US006309361B1

(12) United States Patent
Thornton

(10) Patent No.: US 6,309,361 B1
(45) Date of Patent: Oct. 30, 2001

(54) METHOD FOR IMPROVING MEMORY BY IDENTIFYING AND USING QEEG PARAMETERS CORRELATED TO SPECIFIC COGNITIVE FUNCTIONING

(76) Inventor: Kirtley E. Thornton, 3225 Osborn Ter., Toms River, NJ (US) 08753

(*) Notice: Subject to any disclaimer, the term of this patent is extended or adjusted under 35 U.S.C. 154(b) by 0 days.

(21) Appl. No.: 09/302,321

(22) Filed: Apr. 29, 1999

Related U.S. Application Data
(60) Provisional application No. 60/084,094, filed on May 4, 1998.

(51) Int. Cl.[7] ............................................. A61B 5/04
(52) U.S. Cl. ............................................. 600/544; 600/545
(58) Field of Search ................................ 600/544, 545

(56) References Cited

U.S. PATENT DOCUMENTS

| | | | |
|---|---|---|---|
| 4,913,160 | 4/1990 | John | 128/731 |
| 5,230,346 | 7/1993 | Leuchter et al. | 128/731 |
| 5,269,315 | 12/1993 | Leuchter et al. | 128/731 |
| 5,282,474 | 2/1994 | Valdes Sosa et al. | 128/670 |
| 5,287,859 | 2/1994 | John | 128/731 |
| 5,307,807 | 5/1994 | Valdes Sosa et al. | 128/653.1 |
| 5,309,923 | 5/1994 | Leuchter et al. | 128/731 |
| 5,363,858 | 11/1994 | Farwell | 128/731 |
| 5,392,788 | 2/1995 | Hudspeth | 128/731 |
| 5,467,777 | 11/1995 | Farwell | 128/31 |
| 5,564,433 | 10/1996 | Thornton | 128/731 |
| 5,662,117 | 9/1997 | Bittman | 128/732 |
| 6,016,444 | * 1/2000 | John . | |
| 6,044,292 | * 3/2000 | Heyrend . | |
| 6,052,619 | * 4/2000 | John . | |
| 6,067,467 | * 5/2000 | John . | |
| 6,097,980 | * 8/2000 | Monastra . | |
| 6,132,724 | * 10/2000 | Blum . | |

OTHER PUBLICATIONS

Hall Our Memories Our Selves Feb. 8, 1998.

* cited by examiner

Primary Examiner—Mark Bockelman

(57) ABSTRACT

Mental abilities are labeled with terms such as memory, problem solving, spelling, etc. and can be measured by psychological measures such as recall score, etc. The physical correlates of brain functioning employ such measures as blood flow, electrophysiological events, etc. The relationship between these different scientific domains is called the mind-body problem. The submitted patent addresses the empirically obtained correlative relationships between a number of cognitive capabilities and the Quantitative EFG (QEEG) measures (coherence, phase, magnitude, etc.) during cognitive activation conditions. The QEEG measures reflect the electrophysiology of the gray matter of the brain underlying the scalp. The cognitive abilities addressed include memory for auditory (paragraphs, word lists) and visual (faces, Korean characters, reading material) information (immediate and delayed recall ability), spatial problem solving (Raven's Matrices), spelling, mathematical ability (multiplication, internal spatial addition), pronunciation of nonsense (not real) words, memory for autobiographical information, intentions and where objects have been placed. The patent addresses the different patterns which are responsible for effective cognitive functioning in the adult and child population as well as the normal response patterns across the tasks for the two groups. The relationship between cognitive success of auditory memory ability (paragraphs, word lists) was examined for the eyes closed and auditor, attention condition. The analysis reflected the positive relationship between certain QEEG variables across different cognitive conditions. The value of the patent resides in providing the specific QEEG parameters which are responsible for specitic cognitive abilities. These QEEG variables can be effectively changed through an operant biofeedback conditioning methodology.

7 Claims, 206 Drawing Sheets

| Subject Descriptions | Tot | Hand-edness | | Male | | Female | | Yrs. Educ. | Av. IQ* | Av. Age |
|---|---|---|---|---|---|---|---|---|---|---|
| | | Right | Left | Right | Left | Right | Left | | | |
| Head Injured | 38 | 33 | 5 | 10 | 3 | 23 | 2 | 13.5 | 106 n=33 | 41.6 |
| Normals | 83 | 68 | 15 | 38 | 8 | 30 | 7 | 12.2 | 114 n=59 | 30.7 |
| Children under age 13 | 30 | 25 | 5 | 13 | 2 | 12 | 3 | 4.6 | | 10.4 |
| Total | 151 | 126 | 25 | 61 | 13 | 65 | 12 | 11 | 111 n=92 | 29.3 |

FIGURE 1

| Subject Descriptions | Tot | Hand-edness | | Male | | Female | | Yrs. Educ. | Av. IQ* | Av. Age |
|---|---|---|---|---|---|---|---|---|---|---|
| | | Right | Left | Right | Left | Right | Left | | | |
| Head Injured | 38 | 33 | 5 | 10 | 3 | 23 | 2 | 13.5 | 106 n=33 | 41.6 |
| Normals | 83 | 68 | 15 | 38 | 8 | 30 | 7 | 12.2 | 114 n=59 | 30.7 |
| Children under age 13 | 30 | 25 | 5 | 13 | 2 | 12 | 3 | 4.6 | | 10.4 |
| Total | 151 | 126 | 25 | 61 | 13 | 65 | 12 | 11 | 111 n=92 | 29.3 |

FIGURE 2

| TOTAL | f1 | f2 | f7 | f8 | f3 | f4 | fz | t3 | c3 | c2 | d4 | t4 | t5 | p8 | pz | p4 | t6 | d | c2 | total |
|---|---|---|---|---|---|---|---|---|---|---|---|---|---|---|---|---|---|---|---|---|
| c1 | 4 | 2 | 2 | 3 | 3 | 0 | 0 | 5 | 0 | 0 | 1 | 0 | 5 | 1 | 0 | 0 | 0 | 0 | 0 | 26 |
| ca | 1 | 1 | 4 | 1 | 0 | 0 | 1 | 5 | 6 | 0 | 0 | 1 | 2 | 3 | 1 | 0 | 1 | 1 | 1 | 31 |
| db1 | 2 | 0 | 8 | 3 | 2 | 1 | 1 | 8 | 0 | 0 | 0 | 1 | 1 | 0 | 0 | 0 | 2 | 1 | 0 | 22 |
| db2 | 4 | 4 | 8 | 5 | 3 | 0 | 1 | 0 | 0 | 0 | 1 | 1 | 1 | 0 | 0 | 0 | 1 | 1 | 1 | 32 |
| p1 | 1 | 0 | 2 | 0 | 0 | 0 | 2 | 1 | 1 | 1 | 0 | 3 | 1 | 2 | 1 | 0 | 0 | 2 | 1 | 21 |
| pa | 2 | 1 | 1 | 1 | 0 | 0 | 0 | 2 | 4 | 0 | 0 | 0 | 3 | 1 | 1 | 0 | 1 | 4 | 2 | 32 |
| pb1 | 1 | 1 | 1 | 3 | 2 | 2 | 2 | 3 | 1 | 0 | 0 | 0 | 7 | 1 | 0 | 0 | 1 | 1 | 0 | 20 |
| pb2 | 2 | 1 | 1 | 0 | 0 | 0 | 1 | 1 | 0 | 0 | 0 | 2 | 1 | 0 | 0 | 1 | 2 | 0 | 0 | 11 |
| total | 17 | 10 | 27 | 16 | 10 | 3 | 8 | 27 | 12 | 1 | 2 | 7 | 20 | 8 | 3 | 1 | 8 | 10 | 5 | 195 |

FIGURE 3

| | fp1 | fp2 | f7 | f8 | f3 | f4 | fz | t3 | c3 | cz | c4 | t4 | t5 | p3 | pz | p4 | t6 | o1 | o2 | VIS | AUD |
|---|---|---|---|---|---|---|---|---|---|---|---|---|---|---|---|---|---|---|---|---|---|
| ct-vis | 1 | 0 | 1 | 2 | 2 | 0 | 0 | 2 | 0 | 0 | 1 | 0 | 3 | 0 | 0 | 0 | 0 | 0 | 0 | 12 | |
| aud | 3 | 2 | 1 | 1 | 1 | 0 | 0 | 3 | 0 | 0 | 0 | 0 | 2 | 1 | 0 | 0 | 0 | 0 | 0 | | 14 |
| ca-vis | 0 | 0 | 0 | 0 | 0 | 0 | 0 | 0 | 2 | 0 | 0 | 0 | 0 | 0 | 0 | 0 | 0 | 0 | 1 | 3 | |
| aud | 1 | 1 | 1 | 1 | 0 | 0 | 1 | 8 | 4 | 0 | 0 | 0 | 2 | 3 | 2 | 0 | 1 | 1 | 0 | | 26 |
| cb1-vis | 2 | 0 | 1 | 1 | 1 | 1 | 0 | 0 | 0 | 0 | 0 | 1 | 1 | 0 | 0 | 0 | 0 | 0 | 0 | 8 | |
| aud | 0 | 0 | 2 | 2 | 1 | 0 | 1 | 0 | 0 | 0 | 0 | 1 | 1 | 0 | 0 | 0 | 2 | 1 | 0 | | 9 |
| cb2-vis | 2 | 2 | 2 | 2 | 1 | 0 | 0 | 1 | 0 | 0 | 0 | 0 | 0 | 0 | 0 | 0 | 0 | 1 | 1 | 15 | |
| aud | 2 | 2 | 3 | 3 | 2 | 0 | 1 | 0 | 0 | 0 | 0 | 0 | 2 | 0 | 0 | 0 | 0 | 0 | 0 | | 14 |
| pt-vis | 0 | 0 | 0 | 0 | 0 | 0 | 0 | 1 | 1 | 1 | 0 | 1 | 1 | 1 | 1 | 0 | 0 | 1 | 1 | 7 | |
| aud | 1 | 0 | 1 | 1 | 0 | 0 | 1 | 1 | 1 | 0 | 0 | 2 | 3 | 0 | 0 | 0 | 0 | 2 | 0 | | 11 |
| pa-vis | 1 | 0 | 0 | 1 | 0 | 1 | 0 | 6 | 3 | 0 | 0 | 0 | 5 | 1 | 0 | 0 | 1 | 2 | 1 | 10 | |
| aud | 1 | 1 | 2 | 1 | 2 | 1 | 2 | 1 | 0 | 0 | 0 | 0 | 0 | 1 | 0 | 1 | 0 | 1 | 0 | | 22 |
| pb1-vis | 0 | 0 | 0 | 1 | 0 | 0 | 0 | 2 | 0 | 0 | 0 | 0 | 0 | 0 | 0 | 0 | 0 | 0 | 0 | 9 | |
| aud | 2 | 1 | 0 | 0 | 0 | 0 | 0 | 1 | 0 | 0 | 2 | 2 | 0 | 0 | 0 | 0 | 0 | 0 | 0 | | 12 |
| pb2-vis | 0 | 0 | 0 | 0 | 0 | 0 | 0 | 0 | 0 | 0 | 0 | 0 | 0 | 0 | 0 | 0 | 2 | 0 | 0 | 4 | |
| aud | 0 | 0 | 0 | 0 | 0 | 0 | 0 | 0 | 0 | 0 | 0 | 0 | 0 | 0 | 0 | 0 | 0 | 0 | 0 | | 4 |
| AUD | 8 | 6 | 10 | 10 | 6 | 1 | 6 | 20 | 8 | 1 | 0 | 4 | 10 | 6 | 3 | 1 | 6 | 5 | 1 | 112 | |
| VIS | 9 | 4 | 5 | 6 | 4 | 2 | 0 | 7 | 3 | 0 | 2 | 3 | 10 | 2 | 0 | 0 | 2 | 5 | 4 | 68 | |

FIGURE 4

| Vis&Aud | | fp1 | fp2 | f7 | f8 | f3 | f4 | fz | t3 | c3 | cz | c4 | t4 | t5 | p3 | pz | p4 | t6 | o1 | o2 | |
|---|---|---|---|---|---|---|---|---|---|---|---|---|---|---|---|---|---|---|---|---|---|
| Input | ct | 1 | 0 | 1 | 1 | 1 | 0 | 0 | 1 | 0 | 0 | 1 | 0 | 0 | 1 | 0 | 0 | 0 | 0 | 0 | 7 |
| Recall | | 2 | 2 | 1 | 2 | 2 | 0 | 0 | 3 | 0 | 0 | 0 | 0 | 5 | 0 | 0 | 0 | 0 | 0 | 0 | 17 |
| Delay | | 1 | 0 | 0 | 0 | 0 | 0 | 0 | 1 | 0 | 0 | 0 | 0 | 0 | 0 | 0 | 0 | 0 | 0 | 0 | 2 |
| Input | ca | 1 | 1 | 2 | 1 | 0 | 0 | 1 | 4 | 3 | 0 | 0 | 0 | 1 | 2 | 1 | 0 | 0 | 0 | 1 | 14 |
| Recall | | 0 | 0 | 1 | 0 | 0 | 0 | 0 | 2 | 1 | 0 | 0 | 0 | 1 | 1 | 0 | 0 | 1 | 1 | 0 | 8 |
| Delay | | 0 | 0 | 1 | 0 | 0 | 1 | 0 | 2 | 1 | 0 | 0 | 0 | 0 | 0 | 0 | 0 | 1 | 0 | 0 | 8 |
| Input | cb1 | 1 | 0 | 5 | 2 | 1 | 0 | 0 | 0 | 0 | 0 | 0 | 1 | 0 | 0 | 0 | 0 | 0 | 0 | 0 | 11 |
| Recall | | 1 | 0 | 1 | 1 | 0 | 0 | 0 | 0 | 0 | 0 | 0 | 0 | 1 | 0 | 0 | 0 | 1 | 0 | 0 | 5 |
| Delay | | 0 | 0 | 2 | 0 | 1 | 0 | 0 | 0 | 0 | 0 | 0 | 0 | 1 | 0 | 0 | 0 | 1 | 1 | 0 | 6 |
| Input | cb2 | 1 | 1 | 5 | 2 | 0 | 0 | 0 | 1 | 0 | 0 | 0 | 1 | 0 | 0 | 0 | 0 | 0 | 0 | 0 | 10 |
| Recall | | 1 | 1 | 1 | 1 | 0 | 0 | 0 | 0 | 0 | 1 | 1 | 0 | 0 | 1 | 0 | 0 | 1 | 1 | 0 | 8 |
| Delay | | 2 | 2 | 2 | 2 | 3 | 0 | 0 | 0 | 0 | 0 | 0 | 0 | 0 | 1 | 0 | 0 | 0 | 0 | 1 | 14 |
| Input | pt | 0 | 0 | 1 | 0 | 0 | 0 | 0 | 0 | 0 | 0 | 0 | 0 | 0 | 0 | 1 | 0 | 0 | 0 | 0 | 2 |
| Recall | | 1 | 0 | 2 | 0 | 0 | 0 | 1 | 1 | 1 | 0 | 0 | 0 | 3 | 1 | 0 | 0 | 0 | 2 | 1 | 14 |
| Delay | | 0 | 0 | 1 | 0 | 0 | 0 | 1 | 1 | 0 | 0 | 0 | 2 | 0 | 1 | 0 | 0 | 0 | 0 | 0 | 6 |
| Input | pa | 2 | 0 | 1 | 0 | 0 | 0 | 0 | 3 | 2 | 0 | 0 | 0 | 4 | 0 | 0 | 0 | 1 | 3 | 0 | 10 |
| Recall | | 0 | 0 | 0 | 0 | 0 | 0 | 0 | 2 | 1 | 0 | 0 | 0 | 4 | 1 | 0 | 0 | 0 | 1 | 2 | 14 |
| Delay | | 0 | 0 | 0 | 0 | 0 | 0 | 0 | 2 | 1 | 0 | 0 | 0 | 0 | 0 | 0 | 0 | 0 | 0 | 0 | 8 |
| Input | pb1 | 1 | 1 | 5 | 2 | 1 | 2 | 0 | 0 | 0 | 0 | 0 | 0 | 0 | 0 | 0 | 0 | 1 | 0 | 0 | 14 |
| Recall | | 0 | 0 | 4 | 0 | 0 | 0 | 0 | 1 | 0 | 0 | 0 | 0 | 0 | 0 | 0 | 1 | 0 | 1 | 0 | 7 |
| Delay | | 0 | 0 | 1 | 0 | 0 | 0 | 0 | 1 | 0 | 0 | 0 | 0 | 0 | 1 | 0 | 0 | 0 | 0 | 0 | 6 |
| Input | pb2 | 1 | 0 | 2 | 0 | 0 | 0 | 0 | 0 | 0 | 0 | 0 | 0 | 0 | 0 | 0 | 1 | 0 | 0 | 0 | 4 |
| Recall | | 1 | 1 | 1 | 0 | 0 | 0 | 0 | 0 | 0 | 0 | 0 | 0 | 0 | 0 | 0 | 0 | 0 | 1 | 0 | 4 |
| Delay | | 0 | 0 | 0 | 0 | 0 | 0 | 0 | 0 | 0 | 0 | 0 | 0 | 0 | 0 | 0 | 0 | 1 | 0 | 1 | 2 |
| Input | | 8 | 4 | 22 | 9 | 3 | 0 | 1 | 11 | 5 | 0 | 2 | 2 | 0 | 1 | 0 | 0 | 0 | 0 | 1 | 72 |
| Recall | | 6 | 4 | 11 | 4 | 3 | 0 | 1 | 9 | 3 | 1 | 0 | 1 | 15 | 4 | 1 | 0 | 4 | 7 | 3 | 77 |
| Delay | | 3 | 2 | 8 | 2 | 4 | 0 | 4 | 7 | 2 | 0 | 0 | 2 | 5 | 3 | 1 | 1 | 4 | 3 | 1 | 52 |

FIGURE 5

| visual | | fp1 | fp2 | f7 | f8 | f3 | f4 | fz | t3 | c3 | cz | c4 | t4 | t5 | p3 | pz | p4 | t6 | o1 | o2 | | |
|---|---|---|---|---|---|---|---|---|---|---|---|---|---|---|---|---|---|---|---|---|---|---|
| ct | Input | 1 | 0 | 1 | 1 | 1 | 0 | 0 | 0 | 0 | 0 | 1 | 0 | 0 | 0 | 0 | 0 | 0 | 0 | 0 | 5 | Input |
|  | Recall | 0 | 0 | 0 | 1 | 1 | 0 | 0 | 1 | 0 | 0 | 0 | 0 | 3 | 0 | 0 | 0 | 0 | 0 | 0 | 6 | Recall |
|  | Delay | 0 | 0 | 0 | 0 | 0 | 0 | 0 | 1 | 0 | 0 | 0 | 0 | 0 | 0 | 0 | 0 | 0 | 0 | 0 | 1 | Delay |
| ca | Input | 0 | 0 | 2 | 0 | 0 | 0 | 0 | 0 | 1 | 0 | 0 | 0 | 0 | 0 | 0 | 0 | 0 | 0 | 1 | 4 | Input |
|  | Recall | 0 | 0 | 0 | 0 | 0 | 0 | 0 | 0 | 0 | 0 | 0 | 0 | 0 | 0 | 0 | 0 | 0 | 0 | 0 | 0 | Recall |
|  | Delay | 0 | 0 | 1 | 0 | 0 | 0 | 0 | 0 | 1 | 0 | 0 | 0 | 0 | 0 | 0 | 0 | 0 | 0 | 0 | 2 | Delay |
| cb1 | Input | 1 | 0 | 3 | 0 | 1 | 0 | 0 | 0 | 0 | 0 | 0 | 0 | 1 | 0 | 0 | 0 | 0 | 0 | 1 | 7 | Input |
|  | Recall | 1 | 0 | 1 | 1 | 0 | 0 | 0 | 0 | 1 | 0 | 0 | 0 | 0 | 0 | 0 | 0 | 0 | 0 | 0 | 4 | Recall |
|  | Delay | 0 | 0 | 0 | 0 | 0 | 0 | 0 | 0 | 0 | 0 | 0 | 0 | 0 | 0 | 0 | 0 | 0 | 0 | 0 | 0 | Delay |
| cb2 | Input | 1 | 1 | 3 | 2 | 0 | 0 | 0 | 0 | 0 | 0 | 1 | 0 | 0 | 0 | 0 | 0 | 0 | 0 | 0 | 8 | Input |
|  | Recall | 1 | 1 | 1 | 0 | 0 | 0 | 0 | 1 | 0 | 0 | 0 | 1 | 1 | 0 | 0 | 0 | 0 | 1 | 0 | 7 | Recall |
|  | Delay | 0 | 0 | 0 | 0 | 0 | 0 | 0 | 0 | 0 | 0 | 0 | 1 | 0 | 0 | 0 | 0 | 0 | 0 | 1 | 2 | Delay |
| pt | Input | 0 | 0 | 0 | 0 | 0 | 0 | 0 | 0 | 0 | 0 | 0 | 0 | 0 | 1 | 0 | 0 | 0 | 0 | 1 | 2 | Input |
|  | Recall | 0 | 0 | 1 | 0 | 0 | 0 | 0 | 0 | 0 | 0 | 0 | 0 | 2 | 0 | 0 | 0 | 1 | 2 | 0 | 6 | Recall |
|  | Delay | 0 | 0 | 1 | 0 | 0 | 0 | 0 | 1 | 0 | 0 | 0 | 0 | 0 | 0 | 0 | 0 | 0 | 0 | 0 | 2 | Delay |
| pa | Input | 1 | 0 | 0 | 0 | 0 | 0 | 0 | 0 | 0 | 0 | 0 | 0 | 0 | 0 | 0 | 0 | 0 | 0 | 0 | 1 | Input |
|  | Recall | 0 | 0 | 0 | 0 | 0 | 0 | 0 | 0 | 0 | 0 | 0 | 0 | 2 | 0 | 0 | 0 | 1 | 2 | 1 | 6 | Recall |
|  | Delay | 0 | 0 | 0 | 0 | 0 | 0 | 0 | 1 | 0 | 0 | 0 | 0 | 1 | 0 | 0 | 0 | 1 | 0 | 0 | 3 | Delay |
| pb1 | Input | 1 | 1 | 2 | 1 | 0 | 1 | 0 | 1 | 0 | 0 | 0 | 0 | 0 | 0 | 0 | 0 | 0 | 0 | 0 | 7 | Input |
|  | Recall | 0 | 0 | 3 | 0 | 0 | 0 | 0 | 0 | 1 | 0 | 0 | 0 | 0 | 0 | 0 | 0 | 0 | 1 | 0 | 5 | Recall |
|  | Delay | 0 | 0 | 0 | 0 | 0 | 0 | 0 | 0 | 0 | 0 | 0 | 0 | 0 | 1 | 0 | 0 | 0 | 0 | 0 | 1 | Delay |
| pb2 | Input | 1 | 0 | 2 | 0 | 0 | 0 | 0 | 0 | 0 | 0 | 0 | 0 | 0 | 0 | 0 | 0 | 0 | 1 | 0 | 4 | Input |
|  | Recall | 1 | 1 | 1 | 0 | 0 | 0 | 0 | 0 | 0 | 0 | 0 | 0 | 0 | 0 | 0 | 0 | 0 | 0 | 0 | 3 | Recall |
|  | Delay | 0 | 0 | 0 | 0 | 0 | 0 | 0 | 0 | 0 | 0 | 0 | 0 | 0 | 0 | 0 | 0 | 0 | 0 | 0 | 0 | Delay |
|  | Input | 6 | 2 | 14 | 4 | 2 | 2 | 0 | 2 | 1 | 0 | 2 | 2 | 0 | 0 | 0 | 0 | 0 | 0 | 1 | 38 |  |
|  | Recall | 3 | 2 | 7 | 2 | 1 | 0 | 0 | 2 | 0 | 0 | 0 | 1 | 9 | 1 | 0 | 0 | 2 | 5 | 2 | 37 |  |
|  | Delay | 0 | 0 | 2 | 0 | 1 | 0 | 0 | 3 | 2 | 0 | 0 | 0 | 1 | 1 | 0 | 0 | 0 | 0 | 1 | 11 |  |
|  |  | fp1 | fp2 | f7 | f8 | f3 | f4 | fz | t3 | c3 | cz | c4 | t4 | t5 | p3 | pz | p4 | t6 | o1 | o2 |  |  |

FIGURE 6

| auditory | fp1 | fp2 | f7 | f8 | f3 | f4 | fz | t3 | c3 | cz | c4 | t4 | t5 | p3 | pz | p4 | t6 | o1 | o2 |  |  |
|---|---|---|---|---|---|---|---|---|---|---|---|---|---|---|---|---|---|---|---|---|---|
| ct | 0 | 0 | 0 | 0 | 0 | 0 | 0 | 1 | 0 | 0 | 0 | 0 | 0 | 1 | 0 | 0 | 0 | 0 | 0 | 2 | Input |
|  | 2 | 2 | 1 | 1 | 1 | 0 | 0 | 2 | 0 | 0 | 0 | 0 | 2 | 0 | 0 | 0 | 0 | 0 | 0 | 11 | Recall |
|  | 1 | 0 | 0 | 0 | 0 | 0 | 0 | 0 | 0 | 0 | 0 | 0 | 0 | 0 | 0 | 0 | 0 | 0 | 0 | 1 | Delay |
| ca | 1 | 1 | 0 | 1 | 0 | 0 | 1 | 4 | 3 | 0 | 0 | 0 | 0 | 0 | 1 | 0 | 0 | 0 | 0 | 11 | Input |
|  | 0 | 0 | 1 | 0 | 0 | 0 | 0 | 2 | 1 | 0 | 0 | 0 | 1 | 2 | 0 | 0 | 1 | 1 | 0 | 8 | Recall |
|  | 0 | 0 | 0 | 0 | 0 | 0 | 0 | 2 | 0 | 0 | 0 | 0 | 0 | 0 | 0 | 0 | 1 | 0 | 0 | 6 | Delay |
| cb1 | 0 | 0 | 2 | 2 | 0 | 0 | 0 | 0 | 0 | 0 | 0 | 0 | 0 | 0 | 0 | 0 | 0 | 0 | 0 | 4 | Input |
|  | 0 | 0 | 2 | 0 | 0 | 0 | 1 | 0 | 0 | 0 | 0 | 0 | 0 | 0 | 0 | 0 | 0 | 1 | 0 | 1 | Recall |
|  | 0 | 0 | 2 | 0 | 1 | 0 | 0 | 0 | 0 | 0 | 0 | 0 | 0 | 0 | 0 | 0 | 1 | 1 | 0 | 6 | Delay |
| cb2 | 0 | 0 | 2 | 0 | 0 | 0 | 0 | 0 | 0 | 0 | 0 | 0 | 0 | 0 | 0 | 0 | 0 | 0 | 0 | 2 | Input |
|  | 0 | 0 | 0 | 1 | 0 | 0 | 1 | 0 | 0 | 0 | 0 | 0 | 0 | 0 | 0 | 0 | 0 | 0 | 0 | 1 | Recall |
|  | 2 | 2 | 2 | 2 | 2 | 0 | 1 | 0 | 1 | 1 | 0 | 0 | 0 | 0 | 0 | 0 | 0 | 0 | 0 | 12 | Delay |
| pt | 0 | 0 | 0 | 0 | 0 | 0 | 0 | 0 | 0 | 0 | 0 | 0 | 0 | 0 | 0 | 0 | 0 | 0 | 0 | 0 | Input |
|  | 1 | 0 | 1 | 0 | 0 | 0 | 1 | 0 | 1 | 0 | 0 | 2 | 0 | 0 | 1 | 0 | 1 | 0 | 0 | 8 | Recall |
|  | 0 | 0 | 0 | 0 | 0 | 0 | 0 | 1 | 2 | 0 | 0 | 0 | 2 | 0 | 0 | 0 | 0 | 0 | 0 | 5 | Delay |
| pa | 1 | 0 | 1 | 1 | 1 | 0 | 1 | 3 | 1 | 0 | 0 | 0 | 3 | 0 | 0 | 0 | 0 | 0 | 0 | 9 | Input |
|  | 0 | 0 | 3 | 0 | 1 | 0 | 0 | 2 | 0 | 0 | 0 | 0 | 0 | 1 | 0 | 0 | 0 | 0 | 0 | 7 | Recall |
|  | 0 | 0 | 1 | 1 | 1 | 0 | 0 | 1 | 0 | 0 | 0 | 0 | 0 | 0 | 0 | 0 | 0 | 1 | 0 | 5 | Delay |
| pb1 | 0 | 0 | 0 | 0 | 0 | 1 | 0 | 1 | 0 | 0 | 0 | 0 | 0 | 0 | 0 | 1 | 0 | 1 | 0 | 7 | Input |
|  | 0 | 0 | 1 | 1 | 0 | 0 | 0 | 0 | 0 | 0 | 0 | 0 | 0 | 0 | 0 | 0 | 0 | 0 | 0 | 2 | Recall |
|  | 0 | 0 | 0 | 0 | 0 | 0 | 0 | 1 | 0 | 0 | 0 | 2 | 0 | 0 | 0 | 0 | 0 | 0 | 0 | 6 | Delay |
| pb2 | 0 | 0 | 0 | 0 | 0 | 0 | 0 | 0 | 0 | 0 | 0 | 0 | 0 | 0 | 0 | 0 | 0 | 0 | 0 | 0 | Input |
|  | 0 | 0 | 0 | 1 | 0 | 0 | 0 | 0 | 0 | 0 | 0 | 2 | 0 | 0 | 0 | 0 | 1 | 0 | 0 | 3 | Recall |
|  | 0 | 0 | 1 | 0 | 1 | 0 | 1 | 0 | 0 | 0 | 0 | 0 | 0 | 1 | 1 | 0 | 1 | 0 | 0 | 2 | Delay |
|  | 2 | 2 | 8 | 5 | 1 | 1 | 1 | 9 | 5 | 0 | 0 | 2 | 6 | 1 | 1 | 0 | 2 | 2 | 0 | 35 | Input |
|  | 3 | 2 | 4 | 2 | 2 | 0 | 1 | 7 | 3 | 1 | 0 | 2 | 4 | 3 | 1 | 0 | 4 | 3 | 0 | 41 | Recall |
|  | 3 | 2 | 6 | 3 | 3 | 0 | 4 | 4 | 0 | 0 | 0 | 2 | 4 | 2 | 1 | 1 | 4 | 1 | 1 | 43 | Delay |
|  | fp1 | fp2 | f7 | f8 | f3 | f4 | fz | t3 | c3 | cz | c4 | t4 | t5 | p3 | pz | p4 | t6 | o1 | o2 |  |  |

Positive Correlations with Auditory Recall

Negative Correlations with Auditory Recall

Figure 9
Positive Correlations with Auditory Recall
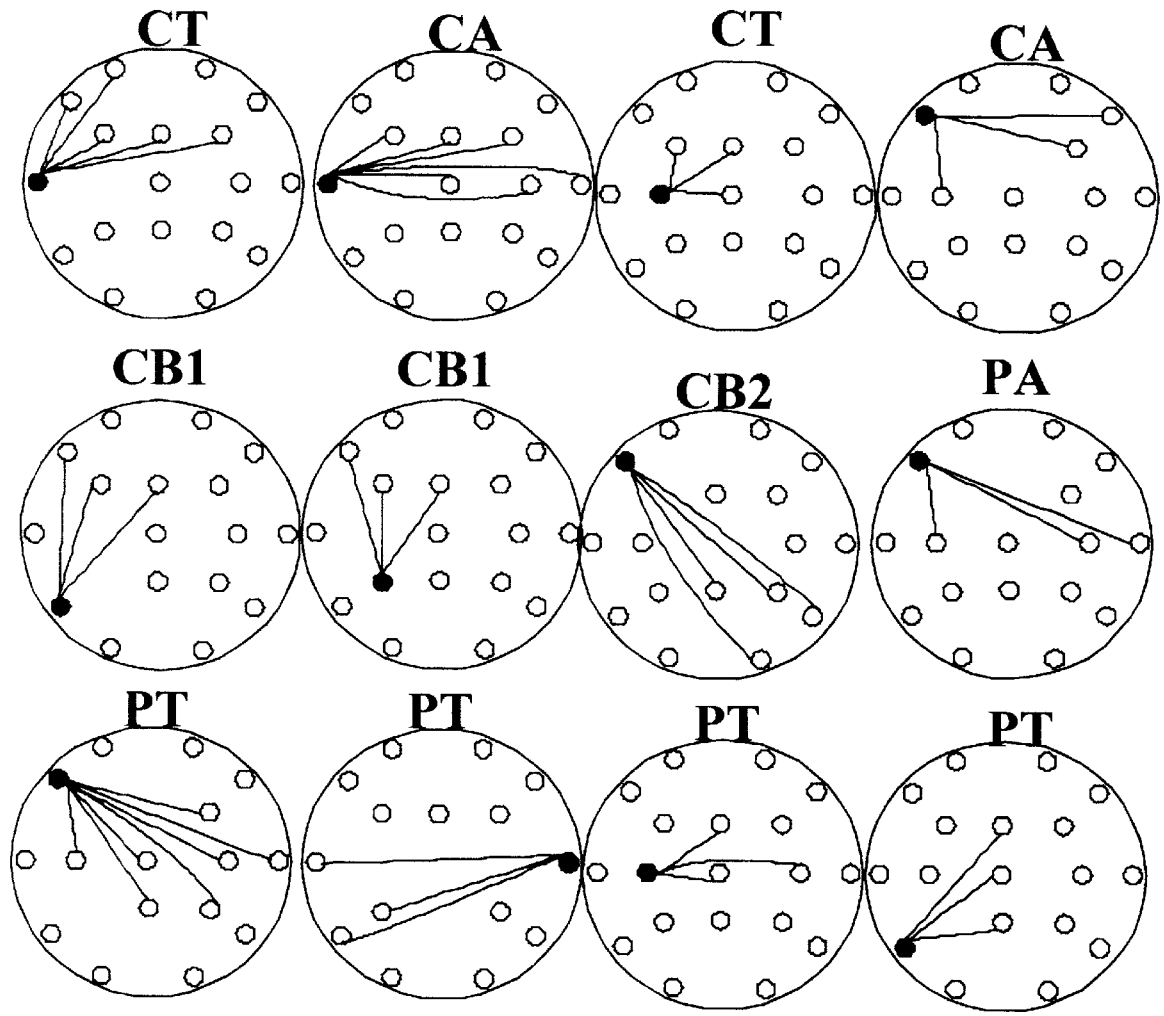
Negative Correlations with Recall
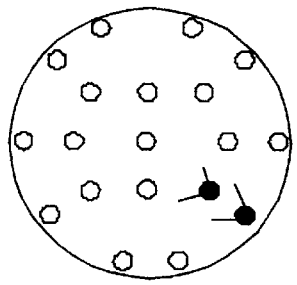

Figure 10
Positively Correlated with Recall
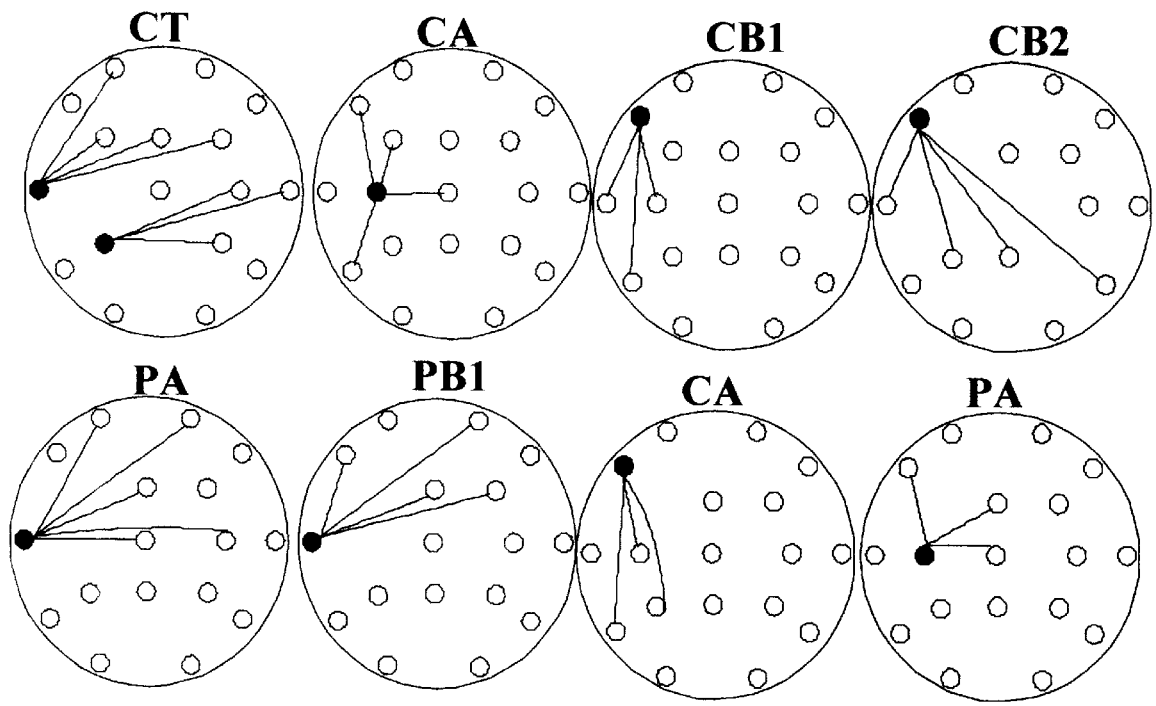
Negatively Correlated with Recall
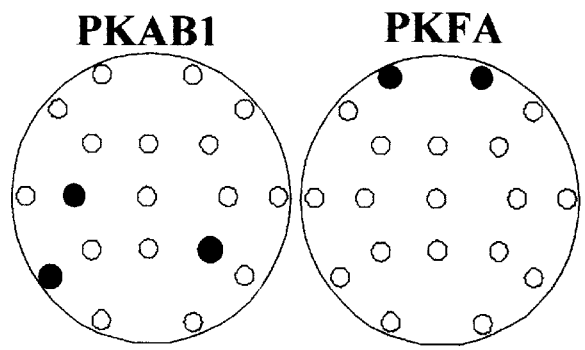

Figure 11
Positively Correlated with Recall
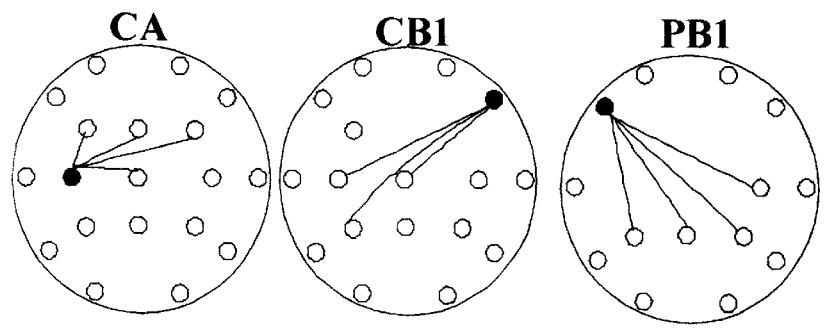
Negatively Correlated with Recall
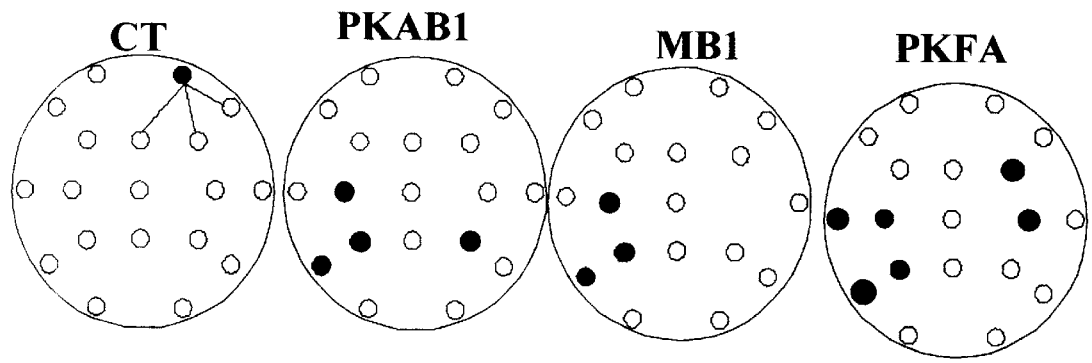

Figure 12
Positively Correlated with Recall
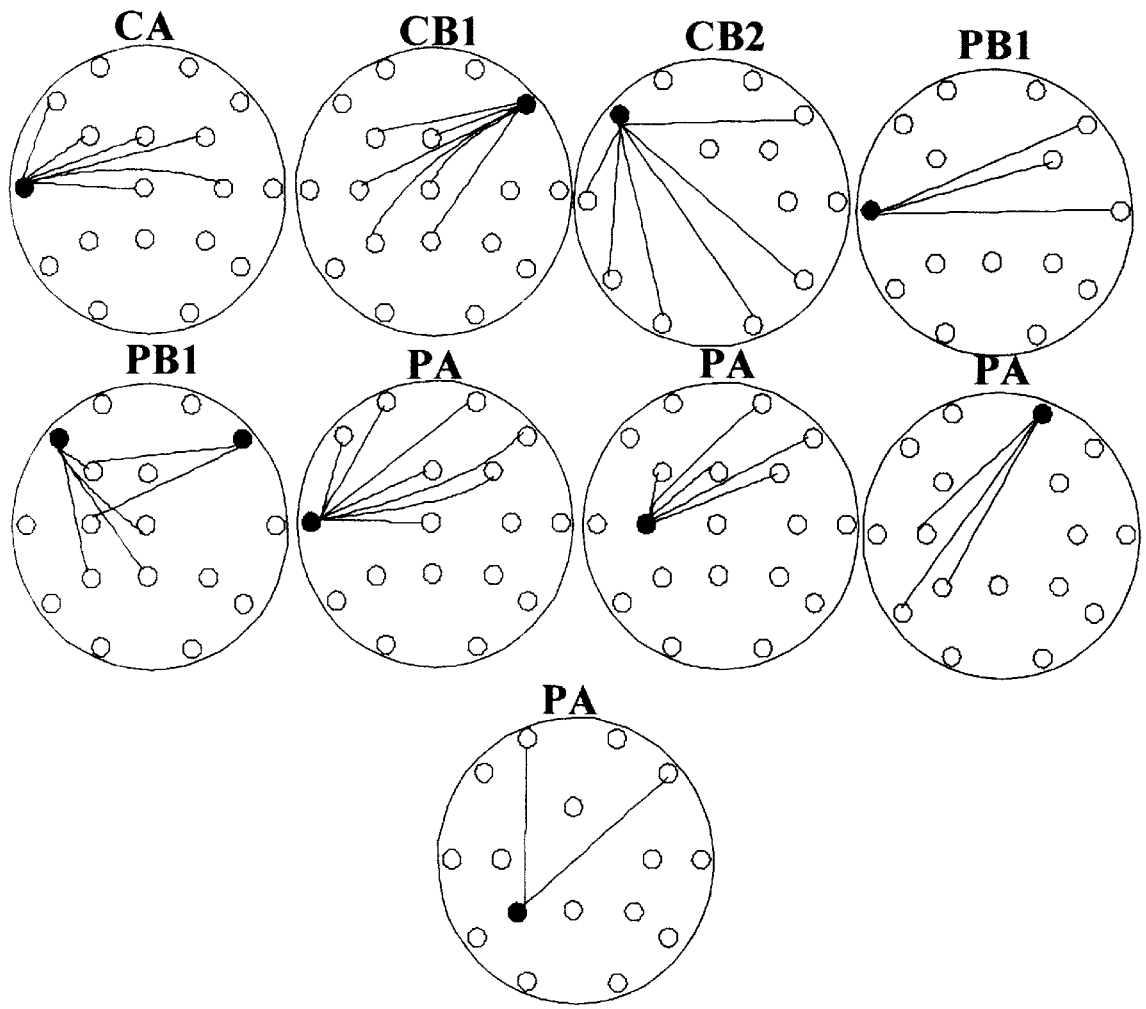
Negatively Correlated with Recall
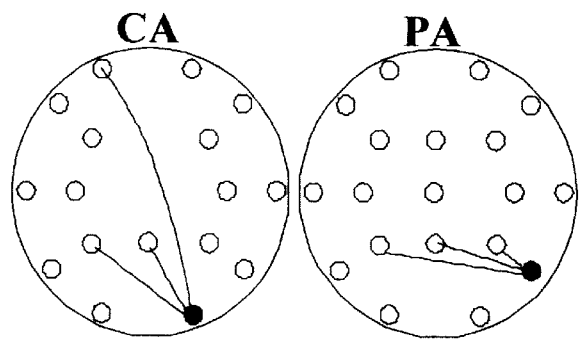

Positively Correlated with Recall

Negatively Correlated with Recall

Positively Correlated with Recall

Figure 14B
Negatively Correlated with Recall
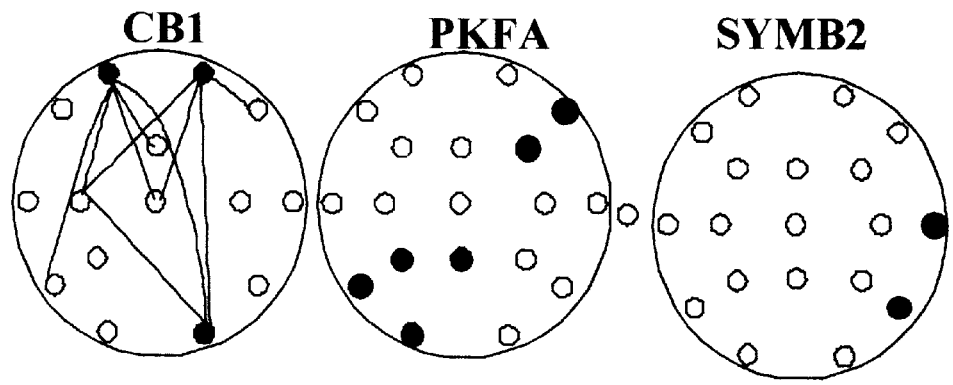
Figure 15
Positively Correlated with Recall
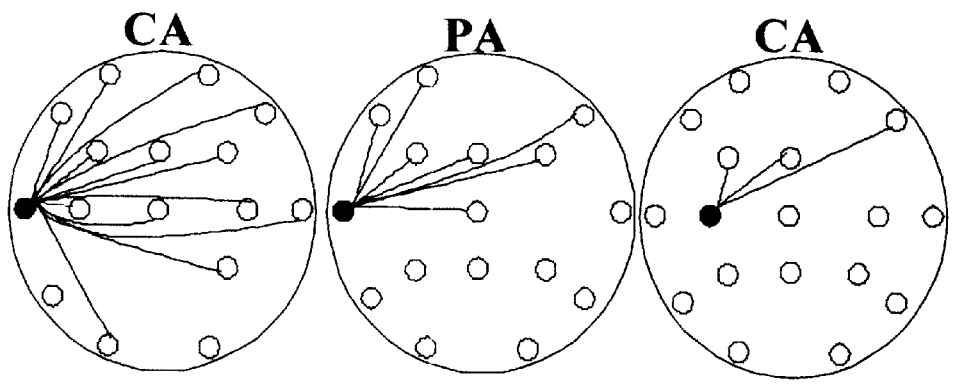
Negatively Correlated with Recall
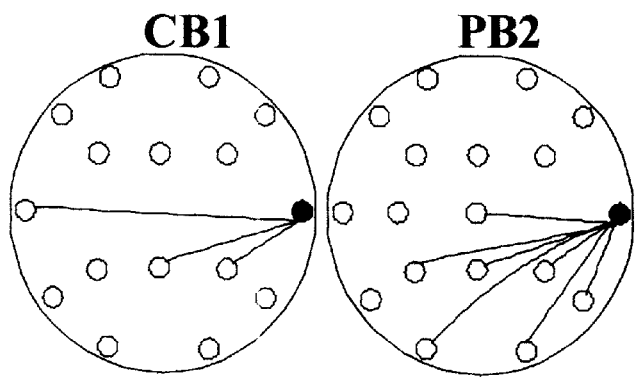

Positively Correlated with Recall**

Figure 17
Positively Correlated with Recall
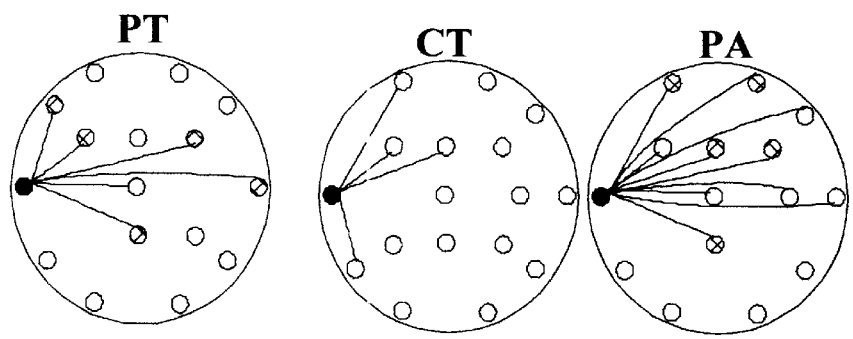
Negatively Correlated with Recall
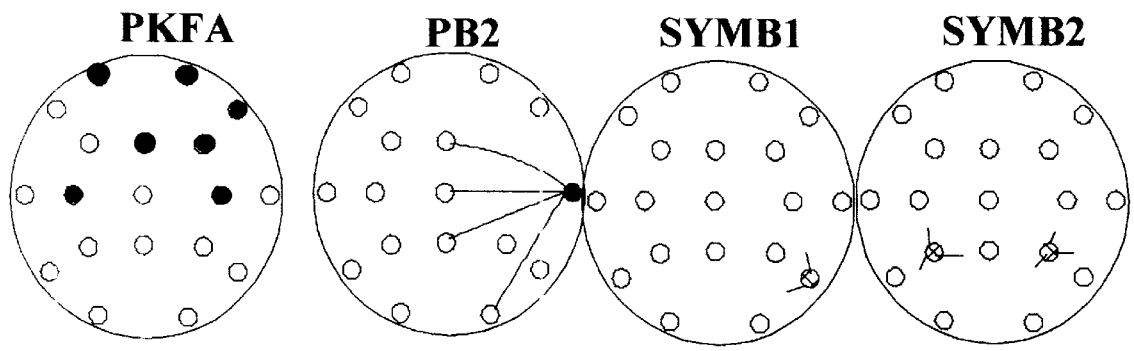

Positively Correlated with Recall

Negatively Correlated with Recall

Figure 19
Positively Correlated with Recall
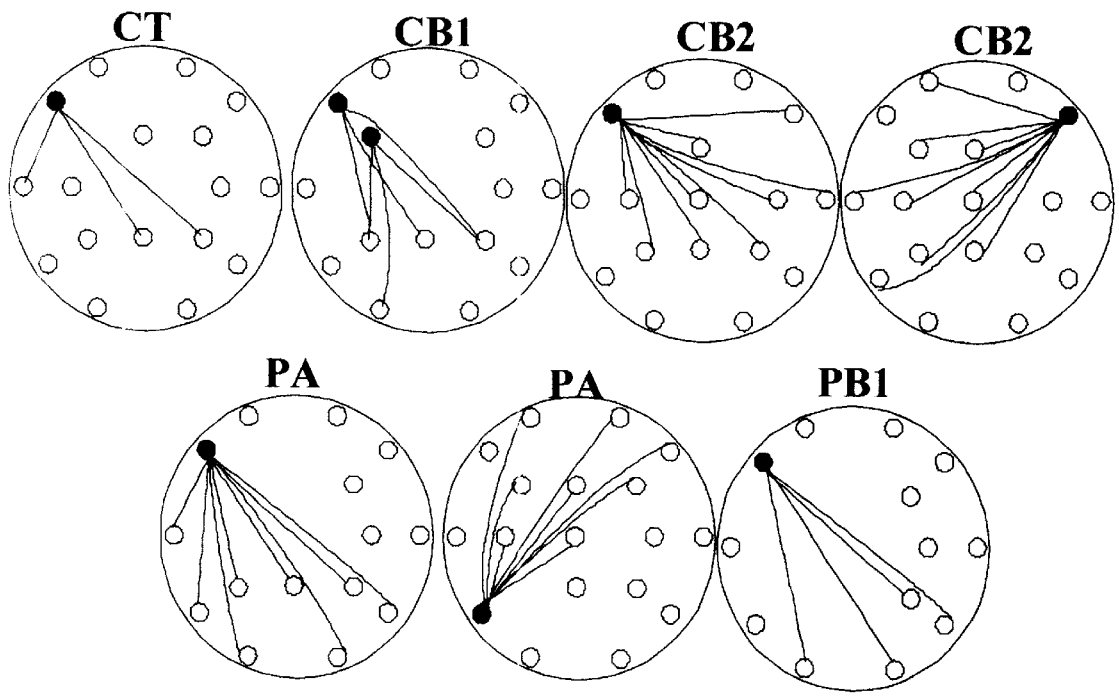
Negatively Correlated with Recall
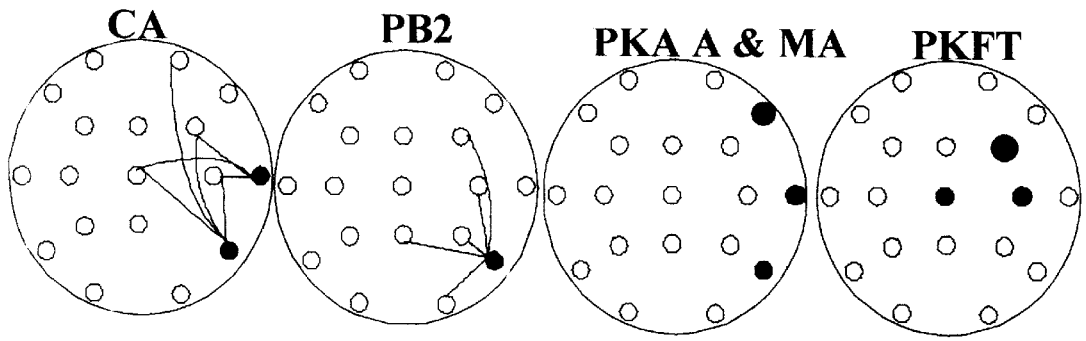

Figure 20
Positively Correlated with Recall
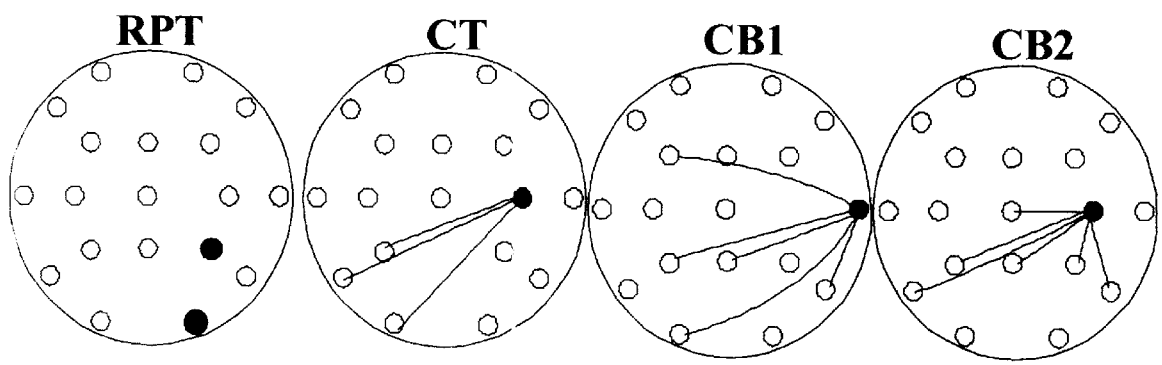
Negatively Correlated with Recall
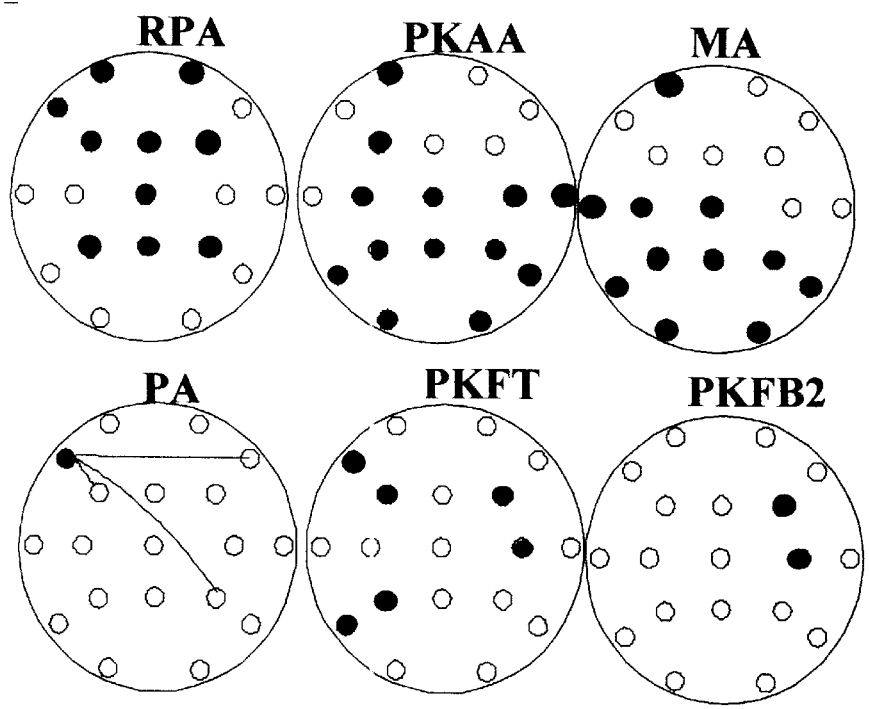

Positively Correlated with Recall**

Negatively Correlated with Recall**

PKFT

Positively Correlated with Recall

Positively Correlated with Recall

Figure 23B
Positively Correlated with Recall
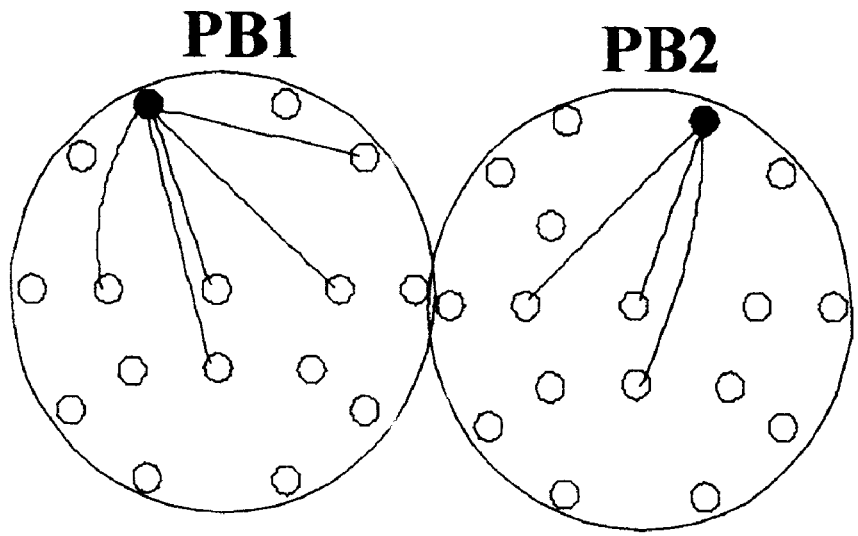
Negatively Correlated with Recall
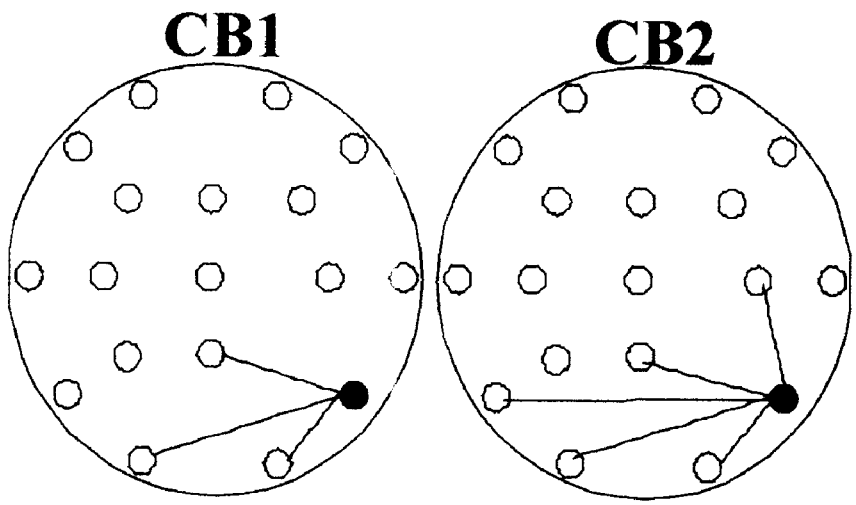

Negatively Correlated with Recall

Figure 25
Positively Correlated with Recall
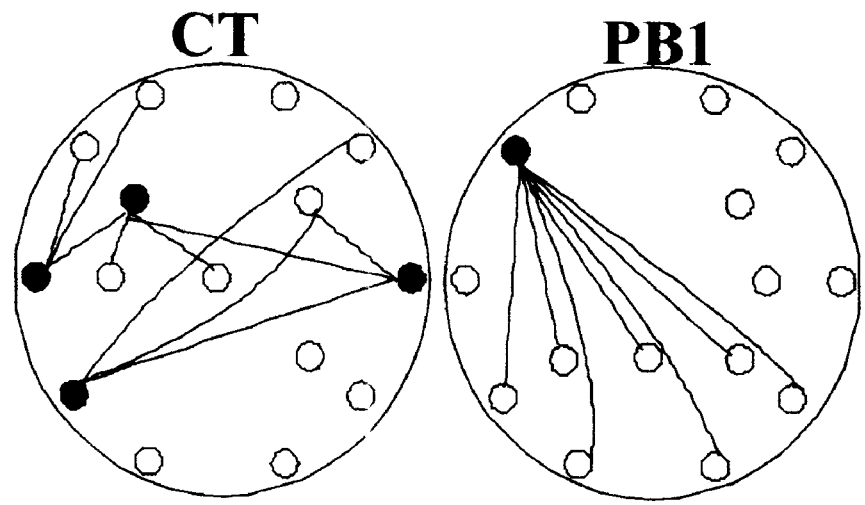
Negatively Correlated with Recall
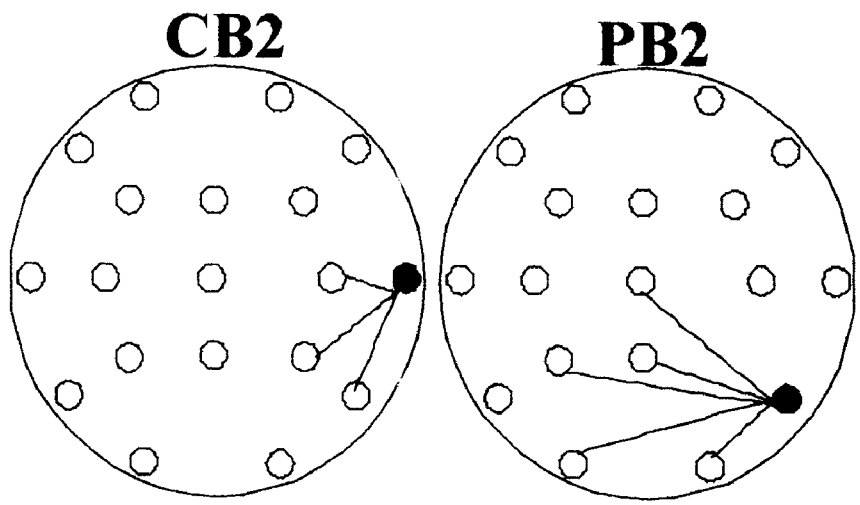

Positively Correlated with Recall**

Figure 27
Positively Correlated with Recall
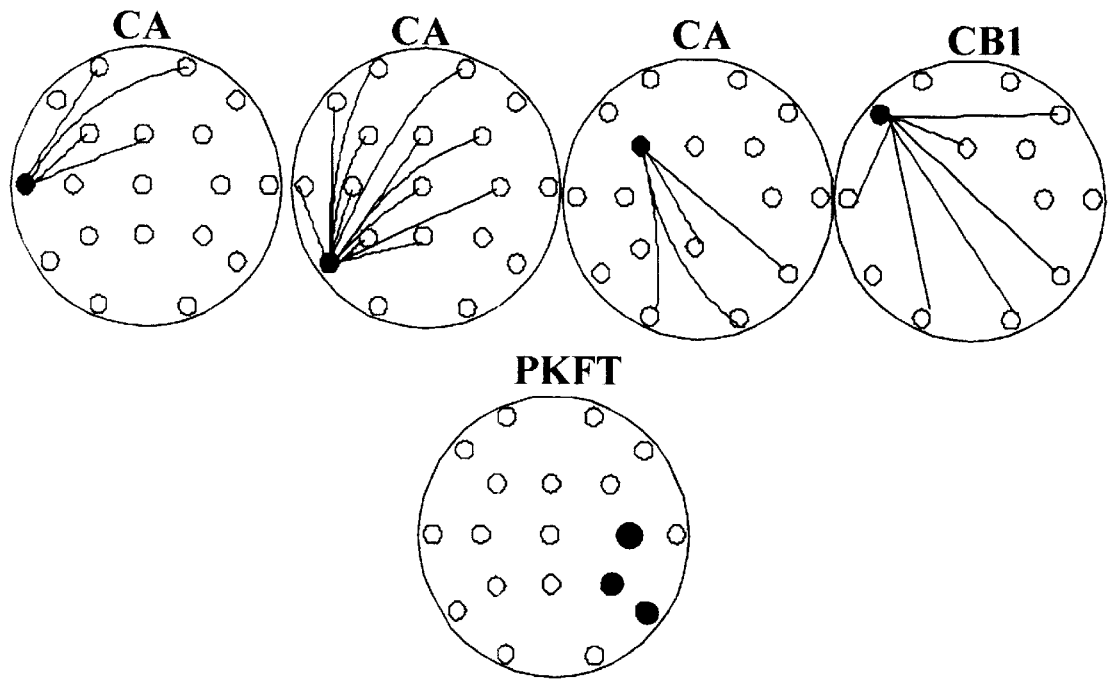
Negatively Correlated with Recall
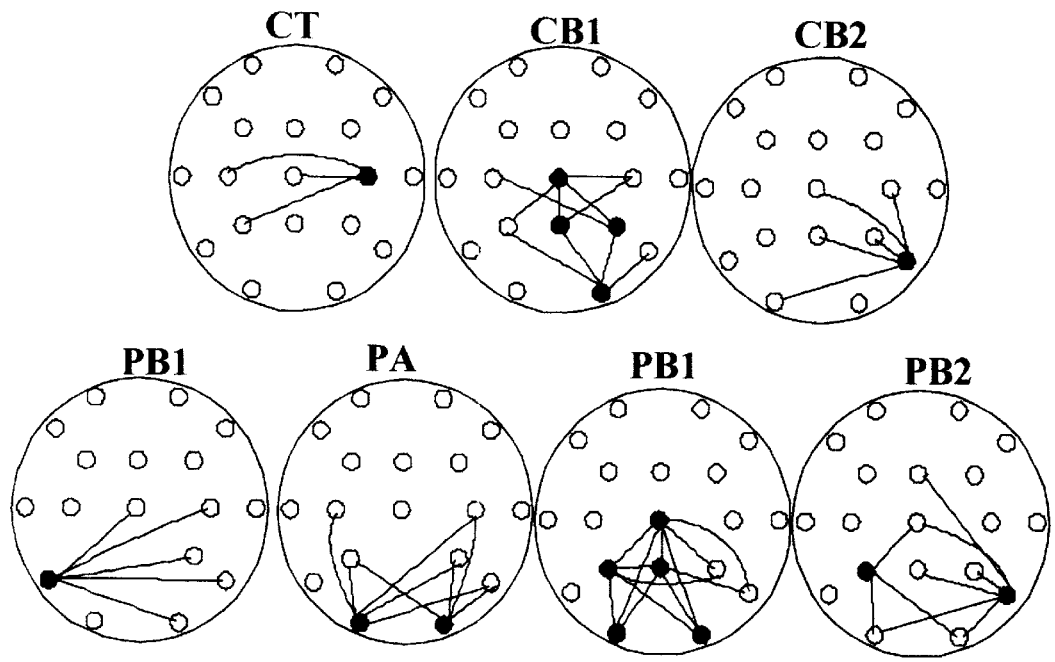

Figure 28
Positively Correlated with Recall
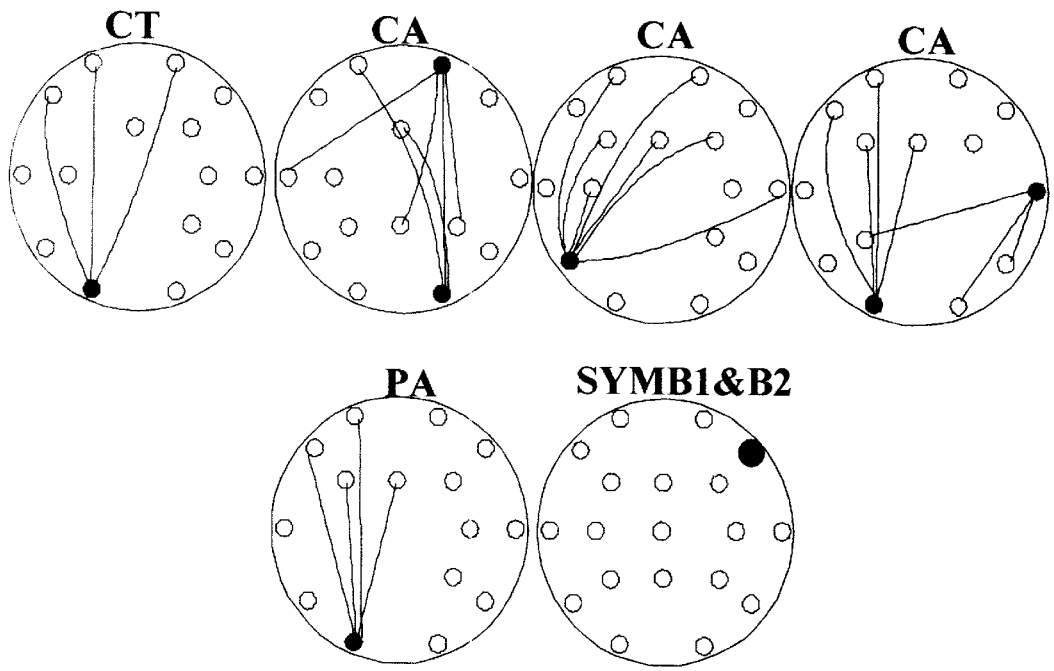
Negatively Correlated with Recall
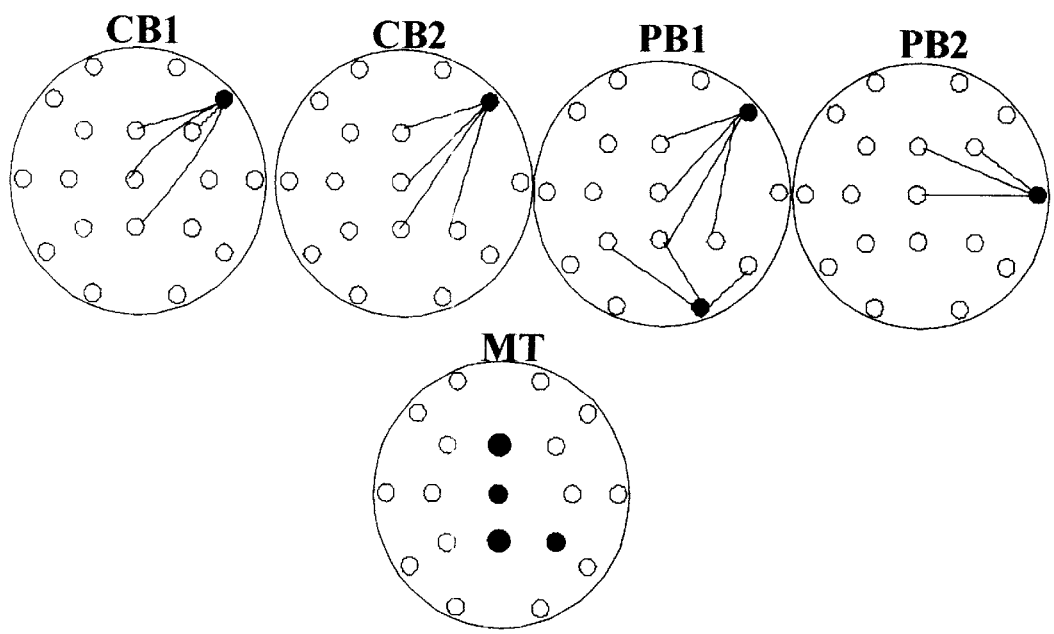

Figure 29
Positively Correlated with Recall
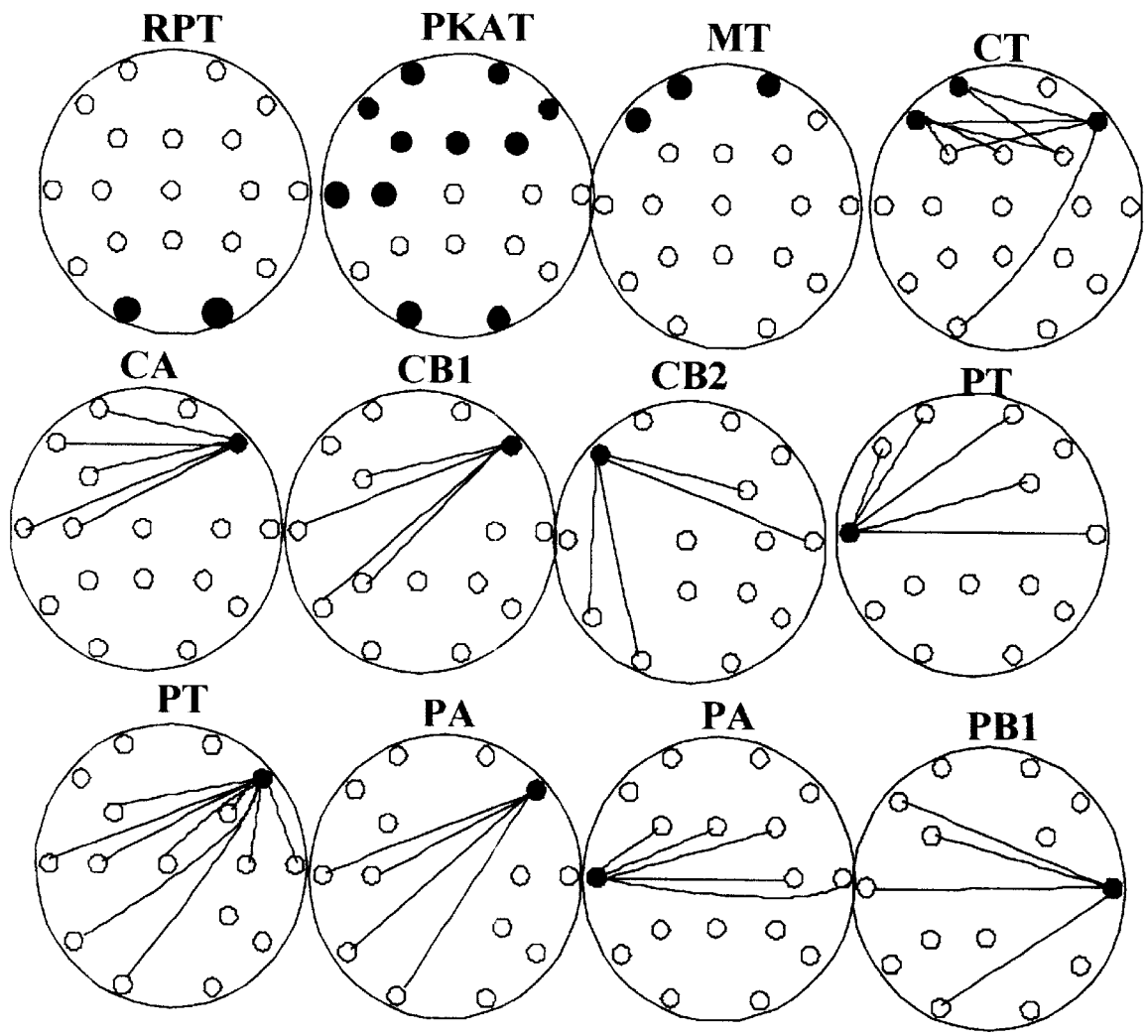
Negatively Correlated with Recall
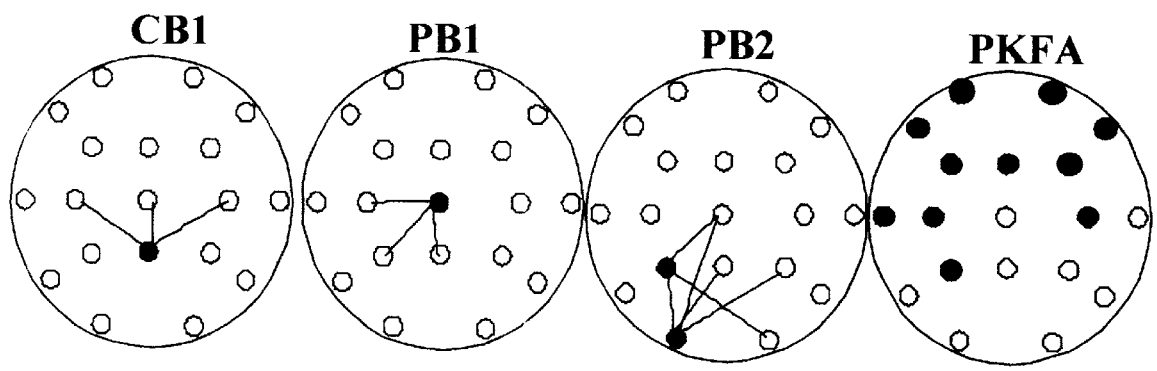

Positively Correlated with Recall

Positively Correlated with Recall

Positively Correlated with Performance

Figure 31B
Positively Correlated with Performance
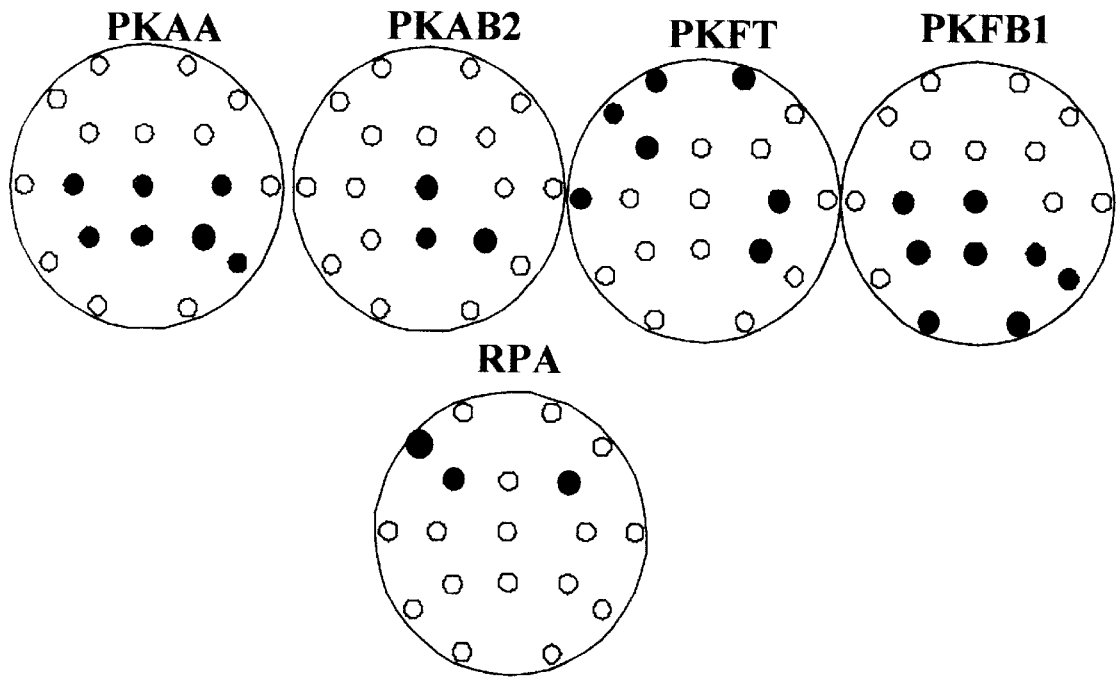
Negatively Correlated with Performance
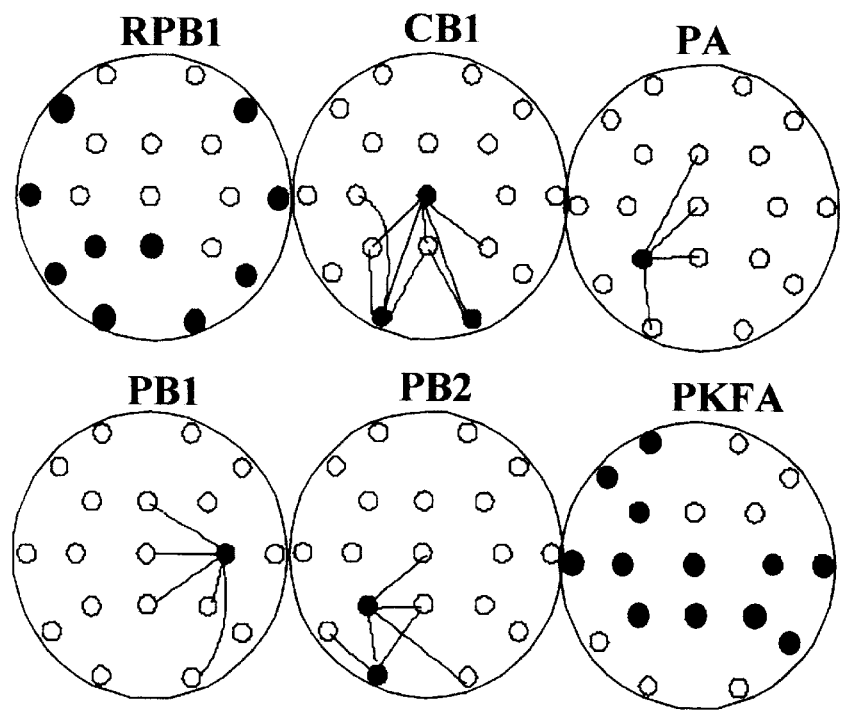

Figure 32
Positively Correlated with Performance
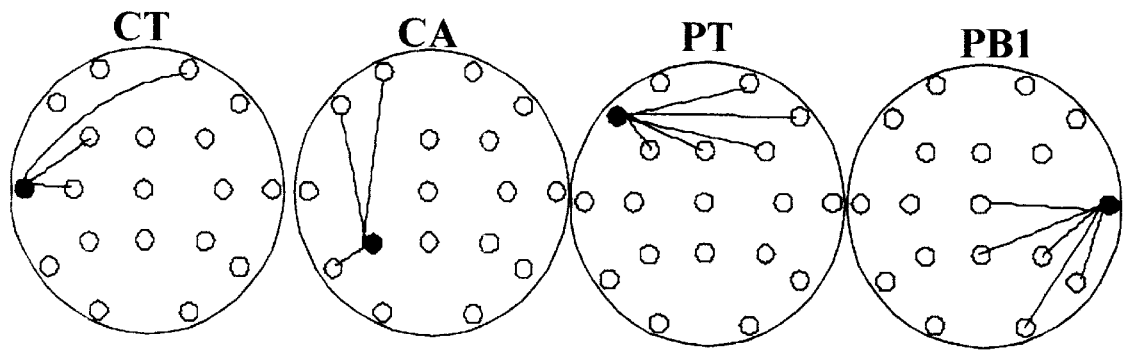
Negatively Correlated with Performance
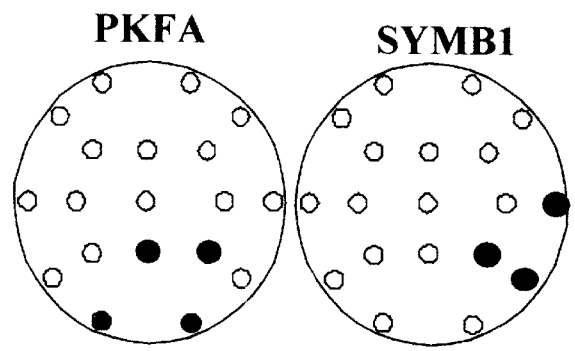

Positively Correlated with Performance**

Negatively Correlated with Performance**

Positively Correlated with Performance**

Negatively Correlated with Performance

Positively Correlated with Performance

Negatively Correlated with Performance

Positively Correlated with Performance**

Negatively Correlated with Performance

Positively Correlated with Performance

Negatively Correlated with Performance

Positively Correlated with Performance

Negatively Correlated with Performance

Positively Correlated with Performance**

Positively Correlated with Performance

Negatively Correlated with Performance

Figure 41
Positively Correlated with Performance
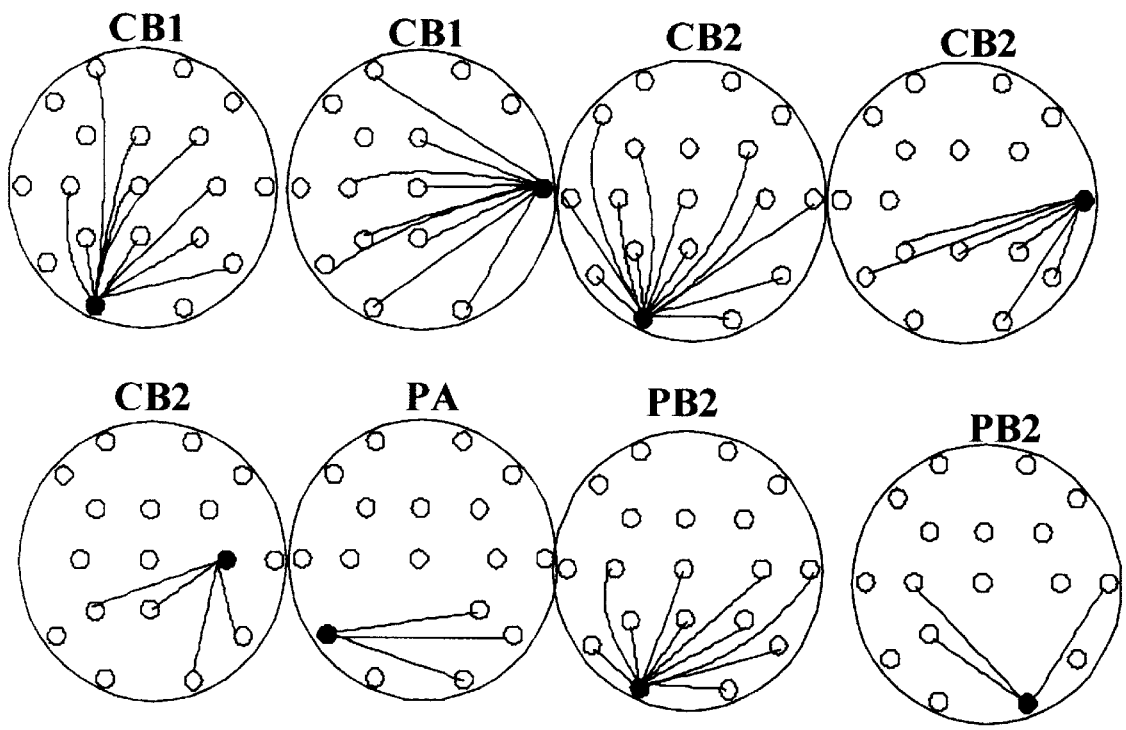
Negatively Correlated with Performance
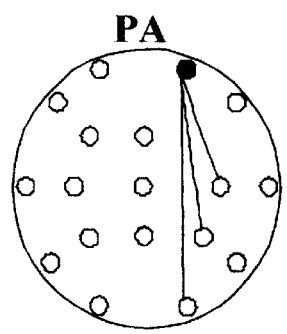

Figure 42
Positively Correlated with Recall
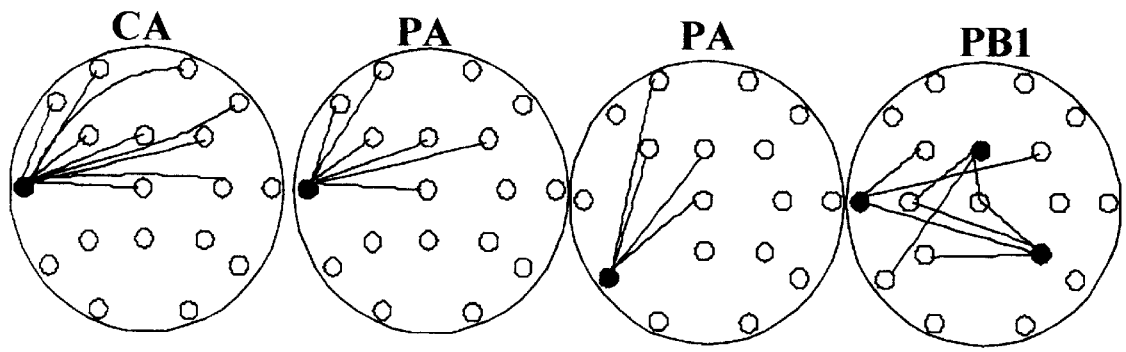
Negatively Correlated with Recall
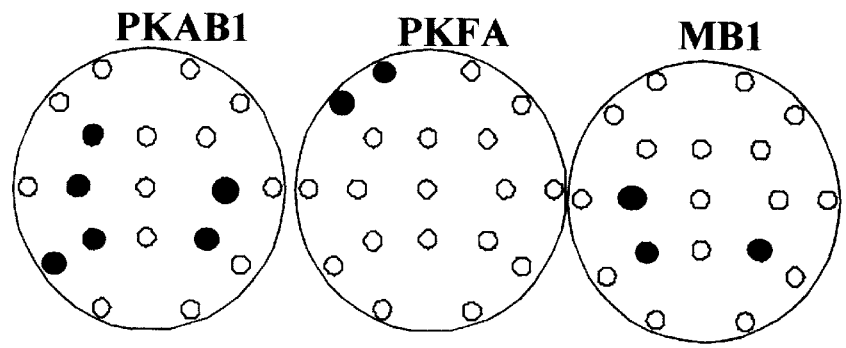

Positively Correlated with Recall

Figure 43B
Negatively Correlated with Recall
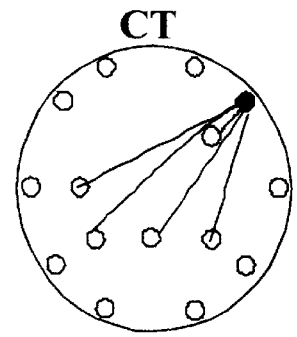
CT
Figure 44A
Positively Correlated with Recall
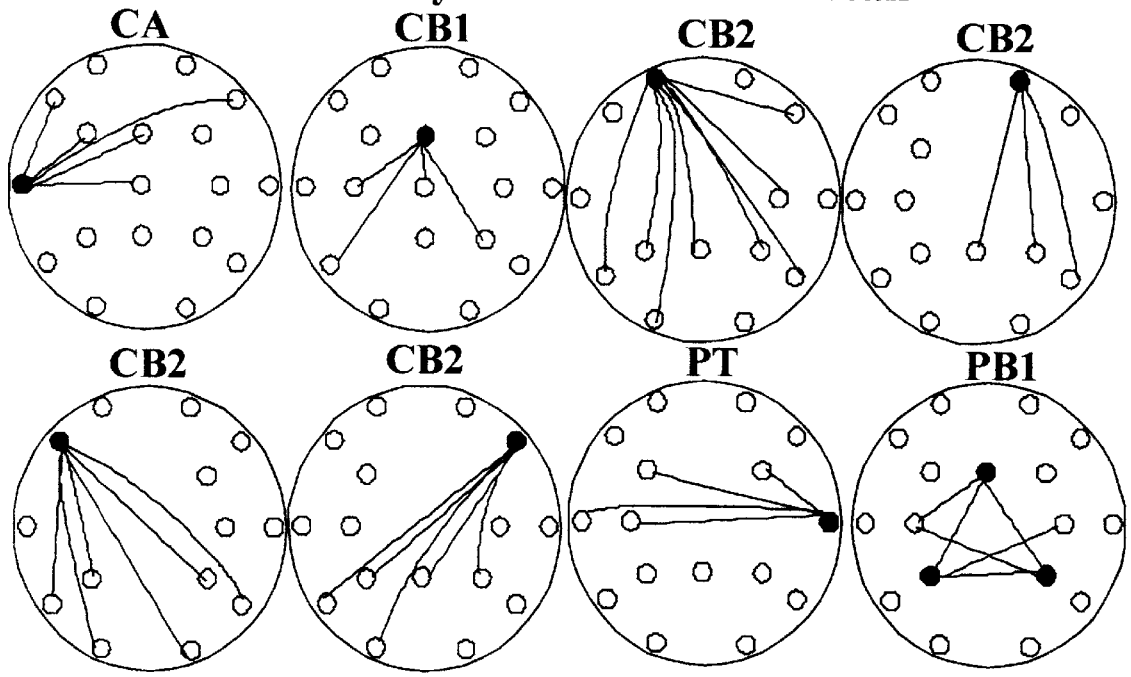
CA  CB1  CB2  CB2
CB2  CB2  PT  PB1
SYMB1&B2
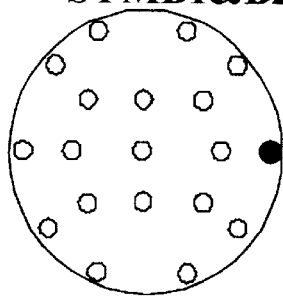

Negatively Correlated with Recall

Positively Correlated with Recall

Figure 45B
Negatively Correlated with Recall
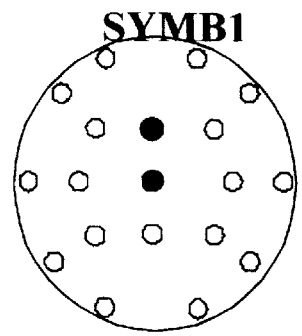
Figure 46
Positively Correlated with Recall
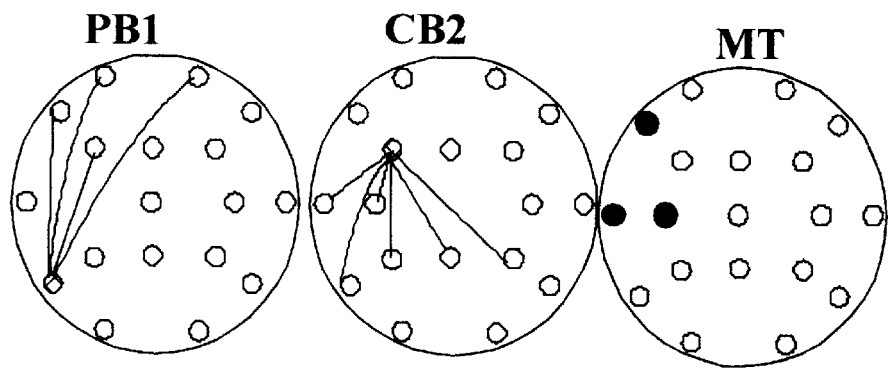
Negatively Correlated with Recall
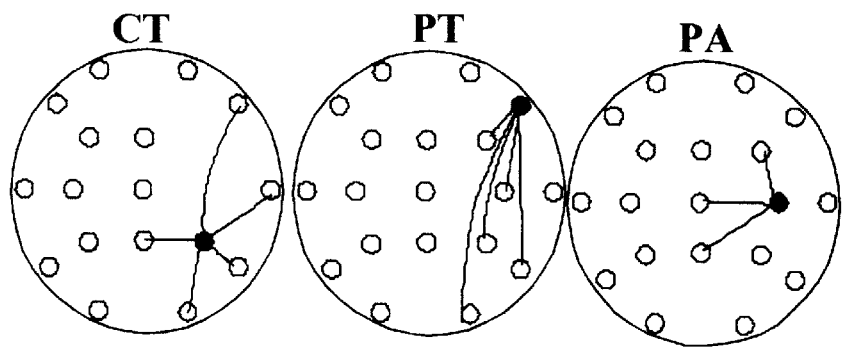

Figure 47
Positively Correlated with Recall
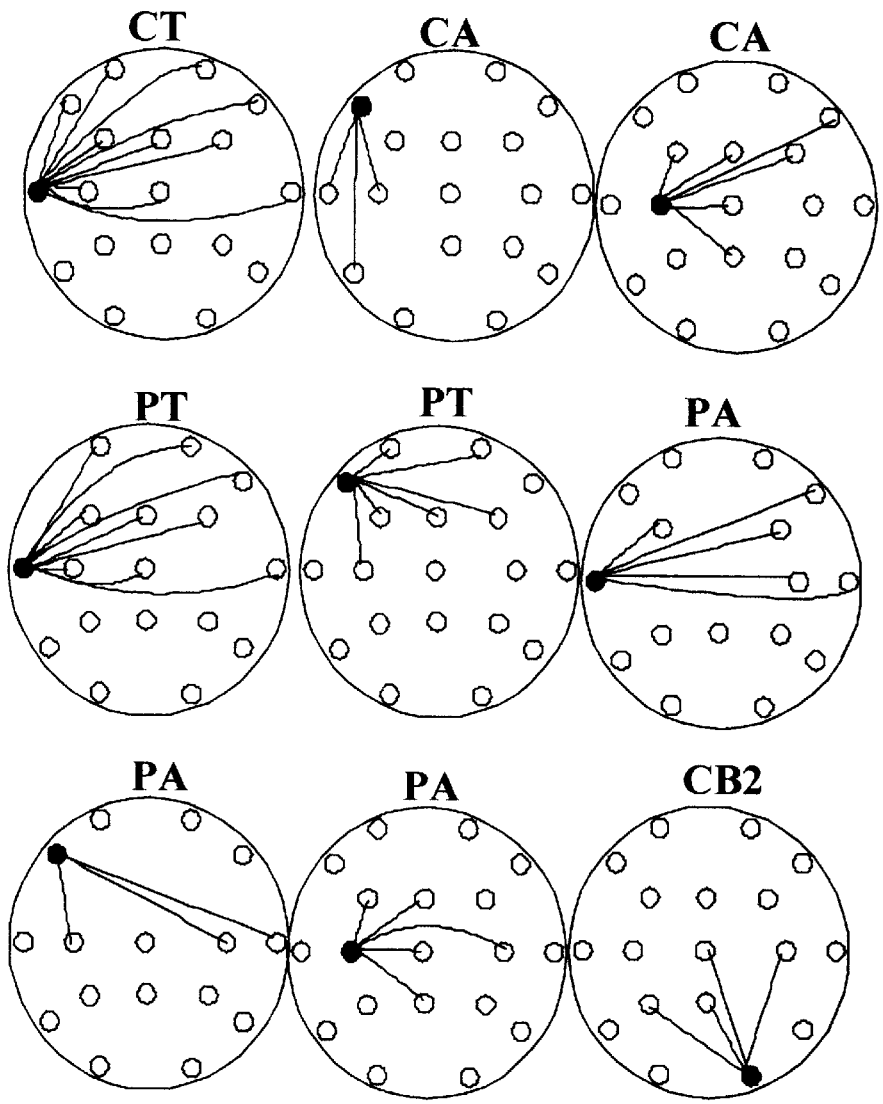
Negatively Correlated with Recall
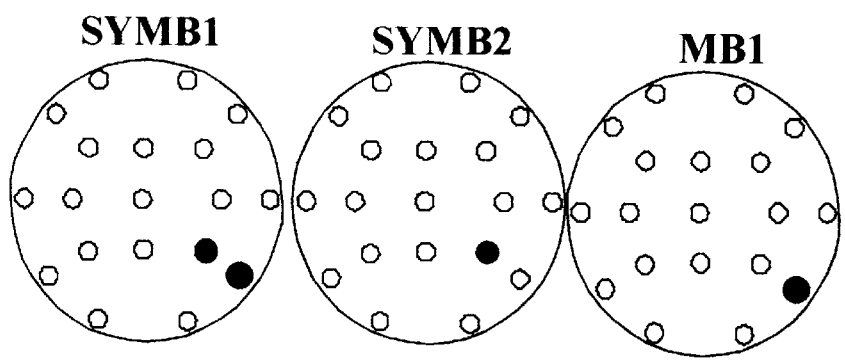

Figure 48
Positively Correlated with Recall
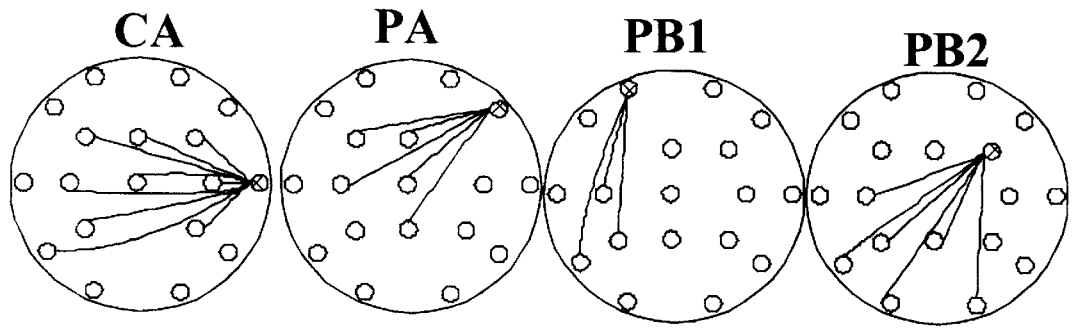
Negatively Correlated with Recall
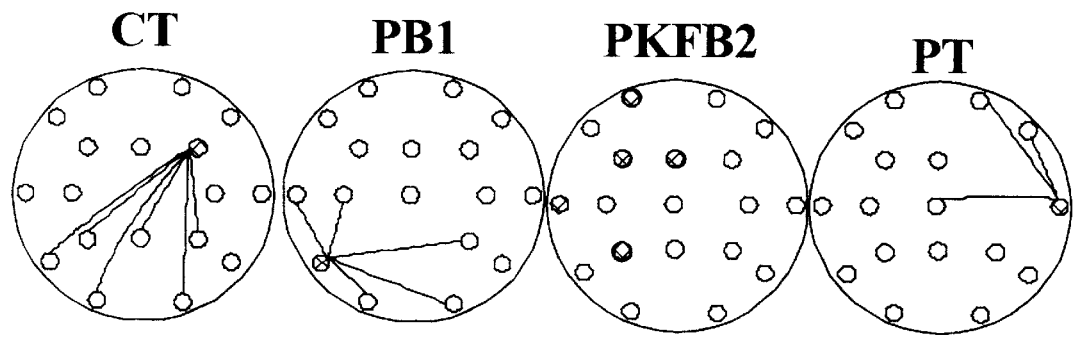

Figure 49
Positively Correlated with Recall
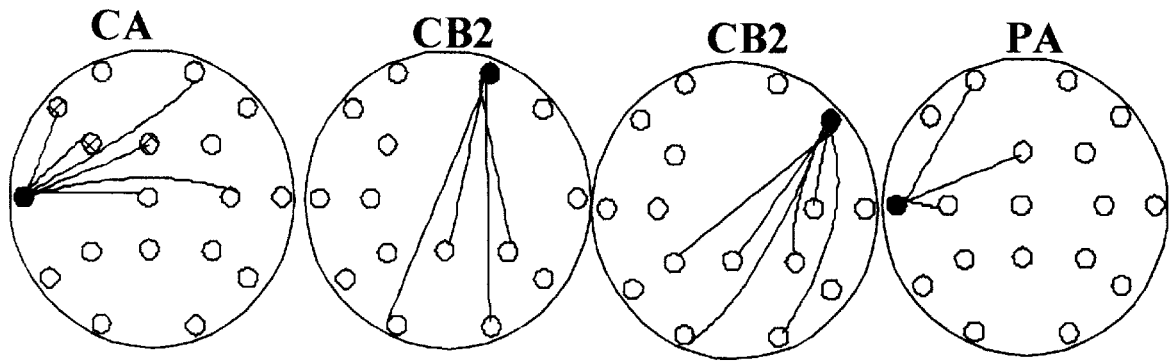
Negatively Correlated with Recall
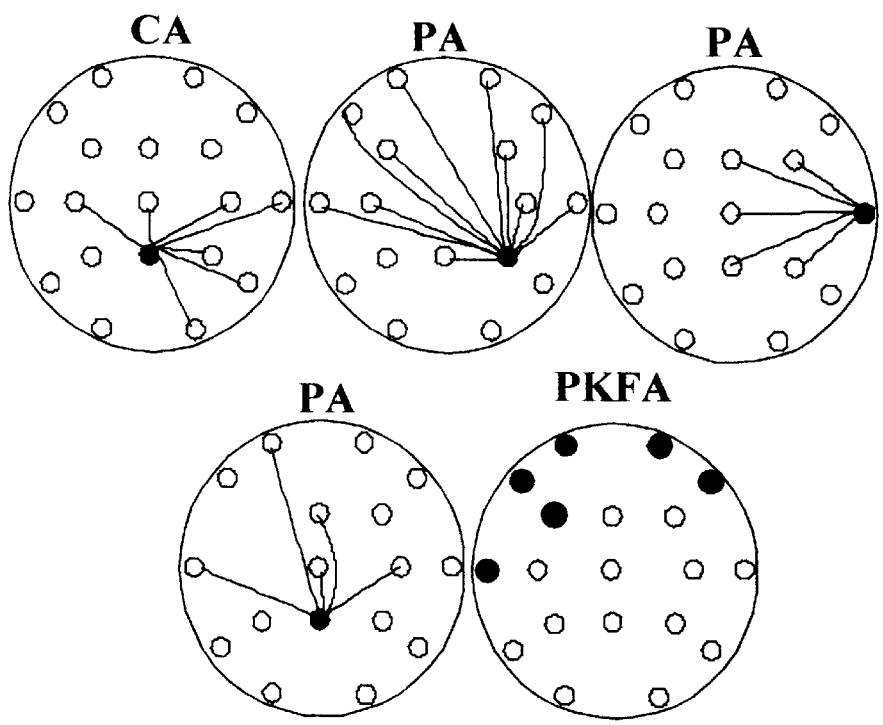

Positively Correlated with Recall

Figure 50B
Positively Correlated with Recall
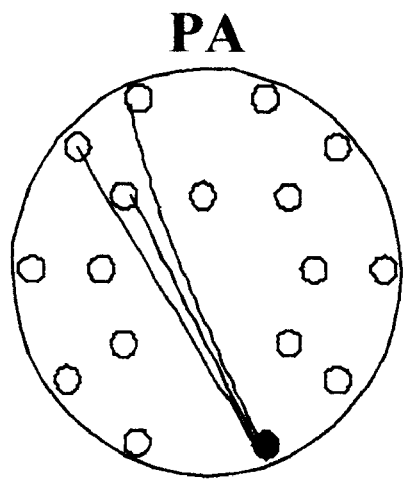
Negatively Correlated with Recall
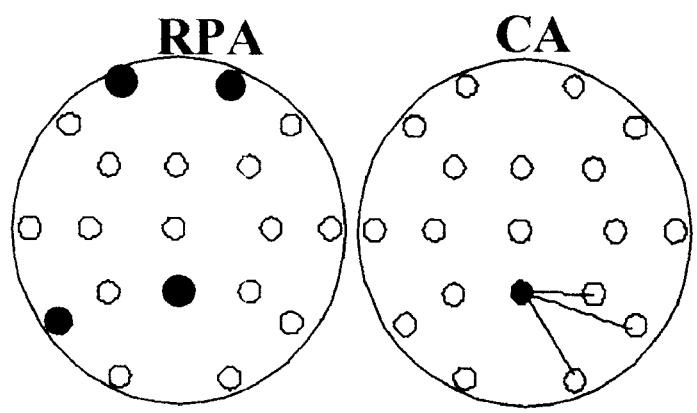

Figure 51
Positively Correlated with Recall
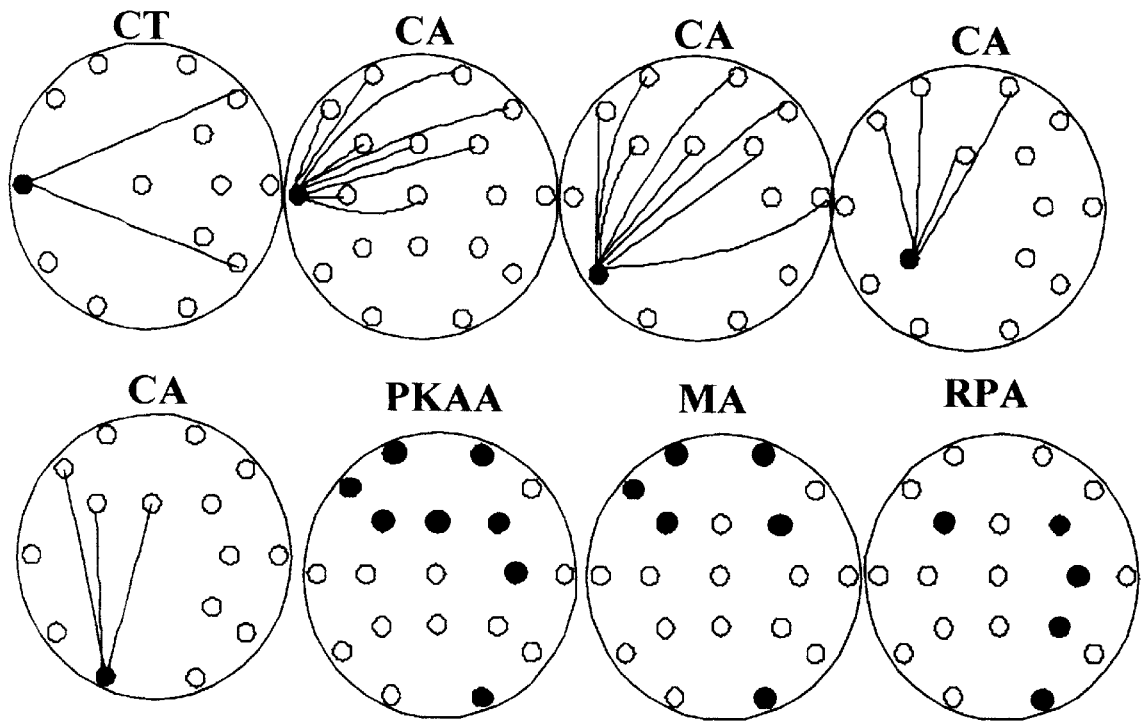
Negatively Correlated with Recall
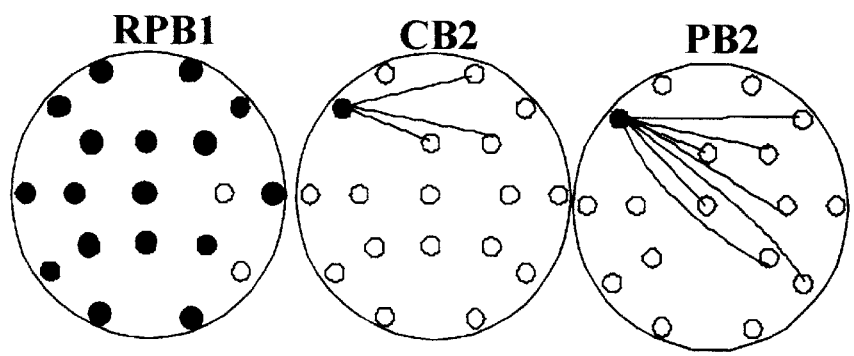

Figure 52
Positively Correlated with Recall
PKFB1
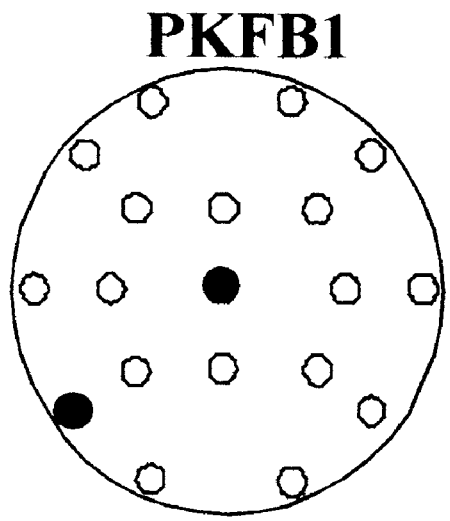
Negatively Correlated with Recall
PB2  SYMB2
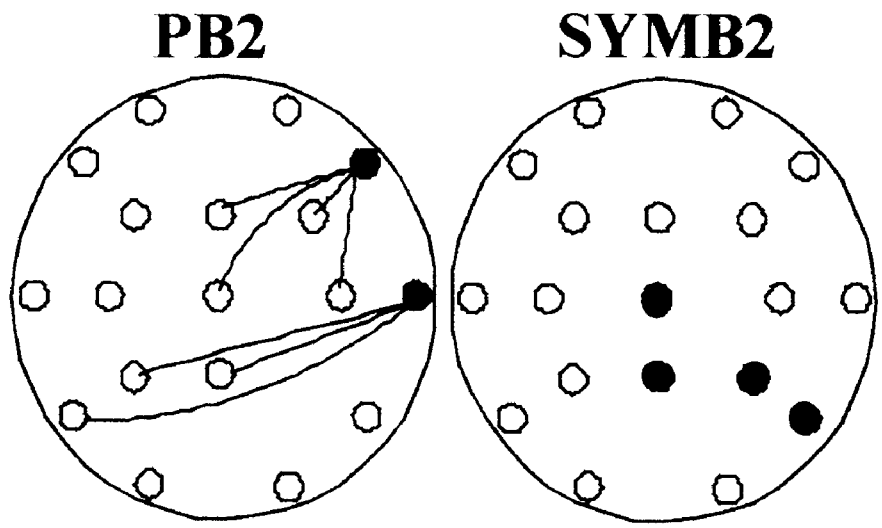

Negatively Correlated with Recall

Positively Correlated with Recall

Negatively Correlated with Recall

PKFB2

Positively Correlated with earliest memory

Positively Correlated with earliest memory

Stepwise Multiple Regression Equations – Normal Adults (N=53) – Paragraph Level of Activation Variables-18 Variables – Coherence Alpha From T3 – Total Memory Score R=.70  $R^2$=.49

Predicted Values-X axis
Observed Values- Y axis
Dependent Variable Short Term Memory Stepwise Multiple Regression Equations – Normal Adults (N=54) – Paragraph Degree of Activation Variables (37) – Total Memory Score R=.81  $R^2$=.65

Figure 59
Positively Correlated with Recall
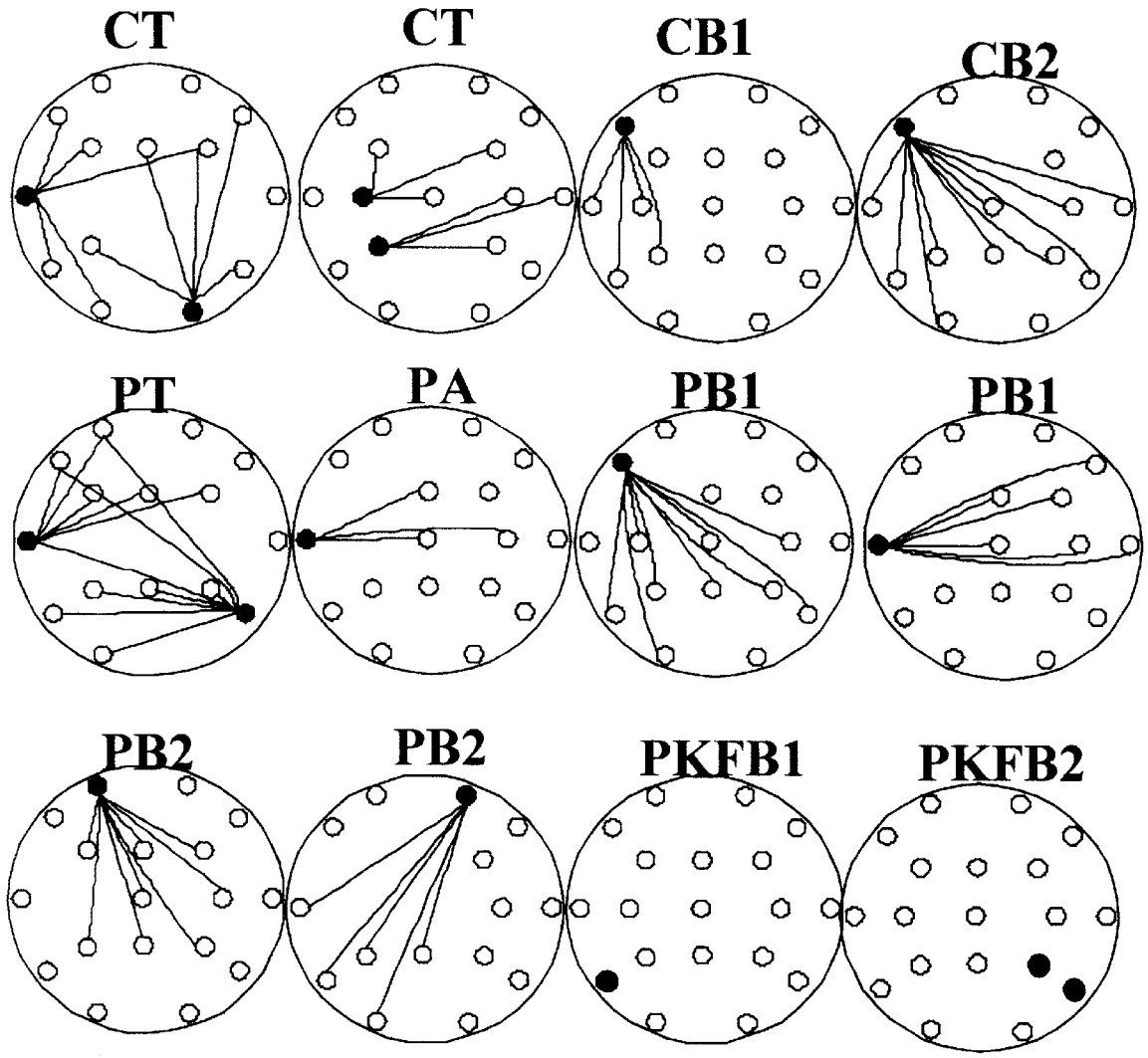
Negatively Correlated with Recall
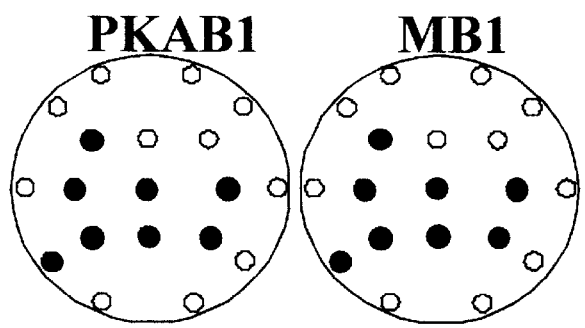

Figure 60
Positively Correlated with Recall
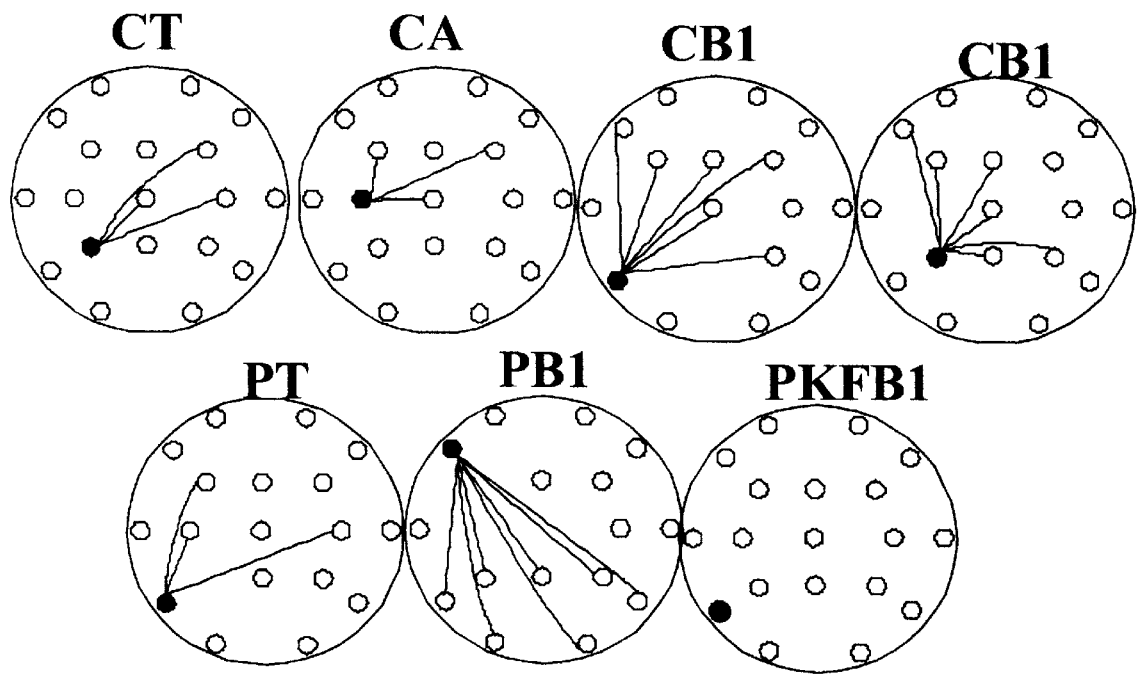
Negatively Correlated with Recall
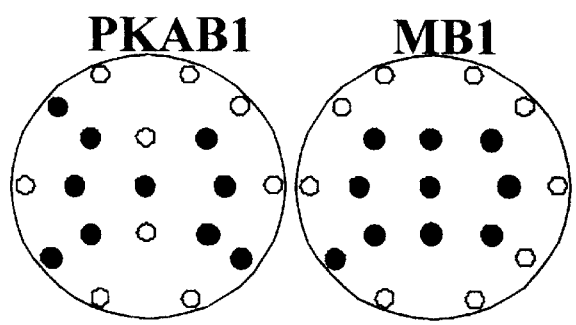

Figure 61
Positively Correlated with Recall
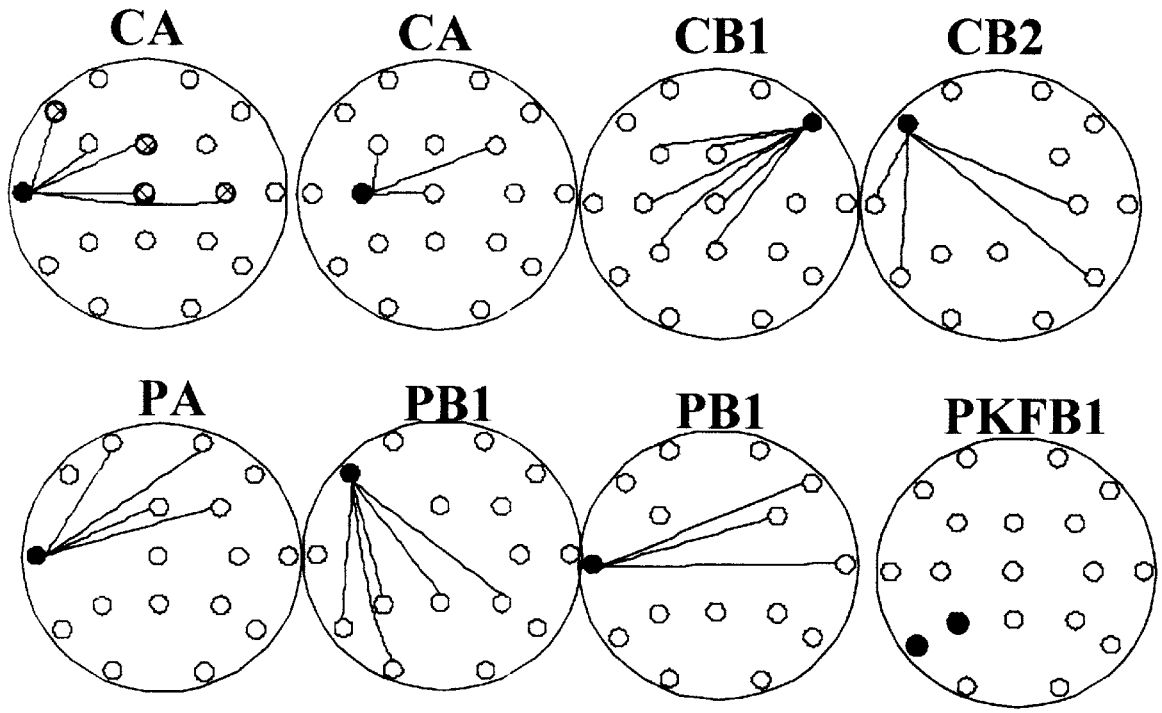
Negatively Correlated with Recall
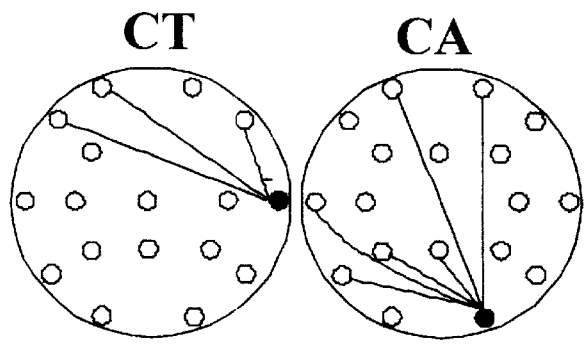

Positively Correlated with Recall

Figure 62B
Positively Correlated with Recall
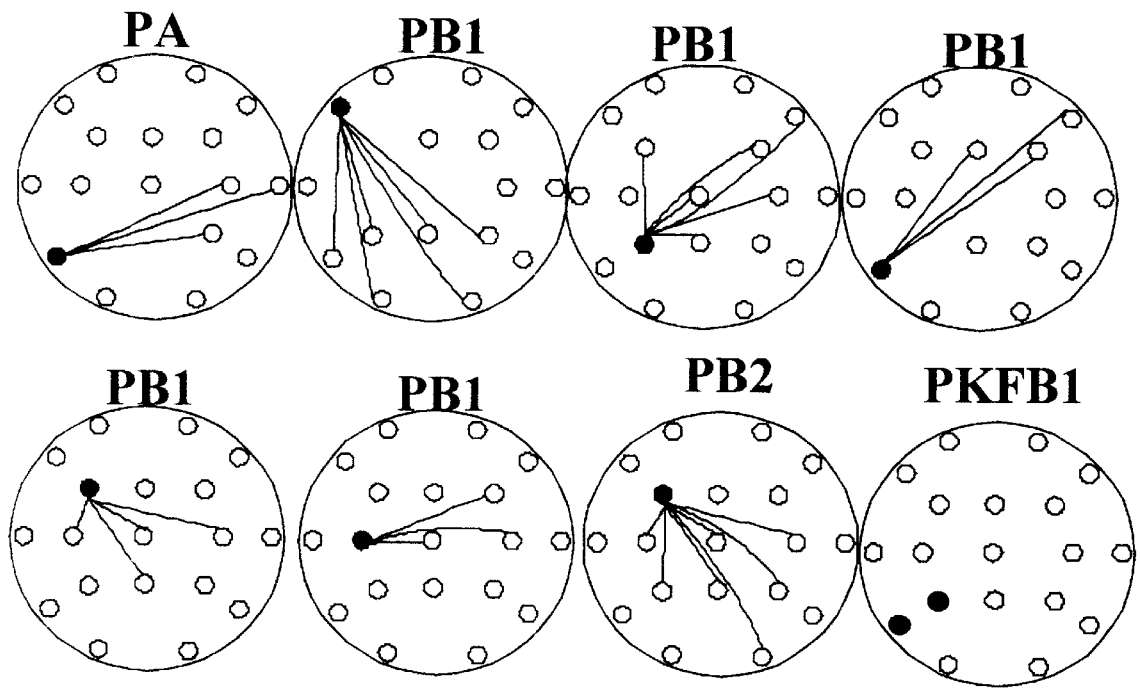
Negative Relationships to Recall
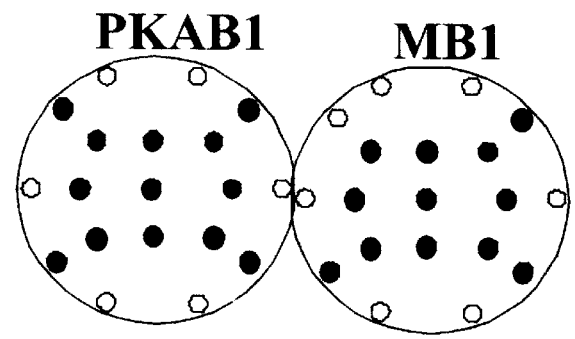

Positively Correlated with Recall

Figure 63B
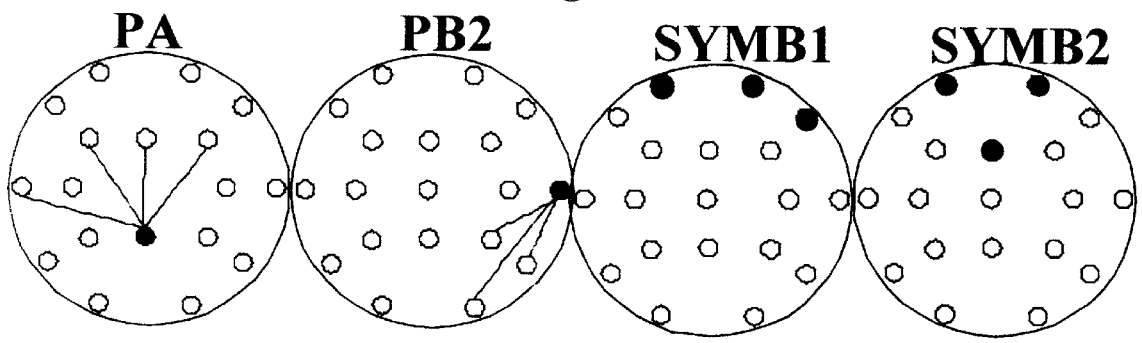
Negatively Correlated with Recall
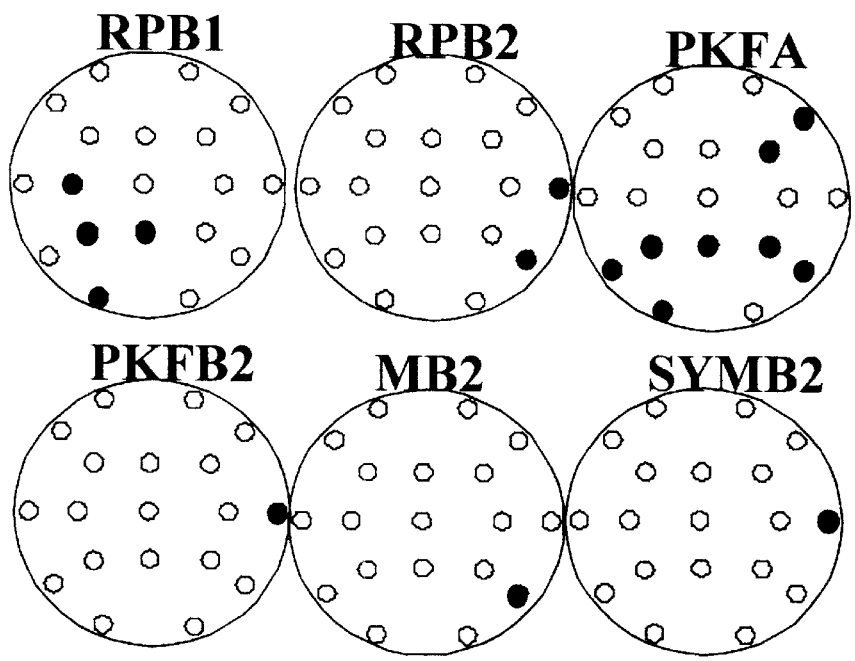

Figure 64
Positively Correlated with Recall
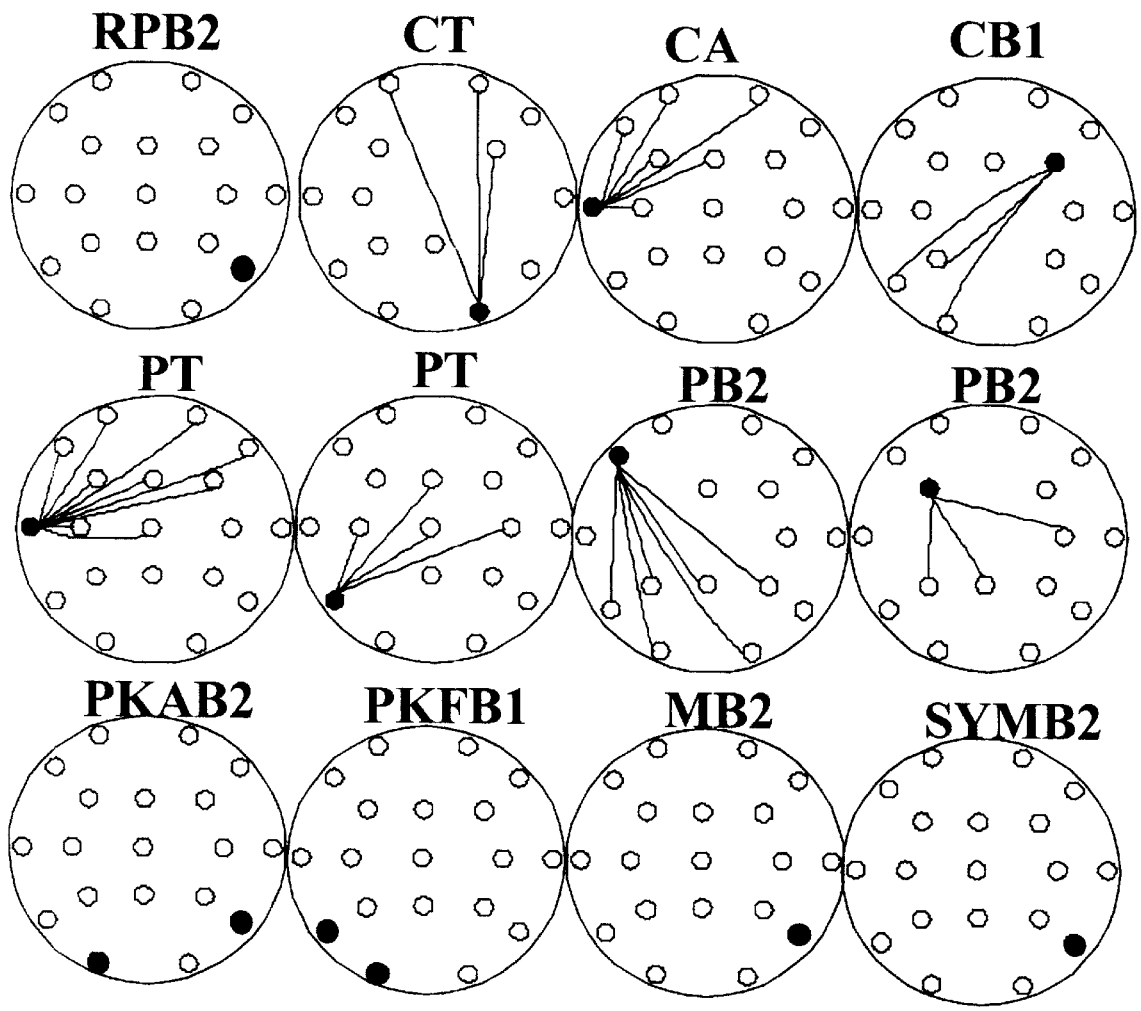
Negatively Correlated with Recall
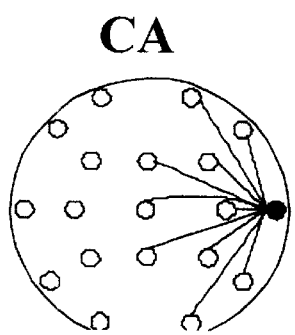

Figure 65
Positively Correlated with Recall
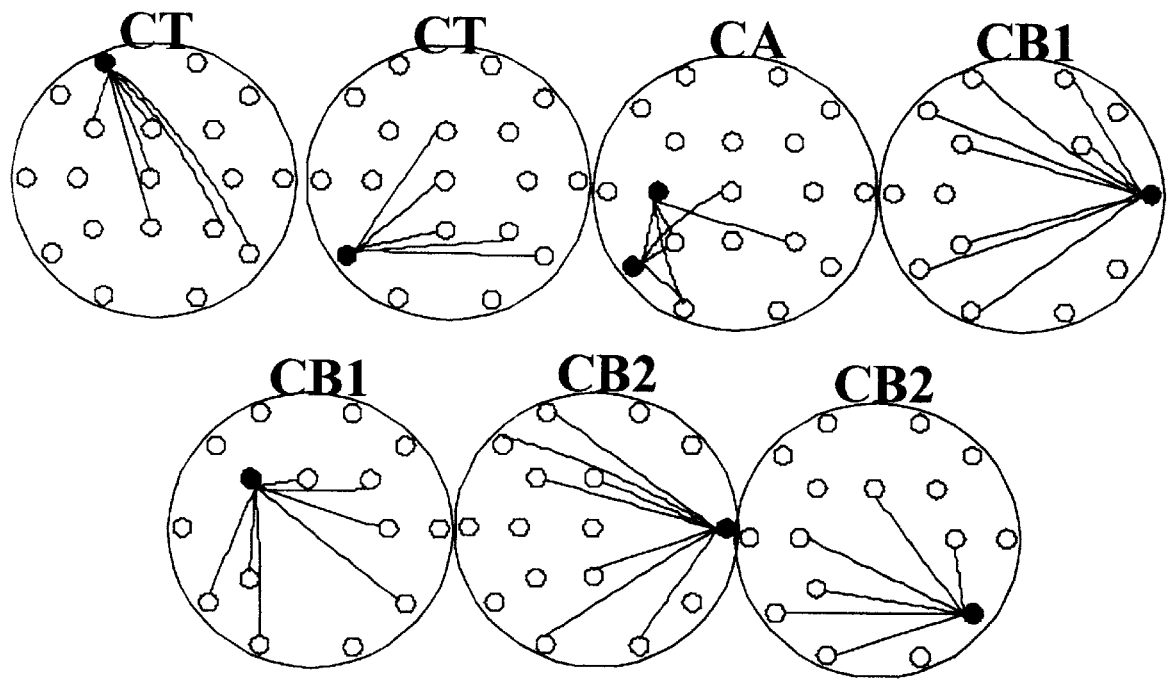
Negatively Correlated with Recall
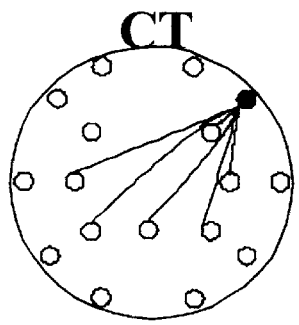

Figure 66
Positively Correlated with Recall
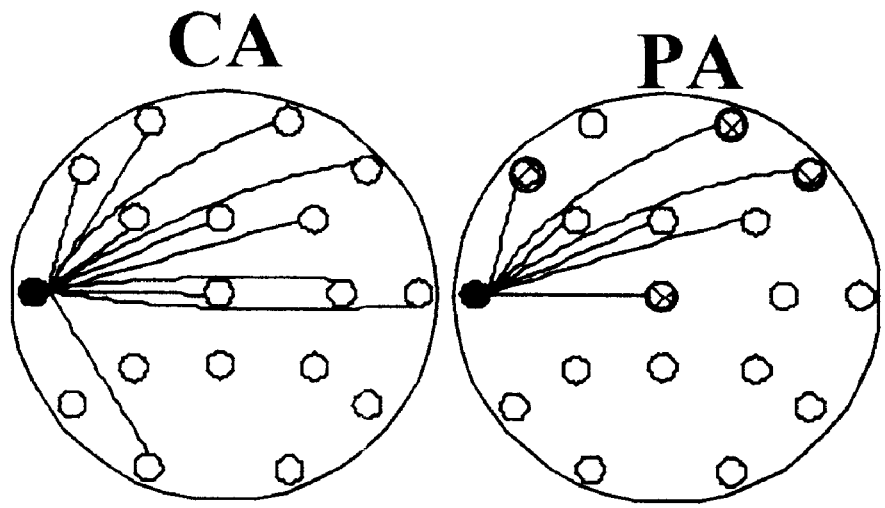
Negatively Correlated with Recall
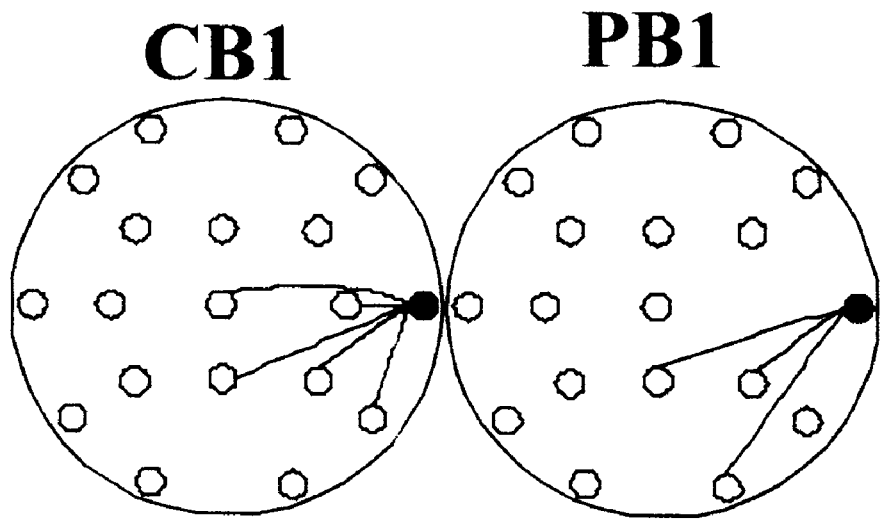

Figure 67
Positively Correlated with Recall
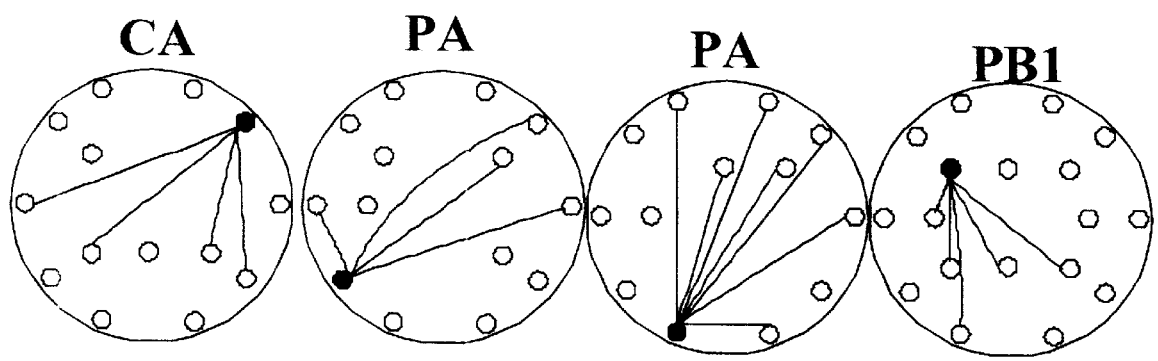
Negatively Correlated with Recall
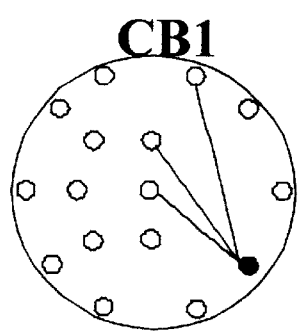

Figure 68
Positively Correlated with Recall
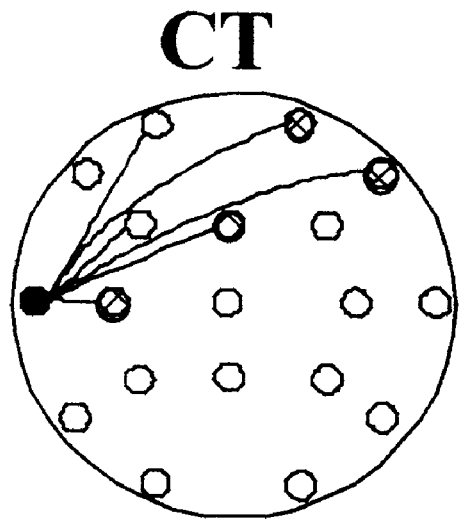
Negatively Correlated with Recall
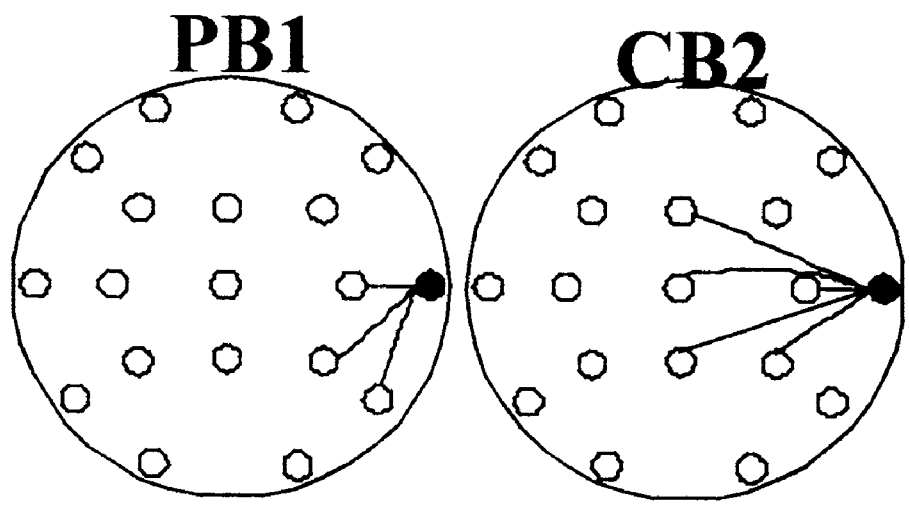

Positively Correlated with Recall

Negative Relationships to Recall

Figure 70
Positively Correlated with Recall
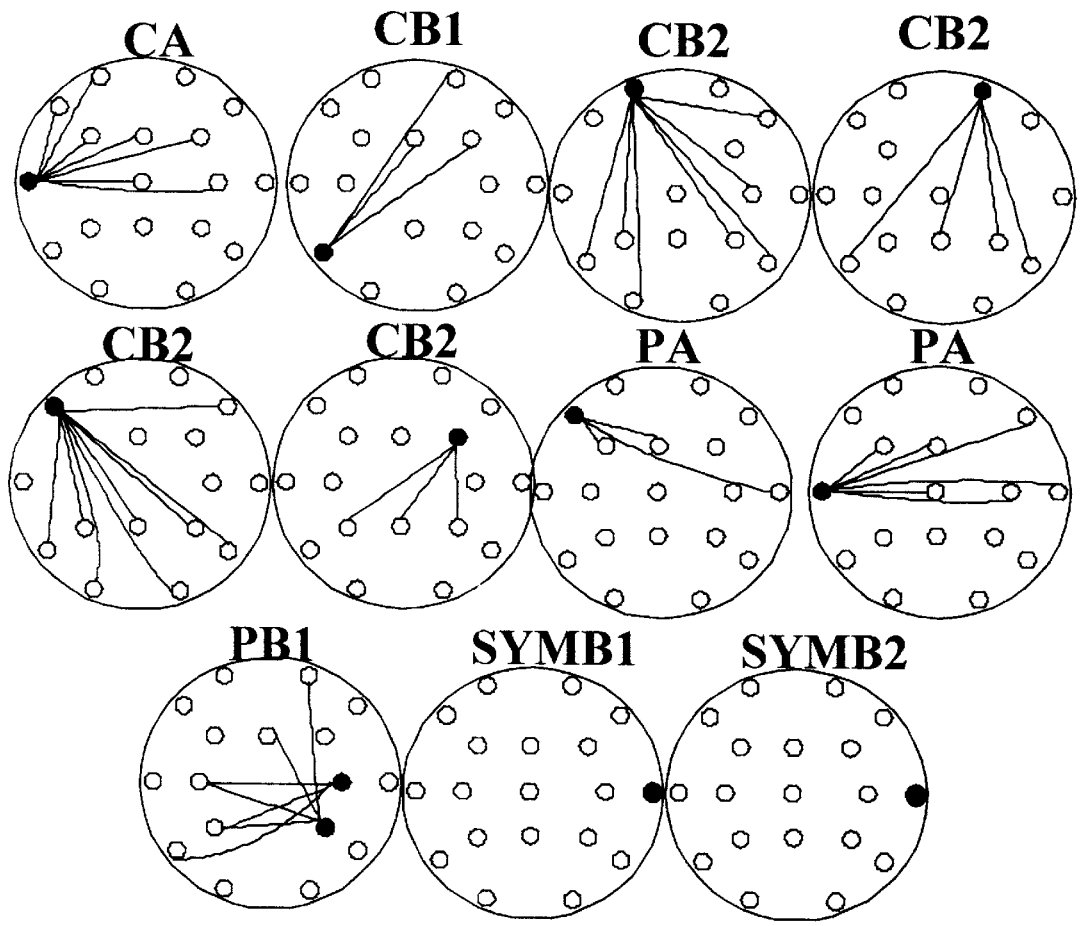
Negatively Correlated with Recall
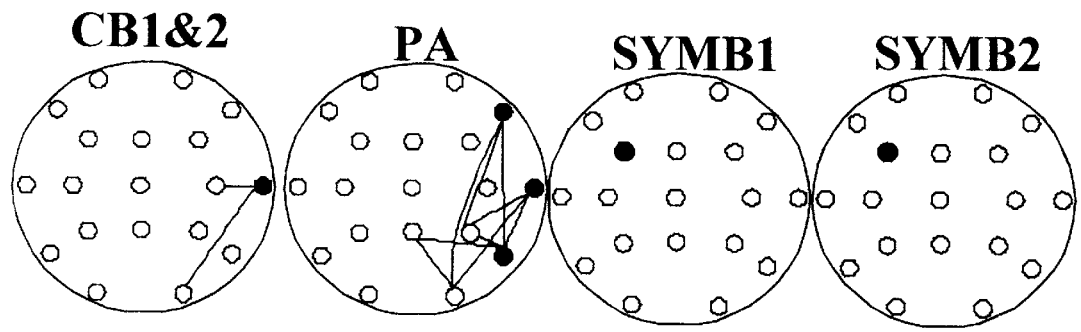

Positively Correlated with Recall

Negative Relationships to Recall

Positively Correlated with Recall

Figure 72B
Positively Correlated with Recall
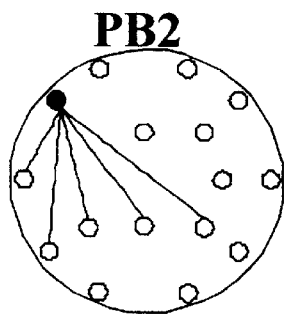
Negative Relationships to Recall
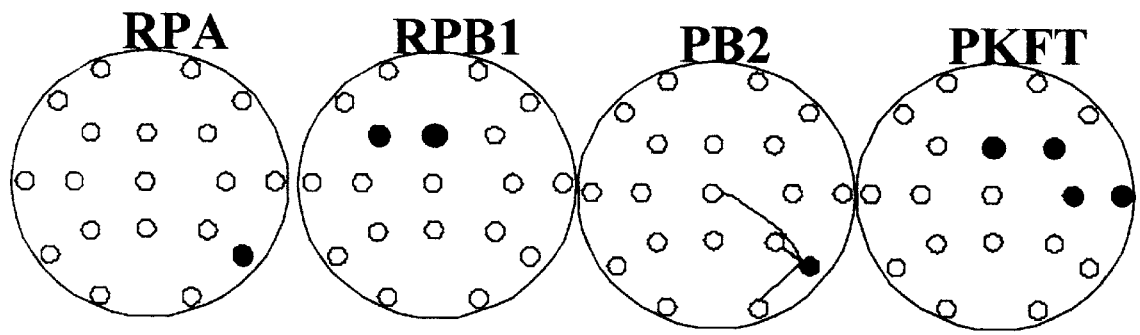

Figure 73
Positively Correlated with Recall
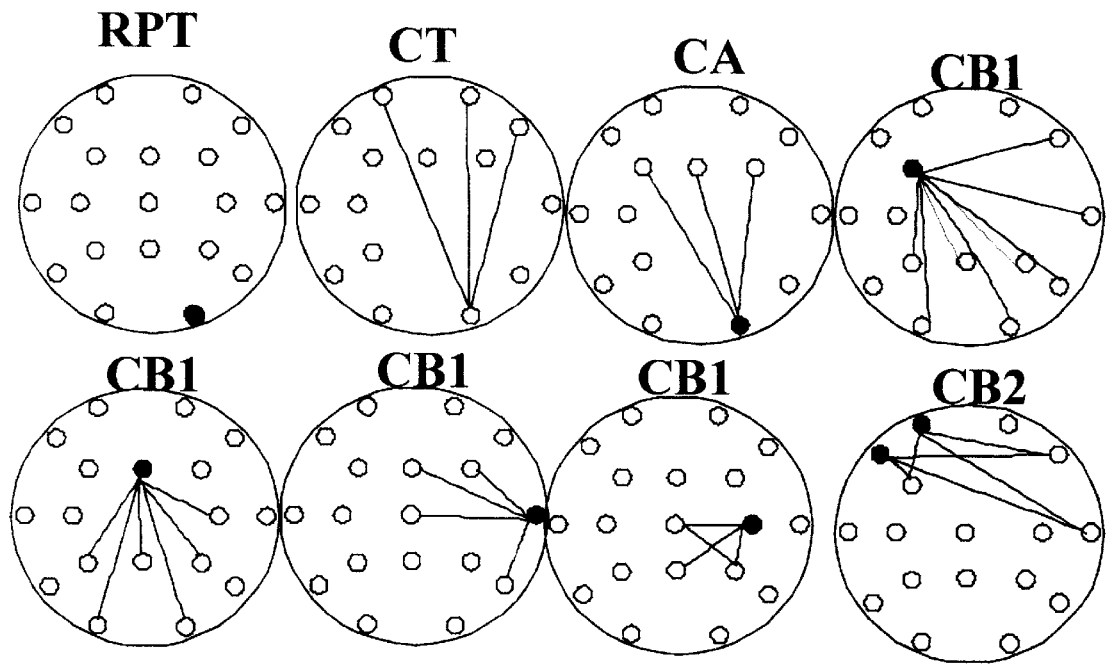
Negatively Correlated with Recall
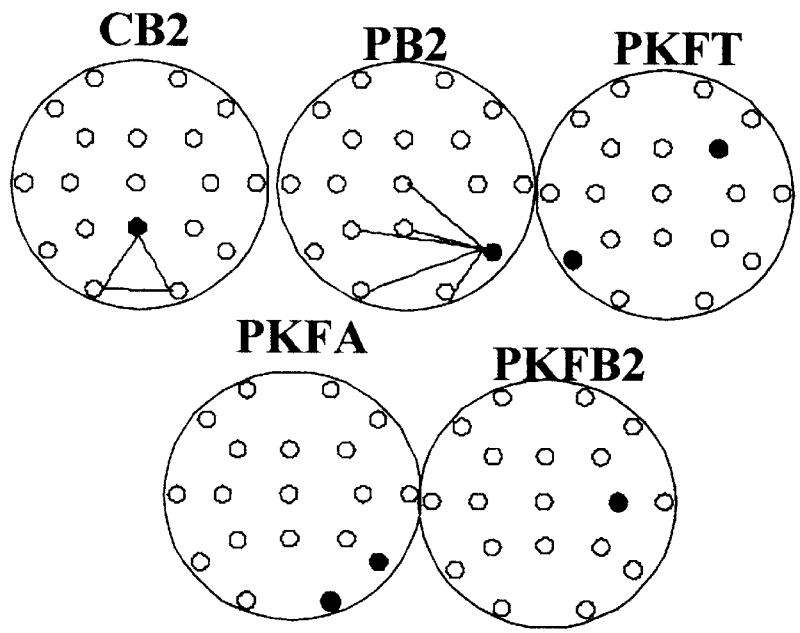

Positively Correlated with Recall

Figure 74B
Positively Correlated with Recall
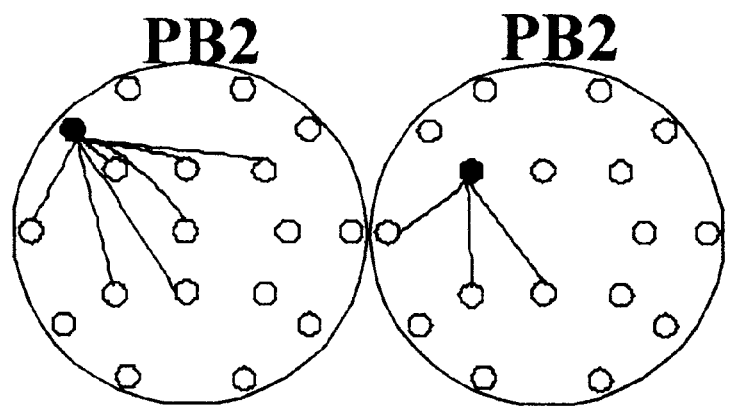
Negative Relationships to Recall
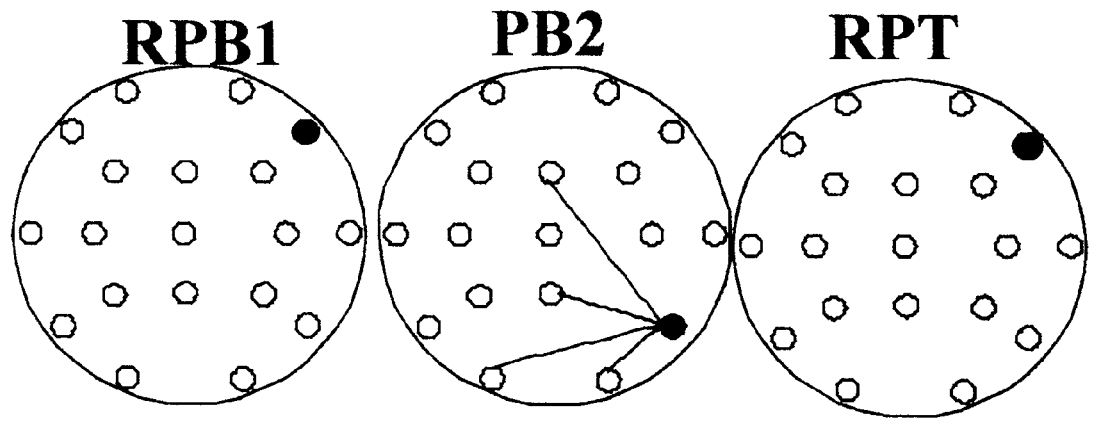

Positively Correlated with Recall

Figure 75B
Positively Correlated with Recall
PB2
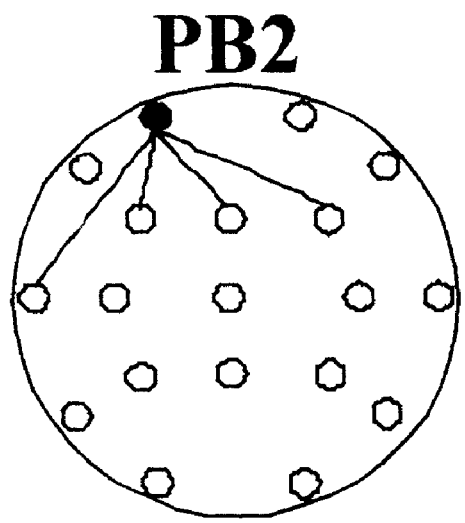
Negative Relationships to Recall
PKAT&MT    PKFT
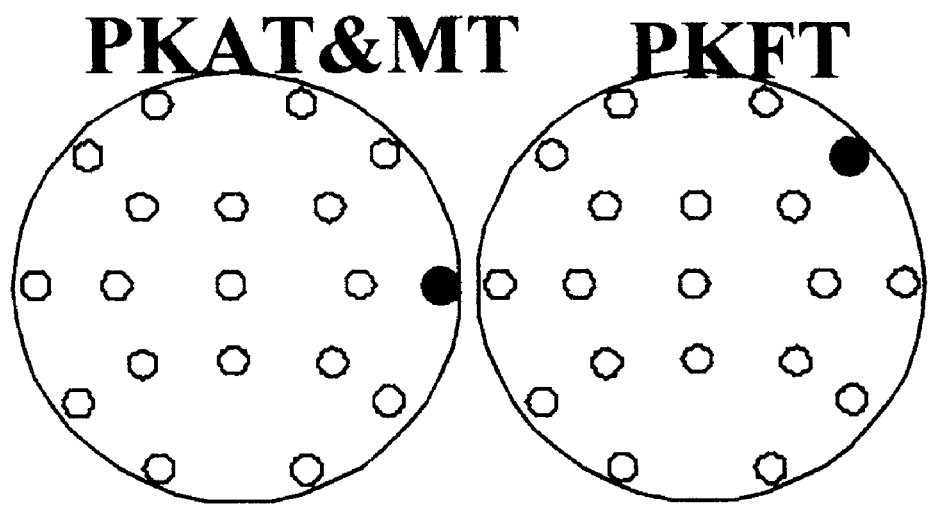

Positive Relationships to Recall

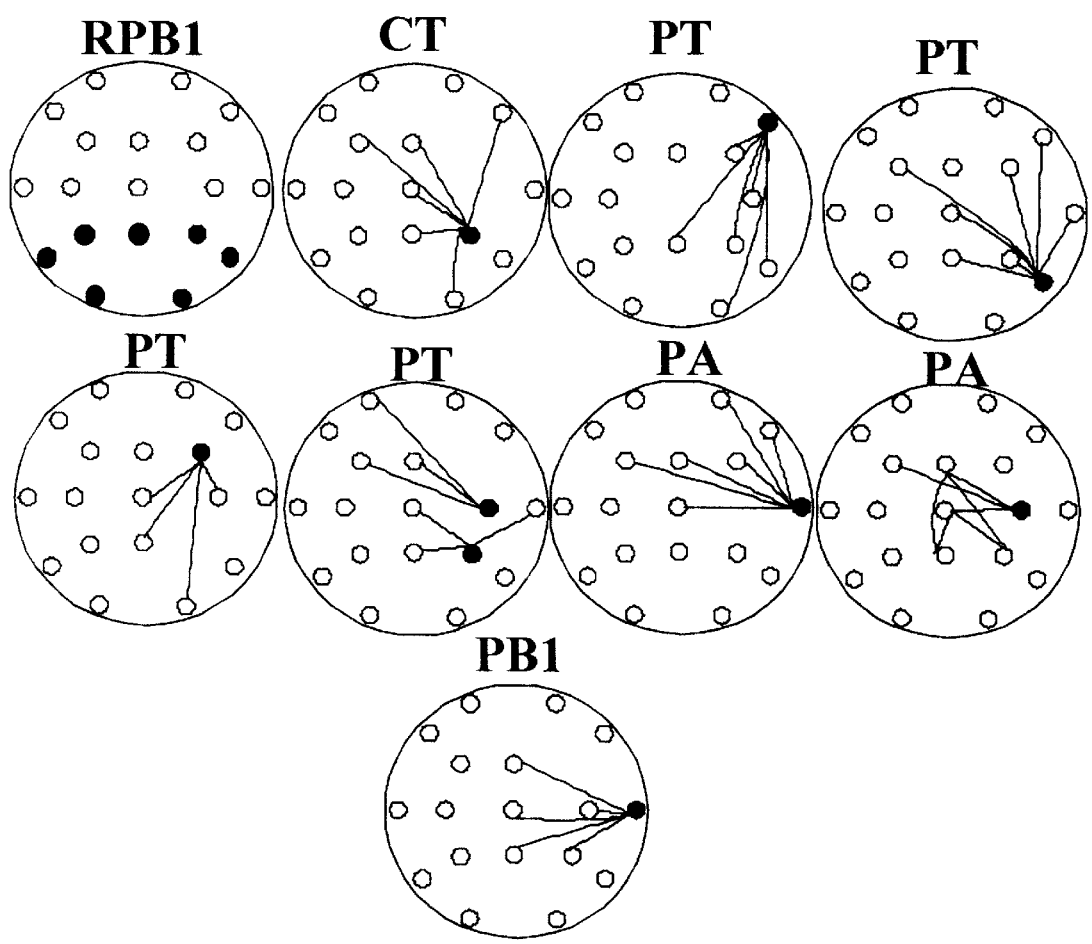

Positive Relationships to Recall

Positive Relationships to Recall

Negative Relationships to Recall

Positive Relationships to Recall

Figure 78B
Positive Relationships to Recall
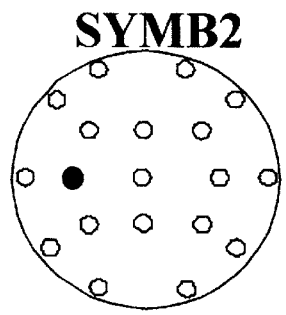
SYMB2
Negative Relationships to Recall
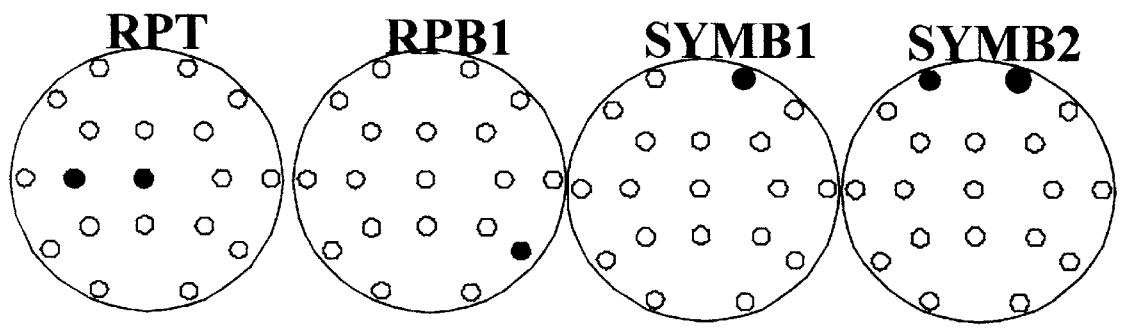
RPT   RPB1   SYMB1   SYMB2

Figure 79
Positive Relationships to Recall
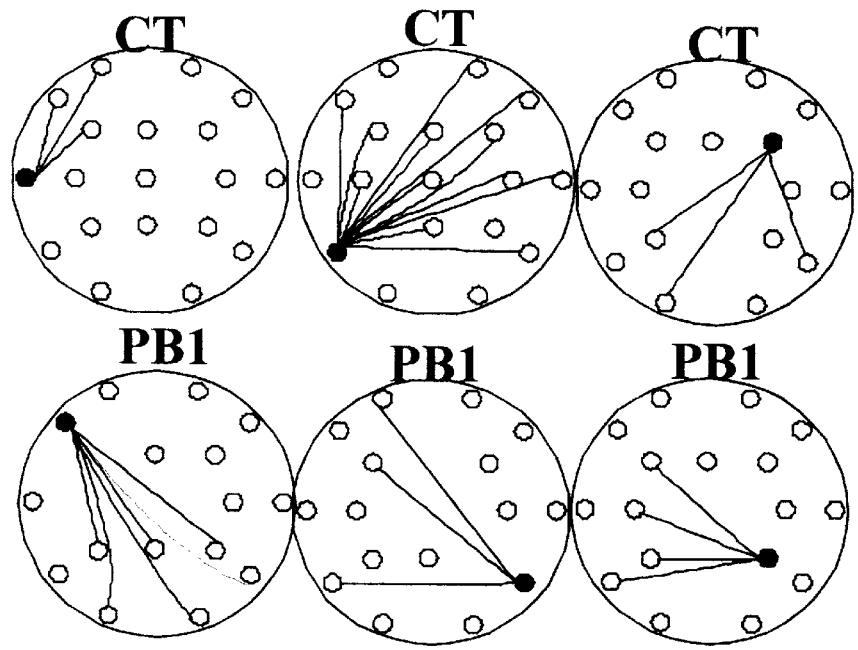
Negative Relationships to Recall
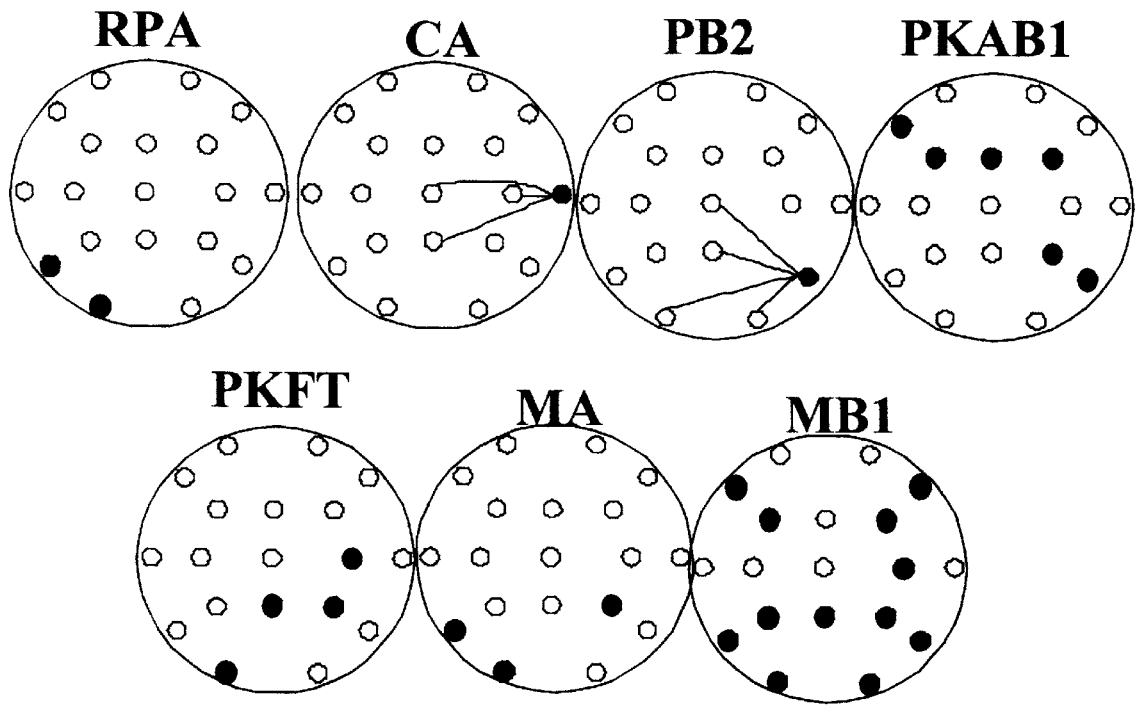

Figure 80
Positive Relationships to Recall
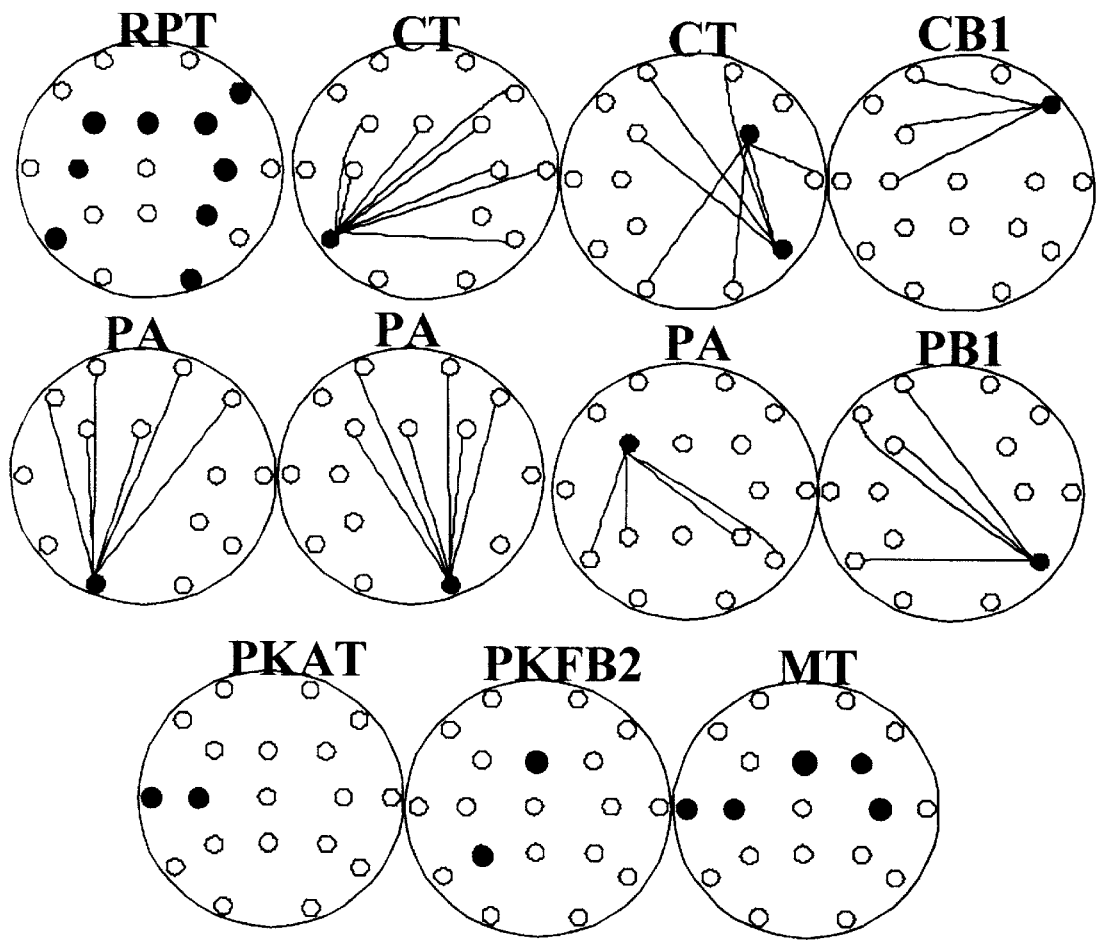
Negative Relationships to Recall
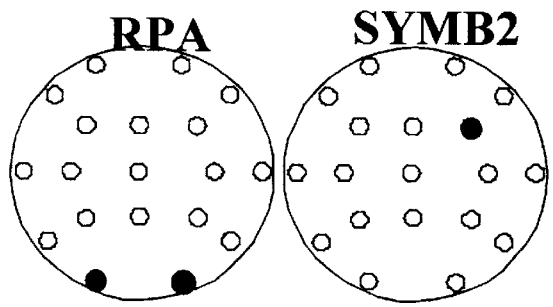

Figure 81
Positive Relationships to Recall
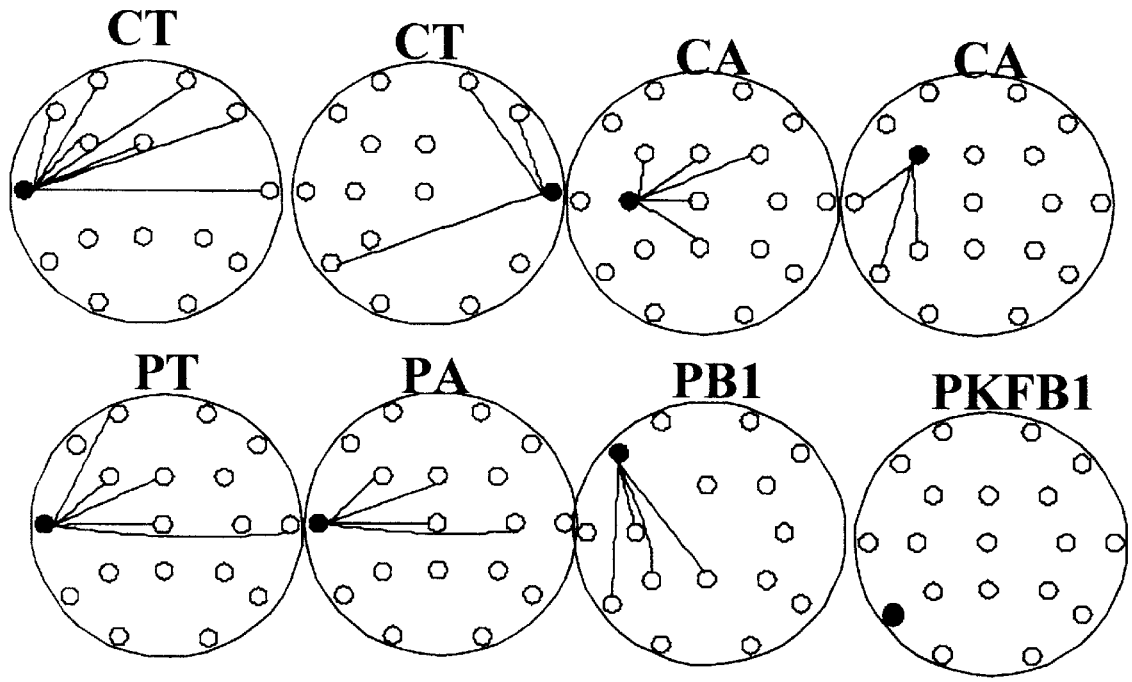
Negative Relationships to Recall
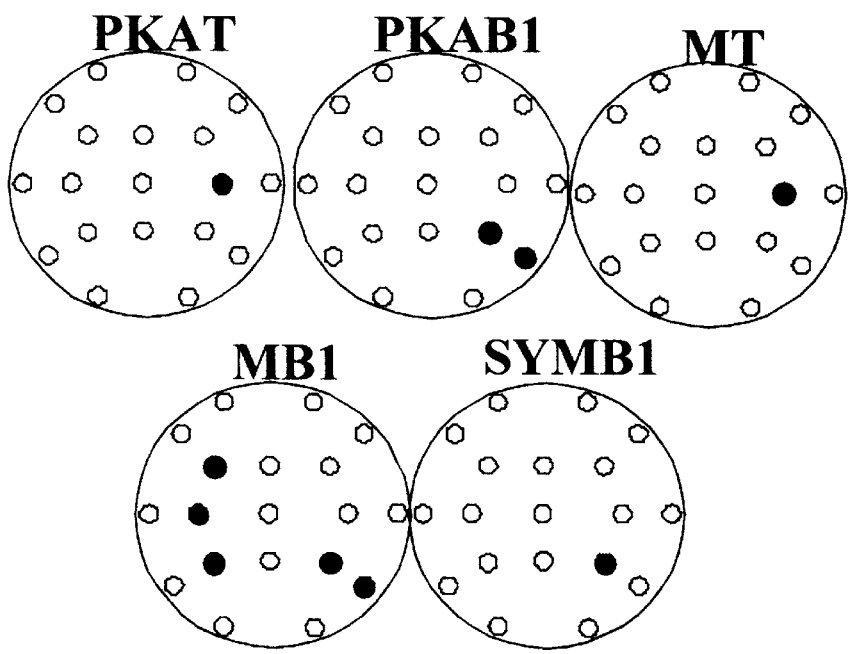

Positive Relationships to Recall

Negative Relationships to Recall

Positive Relationships to Recall

Negative Relationships to Recall

Positive Relationships to Recall

Figure 84B
Positive Relationships to Recall
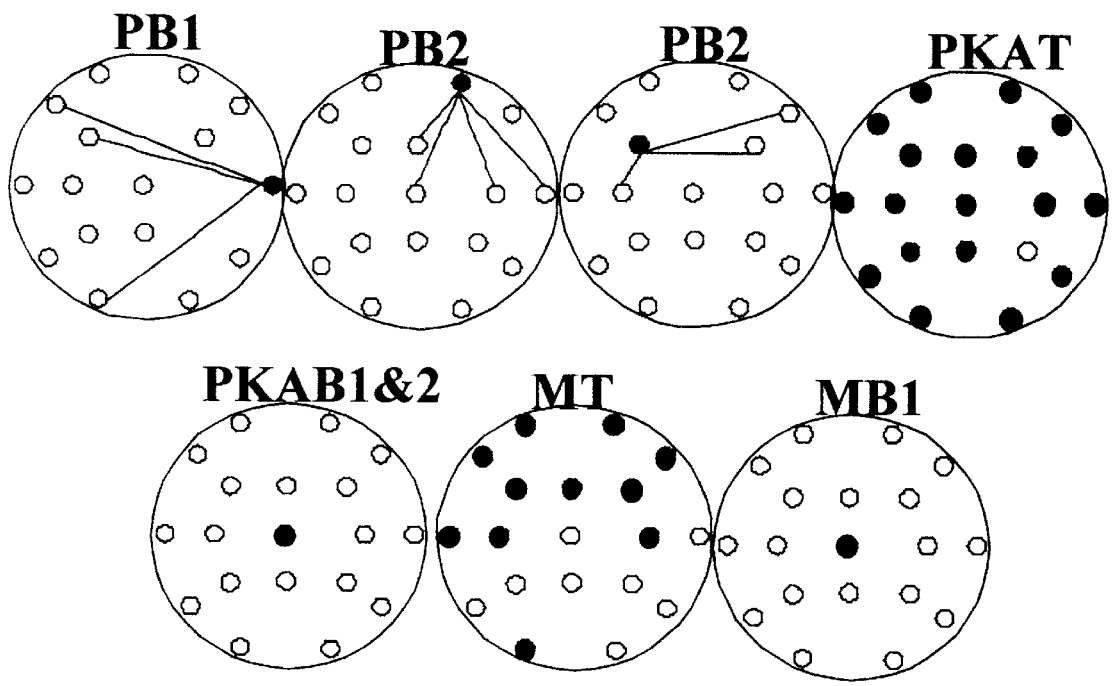
Negative Relationships to Recall
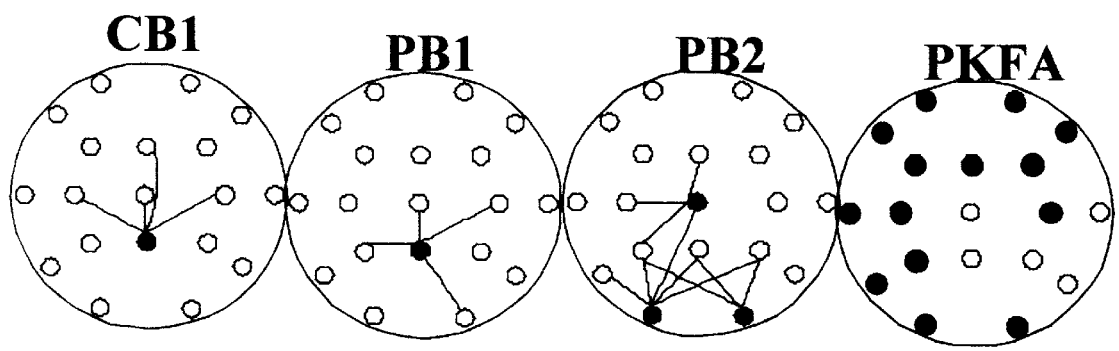

Positive Relationships to Recall**

Positive Relationships to Recall

Figure 85C
Positive Relationships to Recall
MB2
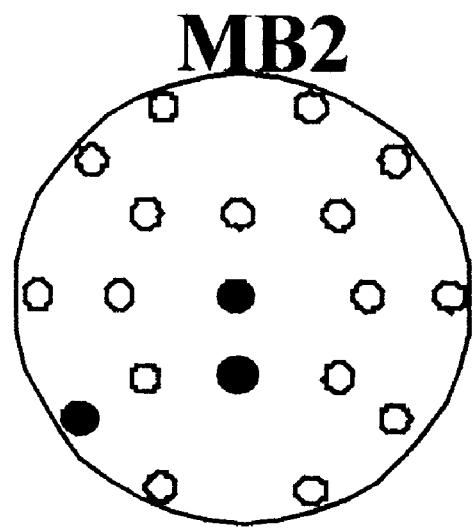
Negative Relationships to Recall
PKFA
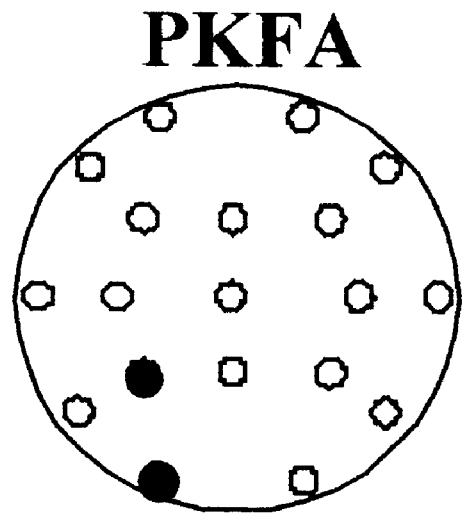

Figure 86
Positive Relationships to Recall
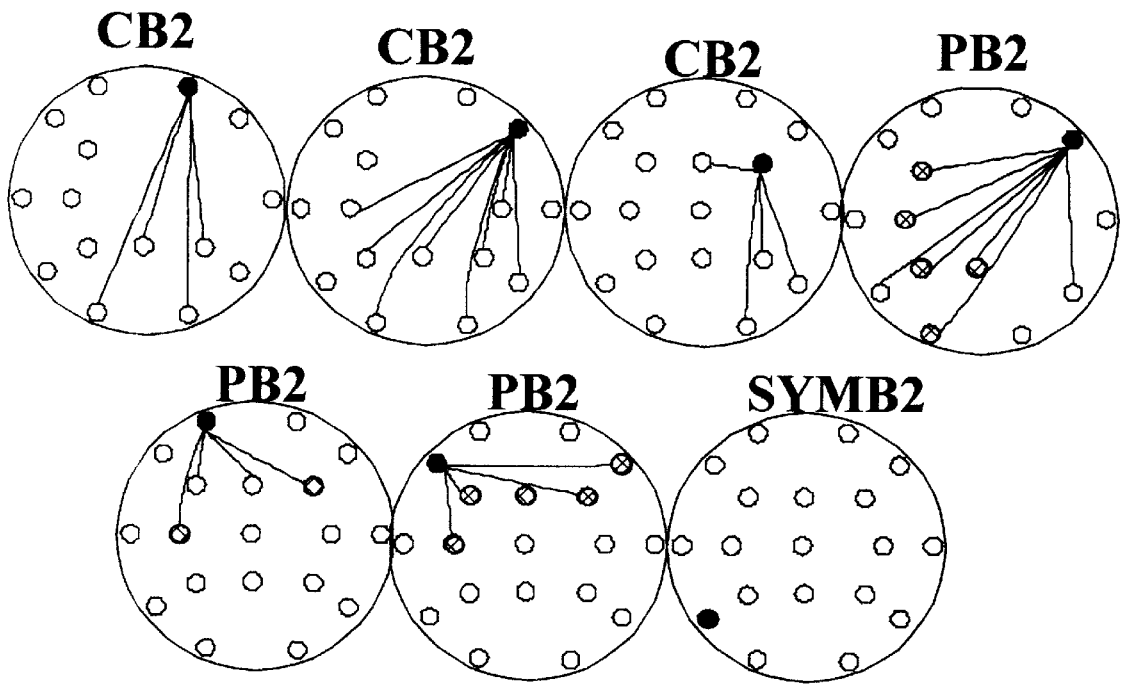
Negative Relationships to Recall
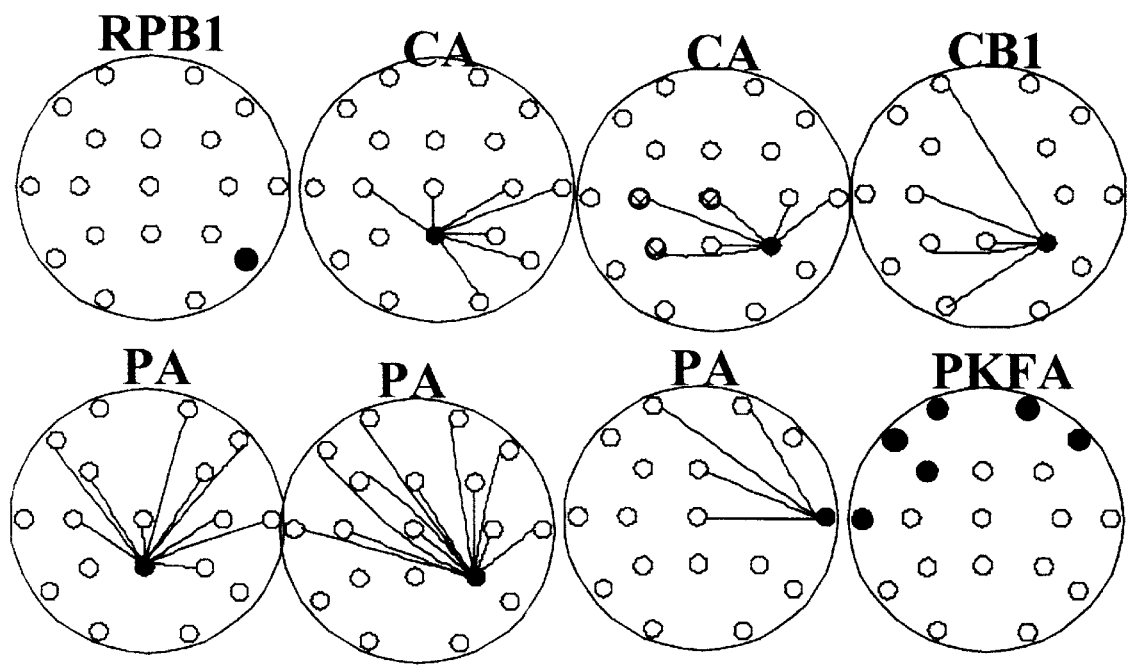

Positive Relationships to Recall

Figure 87B
Positive Relationships to Recall
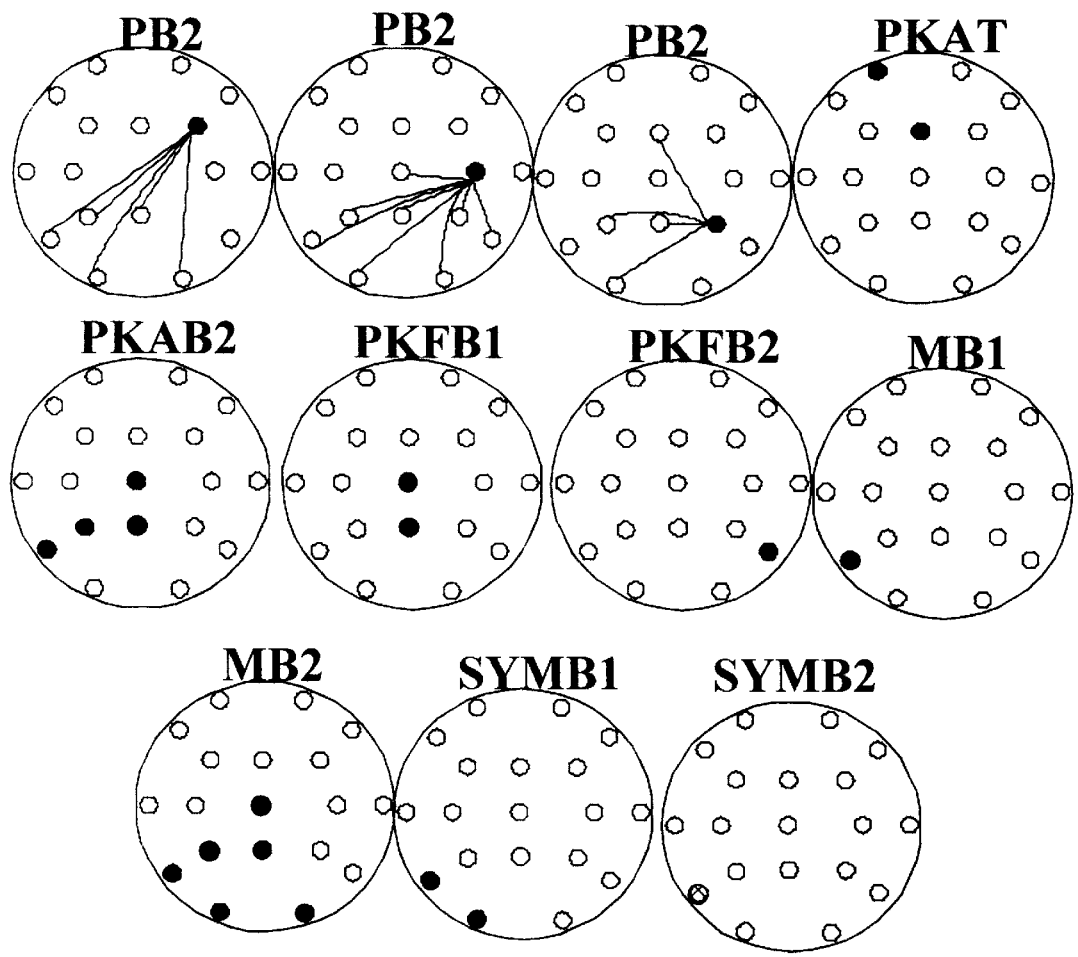
Negative Relationships to Recall
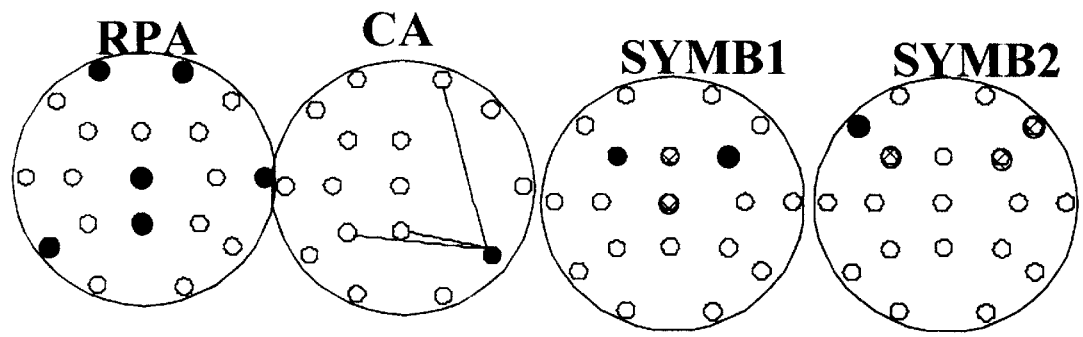

Positive Relationships to Recall

Negative Relationships to Recall

Figure 89A
Positive Relationships to Recall
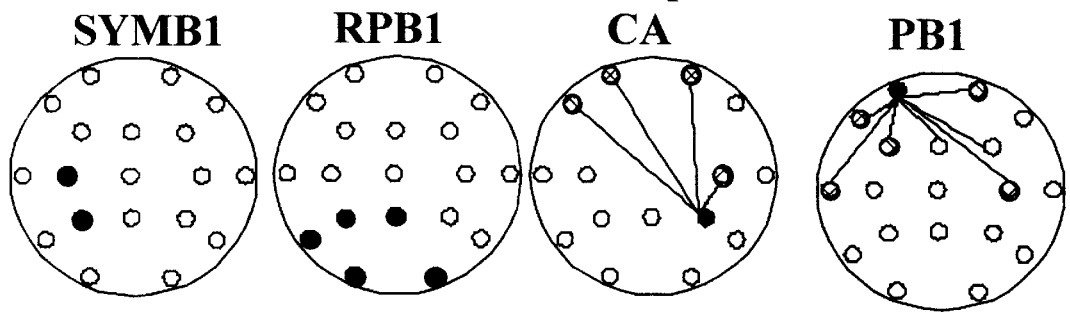
Negative Relationships to Recall
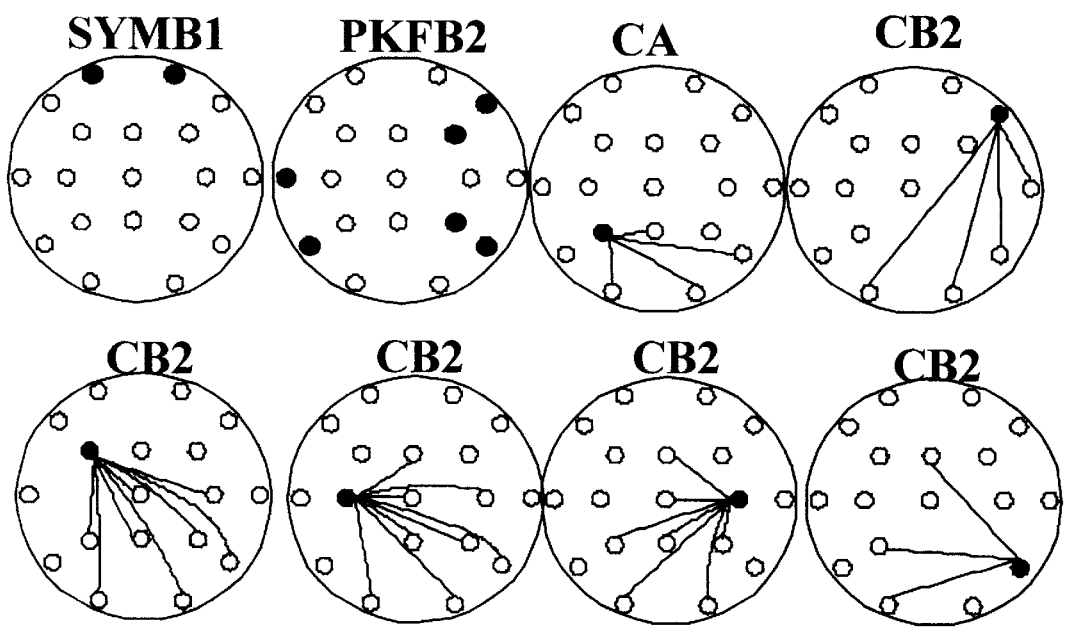

Negative Relationships to Recall

Positive Relationships to Recall

Negative Relationships to Recall

Positive Relationships to Recall

Negative Relationships to Recall

Positive Relationships to Recall

Negative Relationships to Recall

Positive Relationships to Recall

Negative Relationships to Recall

Negative Relationships to Recall

Figure 94
Positive Relationships to Recall
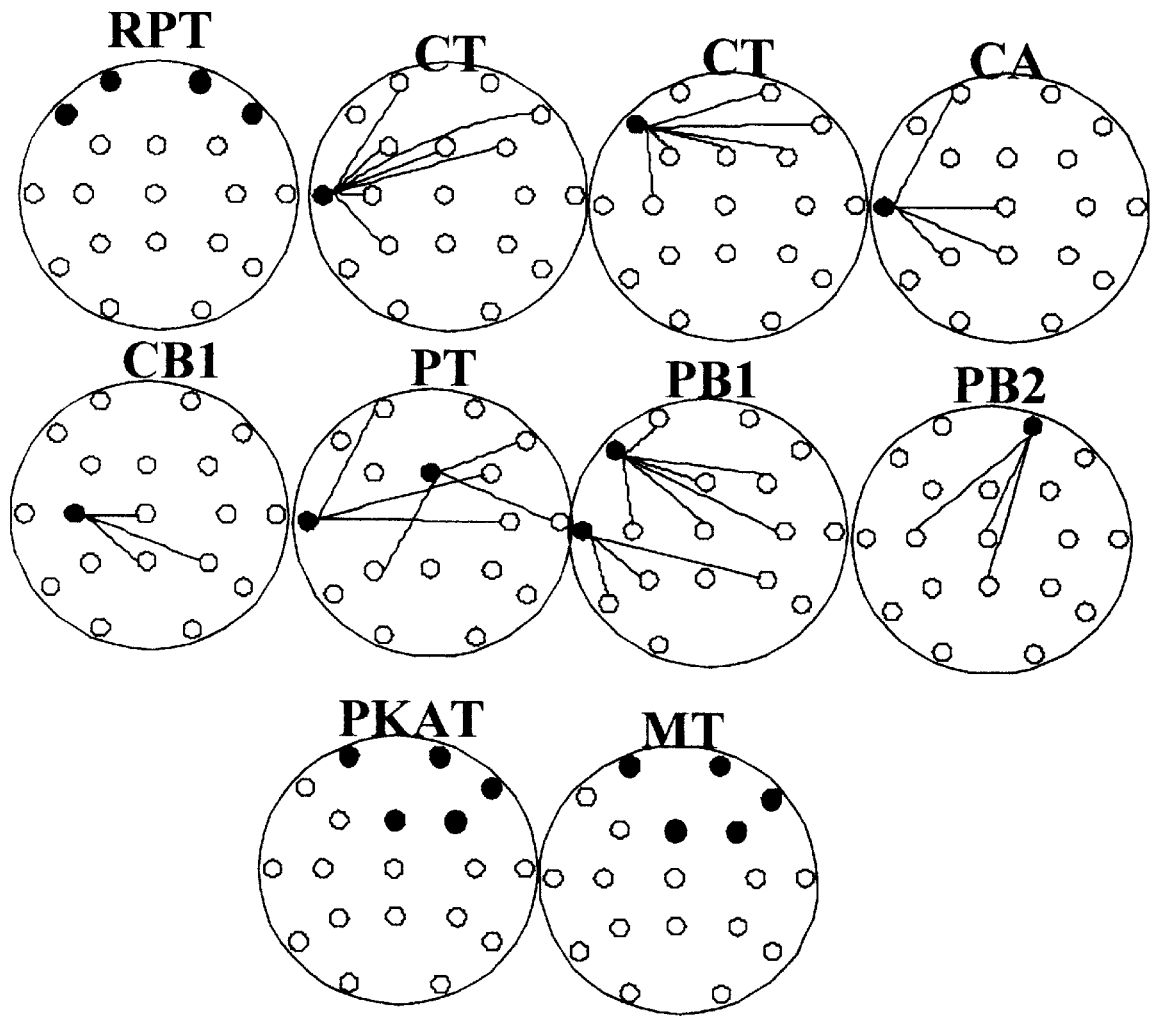
Negative Relationships to Recall
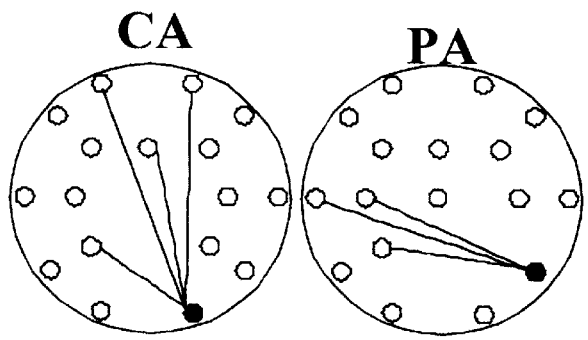

Positive Relationships to Recall

Positive Relationships to Recall

Figure 97
Positive Relationships to Recall
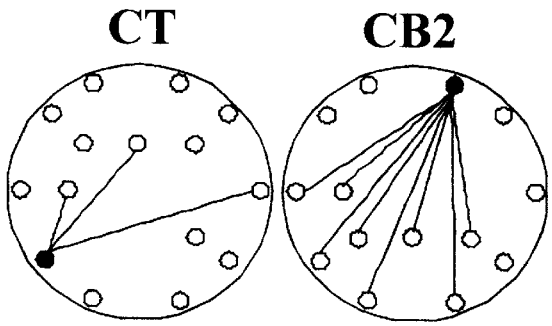
Negative Relationships to Recall
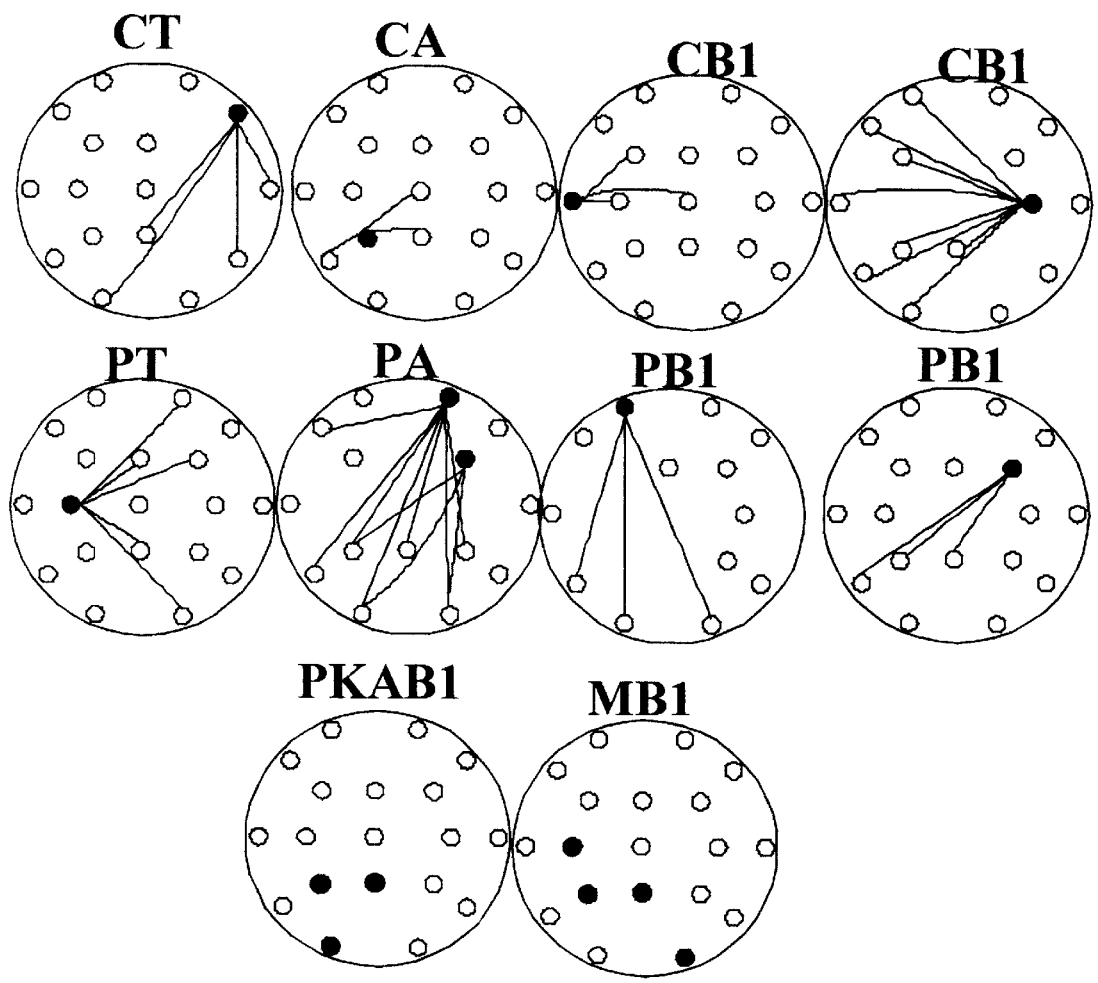

Positive Relationships to Recall

PB1

Positive Relationships to Recall

Figure 99B
Positive Relationships to Recall
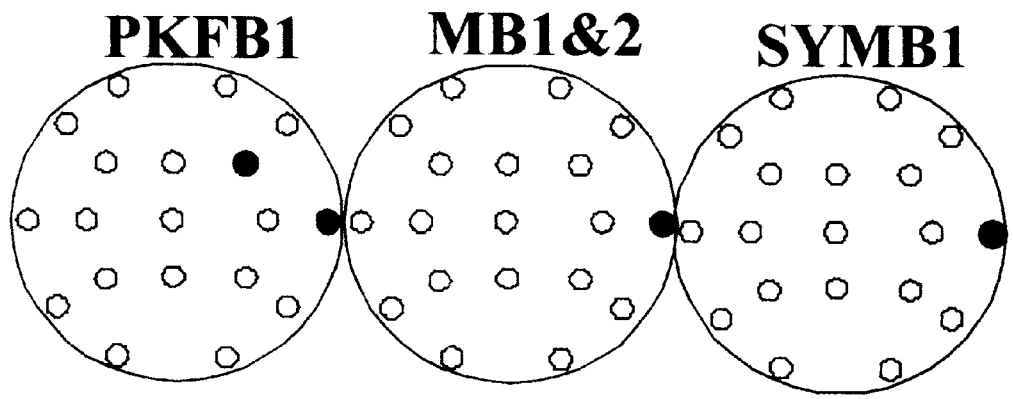
Figure 100
Positive Relationships to Recall
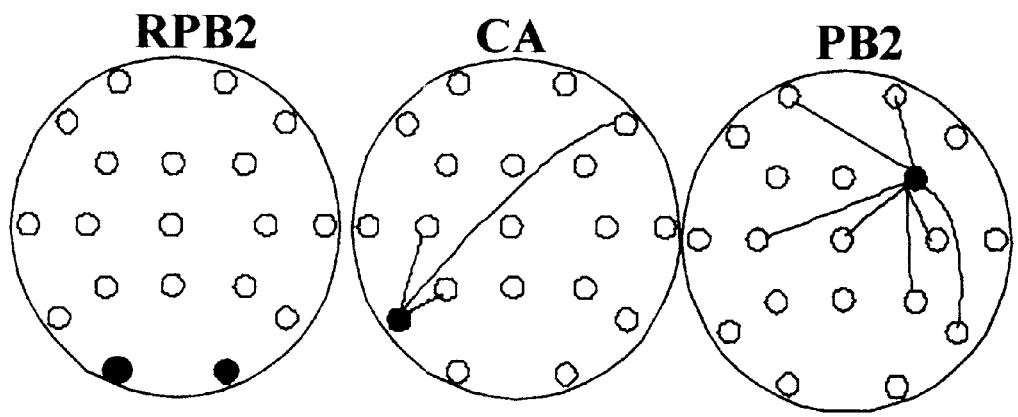
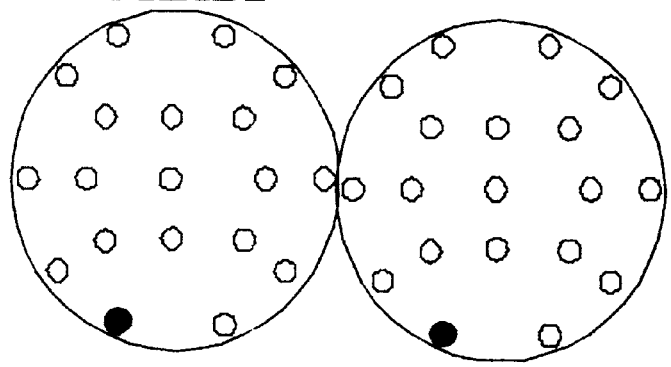

Positive Relationships to Recall

Figure 102
Positive Relationships to Recall
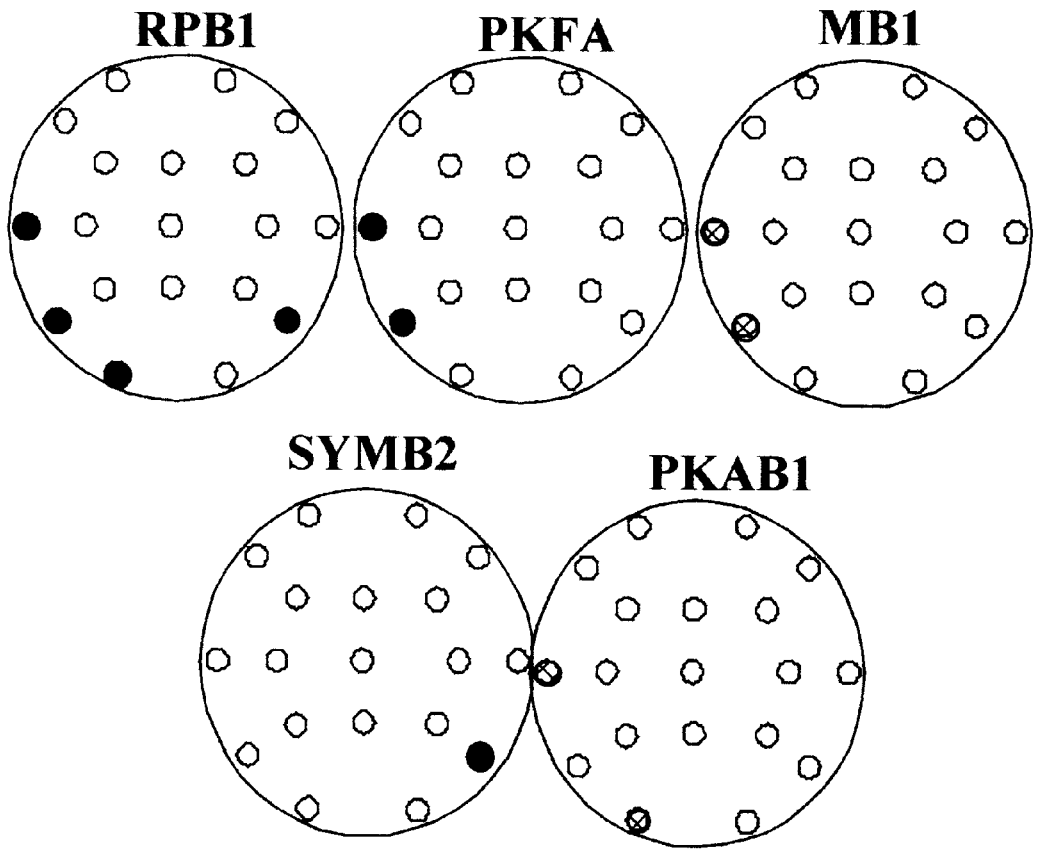
Negative Relationships to Recall
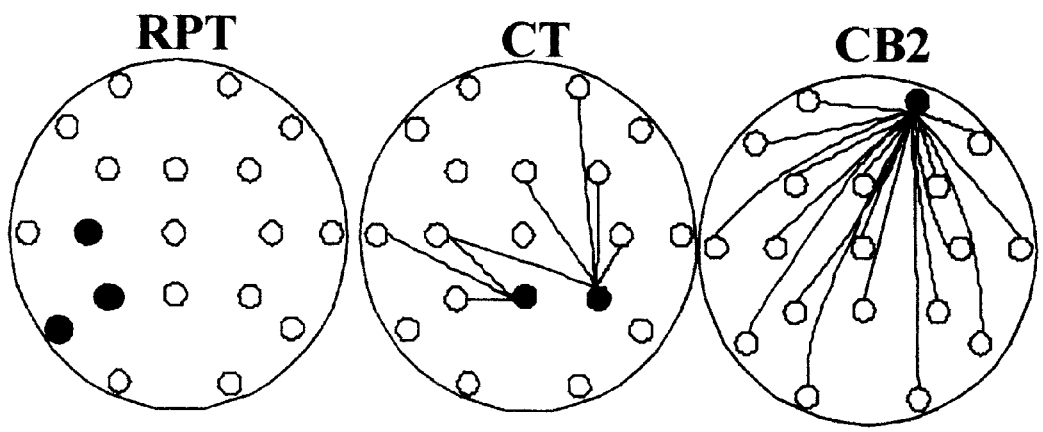

Positive Relationships to Recall

Negative Relationships to Recall

Positive Relationships to Recall**

Positive Relationships to Recall**

Figure 106
Positive Relationships to Performance
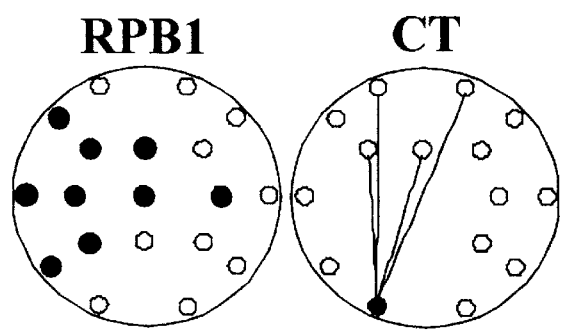
Negative Relationships to Performance
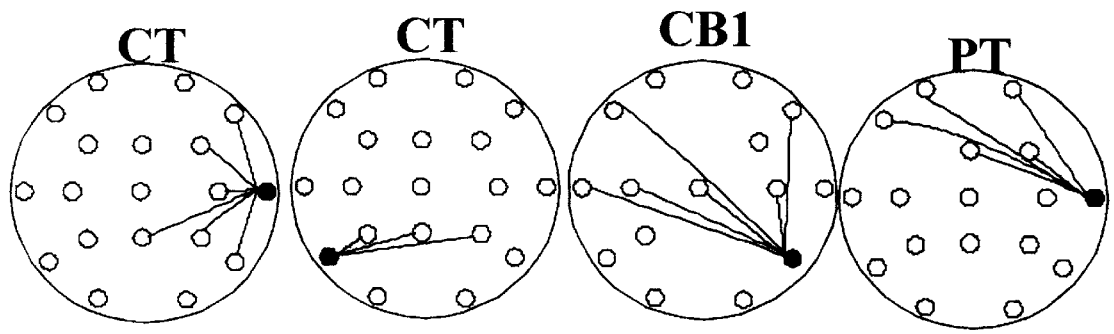

Positive Relationships to Performance

Positive Relationships to Performance

Positive Relationships to Performance

Positive Relationships to Performance

Positive Relationships to Performance

Positive Relationships to Performance**

Positive Relationships to Performance

Positive Relationships to Performance

Positive Relationships to Performance

Positive Relationships to Recall

Positive Relationships to Recall

Positive Relationships to Recall

Positive Relationships to Recall

Positive Relationships to Recall

Positive Relationships to Recall

Positive Relationships to Recall

Positive Relationships to Recall

Positive Relationships to Recall

Figure 148
RPB1
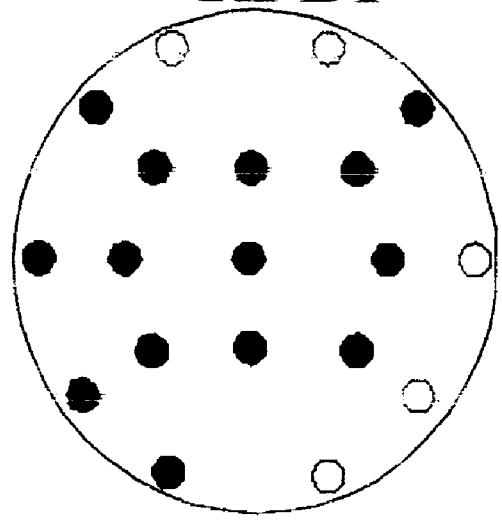
PKAB1
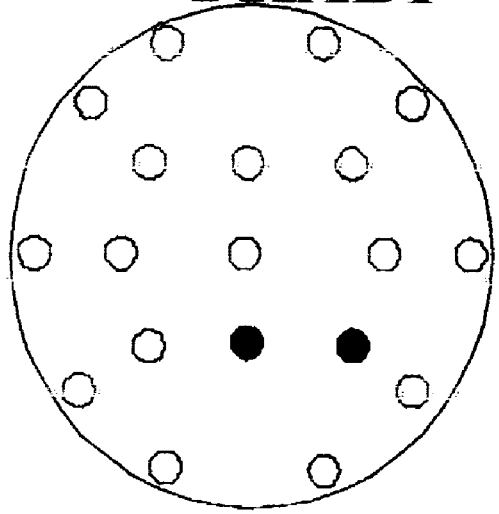
PKFA
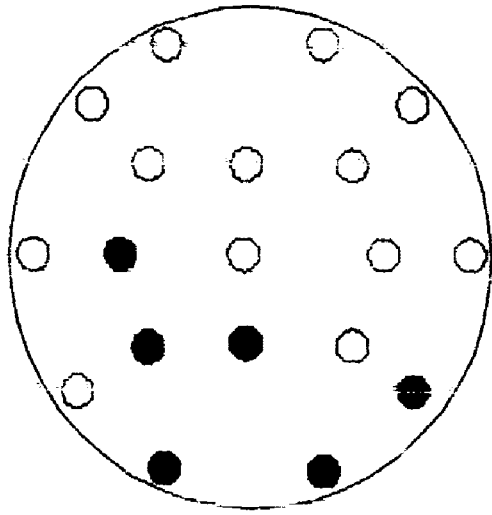
SYMB1
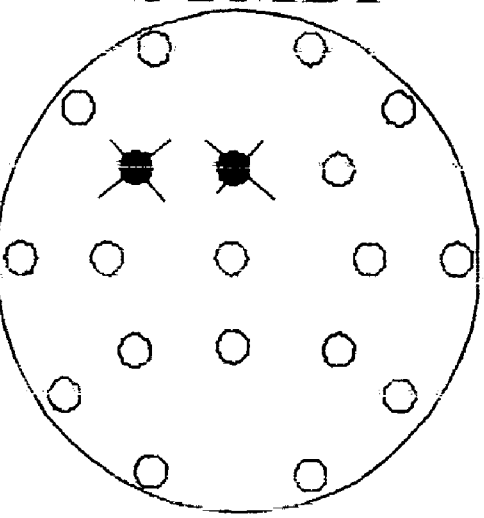

NORMS

Eyes Closed vs Auditory Attention
N=50

Auditory Attention vs Visual Attention
N=50

Eyes Closed vs Silent Recall of Word Lists
N=46

Visual Attention vs Studying Korean Figures
N=49

Eyes Closed vs Recall Korean Figures
N=49

Visual Attention vs Study Names
N=46

Figure AA#8
Eyes Closed vs Recall Names
N=46

Visual Attention vs Reading Silently
N=54

Eyes Closed vs Recalling What Read
N=47

Hearing Silent Numbers vs Spatial Addition
N=53

Visual Attention vs Reading Nonsense Words Silently
N=53

Visual Attention vs Reading Nonsense Words Silently
N=53

Reading Nonsense Words Silently Vs Reading Nonsense Words Outloud
N=50

Eyes Closed vs Recall Earliest Memory
N=28

Auditory Attention vs Listening to Paragraphs
N=55

Eyes Closed vs Delayed Recall of Paragraphs
N=53

METHOD FOR IMPROVING MEMORY BY IDENTIFYING AND USING QEEG PARAMETERS CORRELATED TO SPECIFIC COGNITIVE FUNCTIONING

PRIORITY DATE

A priority date of May 4, 1998 is claimed pursuant to 35 U.S.C. 119(e) based on a provisional application filed in the U.S. Patent Office under Ser. No. 60/084,094 on May 4, 1998 bearing the same title as this application.

BACKGROUND OF THE INVENTION

1. Field of the Invention

The present invention relates to a novel method for improving memory of objects, events, and the like and cognitive functioning related to the objects, events, and the like for the human brain by measuring, determining, recording, and correlating object-related, event-related, recall-related electrical brain potentials ("ERP") with the use of whole skull electroencephalography, using a disposable electrode cap connected to a computer system arrangement and more particularly to a method of measuring and determining a large number of meaningful brain electrical potential changes in response to a continuously presented and varied specific verbal stimulus or verbal stimnuli interspersed with non-significant verbal stimuli concerning memory of objects, events, and the like and cognitive functioning related to the objects, events, and the like by a subject to establish an actuarial or historical base line for use within a predetermined time period and analyzing the measured ERP responses against the historical base line established from the related ERP data established from a group defined as a normal to coaching or feedback to the subject either as a non-verbal (e.g. manual) response or verbal response within the predetermined time period, using a computer.

2. Description of the Prior Art

The research in the area of cognitive functioning and brain physiology is of two general types, blood flow related and electrical activity. The blood flow type studies can employ different types of measures, including, oxygen, glucose or neurotransmitter use as well as other variations. Methodologies include the PET scan, SPECT scan, MRI, etc. Toga, A. W., & Mazziotta, J. C. (1996) have outlined the science and methodology of these and additional approaches of optical imaging, ERP's and transcranial stimulation. Studies of electrical activity will address event-related potentials (ERP) or quantitative EEG measures. ERP's study the activity of the brain within milliseconds following exposure to a stimulus. QEEG studies employ a longer period of time for analysis. The relationship between blood flow and electrical activity has been researched with varied findings. One study indicated that low blood flow is reflected in discordance in the theta (4–8 Hz) and beta (12–18 Hz) bands (Leuchter, A. F., Cook, I. A., Lufkin, T. B., Dunkin, J., Newton, T. F., Cummings, J. L., Mackey, J. K. & Walter, D. O. (1994)). Discordance was a measure developed which analyzes the relationship between relative and absolute power of a bandwidth. However, Leuchter et al. also noted that the associations between EEG power and perfusion or metabolism vary considerably across frequency bands and sites, with some studies showing little or no association.

Hemler, R. J. B., Hoogeveen, J. H., Kraaier, V., VanHuffelen, A. C., Wieneke, G. H., Hijman, R., & Glerum, J. H., (1990) were able to demonstrate that a 60% decrease in blood flow (induced by Indomethacin) resulted in a −0.3 Hz slowing of the alpha (8–13 Hz) peak frequency and a decrease in the relative power of the alpha band. There were no chances in the delta or theta band but there were decreases on memory performance tasks under the low blood flow condition. Jibiki, I., Kurokawa, K., Fukushima, T,. Kjido, H., Yamaguchi, NJ., Matsuda, H., & Hisada, K., (1994) were able to obtain significant negative correlations between blood flow (in group of patients with partial epilepsy) and the relative power of theta (4–7.8 Hz) and a positive correlation between blood flow and alpha (10–12.8 Hz) in the frontal, parietal and temporal regions. In the occipital regions there was a positive correlation between blood flow and relative power of beta1(13–25 Hz). The authors also noted that in previous research there was supporting evidence for the inverse relationship between delta and theta activity and blood flow (studies with cerebral infarction, Alzheimer's, and Pick's disease) as well as positive correlations between alpha power and blood flow.

For both types of methodologies the issue of location is paramount. Blood flow type studies generally employ a longer period of time for analysis, as the technology requires it, while RP studies focus in the millisecond range. QEEG studies will study seconds, not milliseconds. Blood flow studies focus on the difference between the activity under investigation and a control condition, which can be eyes closed or another relevant activation condition. ERP measures employ more of a level, location and time analysis. For example, a response to a stimulus is indicated by time since onset of stimulus, level of amplitude of response, and location of response. Electrophysiological studies enjoy the more precise measurement of the time variable and bypass the problem of the subtraction method. The subtraction method employs two conditions and subtracts the activation in one condition from the activation in another. The result is a degree of activation ditference measure (as indicated by t-tests). This methodology has received criticism due to the difficulty of assuming that its operational assumptions are valid. The discussions of these problems are evidenced in Price, C. J., Moore, C. J., & Friston, K. J. (1997)) and Friston, K. J., Price, C. J., Fletcher, P., Moore, C., Frackowiak, R. S. J., & Dolan, R. J. (1996).

Many studies in this area will focus on pathological states, i.e. Alzheimer's, and will look for differences with normals or activity of the pathological condition. Very few studies have looked at either the degree of activation from an appropriate condition or absolute level in terms of the effectiveness of cognitive functioning. The main emphasis has been on what happens where when we do this. The main cognitive correlates which have been studied include such activities as memory, reading, face recognition, etc.

Theoretical approaches to the understanding of brain dynamics and function have been of five general types. The first type as exemplified by Roland, P. E. (1993) can be described as a modular type, as it indicates what region is activated for a given task. Per Roland describes his approach as the cortical field activation hypothesis. "The cerebral cortex participates in brain work in awake human subjects by activating multiple cortical fields. Each activated field has an area of a few square centimeters. Activation means that the synapses and neurons in a field increase their biochemical activity. This leads to increases in transmembraneous ion transport and in increases in the rate of the regional cerebral metabolism (rCMR) or regional cerebral blood flow (rCBF) . . . The hypothesis states that the neurons in the cerebral cortex always chance their biochemical activity, not in a scattered and singular fashion, but in large distinct ensembles, each covering some 800 mm$^3$ to 3,000 mm$^3$ of the cortex." (Roland, 1993, p. 105)

The second approach is an interactive-regional one, where different regions arc presumed functionally linked for a particular task. Gevins, A., Cutillo, B., DuRousseau, D., Le, J., Leong, H., Martin, N., Smith, M. E., Bressler, S., Brickett, P., McLaughlin, J., Barbero, N., & Lazer, K. (1994) employed a Evoked Potential Covariance measure and conclude that their results suggest the concept of functional networks in that each component cognitive process is associated with a sequence of spatiotemporal patterns of coordinated processing involving widely distributed areas of sensory, association and motor cortices. McIntosh, A. R., Nyberg, L., Bookstein, F. L., & Tulving, E. (1997), (p. 323) expand on this type of analysis in maintaining that "One way to examine whether the same region has a consistent pattern of interactions across retrieval tasks is to explore change in "functional connectivity", loosely defined as the correlation of activity among brain regions . . . the neurobiological interpretation of functional connectivity is simply that two or more regions show correlated activity without reference to how the patterns may be mediated. Further elaboration requires more explicit models to determine the effect regions have on one another, or "effective connectivity"."

The third approach, the flebbian approach is exemplified in some of the research. D. Hebb proposed that knowledge is represented by a collection of neurons, which act as a unit and are required to be activated as a unit for accurate processing. The emphasis on cell assemblies is the theoretical explanation provided for an understanding of the results of Pantev, C. (1995) who maintained that the relationship of rapid (100 ms) event related gamma activity (30–110 Hz, depending upon the stimulus and location) are the activity of the synchronized cell assemblies that are discussed by D. O. Hebb. As an offshoot of the Hebbian concepts, there has also been considerable focus on Neural Network Theory and development (Arbib, M. A.(Ed.) (1995)). This approach attempts to specify the exact nature of the Hebb theory of synaptic change and learning.

In a similar vein "Damasio (1989) made an attempt to integrate findings . . . in his theoretical framework the subcortical structures still have their place for memory functions, however, they are only kind of relay stations which enable storage and retrieval, and do not contain engrams which are assumed to be located in the cortex. However, there they are not stored as holistic units in narrowly circumscribed regions, for example as "grandma cells", but rather was sets of representational fragments in multiple and separate regions. A memory content is accessed if these representational fragments are triggered either by perceptual input or by active memory search. In each case triggering means that the very same activity pattern is recreated in the distributed cortical cell assemblies which was venerated originally, when the entity, a face, etc. was first encountered." (Rosler et al, 1995, p. 301) Damasio (1989) elaborates on this approach by emphasizing that recall of entities and events "1—are activated in time locked fashion; synchronous activations are directed from convergence zones . . . and the process of reactivation is triggered from firing in convergence with and mediated by feedback projections. This proposal rejects a single anatomical site for the integration of memory and motor processes and a single store for the meaning of entities and events. Meaning is reached by time-locked multi-regional retroactivation of widespread fragment records. Only the latter records can become contents of consciousness." (p. 25) Damasio's emphasis upon time locked regional activations places the emphasis upon activated areas. Although he speaks of projections, these projections provide the impetus for activation and are not the focus of recall. For example, he states that "consciousness emerges when retroactivations attain a level of activity that confers salience." (Daamasio, p. 54).

The fourth approach has focused on the electrophysiology of memory and is best exemplified by the research conducted by Klimesch, W., (1996). He notes previous research relating decreased alpha frequency to decreased memory performance in Alzheimer's disease. Klimesch has proposed an integrative memory model, which integrates cognitive psychology, neuroanatomy and neurophysiology and focuses his research and conclusions on variations in synchronizations in the theta and alpha frequency. He defines type 1 synchronization as involving large cortical areas reflecting mental inactivity and type 2 synchronization as the "regular synchronous oscillatory discharge pattern of selected and comparatively small cortical areas" (p. 81). He further elaborates that "the synchronization of very large populations of neurons oscillating with the same phase and frequency reflects a state in which no information is transmitted" (p. 81). He adds "regular type 2 synchronization is that specific oscillatory mode in all of the frequency bands that reflects actual information processing in the brain (p.82)". He further differentiates between low alpha (7–11 Hz) and high alpha (10–13 Hz) and relates desynchronization in these different bandwidths to effective memory performance. His conclusions state that "short term (episodic) memory processes are reflected by oscillations in an anterior limbic system, whereas long-term (semantic) memory processes are reflected by oscillations in a posterior-thalamic system. (p. 61)" The relationship to this patent is that he claims that he focuses on individual alpha frequencies as important to memory (with good memory performers having 1 Hz or higher frequencies), bad memory performance is relate to "a weak or insufficient desynchronization of the lower alpha band. (p. 71)", that alpha is the dominant rhythm reflecting long, term memiory processes . . . hippocampal theta rhythm may reflect the encoding and retrieval of episodic information in working memory (p. 76)." He relates synchronous activity (with implied increased phase relationships) to mental inactivity when he states "the synchronization of very large populations of neurons oscillating with the same phase and frequency reflects a state in which no information is transmitted. (p. 81)." He adds "regular type 2 synchronization is that specific oscillatory mode in all of the frequency bands that reflects actual information processing of the brain (p. 82)." Thus high phase relationship (and presumably high coherence relationships) across broad, long distant relationships in the brain are reflective of low/no information transfer.

A related electrophysiological theory of brain functioning is proposed by Thatcher, R., Krause, P. J., & Hrybyk, M. (1986) where a two compartment model which indicates two separate sources of EEG coherence. The first is coherence produced through the action of short length axonal connections (gray matter connections) and the second is coherence produced through the action of long distance connections (white matter fibers).

The fifth approach has been the employment of the hologram as a theoretical metaphor for brain functioning (Pribram, K., 1994). The optics of hologram science, as put forth by Collier, R. J., Burckhardt, C. B., & Lin, L. H., (1971), indicate that a hologram requires a coherent light source reflecting off both a pure reflecting object and a subject and both reflected back to a recording medium. "Holography is an interference method of recording the light waves diffracted by a subject illuminated with coherent light. The diffracted waves are caused to interfere with a phase-related reference wave. If the waves are highly coherent, the relative phase between subject and reference wave remains constant in time producing an observable effect on the intensity distribution of the resulting interference pattern. The photographic record of this pattern, the hologram, contains sufficient information about both the phase and amplitude of the diffracted waves to permit their reconstruction . . . preservation of relative phase information in a retrievable form between the two sources of information which is recorded onto the medium and allows the creation of a hologram." (Collier, 1971, p. 3)

The theories are generally linked to the type of data they are collecting. For example, blood flow studies indicate locations as results. Thus a theory which attempts to explain blood flow results must necessarily focus upon regional activation, as the data presents itself in this format. The more advanced level of theoretical organization with this type of data is the functionally related orientation. ERP studies will also focus on location and connectivity. QEEG studies also can more appropriately address issues of connectivity and function, as the variables of coherence and phase allow this type of theorizing. QEEG studies, however, can also effectively address issues of activation, as indicated in the measures of magnitude, relative power, etc. Thus the QEEG can allow the integration of activation and connection concerns in theoretical construction of brain dynamics.

A related issue in this discussion is the mind body problem and the level of analysis. These issues come out of the area of the philosophy of science. The studies addressing brain function are generally correlating physiological measures with psychological measures. The two problems here are 1—correlation cannot be inferred to indicate causation and 2—explanation on one level of scientific analysis cannot be employed easily to explain events on a different level of analysis. For example, although we can identify/correlate physiological correlates of fear or love, have we explained these emotions by use of these variables. Each scientific area of study employs certain constructs and operational variables in its study and analysis. To jump across levels of analysis without solid empirical links is an inappropriate theoretical endeavor. Translation of a phenomena to a different level of analysis loses information which is embedded in the original level of analysis. For example, fear and love are psychological constructs, not physiological constructs. Thus we can correlate physiology with psychology, but we cannot say, for example, that increased heart rate is fear.

Within the field of biofeedback applications to problems in human functioning, there is a subspecialty, commonly referred to as Neurotherapy. Neurotherapy is the providing of electrophysiological information (in the form of the QEEG parameters) to a subject for the purpose of changing the parameter being measured. This type of biofeedback has been successfully employed in the remediation of Attention Deficit Disorder (Lubar, J. O., & Lubar, J. F. (1984)(N=6)), the elevation of IQ scores 15 to 25 points (Tansey, M., (1991) (N=21), Othmer, S. & Othmer, S. F., (1992)), addictive conditions such as alcoholism (Peniston, E. G. & Kulkosky, P. J., (1990)(N=30)) and emotional problems such as depression and anxiety (Peniston, E. G., (1993), Peniston, E. G. & Kullkosky, P. J. (1991)) in Veterans (N=20). Peniston (1993) employed an increased theta/decrease alpha protocol at the occipital and frontal positions to induce abreaction.

While these results have been empirically impressive, they have not been based upon a complete theoretical orientation and/or empirical base of brain physiology. The research has primarily focused on the C3-Cz locations (ADD and Learning Disabilities) and occipital leads (alcoholism) and have addressed issues of reducing theta and/or increasing alpha or beta activity (depending upon the problem). None of the research to date has examined or attempted to address the issues of rehabilitation with the coherence and phase relationships.

The research conducted for this patent was explicitly designed to address the whole brain's effective electrophysiological response to specific cognitive tasks. It was the thinking of the inventor that only by studying the problem in this manner can we obtain the findings that are relevant for the Neurotherapy situation. Specific answers to specific questions can allow specific interventions for specific problems in the areas of cognitive rehabilitation as well as increasing cognitive abilities in normal subjects. The fields of application for the findings not only include all rehabilitation facilities engaged in cognitive remediation, all school systems with learning disabled children and Attention Deficit disorders, all mental conditions which have a cognitive component, as well as the general public who might wish to "tune up" their brains. The knowledge presented in this patent application can potentially revolutionize the field of education and cognitive rehabilitation as well as offer to the general public a significantly effective method to improve mental functioning in the workplace, and thus improve the competitive edge of businesses.

Specific Findings Regarding Memory Functioning and Brain Physiology

Findings generated from the blood flow type research are relevant but not particularly prior knowledge with respect to this patent application. This is because 1—blood flow measures are not electrophysiolog,ical measures and 2—the relationship between blood flow measures and electrophysiologyical ones is only partly defined one at present. Therefore, even though a blood flow study may indicate activation in a region for a particular task, it is not a prior knowledge that this finding necessitates a certain type of electrophysiological activity in that region because of that blood flow fiinding. In addition, blood flow studies tell us nothing about connectivity. Thus all blood flow type research is irrelevant to the domain of this patent application. In addition, all Event Related Potential research fails to constitute prior knowledge in this area for a different reason. ERP's study the subject's response in milliseconds. The relationship between activity in the first several hundred milliseconds of a response and the subject's response over a 30 second interval has not been addressed in any research. Although ERP research employs similar type of constructs, such as amplitude, coherence, etc. it is in a different the domain. Therefore all ERP research is irrelevant to the domain of this patent.

In terms of QEEG research, there are generally four types of research that are relevant to this patent.

1. Differentiating Clinical Conditions (i.e. ADD vs. Normals, Learning Disability vs. Normals) on the Basis of Eyes Closed Resting Condition Values The connection in these studies is that, presumably, if a clinical population has differences in electrophysiological functioning then these differences are related to the known cognitive differences.

2. Activation Patterns Under Specific Task Conditions

Research in this are will indicate what happens when a subject reads. Although this approach can tell us what is involved in reading, it cannot tell us the difference between successful and unsuccessful reading (i.e. comprehesion/memory).

3. Analysis of Difference in Activatin/Connection Patterns to Success in Task Condition This is the most relevant to the present patent application as it addresses the same problem. Studies in this area focus on degree and location of activation and/or connectivity patterns. The simultaneous combination of both of these types of measures is what is relevant to this patent.

4. Rehabilitation Efforts With Attention Deficit Disorders, Learning Disabilities and Other Clinical Conditions.

The ability to change electrophysiological parameters and demonstrate increased cognitive functioning is a strong argument for the causal effect of electrophysiological measures on cognitive measures. However, much of the research has not specified what the exact causal route is. The electrophysiological measures and cognitive measures employed have been broad measures. It would be more exacting to be able to state that electrophysiological variable X relates to cognitive variable Y and that if we change X we will find a change in Y.

5. Differentiating Clinical Conditions (i.e. ADD vs. Normals, Learning Disability vs. Normals, Clinical Conditions vs. Normals) on the Basis of Eyes Closed Resting Condition Values While it is the case in first above described type of research that there certainly must be some connection between the eyes closed condition and activation conditions, there is no research, which specifically evaluates that relationship. The type of research conducted under this model includes Giannitrapani, D., (1985) had been able to relate performance on the WISC Arithmetic and Comprehension scores to (not in an activation procedure) to power in the low beta frequencies. Thatcher, R. W., Walker, R. A. (1985) related increased WISC IQ scores (intra-hemispheric analysis) to short inter-hemispheric connections, especially in the posterior regions. The best overall predictors of IQ (hemispheric analysis) were the coherence figures from the frontal and fronto-temporal regions. A multiple regression approach indicated interhemispheric coherenccs were better predictors of IQ than intrahemispheric coherence.

Fein, G., Galin, D., Yingling, C. D., Johnstone, J., Davenport, L., & Heron, J., (1986) (N=113) were able to consistently show decreased beta power (19–24 Hz) in dyslexics (eyes closed condition) but no differences in the other bands.

Harmony, T., Hinojosa, G., Marosi, E., Becker, J., Rodriguez, M., Reyes, A., & Rocha, C., (1990) (N=81) were able to identify children with poor educational evaluations on the basis of absolute power of delta (poor evaluations) and increased alpha at occipital areas (good evaluations). The relative power variables correlated more with the learning problems. Children with very poor evaluation had more delta activity in left frontal and temporal areas, while increased theta activity was found for children (matched for SES) who were lower on the educational evaluations than their matched peers.

Byring, R. F., Salmi, T. K., Sanio, K. O., Orn, H. P., (1991) (N=44) were able to differentiate between spelling disabled children and normals on the visual basis of excess slow activity (especially in temporal regions) and quantitative basis in terms of low alpha and beta powers, and high complexity (spread of frequencies) in the parieto-occipital regions in the spelling disabled children. The authors noted the inconsistent findings in previous research with dyslexics in terms of theta, alpha and beta activity.

Giannitrapani, D., Collins, J., & Vassiliadis, D., (1991) noted that in Alzheimer's and dementia patients there was an increase in slow activity and decrease in fast activity and that the differentiating characteristic on the non-Alzheimer's dementia was a decrease in the frequency of alpha activity.

Marosi, E., Harmony, T., Sanchez, L., Becker, J., Bernal, J., Reyes, A., Diaz de Leon, A. E., Rodriguez, M., & Fernandez, T. (1992) (N=152) were able to demonstrate different patters of maturation of the coherence figure in normal and learning, disabled children under the eyes closed condition.

Mann, C. A., Lubar, J. F., Zimmerman, A. W., Miller, C. A., & Muenchen, R. A. (1992) (N=25) were able to demonstrate increased amplitude theta activity (4–7.5 Hz) and decreased betal (12.75–21 Hz) (compared to normals) in ADD subjects when subjects were reading or drawing. The increased theta activity was more prominent in frontal regions, while decreased beta was significantly decreased in temporal regions. For children with dyseidetic disorders (difficulty with visual spatial processing for whole word recognition) there was increased left temporal theta in the t3-p3 region. Lubar, J. F., Bianchini, K. J., Calhoun, W. H., Lambert, E. W., Brody, Z. H., & Shabsin, H. S. (1985) had obtained similar results.

Leuchter, A. F., Cook, I. A., Lufkin, T. B., Dunkin, J., Newton, T. F., Cummings, J. L., Mackey, J. K., & Walter, D. O. (1994) (p. 208) noted that "pathologic slow waves in the 0–4 or 4–8 Hertz frequency range are known to be caused by partial deafferentation of the cerebral cortex. Deafferentation of the pyramidal cells in lamina II and III is the neurophysiologic principle unifying slow wave production due to tumor, infarction, ischemia, demyelination or degeneration. These cells are responsible for the generation of much of the normal brain electrical activity, and they produce slow waves only in response to a loss of afferent input." This type of analysis would indicate that delta/theta waves are correlated with low cognitive ability due to the loss of input.

Ackerman, P. T., Dykman, R. A., Oglesby, D. M., & Newton, J. E. O. (1995) (N=119) were able to show that dysphonetic readers had significantly higher values in the theta and delta bands. Both phonetic and dysphonetic poor readers had lower beta activity than Attention Deficit Disorder subjects with adequate reading skills.

Chabot, Merkin,Wood, Davenport, & Serfontein, G. (1996) (N=407) who were able to distinguish between normals and ADD/ADHD and Learning Disabilities on the basis of QEEG variables on the basis of coherence, relative power, asymmetry and location issues (eyes closed condition).

Evans, J. R. & Park, N. S., (1996) were able to identify siglificant deviations from a normative database in a group of 8 dyslexic children and 2 adults. These were evident in the left posterior region (in particular the P3 position) in terms of reduced coherences and usually involved the theta bandwidth.

Koyama, K., Hirasawa, H., Yoshiro, O., & Karasawa, A. (1997) noted that age had no effect on interhemispheric coherence but intrahemispheric coherence was found to decrease with age in all bands almost linearly and was a more sensitive indicator of normal aging than relative power.

In summary, this pattern of research findings implies that cognitive abilities reside in increased beta (13–21 Hz) activity, decreased theta and delta activity and increased coherences.

With regard to the aspect of research involving activation patterns under specific task conditions. Sklar, B., Hanley, J., & Simmons, W. W., (1973) (N=25) demonstrated that dyslexic children had more theta activity (3–7 Hz) in the parietal region (rest condition) as well as more activity in the 16–32 Hz range than normals, who had more 9–14 Hz activity (alpha). Under the reading task condition, however, the normals increased activity in the 16–32 Hz range, while the dyslexics decreased activity in this Hertz range. Within the same hemisphere, the coherences were higher for the dyslexics but lower between homologous connections (similar positions) across the hemispheres than normals (reflecting possible problems in the corpus callosum).

Gevins, A. A., Zaeitlin, G. M., Doyle, J. C., Dedon, M. F., Schaffer, R. F. & Yeager, C. L., (1979) and Gevins, A. A., Zaeitlin, G. M., Doyle, J. C., Schaffer, R. E., & Gallaway, E., (1979) found slightly higher theta spectral intensities in frontal and occipital cortex during serial addition, letter substitution and block rotation tasks.

Duffy, F., Denckla, M. B., Bartels, P. H., Sandini, G., (1980) (N=18) found differences between normals and dyslexics in terms of the bifrontal areas as well as the expected left temporal and left posterior quadrant. The activation tests produced more prominent group differences. Dyslexics were noted to have increased alpha during activation conditions (relative to controls).

Dykman, R. A., Holcomb, P. J., Oglesby, D. M., & Ackerman, P. T., (1982) (N=10) employed a complex visual search task and recorded over the central and parietal sites and were able to differentiate between the groups (hyperactive, learning disabled, mixed and normal children) on the basis of two frequencies—16–20 Hz and 7–10 Hz.

Grunberger, B. S., & Grunberg, J., (1985) were able to demonstrate that elderly subjects with poor memory exhibited slow activity and less alpha and alpha adjacent beta activity than elderly subjects with good memory.

Duffy, F. H., Denckla, M. B., McAnulty, G. B., & Holmes, J. A., (1988) were able to demonstrate increased alpha in dyslexics under rest and activation conditions as compared to normals in the left posterior, left anterolateral frontal, left midtemporal and bilateral medial frontal areas.

Gutierrez, S., & Corsi-Cabrera, M., (1988) (N=8) monitored EEG activity during spatial, verbal and one demanding mixed task to determine possible hemisphere and performance effects. They found no significant differences between performance levels but increased beta power in the left posterior region across all tasks, as well as decreased alpha relative power and increased theta relative power.

Randolph, C., & Miller, M. H. (1988) (N=20) examined head injured and normal subjects during several cognitive tasks and employing T3, F4, O1, & O2 electrode placements. They found significantly worse performance in the head-injured subjects and increased (in comparison to normals) EEG amplitudes and amplitude variances. They were able to correlate decreased performance with increased amplitude variances at the temporal lobes for 2 of the 4 cognitive tasks they administered.

Matsuoka, S.,(1990) examined the midline frontal theta and noted the clinical observation that there is the appearance of this theta activity under various conditions which include simulated driving, brain tumor, chemical intoxication, exercise, mental calculation sleep and meditation.

Galin, D., Raz, J., Fein, G., Johnstone, J., Herron, J., & Yingling, C., (1992) (N=113) concluded in an activation procedure for dyslexic and normal readers that the theta activity in the temporal lobes was the main discriminating variable between the two groups.

Valentino, D. A., Arruda, J. E., & Gold, S. M., (1993) conducted an auditory continuous performance task (N=27) and compared performance levels with EEG variables. They found an increase in beta power (especially in frontotemporal and left temporal sites) decreases in alpha and posterior theta, and increased anterior theta and delta. The lower performing group had decreased left temporal heta power, while the good performers had, in addition, more anterior beta and less posterior alpha and theta.

Klimesch, W., Schimke. H., & Pfurtscheller, G., (1993) were able to show that during retrieval the alpha frequency (frequency range not stated) of good performers is 1.25 Hz higher than for bad performers. During retrieval, alpha desynchronization is more pronounced for bad performers than good performers. Special cognitive tasks such as reading, classification and recognition as well as attentional demands tend to reduce the power within the alpha band. They also noted that mental tasks and task difficulty in particular lead to an increase in alpha frequency but only for difficult but not for easy tasks. They also noted that alpha frequency increases selectively in that hemisphere which is dominant for a particular task.

Lutzenberger, W., Pulvermuller, F., & Birbaumer, N., (1994) were able to demonstrate significant differences in activation of the 30 Hz range in subjects between the presentation of words and pseudowords with words eliciting a synchronous activation of large cortical cell assemblies.

Klimesch., W., Schimke, H., & Schwaiger, J. (1994) employing an ERP methodology noted that semantic memory process are reflected primarily in alpha band and episodic memory is related to activity in theta band.

Fernandez, T., Harmony, T., Rodriguez, M., Bernal, J., Silva, J., Reyes, A., & Marosi, E. (1995) (N=25) analyzed the EEG up to the 19 Hz range in terms of the differences between the task conditions (subtracting 7s) and resting condition. They round significant differences in the delta (1.5–3.5 Hz) and theta (3.5–7.5 Hz) bands in the right posterior areas and in the beta (12.5–19 Hz) band in the frontal area.

Klimesch, W., Doppelmayr, M., Schimke, & H., Ripper, B., (1997) noted in another ERP study that episodic encoding and retrieval processes are primarily reflected by a task related increase in theta power. With subjects performed a recognition task the results indicated that only those words that were later correctly recogized produced a significant increase in theta power during the encoding stage. During the actual recognition processes there was significant theta synchronization (increase in band power) for correctly remembered words only. Employing an immediate recall procedure, they found theta relative power increases during the recall period.

Rosler, F., Heil, M., & Hennighausen, E., (1995) studied whether long term memory retrieval is correlated with specific changes in slow, DC like event-related brain potentials. The results indicated a positive relationship to slow negative shifts of 5–10 mV, which prevails about as long as the retrieval process lasts (several seconds). When different types of representations have to be reactivated in memory the slow negative wave shows a clearly distinct topography. The maximum was found in a verbal condition over the left frontal, in a spatial condition over the parietal, and in a color condition over the right occipital to temporal cortex. The amplitude of the topographic maximum increase with the number of representations which have to be reactivated.

Sterman, M. B., (1996) was able to relate (in an event related paradigm) decreased posterior 7–9 Hz at time of presentation (125–250 msec) to effective subsequent recall in a target recall task. At time of recall the ERD (event related desynchronization) was significantly increased (500–625 msec) for the good performers. This article is included to reflect at least one of the studies that have related ERP measures to performance.

Leuchter, A., (U.S. Pat. No. 5,309,923—May 10, 1994) employed a cordance method in analyzing the responses of 11 subjects (mixed group of 5 normal elderly, 4 major depressives, and 2 early dementia) during a memory task (analyzing 4 second periods). The subjects were show slides of pen and ink drawings of common objects for 5 seconds. QEEG data was collected during presentation. Subjects were asked to spontaneously recall the items at both a 3-minute lapse and again at 7 minutes post testing. Subjects were scored on their recall ability during both testings. Leuchter, A. pooled the recordings according to whether the objects were recalled later consistantly (both recall tests) or not at all (recalled at neither of the recall periods). The results were analyzed according to his cordance system and further scored in terms of their overall recall ability. He defines cordance by the relationship between the absolute power and relative power of a bandwidth. When these figures are not consistent (as defined by a midpoint or selected base) there is discordance. For example, when the relative power of alpha is high versus its selected base as well as its amplitude, then there is a condition of cordance. If Alpha relative power is high, but its amplitude is low, then discordance exists. In his study he demonstrated that the concordance of the Alpha frequency (8–12 Hz) in the left temporal lobe was associated with good visual memory performance.

The neurophysiologic activation pattern that was associated with (good recall involved the temporal regions (T3, T5 and T4, T6). A good memory performance was associated with left temporal concordance, while a poor performance was distinguished by a shift to the right temporal concordance. There was also evident a pattern of central discordance or deactivation for two of the good memory subjects. Further analysis by subgroup revealed some differences in cordance, memory and clinical condition, but which were interpreted in line with the general interpretation. He also noted a left/right ratio of Alpha power increasing during the task and that the subjects who failed to obtain this ratio, the memory performance was below the others. Lechter notes that cordance provides information on perfusion (blood flow activity) in that there is a strong relationship between mean perfusion and concordance in the Alpha frequency range.

Although Leuchter claims, in his patent, all possible frequency ranges, all possible time interval periods, channels up to 128, and also lays claim to voltage, amplitude and coherence values. Yet Leuchter only sampled up to 30 Hertz, examined the data in four-second periods for 11 subjects (with differing clinical conditions), analyzed a visual-verbal memory task under a short delay spontaneous recall paradigm. He did not specifically evaluate coherence, phase, peak frequency, peak amplitudes, frequency ranges above 30 Hertz, or memory under different stimiulus conditions separating out the input, immediate and delayed recall conditions.

In summary, the confusing pattern of results is due to the different tasks being employed, different subject populations and different methodologies. The most relevant to this patent are the studies by Klimesch (1993,1994, 1996, 1997) who has discovered the importance of the alpha frequencies, theta relative power and desynchronization patterns to memory performance. There is minimal emphasis in his analysis upon the issues of coherence and phase.

Regarding the third area of research in the area of coherence relationships, Busk, J., & Galbraith, G. C., (1975) demonstrated that coherence increases with the difficulty of the task, while practice reduces coherence as a result of a decrease in task difficulty.

Shaw, J. C., O'Connor, P., Ongley, C. (1977) were able to show that spatial and arithmetic task produces an increase in interhemispheric coherence in a right-handed population.

Gasser, T., Jennen-Steinmetz, C., & Verleger, T. (1987) were able to show in a visual matching task there is a marked increase in interhemispheric coherence in children.

Corsi-Cabrera, M., Gutierrez, S., Ramos, J., & Arce, C. (1988) found increased interhemispheric coherence during unsuccessful cognitive task performance (in the beta band for verbal and visual tasks and in the alpha and theta bands for a mixed task) employing the P3-P4 locations. They summarized some of the literature in the area of coherence noting that coherence increases have been observed in spatial tasks, tasks demaniding high levels of arousal, continuous movement tasks and during human communication and is inversely related to field dependence. Field dependence is a measure of cognitive style with field dependence related to more negative type personality characteristics.

Weiss, S., & Rappelsberger, P. (1998) with a sample size of 16 tried to see if "1—some frequency bands show power and coherence changes only due to the modality of presented stimuli (auditory vs. visual) and 2—if other bands show modality independent effects which should reflect real cognitive-linguistic differences between word classes (either concrete and abstract nouns)." (p. 33) Their results showed that the alpha1 band (8–10 Hz) revealed no difference between word classes (concrete vs. abstract nouns) but did demonstrate an influence of modality of stimulus presentation in that during memorization of auditorily presented nouns compared to rest alpha1 amplitudes decreased at left and right temporal electrodes. This finding was in contrast to all other electrode positions, which showed increases in amplitude. During the memorization of visually presented nouns all electrodes showed alpha1 desynchronization, mostly in the posterior regions. In terms of coherence and alpha1 changes, the auditory condition produced intrahemispheric coherence increases but during visual processing there was a coherence decrease except between central and temporo-cential electrodes. During the auditory noun processing both hemispheres showed increased coherence changes, especially in the frontal and central region. In the visual noun processing the interhemispheric coherences mainly increased in the posterior regions. There were no differences in the comparison of concrete versus abstract nouns within the alpha1 band. However, concrete nouns tended to show higher coherences within both modalities.

The only modality independent different between concrete and abstract noun processing were found in the delta (1–4 Hz), theta (5–7 Hz), and beta-1 (13–18 Hz) band at the left frontal electrodes with increased coherences for the concrete nouns. They also noted better recall (35.5%) for the concrete nouns versus 22% for the abstract nouns.

Previous research (Weiss, S., & Rappelsberger, P. (1996) had indicated higher number of coherences between different brain regions fori auditorily presented concrete nouns compared to abstract nouns in the beta1 frequency (13–18 Hz) and no differences in the alpha1 frequency (8–10 Hz).

In summary, activation conditions will increase coherences. Particular tasks will produce differences in coherence patterns, with increased coherences sometimes causing decrements in location (short posterior connections).

With regard to the research area where both activity and connectivity are simultaneously measured, Tucker, D. M., Dawson, S. L., Rothi, D. L., Penland, J. G., (1985) studied two individuals over several months on two cognitive tasks (with a 8 channel EEG) to determine if there were a characteristic pattern of activation which was stable over time. They found consistent changes in spectral information over the anterior left hemisphere during the word fluency task in terms of relative power and coherence measures. The specifics of the findings are not important for this discussion, as they are complex and represent only two subjects.

Corsi-Cabrera, M., Herrera, P., & Malvido, M. (1989) in summarizing the relationship between power and coherence across a number of studies noted that changes in coherence occur independently from changes in EEG power.

Shepard, W. D., (1990) was able to demonstrate that the coherence values of alpha in the left posterior parietal and right hemisphere predicted speed of response in a lexical decision task. There were no effects of relative power variables (2–30 Hz range).

Inouye, T., Shinosaki, K., Iyama, A., & Matsumoto, Y. (1993) (N=11) measured activation and connection issues (N=10) during mathematical tasks employing all of the 10–20 system placements and examined up to 50 Hz with a frequency resolution of 0.78 Hz. Subjects were instructed to serially subtract 7 from 1000 for 2 minutes with eyes closed. They found specific patterns of activation (left temporo-central-parietal regions) and connectivity (conceptualized as directional EEG) from the same region and within the frontal regions (especially left temporal and mid frontal)

Thornton, K., (1996) (N=3) was able to demonstrate diferences in phase, coherence and activation patterns to effective auditory memory recall. The pattern of results indicated that increases in phase and coherence are associated with better recall. As the results are complex, sample size small and this patent application represents a more refined analysis with a greater number of subjects in similar conditions, the specific results of that experiment will not be presented.

Benham, G., Rasey, B. A., Lubar, J. F., Frederick, J. A., Zoffuto, A. C. (1998) reported on the differences in power spectra and coherence in terms of subjective levels of engrossment in an auditory listening condition (listening to paragraphs). They found increased mean power in the theta (4–8 Hz) and beta1 (13–21 Hz) bands during engrossed states. There were significant increases in theta coherences from the FP1 position to F7 and T3 and from the O2 location to F4,C4,T4, & P4. Increases in alpha (8–13 Hz) coherence were evident in the Fp1-F7 relationships and T3-O1 relationships. Significant decreases in coherence were observed in the Fp2-C4 relationship.

The pattern of results indicates that increased coherences yield better performance and that there is no significant relationship between activation variables and coherence variables.

In the area comprising analysis of difference in activation to success in performance, Gale, A., Davies, I., Smallbone, A. (1978) (N=21) visually presented subjects with 9 digit strings to memorize. Subjects who recalled well were more activated in the left hemisphere and the level of EEG activity (7–20 Hz) in the early trials (left hemisphere) predicted overall recall. The amplitudes were associated with superior recall when the information was new, but decreased amplitudes when the subjects had practiced more. Only posterior leads were employed (occipital). Earle, J. B. (1988) (N=20) found increasing mathematical task difficulty (activation conditions) led to changes in parietal amplitude asymmetries in the alpha band with the locations under investigation (P3, P4, T4, and T6 referenced to Cz). He found performance differences related to these asymmetries (left greater than right) with greater asymmetries related to better performance. He also found that right temporal activation was significantly related to overall performance as well as high mean alpha frequencies. In the verbal activation condition, he found a decreasing alpha frequency with improved performance in the parietal regions as the difficulty of the task increased.

In the fourth area involving rehabilitation efforts toward cognitive functioning, the rehabilitation efforts of Lubar, J. O., & Lubar, J. F. (1984), Tansey, M., (1991) & Othmer, S. & Othmer, (1992) (N=14) have been directed towards the specific clinical problems of Attention Deficit Disorder and Learning Disability. The results have indicated improvement in cognitive functioning in terms of IQ scores (15 to 25 points) and school performance (as well as attitudinal and behavioral changes). However, the specific link between successful cognitive task pertormance and QEEG variables is inferred from the improvement and not demonstrated empirically. The locations employed have focused on the C3-Cz positions predominantly and have augmented beta activity (13–21 Hz) and inhibited theta activity (4–8 Hz).

Thompson, L., & Thompson, M., (1985) were able to demonstrate significant improvement with Asperger's syndrome by providing feedback which reduced theta activity (4–8 Hz) and increased beta (13–15 Hz & 16–20 Hz) activity. Improvements were noted in social interaction, decreased use of medication and improvement in academic functioning and on standardized tests.

SUMMARY OF THE INVENTION

The novel method of the invention is the discovery that the step of rewarding of the beta frequency (13–21 Hz) and inhibiting theta activity (4–7 Hz) at the C3, Cz or C4 locations results in improved academic functioning, improvement in memory and improvement in cognitive skills using the QEEG measurements and therefore that coaching or feedback to a human subject which enhances the beta frequency and inhibits theta activity at the aforesaid locations improved memory and cogniitive ability or performance by the subject. The method of the invention is predicated on derived intormation which indicates that low frequencies (delta) are associated with lowered cognitive functioning, that the theta and alpha frequencies are related to good memory performance, that beta activity is associated with better cognitive abilities and that increased coherences are generally related to improved cognitive abilities and performance. The problem solved and object of the invention is a method of psychological therapy for improving memory and cognitive skills by verbal feedback and coaching along with monitoring of the low frequencies and the theta and alpha frequencies and employing and delivering to a human subject more of the type of verbal or type of communicative feedback regarding a body of subject matter which diminishes the low frequencies and enhances the quantitative level of the theta and alpha frequencies in terms of their frequency of occurrence and electrical power.

DESCRIPTION OF THE DRAWINGS

FIG. 1 is a chart summarizing the data upon which the novel method is predicated.

FIG. 2 presents the summary of the just described analysis in terms of all the different tasks (except Raven's Matrices).

FIG. 3 compares two auditory memory conditions (paragraphs, word lists) with two more visually oriented tasks (Korean Figures, Names of Faces) to discern if there is a distinction between the two modes of processing.

FIG. 4 analyzes the differences between the input stage, immediate recall stage and delayed recall across four conditions (two auditory and two visual).

FIG. 5 presents the analysis of this three-stage analysis in terms of the two visual tasks the important considerations.

FIG. 6 presents the same analysis employing the two auditory tasks.

FIG. 9 represents a relationship between the auditory attention condition and future auditory memory ability (word lists and paragraphs).

FIG. 10 reflects the absolute level when listening to word lists, when processing word lists and absolute levels for the words which were recalled successfully under the long term memory condition for the list learning condition (hearing activatioin issue).

FIG. 11 represents the absolute decree of activation under the processing condition, the one second period of time after a word was heard and prior the presentation of the next word.

FIG. 12 represents the variables, which were significantly related to the long term, recall condition in terms of absolute level.

FIG. 15 presents the respective significant levels of activation for successful recall in terms of level of activation.

FIG. 17 presents certain significant levels of absolute activation and degree of activation from the subject's respective listening condition when the subject was quietly recalling the paragraphs to himself.

FIG. 19 represents the level of activation for the variables which had a significant correlation with total recall (immediate and delayed) during the 60 studying period the subjects were asked to study the figures.

FIG. 20 represents the degree of activation from the visual attention comparison condition and the variables, which were significantly correlated with total memory.

FIG. 25 presents the significant variable whose level of activation correlated with total recall during the 30-second silent recall condition.

FIG. 27 presents the significant correlations between the total recall of the reading material and the level of activation of variables during the silent reading task.

FIG. 28 compares the degree of activation from the visual attention condition and recall ability.

FIG. 29 presents the correlations between the absolute level of the variable during the silent recall period and total recall ability.

FIG. 32 presents the variable whose absolute level correlated with success the spelling task.

FIG. 41 presents the relationships between the degree of activation over the visual attention condition and accuracy in pronunciation.

FIG. 42 present the relationship between absolute level of a variable and degree of success in terms of delayed recall (not including the short term recall score).

FIG. 46 presents the significant relationships between the absolute level of a variable and successful recall of the Korean figures.

FIG. 47 present the significant relationships between the level of a variable and successful recall of the names of the faces presented in the beginning of the experimental procedure.

FIG. 48 presents the comparison between immediate recall of names and delayed recall.

FIG. 49 presents the significant relationships between the absolute level of a variable and subsequent recall ability.

FIG. 51 presents the significant relationships between the level of a variable and subsequent successful recall of the object's location in the room.

FIG. 52 presents the significant relationships between successful recall of intentions and the level of a variable.

FIGS. 59 to 87 present memory recall of various tasks—has been inserted.

FIGS. 88 to 124 present the results of the analysis of the children under the age of 13 who were involved in the experimental procedure(biofeedback of the QEEG signal).

FIG. 88 presents the variables, which were important for memory during the initial presentation of the words in the word list task and represents the relative power if the Beta 1 figures for the posterior portion of the head.

FIG. 89 presents those variables, which were important for the one-second intervening processing period and is another representation of the relative power of Beta 1 figures for the posterior portion of the head.

FIG. 90 presents the variables, which predicted recall ability under the delayed recall condition and is yet another representation of the relative power of Beta 1 figures for the posterior portion of the head.

FIG. 91 presents those variables (levels of activation) which accurately predicted recall under the quiet 30-second recall condition in between each word list.

FIG. 92 presents those variables whose degree of activation from the eyes closed condition predicted recall.

FIG. 93 represents those variables whose absolute level of activation predicted recall.

FIG. 94 shows those variables whose degree of activation from the auditory attention condition predicted recall.

FIG. 95 presents those variables whose level of activation under the immediate silent recall condition predicted recall.

FIG. 96 shows those variables whose degree of activation from the eyes closed condition predicted recall.

FIG. 97 presents the variables that were important for recall in terms of the degree of activation from the visual attention condition.

FIG. 98 presents the variables during the quiet recall of Korean characters were important.

FIG. 99 presents variables signifcant in studying names.

FIG. 100 presents variables significant in silent recall of names.

FIG. 101 presents variables significant in silent recall of names with eyes closed.

FIG. 102 presents those variables whose level of activation at the time of studying the names of faces were important.

FIG. 103 presents those variables whose degree of activation from the visual attention condition predicted recall ability.

FIG. 104 presents the variables whose level of activation, during the 30-second quiet recall period for the names of faces, predicted subsequent recall.

FIG. 105 presents the degree of activation from eyes closed analysis and recall for the same period of time.

FIG. 106 presents the variables whose level of activation during the quiet reading period predicted subsequent recall.

FIG. 107 presents those variables that were positively and significantly related to effective problem solving (Raven's Matrices).

FIG. 108 presents variables significant in spelling success from hearing words.

FIG. 109 presents the variables whose level of activation during the spelling task positively correlated with subsequent success.

FIG. 110 presents the variables whose degree of activation from the hearing words silently condition successfully predicted spelling ability.

FIG. 111 presents the variables whose level of activation during the silent multiplication period predicted subsequent ability.

FIG. 112 presents the variables whose degree of activation from the hearing silent numbers condition predicted success on multiplication tables.

FIG. 113 presents the variables whose degree of activation from the silent hearing of numbers condition predicted subsequent addition ability.

FIG. 115 presents those variables whose level of activation during the silent reading of nonsense words predicted subsequent ability in the outloud condition.

FIG. 116 presents the degree of activation from eyes closed and the variables, which related to success.

FIG. 117 presents the variables whose level of activation during the silent recall of paragraphs predicted success.

FIG. 118 present the degree of activation from the respective eyes closed condition. Those variables, which correlated with subsequent success are presented.

FIG. 119 presents certain variables whose level of activation predicted subsequent recall ability.

FIG. 120 present the results for those variables whose level of activation during the silent recall of reading material predicted subsequent recall ability.

FIG. 121 present additional results for those variables whose level of activation during the silent recall of reading material predicted subsequent recall ability.

FIG. 122 presents the results for the degree of activation from the eyes closed condition.

FIG. 123 presents the variables whose level of activation during the silent recall condition predicted subsequent recall ability.

FIG. 124 present the variables whose level of activation during the silent recall period predicted subsequent success in recall.

FIGS. 143 to 178 present data for children under age 13.

DESCRIPTION OF THE PREFERRED METHOD OF THE INVENTION

Figure 7:
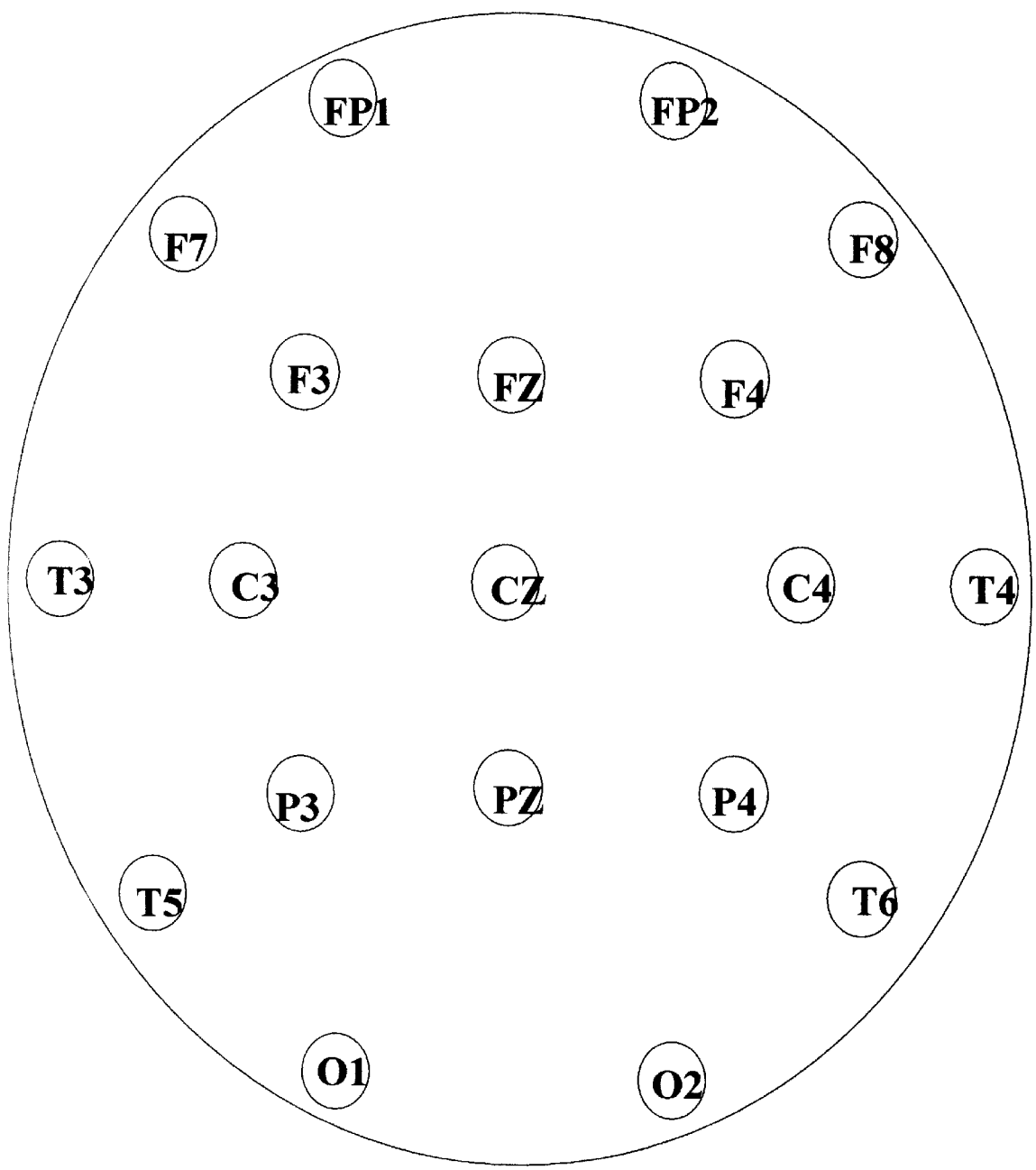
FIG. 7 is a chart of showing the standard nomenclature for positions in the 10–20 QECG measurement system used in the method.

A total of 151 subjects underwent the experimental procedure. As shown in FIG. 1 the following breakdown represents the demographics of the subjects involved. Two of the normal group had a head injury over 20 years previous to the evaluation. As their electrophysiological functioning and cognitive functioning was not demonstrating deficits or showing a particular electrophysiological pattern, which this study discovered, they were included in the normal group. Subjects were paid for their participation and signed an informed consent form as required in human research situations. As shown in FIG., the IQ* figures were obtained from Shipley Institute of Living Scores and employed the Paulson, M. J. & Lin, L. (1970) formula. The formula was averaged across all age groups. As formulas were developed on subjects age 15 and above, the Av. IQ cell also indicates the number of subjects that were above age 15 and the formula could be applied.

Twenty six of the subjects were on medication at the time of testing. The medications ranged from antidepressants, tranquilizers to blood pressure medication. There were 125 Caucasians, 10 Black individuals, 10 Spanish individuals, 2 Oriental and 4 of Indian origins. The analysis of the results involved breaking down the subjects into four groups. The first group (presented in FIG. 1 under subject description "Head Injured") included subjects with no history of significant head injury or head injury within the past ten years. Subjects who demonstrated a history of learning disability were included and subjects with mild head injuries greater than 10 years prior the research. If memory is dependent upon certain connections and activations, then the inclusion of individuals who have difficulty in this area would help identify the problem areas more clearly. However, the contrary argument to this position, is that an individual may not have undergone optimal cortico-genesis (in the case of the learning disabled child) and thus learned to develop other approaches to recall. The head injured subject may have injured an important area for recall and then is forced to call upon other connections or activations to the task for success. The second group (presented in FIG. 1 under subject description "Normals") was comprised of all subjects of all ages and disregarded issues of medication, head injury, learning disabilities or psychiatric problems. The reasoning behind this approach was to ascertain 1—if there are parameters which cut across all conditions and 2—to increase the sample size to provide more stable results. The third group (presented in FIG. 1 under subject description "Children under age 13") consisted of children under the agre of 13.

The summary analysis of the data obtained to support the utility of the method was integrated across different comparisons.

While the subjects underwent the experiment, they were videotaped and recorded with a device developed and described in U.S. Pat. No. 5,564,433 entitled Method for the Display, Analysis, Classification and Correlation of Electrical Brain Function Potentials incorporated herein by referenced thereto. The device is a combination of computer, video, audio recording equipment which allows an experimental recording session to be saved to a hi 8 mm tape with all pertinent information. The videotape, which is saved, is a split screen videotape, with the left side reflecting the EEG recording with the appropriate epoch number and the right side of the screen showing the subject during the experiment. The epoch number refers to a one-second period of time, which is occurring. Thus, epoch number 1 is the first one second period of the recording and epoch number 60 is the $60^{th}$ second of the recording. This device enables the inventor to review the tape to check and confirm the scoring of the subject's responses during the experiment. The method for scoring the responses is also presented as well as a brief rationale for the scoring and procedure.

The EEG recording equipment of Lexicor Medical Technologies was enmployed. The sampling rate was set to 256 to allow for examination of up to the 64-Hetz range. The bandwidths were divided according to the following, divisions Delta: 0–4 Hertz
Theta: 4–8 Hertz
Alpha: 8–13 Hertz
Beta1: 13–12 Hertz
Beta2: 32–64 Hertz All available measurements available through the software provided by Lexicor Medical Technologies were employed. These included the following for each bandwidth:

Absolute Magnitude—the absolute magnitude (as defined in microvolt) of a band over the entire epoch (one second)

Relative Magnitude—the relative magnitude of a band (absolute magnitude of the particular band divided by the total microvolt generated at a particular location by all bands)

Peak Amplitude—the peak amplitude of a band during an epoch (defined in microvolts)

Peak Frequency—the peak frequency of a band during an epoch (defined in frequency)

Symmetry—the peak amplitude symmetry between two locations in a particular bandwidth—i.e. defined as peak amplitude of band at location #1 divided by peak amplitude of band at location #2.

CONNECTION MEASURES

Coherence—the average similarity between the wave forms of a particular band in two locations over the one second period of time. Conceptualized as the strength/number of connections between two positions.

Phase—the time lag between two locations of a particular band as defined by how soon after the beginning of an epoch a particular waveform at location #1 is matched in location #2.

Roland, P. E., (1993) discusses the issues of connectivity of the brain in terms of the anatomical organization of the neocortex, which contains six lavers (with layer I being closest to the scalp) and is approximately 3 mm thick. The pyramidal cells (excitatory) in layer II and the upper part of layer III send their axons to the cortex in the same hemisphere while the pyramidal neurons in the lower part of layer III send their axons to the other hemisphere or over longer distances intercortically. Thus, apart from other subcortical considerations, these are the physiological foundations of the coherence and phase figures.

The total number of activation variables resulting from 19 locations, 5 bandwidths and 4 parameters (excluding symmetry) is 380. The symmetry nesures produce 855 variables. The total number of connection measures resulting from 19 locations, 5 bandwidths and two parameters is 1710. The resulting total number of variables under consideration is 2945. For each of the 151 subjects the resulting approximately 3000 epochs were visually analyzed for artifacts and marked for deletion if they appeared to be significantly affected by artifact issues (eye movements, muscles activity). Minor eye movement activity was included in the data. The reasoning for this inclusion was three fold: 1—Many of the procedures are of a short duration (i.e. 30 seconds). To exclude minor eye movement could effectively reduce the number of epochs under consideration to unacceptable low levels. 2—Cognition continues during eye movement as evidenced by visual examination of the locations not affected by the eye movement. 3—Eye movement is related to cognitive functioning as reflected in research which indicates left lateral eye movements activate the right posterior region of the brain and vice-versa.

The subjects underwent approximately 1 to 1½ hours of testing during which a total of 28 tasks were administered. The following list presents the tasks in the order in which they were presented, the approximate period of time the tasks and a brief description of the task and instructions to the subject.

To aid in understanding the results, a conceptual discussion of the possible meaning of the results (in terms of brain functioning) is presented to aid in understanding the figures.

The results of this experiment appear to present a formidable problem in conceptualizing. The concept of parsimony is relevant in this situation. The holographic model is a useful one in this context, but cannot be employed in the same manner as used in optical science.

Concerning the bandwidths, the study employed broad Hertz bands in its analysis., Recall implies conscious awareness. Some of the data with adults that projection to the frontal lobes is what has been correlated with conscious awareness. Children do not show this pattern as strongly. In children it appears that the degree of activation of the activation variables (relative power, magnitude, etc.) are the more effective parameters of cognitive functioning than the connection issues. The onset of the effective use of coherence and phase parallels modern theories of the cognitive development of children in terms of age, as Piaget considers the age of 13 to be critical for the development of analytical thinking.

The results are presented in terms of absolute level of activation and degree of activation from a relevant comparison condition. The logic of the correlation analysis is that the higher the value the greater the recall. In PET (Positron Emission Tomography—Blood Flow) studies the degree of activation is generally the critical variable. The logic involved in these studies is that greater activation implies greater involvement of that region in the task, generally without respect to success in that task. The results set forth herein imply some linear relationships (i.e. the greater the value the better the memory).

In further analyzing the results presented (paragraphs—where both the level and degree of activation results are very similar), the correlations between level and degree of activation are significant and positive, by and large.

In summary, the method of the invention employs the empirical results of the research which indicate that the effective parameters of cognitive functioning are determined by the 1—the locations of the projectors, 2—the Hertz range, 3—the level and degree of activation of connections and 4—the task (visual vs. verbal—input, immediate & delayed recall, problem solving, etc.).

For the following analysis the two auditory (word lists and paragraphs) and two more visually oriented tasks (Korean figures and Names of Faces) were examined.

Five tables are presented in FIGS. 2–6 which represent an analysis and summary of the total results (group 1) in terms of position, band width, type of information presented (auditory or visual) and nature of task (input, immediate recall, delayed recall). For the following analysis all the significant phase and coherence generators for all the tasks (FIG. 2) were organized by location and bandwidth to discern if there was a particular pattern. Both absolute level of activation was employed as well as degree of activation from the respective relevant condition.

FIG. 2 presents the summary of the just described analysis in terms of all the different tasks (except Raven's Matrices). The top three locations and bands were bolded in red to indicate the locations and bandwidths, which are the most important overall. The results indicate that the F7, T3, and T5 positions are the most involved in terms of effective cognitive functioning and memory and that the Coherence Alpha, Coherence Beta2 and Phase Alpha variables are the most relevant band considerations.

FIG. 3 compares two auditory memory conditions (paragraphs, word lists) with two more visually oriented tasks (Korean Figures, Names of Faces) to discern it there is a distinction between the two modes of processing. The highest figures per category are bolded in red. The results indicate that for Visual Memory the important locations are F1, T3, T5 and the relevant band information is Coherence Theta and Coherence Beta2. For Auditory information, the relevant positions are F7, F8, T3 and T5 while the important band considerations are Coherence and Phase Alpha.

FIG. 4 analyzes the differences between the input stage, immediate recall stage and delayed recall across four conditions (two auditory and two visual, as in FIG. 3). For the input stage the top three locations are F7, F8 and T3 and the bands are Coherence Alpha and Phase Beta1. For the immediate recall condition it is F7, T3 and T5 which are the three most important locations and Coherence Theta, Phase Theta, and Phase Alpha being the three most important band considerations.

FIG. 5 presents the analysis of this three-stage analysis in terms of the two visual tasks. For the input stage the two most important locations are FP1 & F7 and the relevant band information is Coherence Beta1, Coherence Beta2 and Phase Beta1. For the immediate recall condition it is F7 and T5 which are the relevant locations and Coherence Beta2 as the most relevant band. For the delay condition it is T3 and Phase Alpha which are the important considerations.

FIG. 6 presents the same analysis employing the two auditory tasks. For the input stage, it is F7, T3, & F8, which are the relevant positions and Coherence and Phase Alpha as the relevant band information. For the recall stage it is T3 and T5 which are the most important locations and Coherence Theta as the relevant band. For the delayed recall condition it is F7 and Coherence Beta2 which present themselves as the most important location and band.

An examination of FIG. 2 indicates the relative importance of three locations, F7, T3 and T5 and three bands, coherence and phase Alpha and coherence Beta2 in the successful completion of memory tasks.

FIG. 3 reflects the importance of T3 projectors (in terms of coherence and phase Alpha) for the auditory input tasks as well as F7 & F8. Visual tasks are dominated by the FP1, T3 and T5 locations (coherence Theta and coherence Beta2). However, closer inspection of the table indicates that the greatest ratio difference favoring visual tasks is the O1, C4, F4 and Fp1 positions.

FIG. 4 indicates that across visual and verbal tasks the FP1, F7 and T3 dominant in importance in terms predominantly of the coherence Alpha and phase Beta1 bands. In terms of immediate recall it is the F7, T3 and T5 locations that dominate in terms of coherence Theta, phase Theta and phase Alpha. In terms of delayed recall it is the F7 and T3 locations that are the most important and in terms of the coherence Beta2 band.

FIG. 5 presents the visual tasks. In terms of the visual input stage it is F7 and Fp1 and the coherence Beta1 & Beta2 and phase Beta1, which are the most important. For visual immediate recall it is F7 and T5 in terms of coherence Beta2, phase Theta and phase Alpha. For the delayed visual recall condition it is T3 and the phase Alpha and coherence Beta1 bands which dominate.

FIG. 6 presents the analysis for the two auditory tasks. In the input stage it is F7 and T3, which dominate, in the coherence and phase Alpha bands. In the immediate recall aspect of the task it is T3 and T5 which dominate in terms of coherence Theta and Alpha and phase Theta. With respect to the delay condition it is the F7 position in terms of coherence Beta1 and Beta2 which are the strongest contributors to the results.

A broad analysis of the frontal versus posterior projectors reveals the following results for the four tasks under consideration. There are 49 projectors from the frontal lobe (all F positions) involved in the input stage and 2 from the posterior regions which are identified with the T5,P3,O1, PZ,P4,T6, & O2 positions. The immediate recall involves 29 projectors from the frontal region and 34 from the posterior region, while the delayed recall involves 23 from the frontal area and 18 from the posterior region.

A breakdown of the four tasks in terms of left (P3,O1,T5) and right (P4,T6,O2) posterior projectors indicated an overall dominance of the left posterior over the right posterior at a 30 to 13 rate. The Korean characters reflected the greatest degree of right posterior involvement with a 9 (LP-left posterior) to 6 (RP-right posterior) ratio. Thus the results reflect the greater involvement of the left posterior in general (for the tasks analyzed) and a greater involvement of the right posterior for the more visually oriented task. Interestingly, reading involved an 11 (LP) to 5(RP) ratio across all the conditions, which was a higher ratio for the RP than either the word list, paragraphs, or names Successful reading also engaged the right frontal projectors as well as the T4 projectors more than all the other tasks.

Lower frequencies are more relevant to the rear projection system and higher frequencies to the frontal systems. An analysis of frontal/posterior lower bands (Theta & Alpha) vs. beta bands yields the following results. The frontal positions generated 32 generators in the lower frequencies and 62 in the beta frequencies. The posterior positions generated 40 generators in the lower frequencies and 17 in the upper frequencies.

The projection systems favors the long-distance connections and disfavors the short connections in terms of effective cognitive functioning. Even a superficial inspection of the results indicates that the long distance connections are the critical components in terms of successful recall and successful cognitive functioning (see Ravens Figure). In examination of the connective activity, which interfered with effective recall, the following list demonstrates the negative influence the short and sometimes medium distance connections have upon cognitive functioning. Also of note in this list is a tendency for the right hemisphere projectors to interfere in these predominantly verbal memory tasks.

FIG. 11—Processing, word lists—Level of Activation
    F2-CT to Right frontal

Figure 14A:
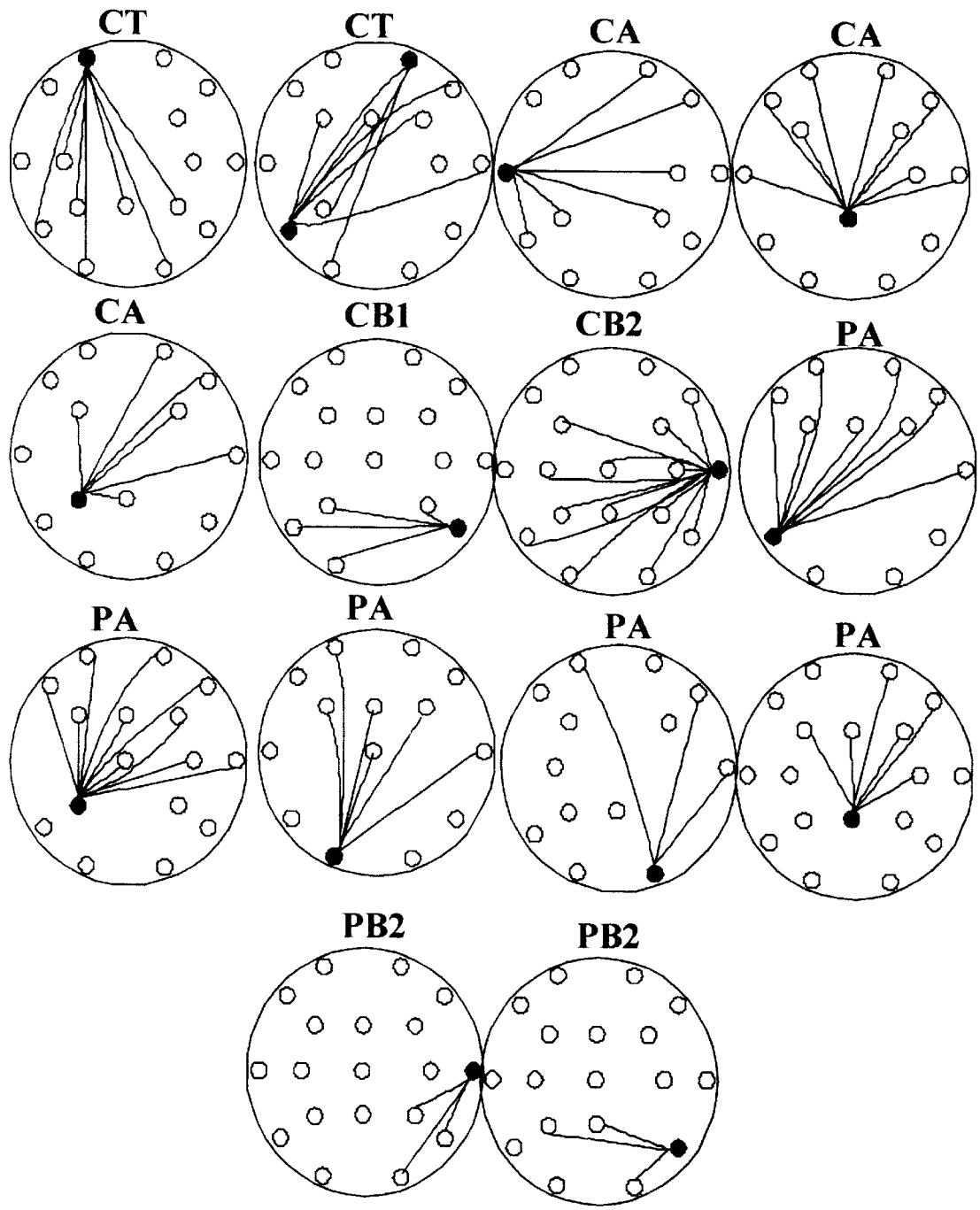
FIG. 14 represents the results of the analysis of the 30-second quiet period when the subject was trying to recall the just administered word list (degree of activation from the subject's respective eyes closed condition) and presents additional data representative of the results of the analysis of the 30-second quiet period when the subject was trying to recall the just administered word list.
Figure 18A:
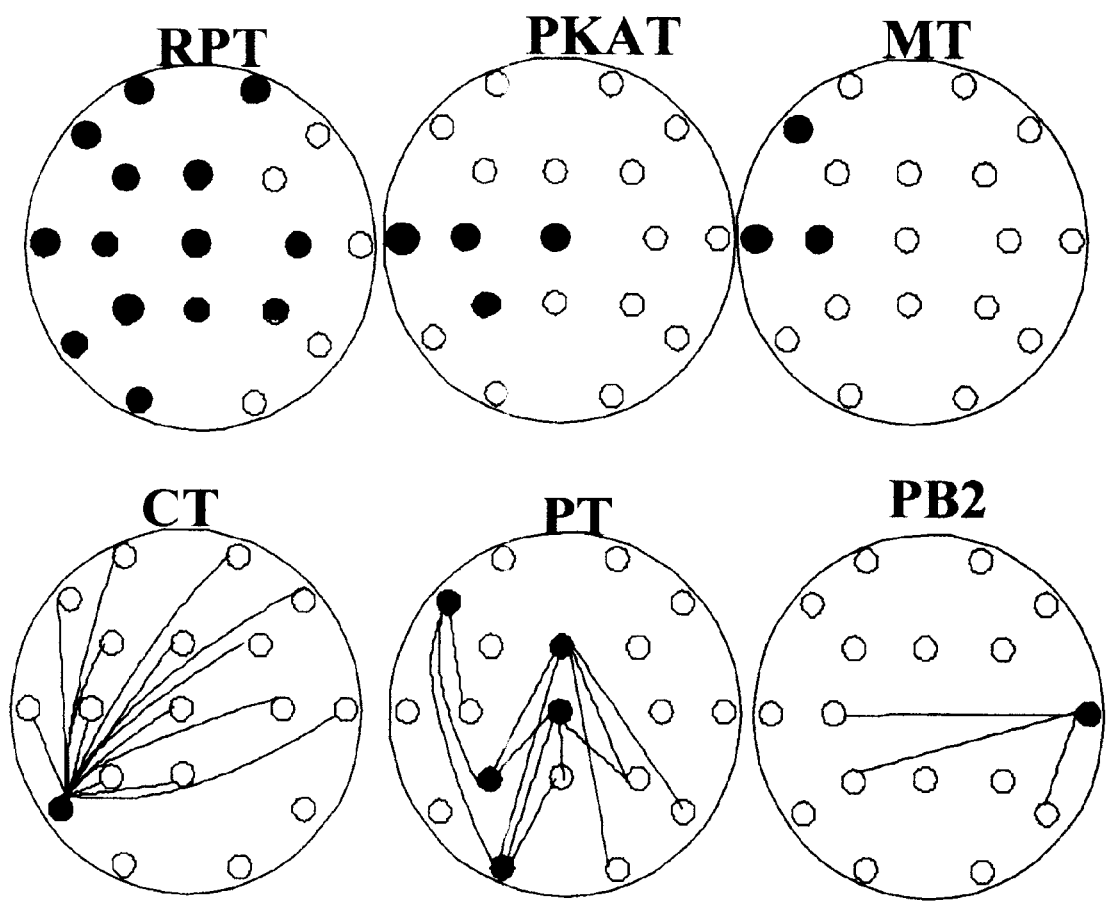
FIG. 18 presents additional significant levels of absolute activation and degree of activation from the subject's respective listening condition when the subject was quietly recalling the paragraphs to himself.
Figure 18B:
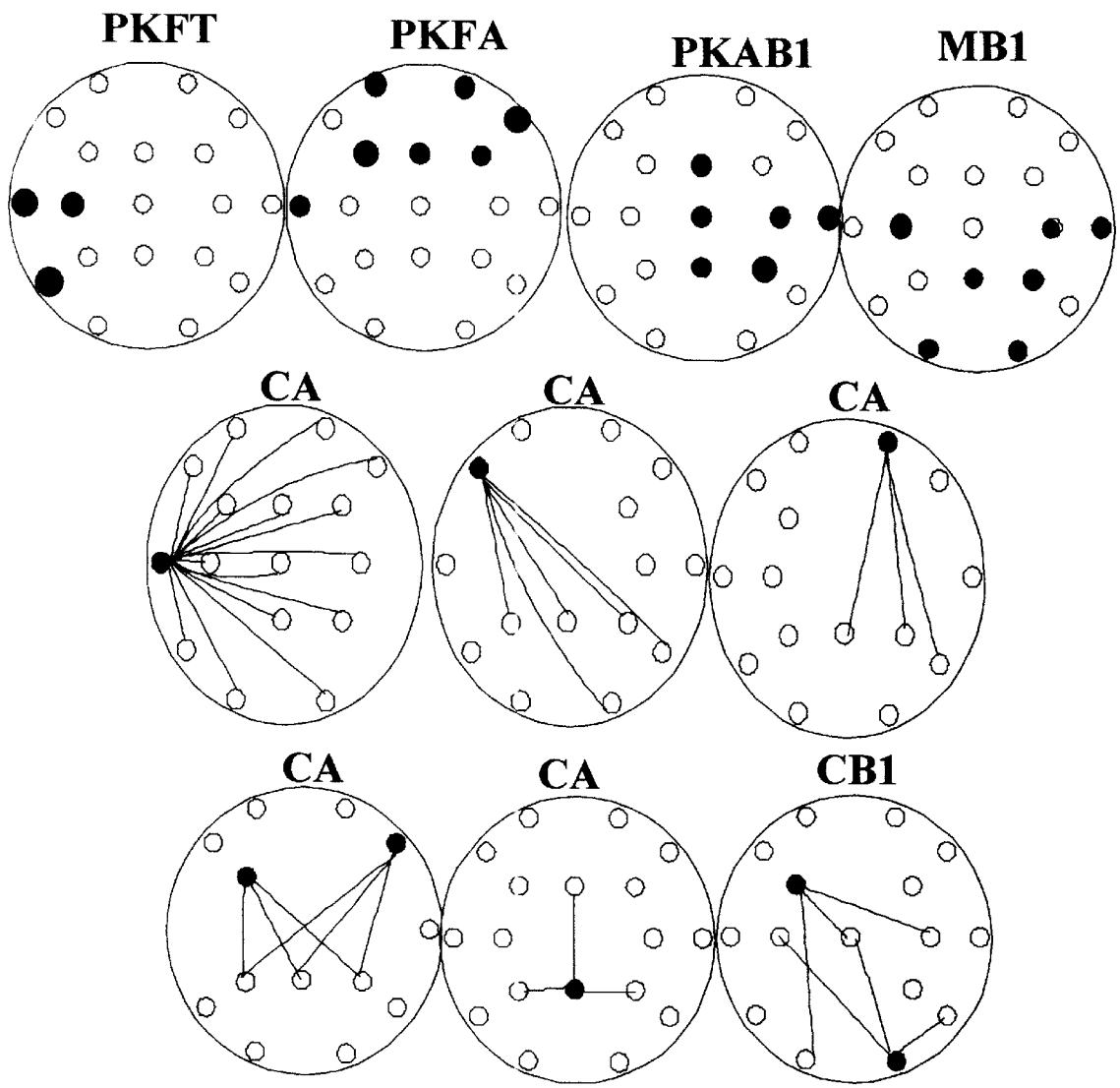
Figure 23A:
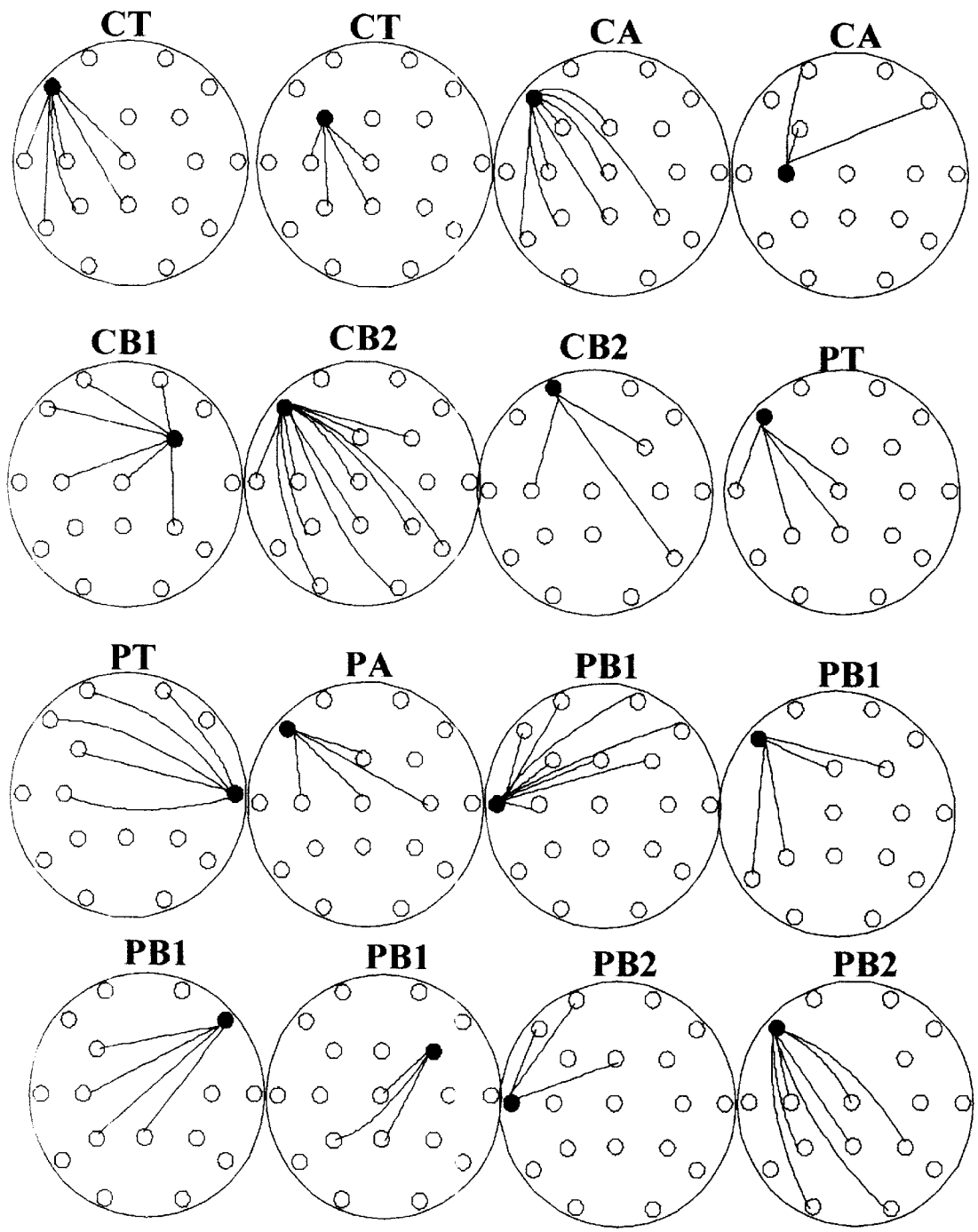
FIG. 23 presents the significant correlations between the total recall (short and delayed) of the names of the faces and the studying period (15 seconds per association).
Figure 24:
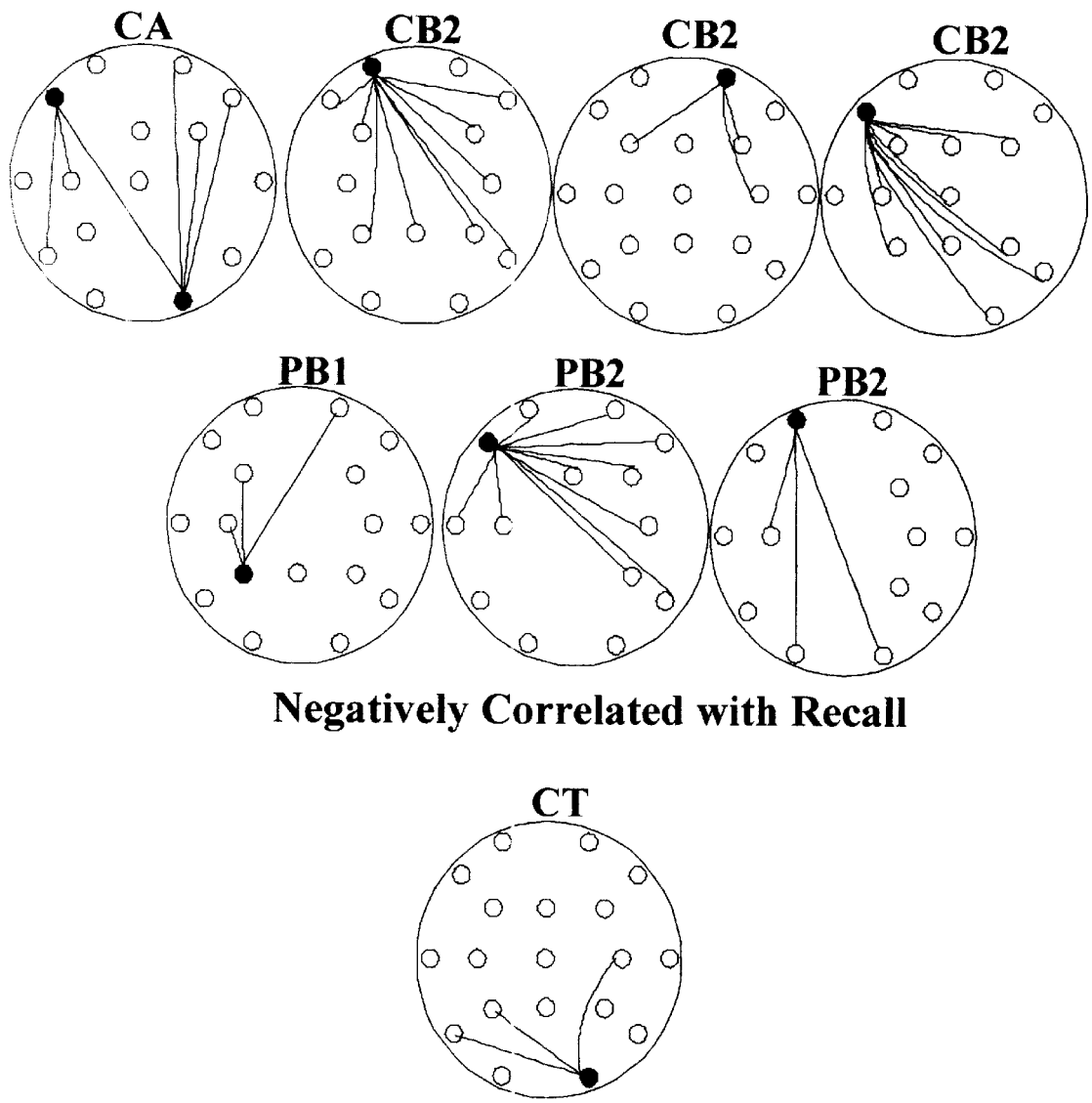
FIG. 24 presents the variables whose degree of activation from the visual attention condition correlated with total recall. In terms of level of activation variaibles, it was the F7, FP1, FP2, F3, F4, & F8 projection system from coherence Theta to phase Beta2 which was relevant, in addition to both the T3 & T4 projection systems.
Figure 31A:
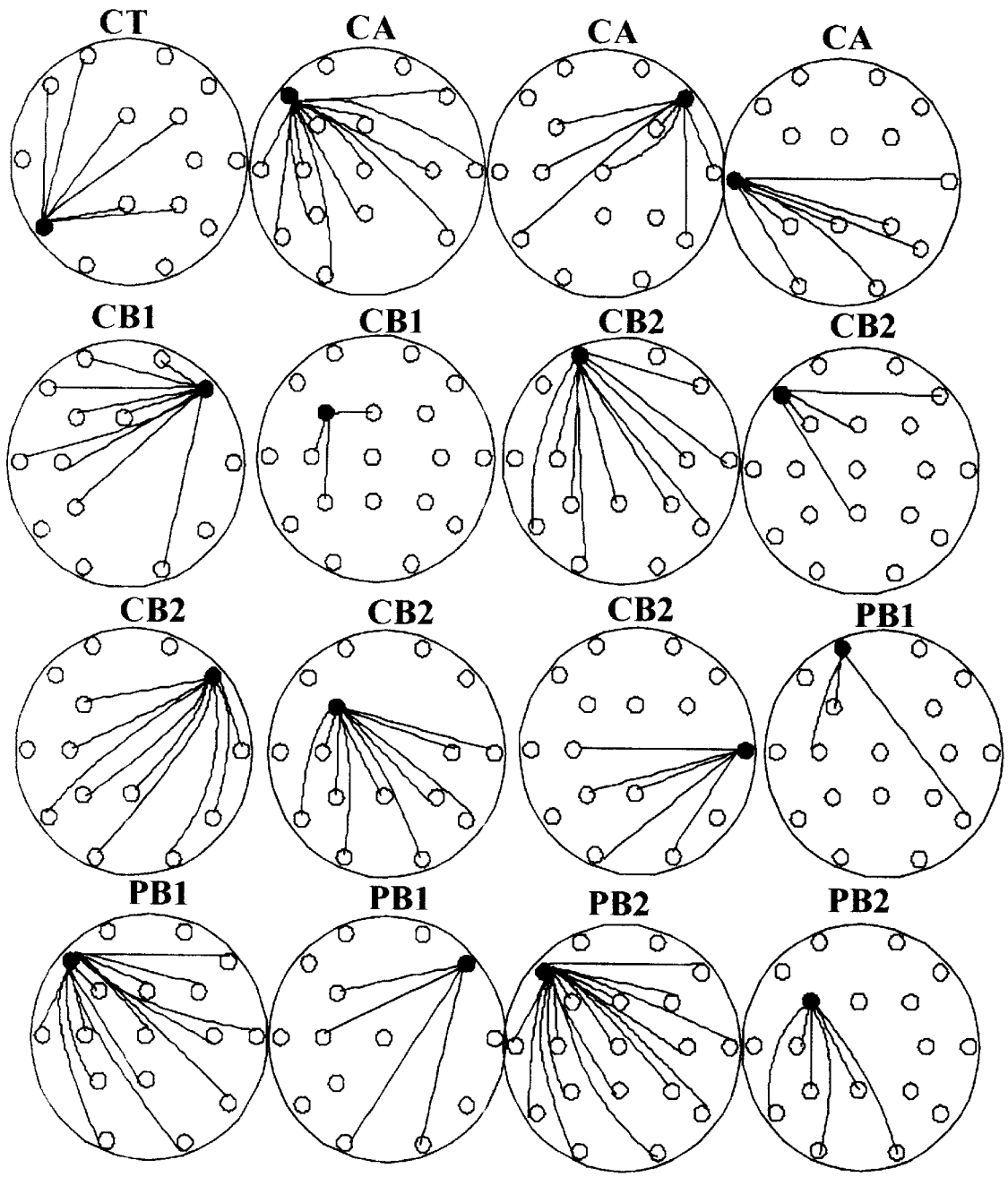
FIG. 31 presents the summed data for 9 of the eleven Raven's matrices (N=628).
Figure 38A:
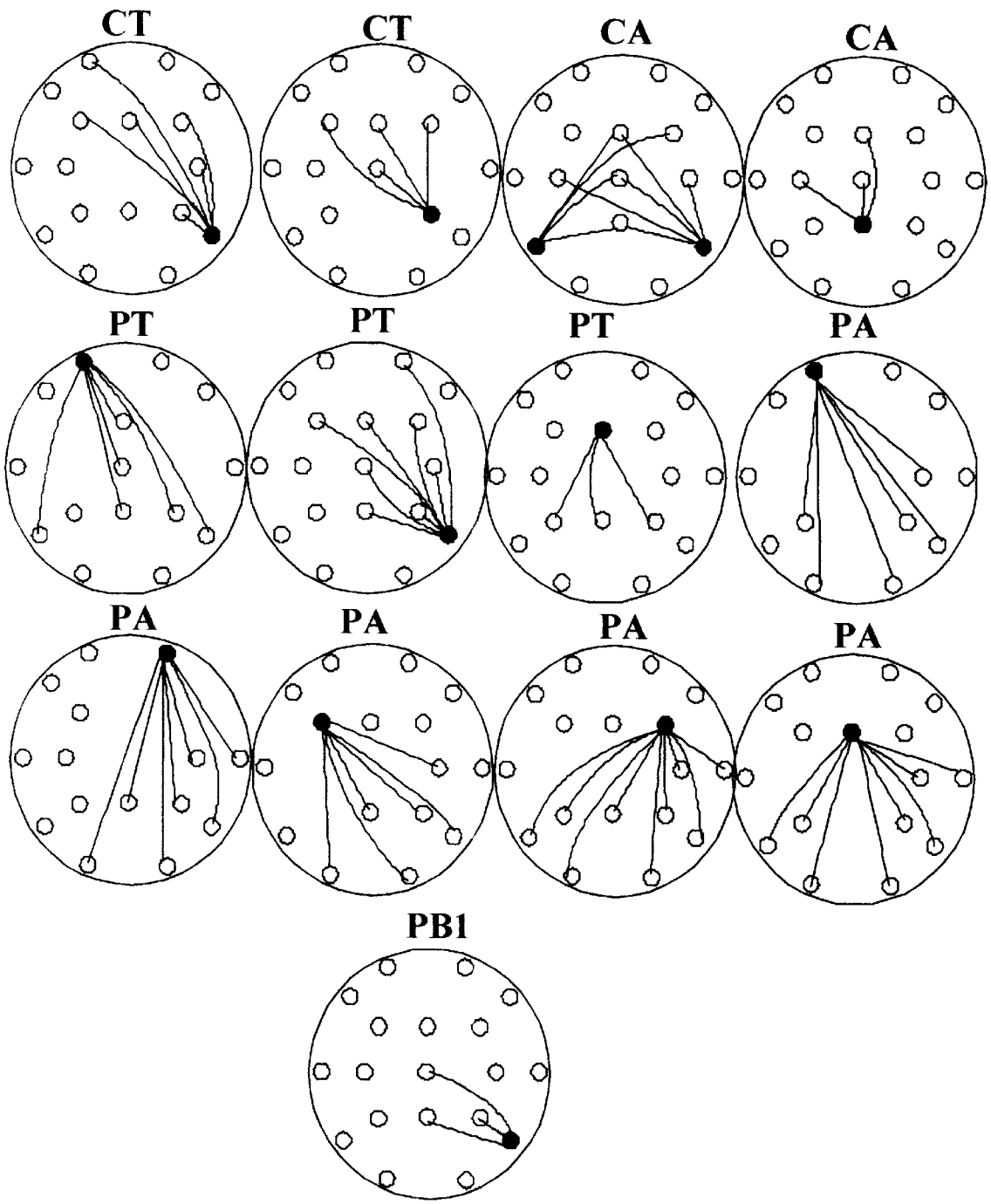
FIG. 38 presents the relationship between successful silent reading of nonsense words (as measured by accuracy during reading outloud) and degree of activation of the variables displayed.
Figure 38B:
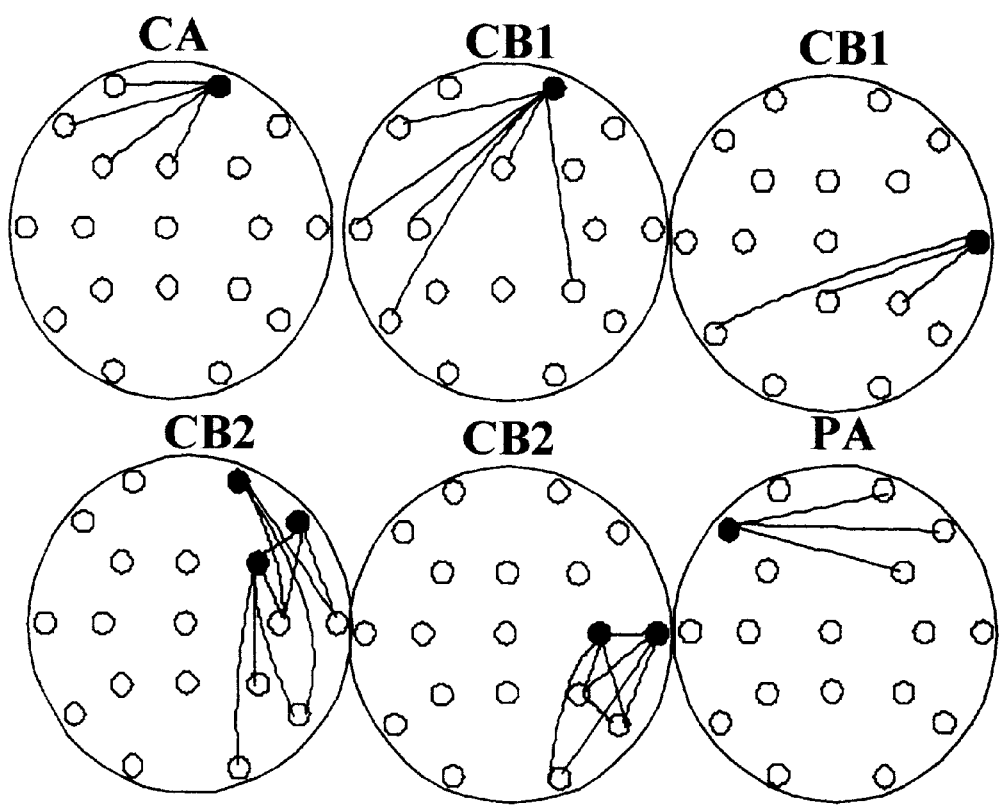
Figure 43A:
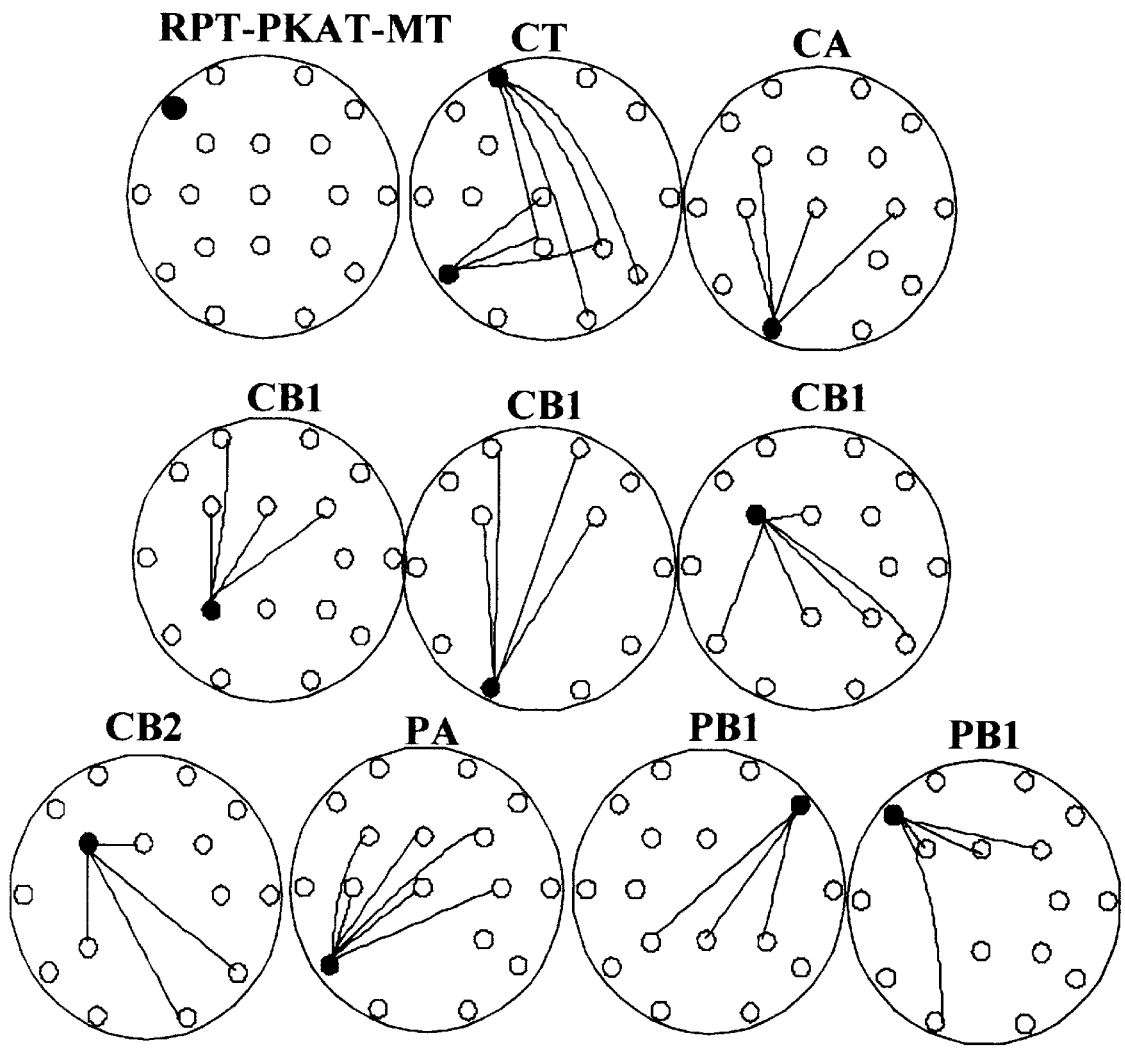
FIG. 43 presents the significant relationships between the degree of activation from the eyes closed condition and delayed recall ability.
Figure 44B:
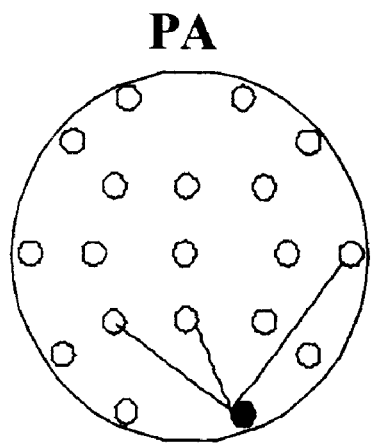
FIG. 44 presents the relationship between level of activation during the quiet recall period and subsequent recall outloud in terms of long term memory performance.

FIG. 12—Long Term Recall of Word Lists
    O2-CA to central posterior
    T6-PA to central posterior FIG. 14 Recall of Word lists
    Fp1/Fp2-CB1 to frontal/central FIG. 15 Listening to Paragraphs
    T4-CB1 & PB2 to posterior FIG. 17 Immediate Recall of Paragraphs
    T4-PB2 to central region FIG. 18 recall paragraphs some right and some left—look at this one again FIG. 20 Korean Figures
    F7-PA to RH FIG. 23 Studying Faces
    T6-CB1 & CB2 to posterior FIG. 24 Studying Faces
    O2-CT to left posterior FIG. 25 Recall of Names
    T4-CB2 to right posterior
    T6-PB2 to left posterior FIG. 27 Reading
    T5-PB1 right posterior
    O1/O2-PA & PB1 to posterior
    T6-PB2 to posterior FIG. 28 Reading
    F8-CB1 & CB2 & PB1 to central
    T4-PB2—right frontal/central
    O2-PB1 to posterior FIG. 29 Recall of Reading
    CB1,PB1, PB2 short posterior connections FIG 31 Ravens
    O1/O2-CB1 to posterior
    P3-PA to central, C4-PB1 to central
    PB2—short left posterior FIG. 38—Silent Reading Of Nonsense Words
    9/10 generators were from the right hemisphere FIG. 43—Delay Recall/Words
    F8-CT to posterior FIG. 44—Delay Recall/Paragraphs
    O2-PA to posterior FIG. 46—Delay Recall/Korean
    3 right hemisphere generators: P4,F8,C4

FIG. 49—Delay Recall/Reading
    T4,P4, and 2 at PZ short and long posterior to frontal bands In Conclusion, although not always exact, the pattern of interference in effective recall comes from short posterior connections and right hemisphere activity. Interference also comes from activations at locations.

In making theoretical considerations in interpreting the data, it must be understood that the locations of the 10–20 system are only one set of locations and are defined by geometric not anatomical considerations. Thus the locations present only a tip of an underlying mass of electrical activity. FIG. M#1 (Raven's Matrices) presents 11 phase and coherence generators emanating from the frontal lobes and only one from the left posterior. It is not difficult to infer from these 11 positions that it is the entire frontal lobe which is sending predominantly high frequency signals to the back of the head. A similar analysis can be employed for all the results, albeit with a more limited area of spread as defined by the activity of the neighboring positions. These electrophysiological parameters are cortical parameters.

Holographic theory requires a single coherent light source, which is projected simultaneously onto a reflector and the subject of interest. The two beams (from the subject and the reflector) are reflected to a recording medium. It is the angle of deflection or phase shift in the two sources of light that allow the hologram to be created. It is this phase shift information which is recorded in the recording medium.

The following more technical discussion of holographic theory may be useful. The creation of a holograph is a result of the measurement of the interference pattern of two light sources. "A hologram is a diffracting record of the interference of a particular subject and a particular (coherent) reference beam." (Collier, R. J., Burckhardt, C. B., Lin, L. H., (1971) (p.17) It is a record of the phase shift. "spatially modulated wave propagation may be analyzed in either of two domains: a spatial domain or a temporal-frequency domain . . . in the spatial domain the light complex amplitude is expressed as a function of the x, y spatial coordinates of an observation plane through which the light propagates. According to the basic theorem of Fourier analysis, as applied to light distributions, any two dimensional complex amplitude pattern can be considered as a discrete or continuous set of sinusoidally varying patterns (periodic components). (Collier et. al. (1971) (p. 79) "We may express the light complex amplitude distribution in the spatial domain as another function in the spatial frequency domain." (Collier p. 80) Fourier transformation from the spatial domain to the spatial frequency domain can often provide physical insight into the working of optical systems. The transformation can be regarded as a decomposition of a general light wave into many plane waves whose direction cosines correspond to the spatial frequencies." (Collier, p. 80) The spectrum of the output function of a linear space invariant system is the product of the spectrum of the input function and the frequency transfer function. (Collier, R. J., Burckhardt, C. B., Lin, L. H., (1971)(p. 83)

The holographic theory was developed upon considerations with a solid recording medium. The brain is a fluid, electrical environment enables flexibility in the creation of the hologram. One such consideration would be the ability of the brain to employ different frequencies (not necessarily coherent sources) from different locations and different frequencies from the same location.

In examination of the usefulness of holography to brain function, the results from the paragraph task (group 1) were employed.

Figure 16:
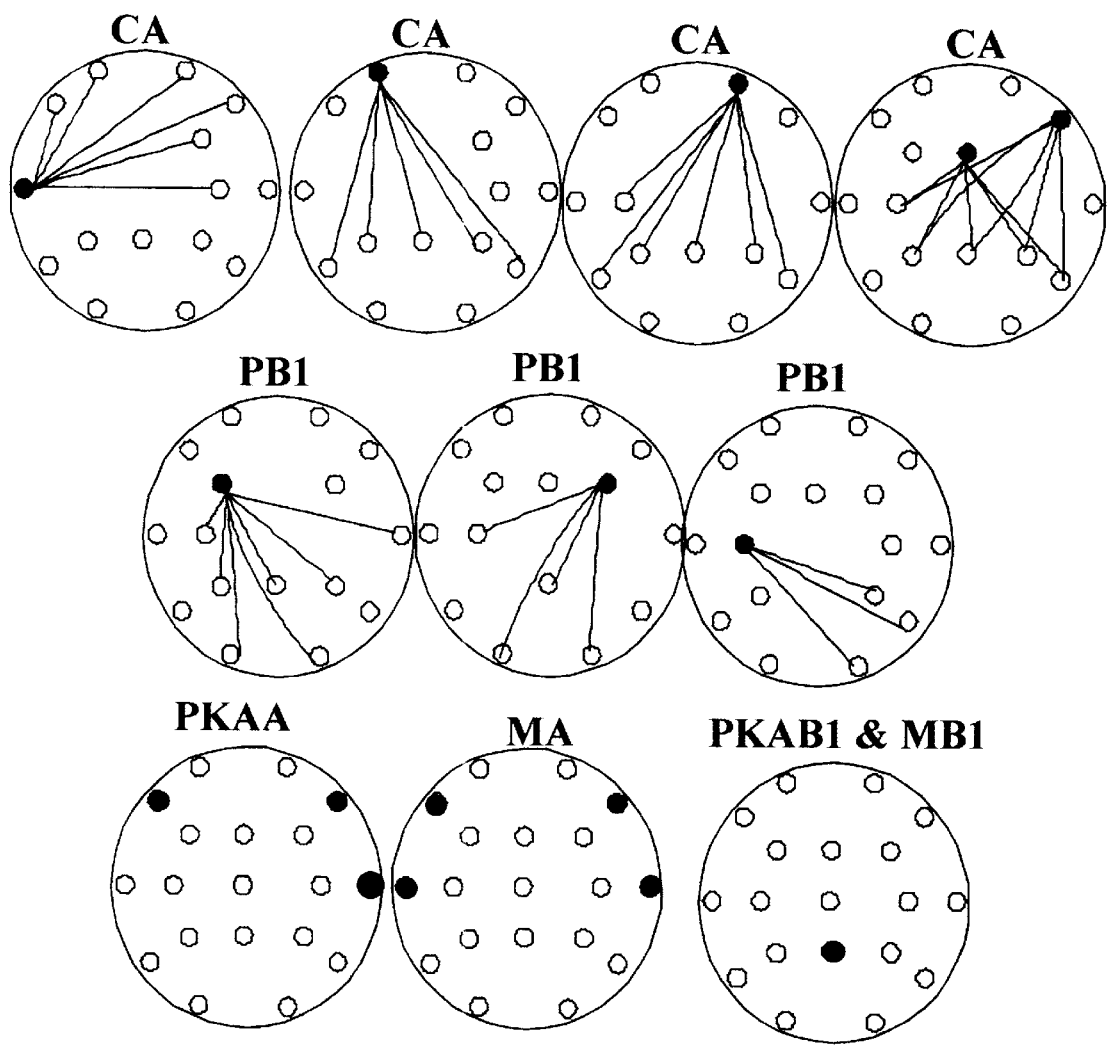
FIG. 16 presents the respective significant levels of activation for successful recall in terms of degree of activation from the auditory attention task.

FIG. 15 presents the level of activation results and indicates that the temporal lobe (T3) is the primary correlate of memory performance in the input stage (phase and coherence) in terms of the level of the variable. FIG. 16 indicates that coherence Alpha and phase Beta1 are the primary determinants and are almost all frontally located. Of additional interest is the magnitude Alpha significant relationships from the T3, T4, F7 & F8 positions as well as 3 of these positions involved in terms of significant peak amplitude of Alpha (F7, F8, T4). The Fourier transform employs frequency and amplitudes to represent the information. In holographic theory the source (laser) is projected onto two different objects (a reflector and the subject). Here in the brain the source (temporal lobe coherence Alpha) is projected upon the frontal positions, which in turn project to the posterior portions of the brain. Note, in particular, that Fp1, Fp2, Fz and F8 project to the T5, P3, Pz, P4, and T6 positions, while the F3 and F4 positions (receiving the Alpha waves from the temporal lobe) project more to the occipital regions (O1 & O2), in addition to the midline posterior positions (P3,Pz,P4).

Examination of the entire subject population (A11-A8-9) of 150 subjects demonstrates a similar finding in terms of level of activation of the alpha frequency, with a difference in terms of alpha coherence projecting to almost the entire cortex while phase alpha focuses upon the frontal region.

Thus the system is satisfying the requirements of the holographic theory in that coherent wave forms are being projected to separate regions which are, in turn, projecting the same wave forms to similar positions in the posterior portion of the head. Thus the requirements of waves from different sources (frontal or frontal/temporal) converging upon the recording medium (the posterior portion of the head) is met. FIG. A11-A8-9 indicates almost an exact replication of the holographic criteria as the original source beam from T3 is projected posteriorly and the reflection of the source beam off the frontal locations is projected posteriorly where it interacts with the undistorted original coherent source beam from the T3 location. An additional feature is the phase Beta1 projections to the posterior occipital areas. Thus the projection pattern is mirrored in a different frequency to different positions. It is uncertain whether the information from T3 is being spread or mirrored. From the positions involved, the entire frontal region (or as is the case with A11-A8—the entire cortex) is receiving the Alpha waves. Each position is receiving the entire set of information required to represent the stimulus. Therefore the temporal lobes send pieces of the necessary information to represent the stimulus to different areas.

Thus, the partial information is then projected in a mirror type function to the posterior regions. Holography requires a mirror function. There is a difference between the brain's approach and holographic theory. In holographic theory it is the difference between pure reflection of the light source (laser) and the diffraction process of the light upon the subject (and their respective projections to the recording medium) that is critical. It is the phase angle which is recorded in the holographic medium. In theory the brain would not need an external coherent source, but only differences in the origin of a coherent beam representing the same object upon a single destination. The additional aspect of different frequencies being projected posteriorly raises the level of complexity and thus information. As the informational content becomes more complex, a system can differentiate better. In principle, the systems could generate different frequency waves from the same location to similar posterior positions and generate a discrepancy on the recording medium. To activate the memory for the stimulus, the frontal projection system merely reactivates (not necessarily in terms of amplitudes, etc.) the areas and recreates the hologram.

The different posterior regions code different aspects of the stimulus (tactile associations, verbal meaning, etc.) and that the purpose of the posterior projections is to make those associations and were not apparent until the research had been completed.

In terms of immediate recall the temporal lobe (T3) dominants success (level of activation of phase Alpha) while posterior projections to the frontal region (degree of activation) add to success. Both the T5 and T3 locations (see empirical summary discussion) are strongly related to recall. The immediate short term recall task calls upon the information which is still stored in the temporal lobe system (T3 and T5). This result gives the appearance of a holograph being created in the frontal areas. The requirement of coherent beams from different sources is met as the T5 beam is Theta and the T3 beam is Theta. The T3 phase Alpha generator provides any differences. This pattern of projection from the left temporal lobe is strongly involved in all of the auditory memory tasks. Short term memory, in this model, consists of the ability of the input source location to create the hologram. In the case of auditory memory it is the T3 location. Long term memory, resides more on the posterior projection system and the temporal projections. Consciousness resides in the frontal lobes.

Figure 45A:
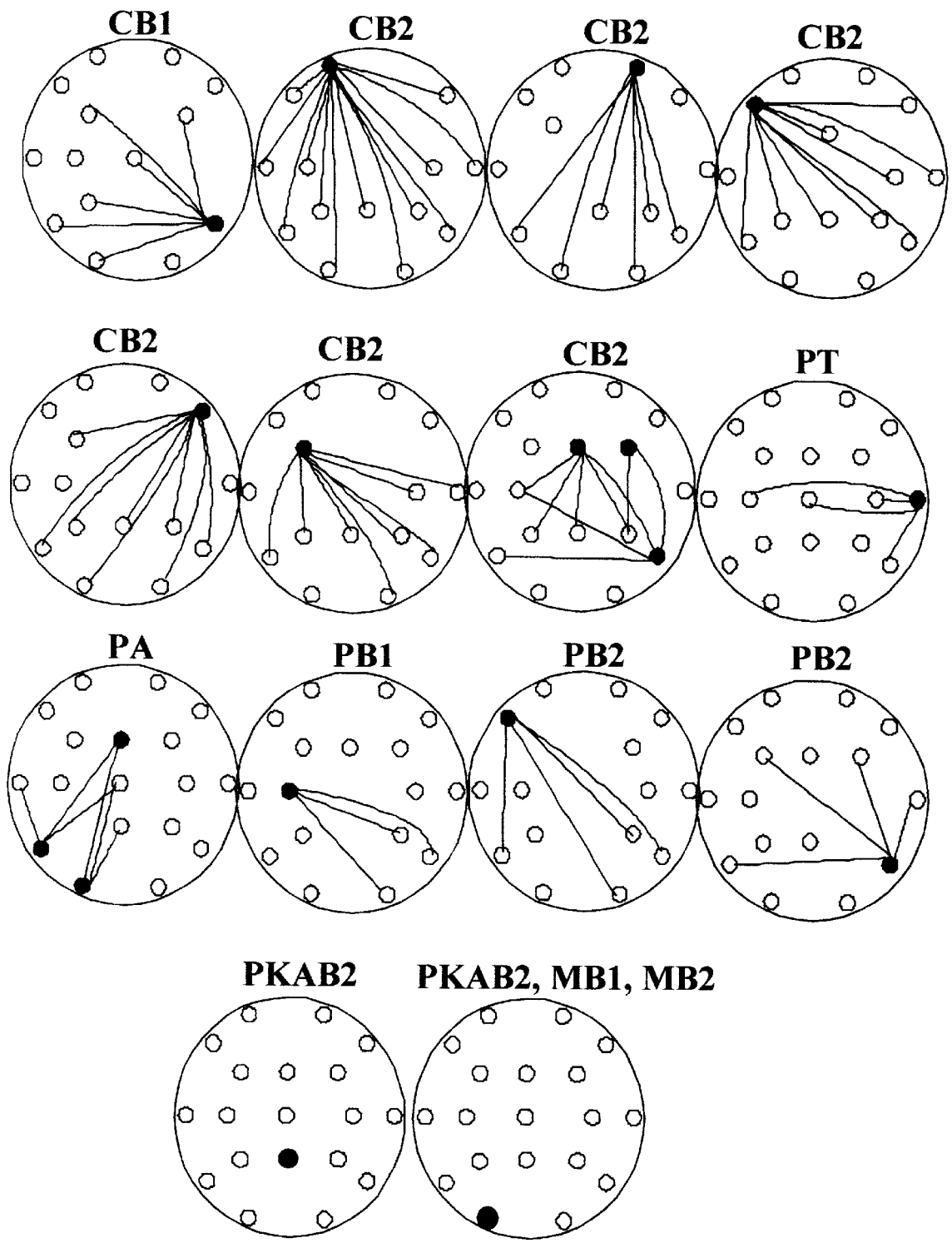
FIG. 45 presents the relationship between the degree of activation from the eyes closed condition and long term recall.

In terms of the delayed recall of the paragraphs (See, FIGS. 44 and 45) there are 12 projectors from the frontal area (in terms of level and degree of activation) and four posterior projectors, in addition to two temporal projection systems. The frontal (absolute level) projectors focus again on the posterior portion of the head, while the temporal project more frontally (similar to input stage). FIG. 45 (degree of activation) shows a similar pattern with the exception of the temporal lobes. Thus the requirements of different projectors from different locations projecting at different angles to the same positions is met.

The reading task situation offers the opportunity of the analysis of a different input modality (visual). In this situation (see, FIGS. 27 and 28) there is (in the absolute level analysis) projections from the left temporal areas (T3 and T5) and frontal projections from F7 & F3, predominantly projecting to the occipital regions. The temporal areas, although predominantly known for verbal memory, are also a part of a myelinated bundle of fibers from the occipital regions. In the degree of activation analysis, FIG. 28, there are four projections from the occipital lobes (O1, O2) in the Alpha and Theta range and one frontal projection system from F2 (Alpha range).

The immediate reading recall condition (see, FIGS. 29 and 30) predominantly involve five projection systems from the frontal lobe (primarily projecting to the left posterior) and three temporal lobe systems (primarily projecting to the frontal area, in terms of level of activation). The degree of activation (FIG. 30) analysis reveals 6 projections from the frontal lobes (five to the posterior portion of the head), 6 from the temporal lobes with the left temporal going to the frontal and right temporal diffusely projecting, and five from the posterior head (T5,O1,O2,T6).

Figure 50A:
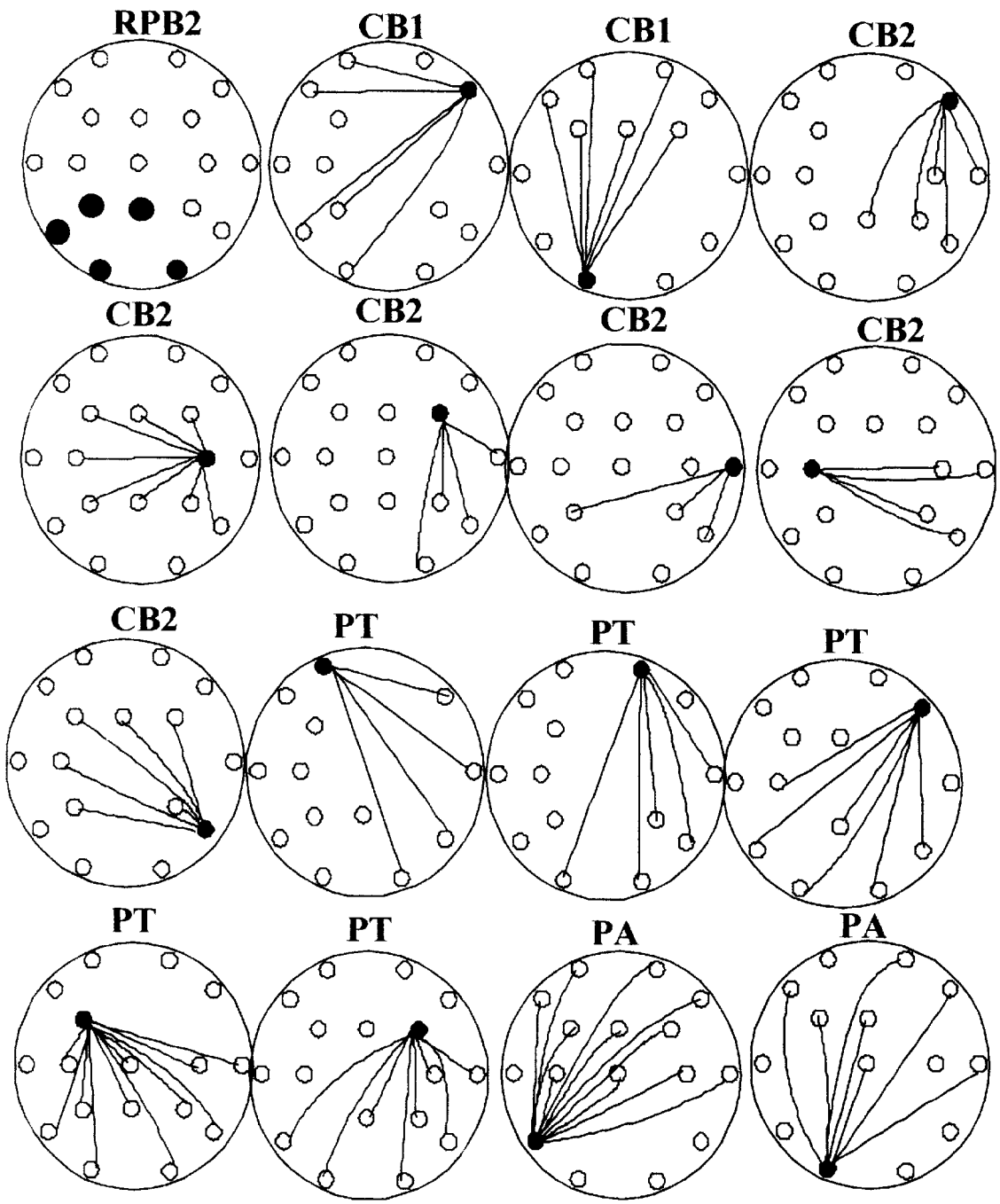
FIG. 50 presents the significant relationships between the degree of activation from the eyes closed condition and recall ability.

The reading-delayed recall condition (FIG. 49) activates the left temporal (to the frontal), and right frontal to posterior (absolute level of variable). In FIG. 50, there are 8 projections from the frontal area (to the posterior portion of the head), and 5 from the posterior region (again, T5,O1,O2, and T6) predominantly projecting to the frontal lobes.

The exact specifics of the projection systems required vary by task. The additional problem of consciousness and children is addressed in FIG. 14. This Figure depicts the recalling of word lists (degree of activation from eyes closed). The multiple projections from the posterior to the frontal areas would give the initial impression that consciousness resides in the frontal lobes and what the projections are doing is recreating the "image" in the frontal lobe. The projection systems do not have to be all completely operational, as the ambiguous figure phenomena demonstrates. Previous knowledge can fill in the gaps of information. Consciousness of the object, thus, requires only that a sufficient number of these systems be in effect.

There are very few activation variables (relative power, peak amplitude, magnitude, and peak frequency) with the adult subjects that are significant contributors to cognitive performance. The dominant mode of effectiveness resides in the use of the phase and coherence relationships. With children under the age of 13, these activation variables become the dominant means of effective cognitive functioning, particularly in the 13–32 Hertz range.

Prior to the recording the subjects are instructed to hide (out of sight) 14 common objects (eraser, pencil, etc.) throughout the room in different locations. These subjects are also requested to generate a ten item "to do" list of common tasks which they do not engage in on a daily basis. For example, the list might be composed of calling a friend, getting gas for the car, going to the store to purchase milk, etc. At the end of the experiment the subject is asked to quietly recall, during separate 30-second periods of time, both of these lists and then asked to recall outloud what they recalled during the quiet period.

In the task labeled "Eyes Closed") (actually, no task or baseline) the time period is 250 seconds. For the task labeled "Auditory Attention" the time period is 100 seconds. The subject's eyes are closed and they are requested to raise the right index finger about a half an inch when they hear the sound of a pen tapping on a desk.

There is no scoring of this task as it represents a comparison period for other tasks. For example, to separate out the memory component from the attention component of listening to paragraphs, the levels of activation under auditory attention condition is subtracted from the listening to paragraph condition (for each subject individually) and the difference is correlated with the memory score. The correlations reflect what parameters need to be activated, above just paying auditory attention, for auditory memory to be effective. Thus, if variable X (degree of activation from auditory attention) is significantly correlated with memory performance, then the tenet that the higher the variable is able to be activated (above auditory attention levels) the better the memory is demonstrated. The auditory attention task is compared to subsequent tasks involving auditory memory (verbal list learning and paragraphs).

While it will be shown that the absolute level of activation is important for cognitive functioning, it is also the case that the relative activation from an appropriate baseline represents a significant correlate of cognitive functioning. This is the cognitive subtraction approach of PET studies.

The Visual Attention task used a time period of 100 seconds. The subject looks at a sheet of paper with a story in Spanish typed on the page. The page is held upside down. A laser light is flashed onto the center of the page. When the subject sees the light, they are instructed to raise their right index finger about a half an inch. There is no scoring for this condition as it is the comparison condition for several visual memory tasks conducted later during the experiment (Korean characters, names, and reading).

For the Auditory Verbal List Learning task the time period was 300 seconds. The subject is presented with 5 different lists of 15 different common words in each list. A total of 65 words are presented to the subject in groups of 15 words. The subject's eyes are closed and the words are read in a normal and clear tone of voice at the rate of one word every other second. The subject is instructed prior to the presentation of the list that they are to keep their eyes closed after the presentation of the list and try to recall as many of the 15 words quietly to themselves as they can for 30 seconds. Following the 30 seconds they are instructed to tell the inventor all the words they recalled during the quiet period. This procedure is repeated for each of the 5 lists.

The scoring for this task involves labeling each epoch that the subject is listening to the words according to 1—whether they accurately or inaccurately recalled the word during the immediate recall condition and 2—whether they accurately or inaccurately recalled the word during the delayed recall condition (about 45 minutes later). The epochs are further divided into the periods of time when they were hearing the word and the one second period of time during which the brain was processing the word, prior to subsequent presentation of the following word. This scoring results in accuracy/inaccuracy scoring for the one-second period of time during the presentation of the word and the one-second period of time of processing the word. To increase the number of epochs available for analysis, the delayed recall scoring involves both the hearing and processing periods of time. Thus, if a word was subsequently correctly recalled 45 minutes later, both the hearing and processing one second periods are labeled as accurate delayed recall.

The 30-second period of quiet recalled is employed as an additional period for analysis of accurate recall. It is the operational assumption of the experiment that the correlation between the subject's recall during the quiet 30-second recall period and subsequent outloud recall is significantly high to justify the analysis. The word list was drawn from an article on alternate forms of the AVLT by Shapiro, D. M. Harrison, D. W. (1990).

The Paragraph Recall task used a time period of 250 seconds. The subject is read four stories from the Rivermead Behavioral Memory test. Each story has 21 "ideas" available for scoring. The subject's eyes are closed as the story is read. The subjects are instructed in a manner similar to the list learning task. Following the presentation of the material, the subject's are to silently recall whatever they can during a 30-second period. Following the 30 seconds, the subjects are requested to indicate outloud what information they were able to recall.

The scoring follows the recommendations made in the Rivermead manual with the exception that ½ points are granted for partial memories.

For the Visual Memory—Korean Figures task the time period was 60 seconds. The subjects are presented with a piece of paper with 6 Korean words printed on on it. They are instructed to study the figures for 60 seconds and are informed that they will be required to reproduce the figures subsequent to a 30-second quiet recall period.

Scoring for the figures involves giving a score of 1 for each segment of the figures, which represents a distinct figure. A particular word may consist of 3 different segments, which can be viewed as a distinct gestalt. The maximum score possible is 17.

For the Memory for Names task the time period was 150 seconds. The subjects are presented with pictures of ten faces on one page. The faces represent different nationalities and sexes. They are told that a 15-second period of time will be allotted for them to memorize the association between the face and the name (first and last name) for the face that the inventor states in the beginning of the 15-second period. Following the presentation of the ten faces, the subject engages in a 30-second quiet recall period. Following, the 30-second quiet period the subject is presented with a page with all ten faces on it. The faces, however, have been rearranged in terms of their position on the page to avoid the problem of memory for location. The subjects are asked to indicate the names of all the ten faces, starting with the first one in the upper left of the page.

The scoring consists of giving 1 point credit for each name recalled (first or last name). Thus the total maximum score possible is 20.

For the Reading task the time period was 100 seconds. The subjects are presented with a printed story on one page, instructed to read the story quietly to them and told they will be required to tell the story back to the inventor. Following the 100 seconds, the subjects are requested to engage in 30 seconds of quiet recall, which is followed by recalling the material outloud for scoring purposes.

For the Reading out loud task the time period was 60 seconds. The subjects are instructed to read the same material outloud for one minute.

The Raven's matrices are considered in psychological research to be the best culture test of non-verbal intelligence that is available. The subjects were presented with a sample of the Raven's matrices in order to understand the task they would be undergoing. The sample was discussed and the correct answer provided, if the subject was inaccurate in their analysis. The discussion continued until it was clear that the subject understood the task.

The Raven's Matrices involves a set of 6 or 8 figures presented in a rectangular format. The figures change in a vertical and horizontal manner according to a principle, undisclosed to the subject. The subject's task is to understand the two different principles being employed in the changing of the designs. On the bottom right of the design is an empty position. The test material presents the subject with a selection of 8 patterns, which could be placed, into the empty position. Only one of the patterns completes consistently, however, the vertical and horizontal patterning which is occurring in the overall design.

The subjects were allowed to examine the problem until a solution result. If the subjects were appearing to answer too quickly (i.e. under 10 seconds) and were inaccurate, they were told that they were inaccurate and instructed to spend more time on the task. The selection of the 11 problems presented were drawn from the most difficult of the Raven's matrices (series D and E). The purpose of this selection was two fold. (1) to ensure that the subjects spend sufficient time on the task to generate an adequate amount of data and (2) to ensure that the task is not too easy, is tapping intelligence in action and is as demanding of the subject's problem solving ability as can be constructed.

The scoring indicates only whether the subject was accurate or not according to the scoring system provided in the Raven's manual.

For the Hearing Words task the time period was 60 seconds. The subject listens, with their eyes closed, to a series of common words played on a tape recorder. There is no scoring for this condition, as it represents a comparison condition for the spelling task.

For the Spelling task the time period was 60 seconds. The inventor states a word (chosen from the WRAT, Wide Range Achievement Test). The subjects are instructed, prior the task, that they are to spell the word quietly to themselves and raise their index finger after they have completed the spelling. A total of 14 words are read, with the children's list composed of easier words (from the WRAT) than the adult selections. Following the 14 words, the subjects are requested to spell the 14 words outloud. Their performance is scored according to the number correctly spelled in the outloud condition.

For the Silent Numbers task the time period was 50 seconds. The subject listens to a tape on a tape recorder, which is presenting a random list of numbers. This procedure is employed as a comparison condition for comparison to subsequent tasks of multiplication and spatial addition, during which the subjects listen to the inventor present numbers which require of them different operations.

For the Multiplication Tables task the time period was 40 seconds. The subjects are presented, while their eyes are closed, single digit multiplication problems (i.e. 7×9=?). They are asked to answer the problem quietly to themselves. The subjects are provided with 1–2 seconds to answer the question quietly and then an additional problem is presented. Several simple problems are presented initially, to allow the subjects to warm up a little to the task. Following the warm up the subject is presented with 11 problems involving the more difficult single digit multiplication problems (the 6 to 9 series). Following the quiet procedure, the subjects are asked to provide answers to the 11 problem. The maximum score possible is 11.

The subjects are presented, while their eyes are closed, with a sequence of double-digit addition problems (i.e. 16+52=?) and instructed to solve the problem internally. Prior the administration of the task, they are instructed to raise their index finger when they have completed the task. Several simple (i.e. 12+13=?) tasks are presented first to warm up the subjects, which is then followed by 6 difficult spatial addition tasks which involve a carrying operation (i.e. 27+54=?). Following the 6 problems, the subjects are asked to provide the answers outloud. The maximum scoring for this task is 6.

For the Sounding out Nonsense Words Silently task the time period was 60 seconds. A set of nonsense words was selected from a standardized test of nonsense word pronunciation (Decoding Skills Test, Richardson, E. & DiBenedetto, B. 1985). They are presented on a single page and the subject is instructed to sound out the words to themselves quietly. There is no scoring for this task at this point. The rationale for inclusion of this task is that the sounding out of nonsense words represents the fundamental deficit in the reading disability situation.

For the Sounding out Nonsense Words Outloud task the time period was 60 seconds. The same list that was presented for silent reading is presented for reading outloud. The subject is scored according to their number of pronunciation errors.

For the Saying the Word Table silently task the time period was 30 seconds. The subjects are requested to say the word table quietly to themselves for 30 seconds. There is no scoring for this task, as it represents an attempt to understand from an electrophysiological point of view the process of subvocalization. By comparing the eyes closed condition to this condition, the subvocalization pattern can be understand and the role of subvocalization in the other tasks can be addressed.

For the Visualizing a Beach task the time period was 30 seconds. The subjects are requested to visualize a beach for 30 seconds. There is no scoring for this task. As with the subvocalization task, the purpose of the task is to understand how electrophysiologically the visualization process is accomplished. The results can then be analyzed with respect to other tasks, to understand the possible role of visualization in the completion of the task.

For the Autobiographical Memory-Earliest Memory task the time period was 30 seconds. The subjects are requested to recall the earliest childhood memory that they can recall. Following the 30-second period, the subjects are requested to inform the inventor of their age at the time of the memory and provide a brief description of the memory. The results are not presented in the Figures section. An analysis was conducted to ascertain if there was a pattern of electrophysiological functioning which allowed a subject to recall earlier in time. The results were so affected by the current age of the subject that the results were deemed to be unable to answer the question posed.

For the Autobiographical Memory-Facts/Names from Childhood task the time period was 120 seconds. The subjects are instructed that they will be asked to quietly recall answers to questions regarding their childhood memories. They are provided with 5–8 seconds for each question. An example of a question would be "Recall the first and last name of your favorite and worst teacher during elementary school years?" Following the questioning, the subjects are asked the same question and asked to provide the inventor with their recall during the quiet 5–8 seconds. The scoring indicates the number of facts recalled. The level of activation results only indicate T5 & P3 peak frequency of Beta 1 as related to percentage of facts recalled from childhood. The results are not presented in the Figures.

For the Delayed Recall of Auditory Verbal List Learning task the time period was 30 seconds. The subject is asked to recall, quietly to themselves, all the words they can from the list learning task (task #4). Following the 30-second quiet period, the subjects are requested to inform the inventor outloud of all the words they could recall. Scoring is simply the number of words recalled.

For the Delayed Recall of Paragraphs task the time period was 30 seconds. The subjects are requested to quietly recall for 30 seconds as much information from the 4 paragraphs read in task #5. They are then asked to outloud inform the inventor of all the information that they were able to recall. The scoring follows the same principles employed in the original presentation.

For the Delayed Recall of Korean Figures task the time period was 30 seconds. The subjects are asked to recall quietly for 30 seconds the Korean figures that were exposed in task #6. Following the quiet recall period, they are asked to draw the figures. Scoring follows the same principles as the original presentation.

For the Delayed Recall of Names of Faces task the time period was 30 seconds. The subjects are requested to recall quietly and with their eyes closed for 30 seconds all the names and faces of the ten faces that were exposed in task #7. They are then presented with the same sheet that was presented for immediate recall following the initial presentation and asked to indicate the first and last names of the faces. The maximum scoring for this task is 20.

The subject is then presented with a name and asked to indicate which face is associated with the name. The maximum score for this task is 10. This represents a recognition score.

For the Delayed Recall of Reading Material task the time period was 30 seconds. The subjects are requested to recall for 30 seconds, quietly to themselves and with their eyes closed, all of the information they can recall from the material they read in task #8. Following the quiet period, they are asked to say outloud all of the information that they are able to recall. Scoring is conducted in the same manner as the original short-term recall for this task.

For the Delayed Recall of Object Location task the time period was 30 seconds. The subjects are requested to recall (quietly with eyes closed) for 30 seconds where the 14 objects are placed in the room. These are the objects, which the subject hid in the beginning of the procedure. The maximum score for this task is 14.

For the delayed Recall of "To Do" List task the time period was 30 seconds. The subjects are requested to recall (quietly with eyes closed) for 30 seconds the 10 items on the "to do" list. Subsequently, they are asked to indicate outloud to the inventor what are the ten items. The maximum scoring for this task is 10.

Although there were 151 subjects engaged in the procedures, not all procedures were administered to all subjects, as the experiment underwent revision during the data collection process. The data analysis will only examine subjects over the age of 13 with no history of head injury, which had a demonstrable effect (i.e. inclusion of two subjects with minor head injuries who performed well on the tasks). The reasoning for the exclusion of subjects under the age of 13 is that the patterning of results for these subjects is qualitatively different than adults and represents develop-mental aspects of efficient cognitive functioning. In addition delta activity is not being presented in the analysis for two reasons. 1—As minor eye movement was allowed into the included for analysis epochs, the inclusion of delta activity would be misleading as to the nature of the underlying brain activity. 2—The effective QEEG parameters were focused in the higher bandwidths, thus minimizing the probability that Delta activity is an effective cognitive measure. 3—Some of the tasks evoked more globally located delta activity. The inventor decided to allow some of this activity into the analysis on the basis of the need in include as many epochs as possible. Thus, again, to include delta in the analysis would be misleading.

The raw data, once artifacted, was analyzed with the Exporter program available from Lexicor Medical Technologies. The Exporter software program was commissioned by the inventor to solve the cumbersome time problem of obtaining the required figures from the raw data file. The Exporter program was written by the programmer of Lexicor. The program generates the values for the variables under consideration from the raw data file and generates ASCII, comma delimited files which can then be imported into Excel or CSS Statistica. The Exporter program was employed with all the subjects to generate the raw values for the variables. One CSS spreadsheet was generated for each subject. Every epoch of the spreadsheet was labeled according to what activity was occurring at the time. Once the labeling was completed, the file under a series of t-test comparisons, i.e. auditory attention versus listening to paragraphs. A t value was generated for all 2945 variables for each of the comparisons conducted. These comparisons were placed into Excel spreadsheets. Each subject, therefore, had an Excel spreadsheet containing all of the comparison results. Once all the comparisons were completed the results from the Excel spreadsheet were transferred to a CSS statistica file containing similar comparisons for the other subjects. Thus, a CSS file would contain the results of all of the auditory attention (AA) versus listening to paragraph (LP) comparisons. The CSS files for each comparison would consist of 3 files. For example, in the AA vs. LP comparison, one file would contain the absolute levels of the LP condition, one file would contain the degree of activation values (i.e. LP-AA) and a third file would contain the t values resulting from the comparisons (i.e. LP vs. AA). For each subject additional data regarding age, age at time of testing, history of head injury, date of head injury, sex, handedness, education level, scores on the Shipley in terms of raw scores and Verbal and Abstraction IQ were placed in every file in addition to the performance values of the subject on the particular task under consideration. This procedure would enable analysis of all the conditions along a number of dimensions.

With 2495 variables available for inspection, significance by chance alone becomes a significant problem. There were two methods employed to reduce or handle this problem. 1—Summary variables were developed for the beta bandwidths. In terms of the activation dimension, summary activation variables for the four quadrants of the brain were developed. These quadrants included the left frontal, right frontal, left posterior and right posterior. The respective positions, for example, would include for the right frontal the FP1, F7 and F3 positions and for the right posterior quadrant the T6, P4 and O2 positions. Summary activation values involving these three locations were calculated in the Excel spreadsheet (prior importing to CSS) for absolute magnitude, relative power, peak amplitudes and peak frequencies for Beta1 and Beta2. Activation ratios were developed for the four quadrants along these activation measures with respect to their opposite hemisphere, similar quadrant structure and same hemisphere, opposite quadrant structure. For example, the absolute magnitude ratio of the left posterior region (in terms of P3,T5 and O1) was calculated with respect to the right posterior and left frontal regions. The symmetry measure was summarized as follows: for each position the symmetry value was added across all relationships to the other 18 locations and then divided by 18 to obtain an average value for the Beta1 and Beta2 bands. For the Coherence and Phase Values, every location's phase relationship (in the Beta1 and Beta2 bands) to selected other positions were added together and then divided by the total number of relationships examined to produce an average value for that location's relationship to the other locations under consideration. The relationships under consideration involved the short-range connections in the left and right frontal and the left and right posterior regions. Middle connection considerations concerned all homologous relationships, summed and averaged across the frontal, central and posterior regions for the Beta1 and Beta2 bands. The long-range connections under consideration concerned the relationship of the particular location (only frontal locations) to the remaining locations within the same hemisphere and separately the relationship to all locations in the opposite hemisphere. An additional analysis concerned the relationship of a particular location (middle region, i.e. T3,C3,C4,T4) to the left and right frontal and posterior regions (as defined by respectively 3 locations in each region). Posterior locations (by quadrant) were summed and averaged according, to their relationships to their respective hemisphere and separately to the opposite hemisphere as well as to the left and right frontal regions for the Beta1 and Beta2 bands. This summarizing activity resulted in an additional 338 variables concerning the Beta bands. Although this method reduced the overall number of beta variables under consideration, it ignored the Alpha and Theta bands, which subsequently demonstrated significance. The result of the arrangement of the variables in this manner is not discussed or presented in this patent application, but was employed by the author to aid in understanding the data more fully.

Setting the Alpha level to 0.05 would result in 147 significant findings (of the 2945 variables under consideration) by chance alone. To reduce this statistical problem to manageable levels the following considerations were taken into account. Statistical significance was considered in view of the parameter under consideration. For example, in terms of one of the activation measures (relative power, etc.) there are 19 locations and 5 bands, resulting, in 95 possible significant findings. An Alpha level of 0.05 would produce approximately 5 significant findings by chance alone. The inventor decided that at least two adjacent locations are activated in the same bandwidth before a result could be considered significant. Additional criteria included if a location was significant across different activation measures or if there were three locations, which were significant in a particular activation measure. If it assumed that the 5 chance findings are randomly distributed, then they would be distributed equally among the five bands. To require that two locations be activated in the same band and require an additional proximity of location lowers the chance factor significantly. The probability of a second significant finding, the close proximity to the first is determined in part by the location of the first. For example, T3 has 5 locations (of the 18 remaining) which would be close enough, while Cz has 8 locations. Thus the probability for T3 is 0.05*0.27 or 0.0146. All the additional activation measures are handled in a similar manner.

In terms of the relationship variables coherence and phase) the problem is similar. Each band generates 171 relationships between all locations. For the 4 bands under consideration there are a resulting 684 variables. With an Alpha level of 0.05, there would be 34 significant findings by chance alone. To reduce this probability, the inventor required an additional 2 relationships in a single band from a single location to be significant at an Alpha level of 0.05 before significance is accepted. If one assumes that the 34 significant findings are distributed randomly, then there will be 8.5 significant findings in each of the four bands. If these band findings are randomly distributed among the 19 locations, then about 45% of the locations will have significant findings in terms of one location having two of the same band coming from the same location. If the additional criteria of a third similar band from the same location is added, the probability drops to 0%.

If the Alpha level is set to 0.10 there would then be 68.4 significant findings by chance alone. Employing the previous analysis, if one assumes that the 68 findings are distributed randomly among the 684 variables, then there will be 17 findings per band. If the findings are randomly distributed then there is an 89% probability that there will be two significant findings from one location in the same bandwidth. If the criteria is set to three relationships emanating from the same location, the probability of this event occurring by chance alone drops to 0% chance. However, to employ an even more stringent criteria, the experimenter required 4 significant findings at the 0.10 level coming from the same location to quality for significance in the following discussion.

The results are presented herein in support of the utility of the method in graphical format for each of the conditions and summarized across all the conditions by bandwidth and location. For the purposes of the analysis only subjects over the age of 13 and without a head injury are considered. This resulted in a total of 83 possible subjects available for the following analysis.

The figures presented indicate the 19 locations of the 10-20 EEG system. FIG. 7 presents the standard 10-20 system and the standard labeling of positions.

The results of each task (with some exceptions) is represented by the figures in the drawings, the first representing the level of activation and the second the degree of activation from baseline. Below the initial figure label and title is the number of subjects represented in the analysis, i.e. N=75.

The task under consideration is presented above each head figure, followed by descriptive label of the comparison being presented, followed by the subject size.

The circles represent the areas activated (in terms of magnitude, relative power, peak frequency, and amplitude asymmetry) to a significant level according to the previous discussion of significance. The lines represent the significant levels of the respective phase and coherence levels. When indicated dotted lines in red indicate results, which were significant at the 0.10 level. The employment of the color red for the asymmetry values does not indicate any special level of significance, but supplied for visual effect only. The effective and ineffective parameters are noted on the top of each set of figures. Each head figure is labeled on top with the parameter under consideration, according to the following nomenclature.

T-Theta
A-Alpha
B1-Beta1
B2-Beta2
M-Absolute Magnitude
R-Relative Magnitude
PA-Peak Amplitude
PF-Peak Frequency
Sym-Symmetry
P-Phase
C-Coherence The following examples are provided for clarification.

PA—would reflect phase Alpha.
CT—would reflect coherence Theta.
RB2—would reflect relative power of Beta2
MB1—would reflect magnitude of Beta1
PKAA—would reflect peak amplitude of Alpha
PFKB2—would reflect peak frequency of Beta2
SymB1*—would reflect Asymmetry of Beta1 band
   *-Symmetry measures employ the combination method, where a particular location's symmetry measure is calculated in reference to all other positions and is calculated only for the beta bands.

The following is the presentation of the results. The order of presentation is the order of administration of the task to the subject.

Figure 8A:
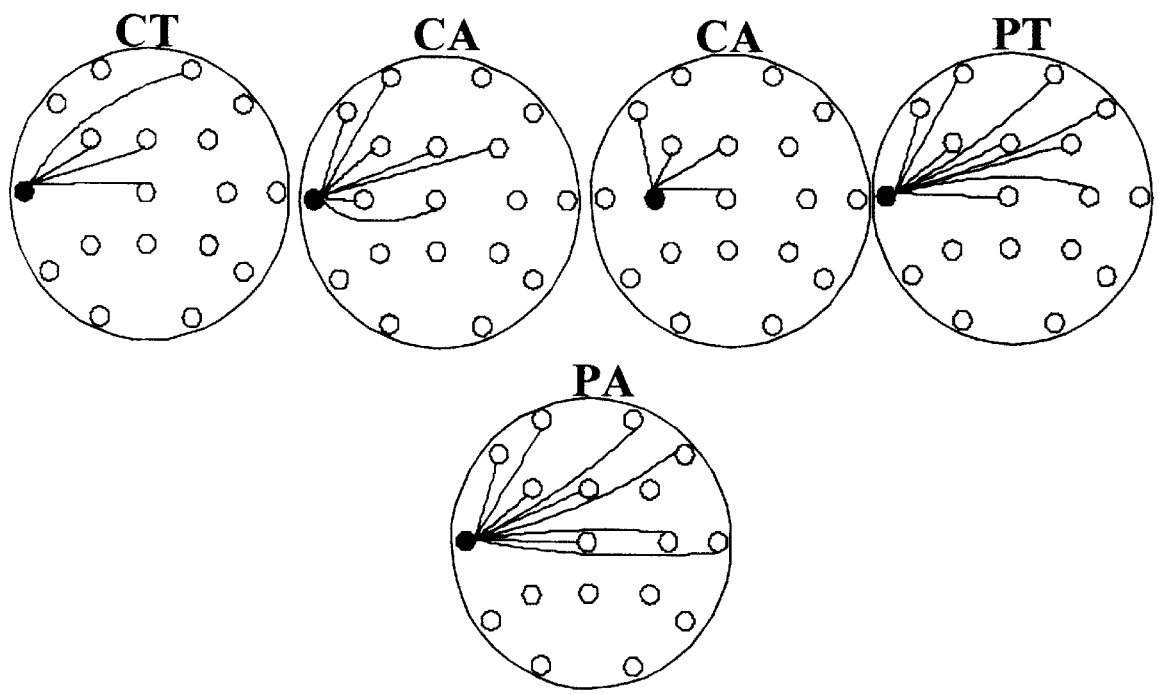
FIG. 8 is an Eyes Closed comparison and represents the significant correlations between the eyes closed condition and combined ability to recall paragraphs and the ability to recall word lists.
Figure 8B:
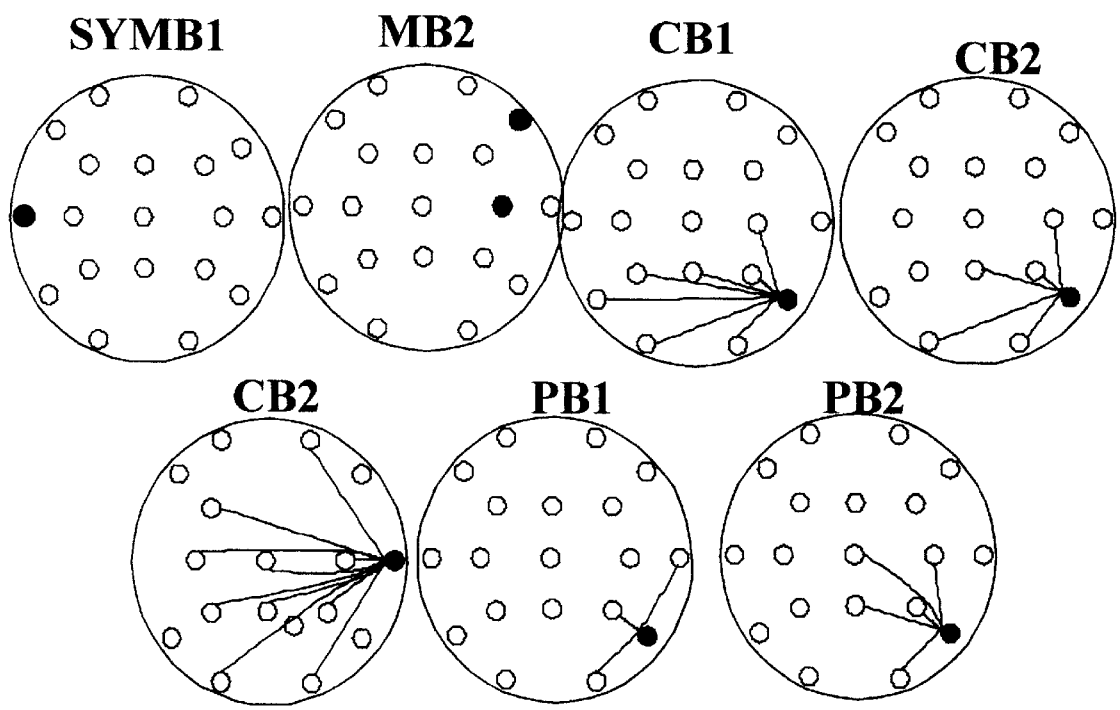

Eyes Closed comparison presented in FIG. 8 (A#1) represented the significant correlations between the eyes closed condition and combined ability to recall paragraphs and the ability to recall word lists. The QEEG variables are correlated with the total memory score for both short and delayed memory for both auditory memory conditions. Both of these tasks involve auditory memory. The reasoning for this type of analysis is to understand if there is a significant relationship between a subject's resting condition and future memory ability. If coherence is conceptualized as the number of connections between two positions then the value of coherence figure between two locations will represent the number/strength of that connection. If that figure correlates with auditory memory, then it may be reasoned that auditory memory ability resides in the strength of the underlying connections and not just the degree or level to which an individual is able to activate the connection.

The figure indicates that 3 positions (F7, T3, T5) are the critical determinants of auditory memory in the Theta to Beta1 frequencies in terms of coherence and phase. As auditory information enters into the temporal lobes first in the cortical representation of information, the T3 position (with 5 of the 9 significant projection systems) is the critical already is a major determinant of their future memory ability.

The relationship between the auditory attention condition and future auditory memory ability (word lists and paragraphs) is presented in FIG. 9 (experiment coding B#1). The reasoning behind this analysis is similar to the eyes closed comparison. The ability of the subjects to raise the levels of the phase and coherence relationships from the T3 position (Theta & Alpha) in a simple auditory attention task is a significant determinant of their future memory ability.

The following series of FIGS. 10 11, 12 (experiment coding C#1, #2, #3) reflect the absolute level when listening (hearing) to word lists, when processing the word lists and absolute levels for the words which were recalled successfully under the long term memory condition for the list learning condition. FIG. 10 represents the level of hearing activation issue. Success at the input junction is determined by the T3 Theta & Alpha coherence and phase generators as well as high frequency (Beta1 & Beta2) phase and coherence activity coming from the F7 position.

FIG. 11 represents the absolute degree of activation under the processing condition, the one second period of time after a word was heard and prior the presentation of the next word. FIGS. 10 and 11 represent the significant correlations with a total memory score. After the word is heard, it is the F7 & F8 positions which appear to solidify the memory by projecting to the posterior portion of the head in the Beta1 band (coherence and phase).

FIG. 12 represents the variables which were significantly relates to the long term recall condition in terms of absolute level. This Figure represents the level of the variable at the time of presentation (including both the hearing and processing condition). FIG. 12 represent the correlations between variable and number of words correctly recalled. The level of activation (at time of input) from T3 position in terms of Alpha (coherence and phase) relationships to the frontal part of the head, as well as F7, F2 and F8 high frequency projections to the back of the back are the main determinants of the subject's ability to recall the words 30 minutes or more later.

Figure 13A:
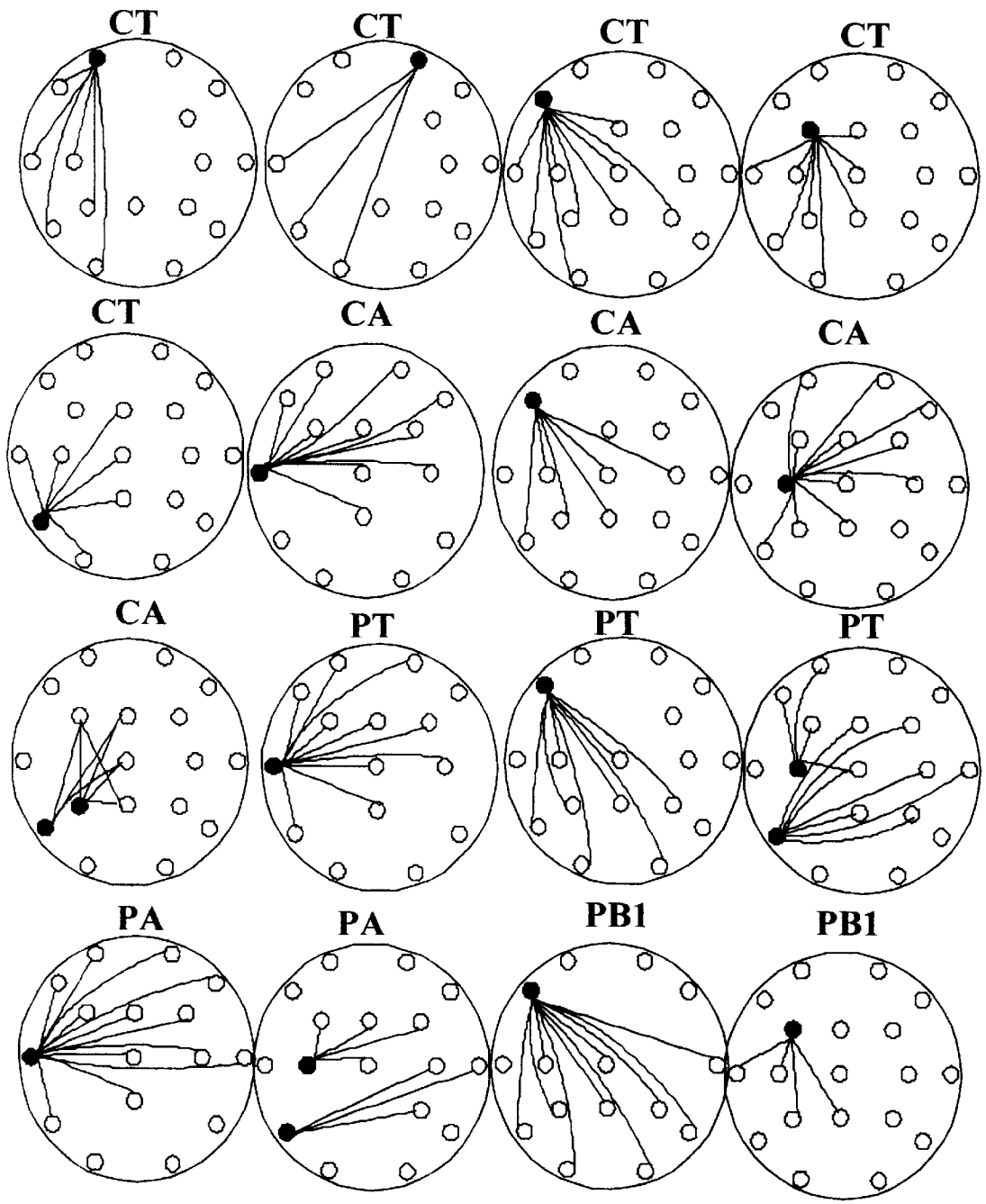
FIG. 13 represents the results of the analysis of the 30-second quiet period when the subject was trying to recall the just administered word list (correlations with the absolute value of a variable).
Figure 13B:
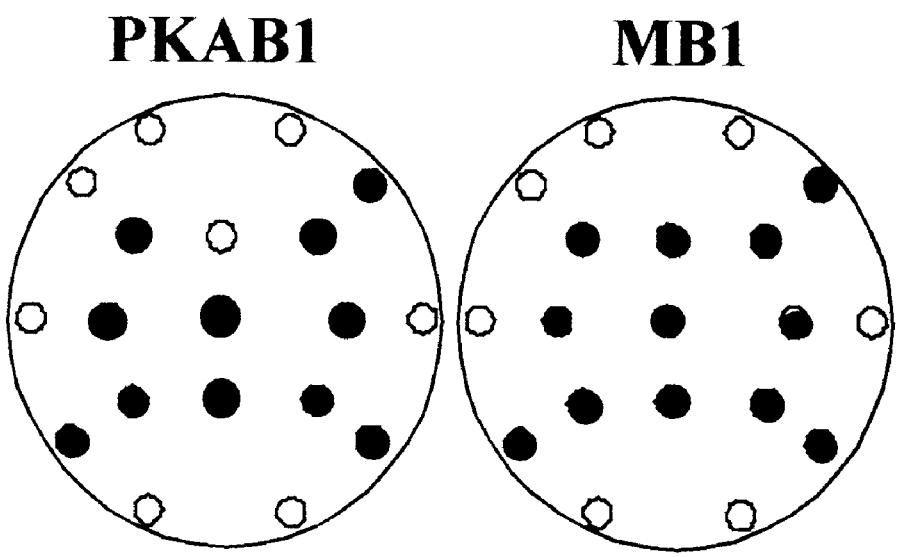

The FIGS. 13 and, 14 (D #1, #2) represent the results of the analysis of the 30-second quiet period when the subject was trying to recall the just administered word list. FIG. 13 represents significant correlations with the absolute value of the variable, FIG. 14 the degree of activation from the subject's respective eyes closed condition. As the subject recalls the words the lower frequencies (Theta and Alpha, coherence and phase) from the frontal and T3, T5, C3 become the critical components as well as the F7 projections system to the back of the head (phase Beta1) Degree of activation results reflect predominantly posterior and temporal projection (11) systems mostly in the Theta and Alpha bands. Of particular interest in the T4 coherence Beta2 projection system. This result suggests that either there might be a narrower band width out of T4 that is important of auditory memory that is not being picked up in the broad band width definitions in terms of original input or the T4 position operates in a different manner in the creation of the hologram.

Figure 57:
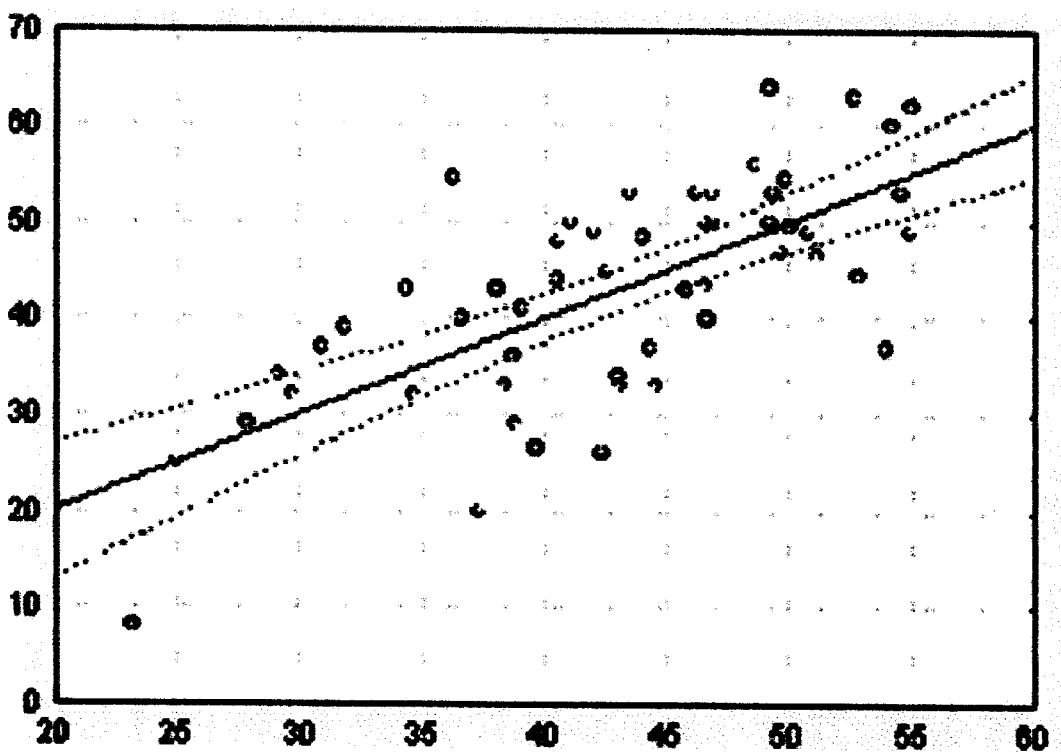
FIGS. 57 and 58 present the stepwise multiple regression equations for predicting total recall memory.
Figure 58:
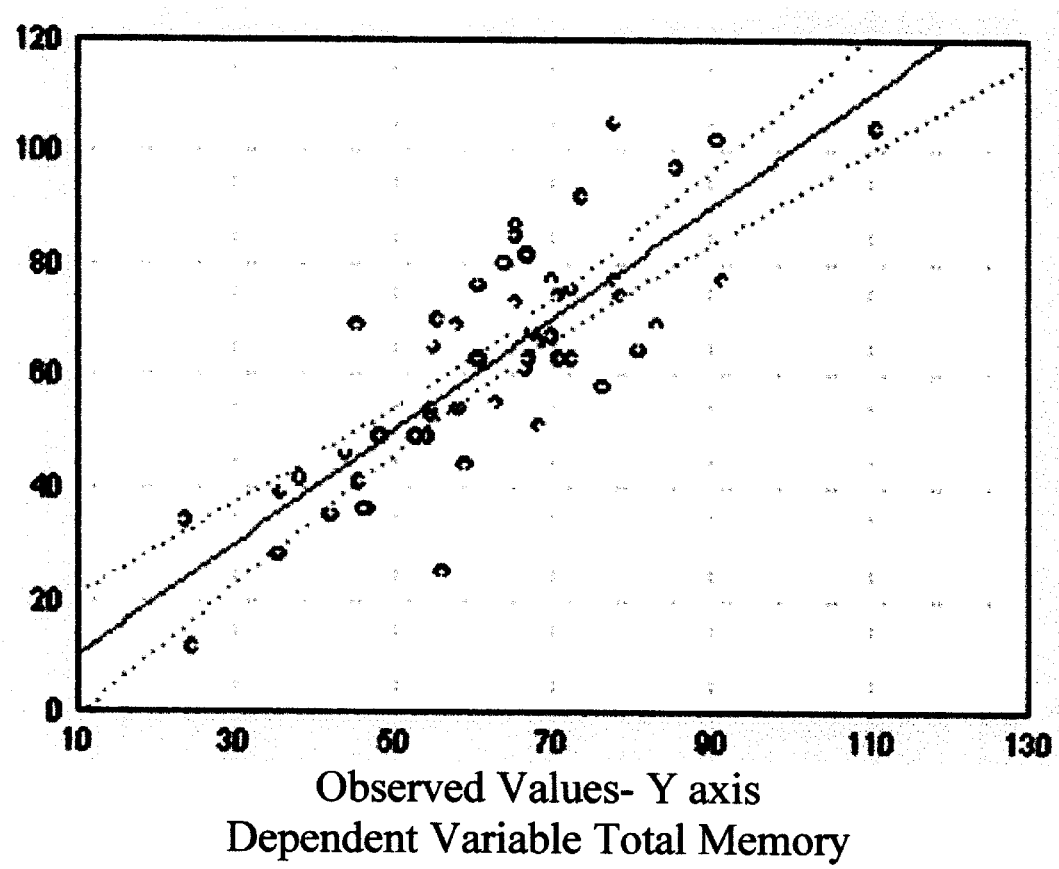
Figure 62A:
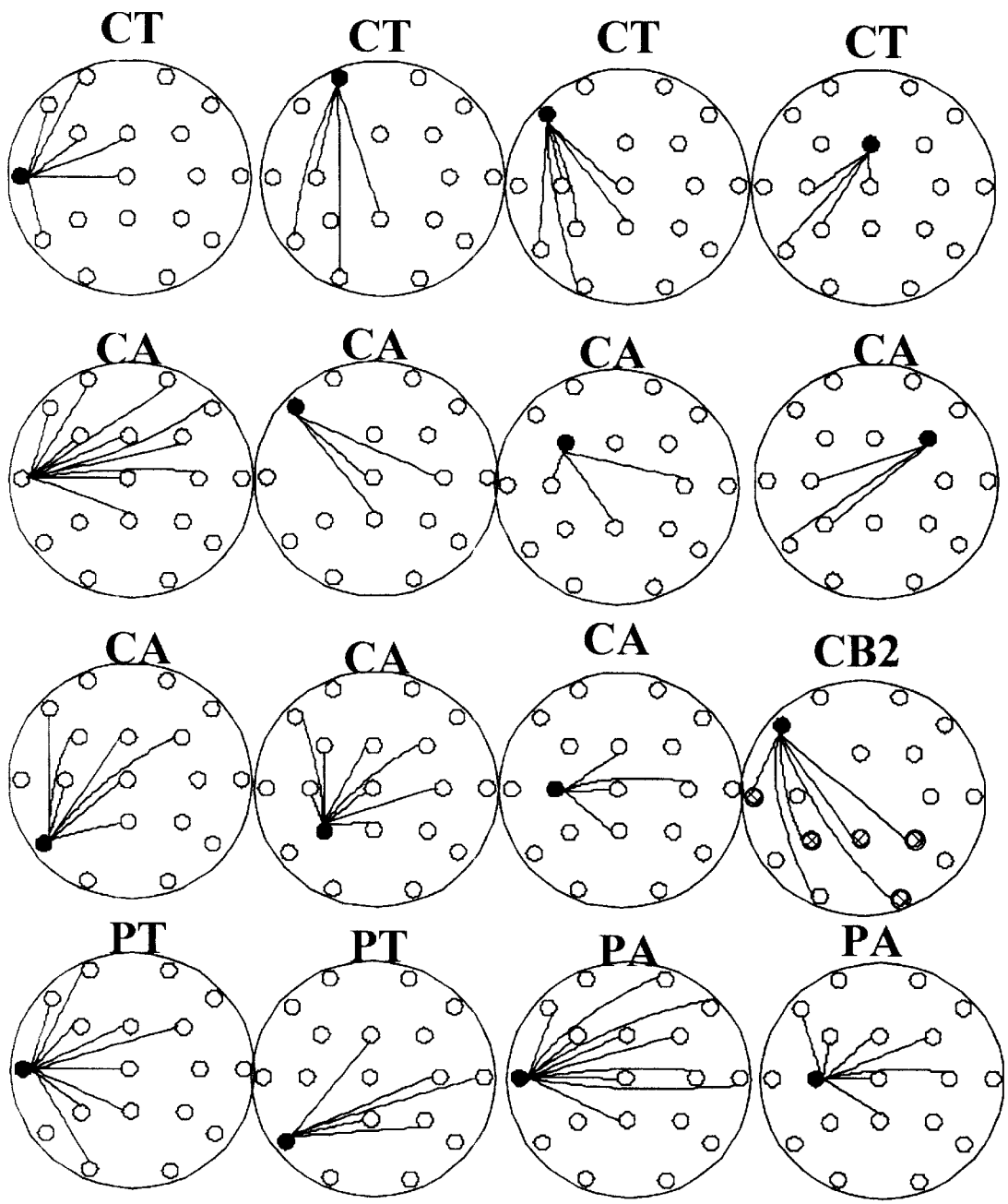
Figure 63A:
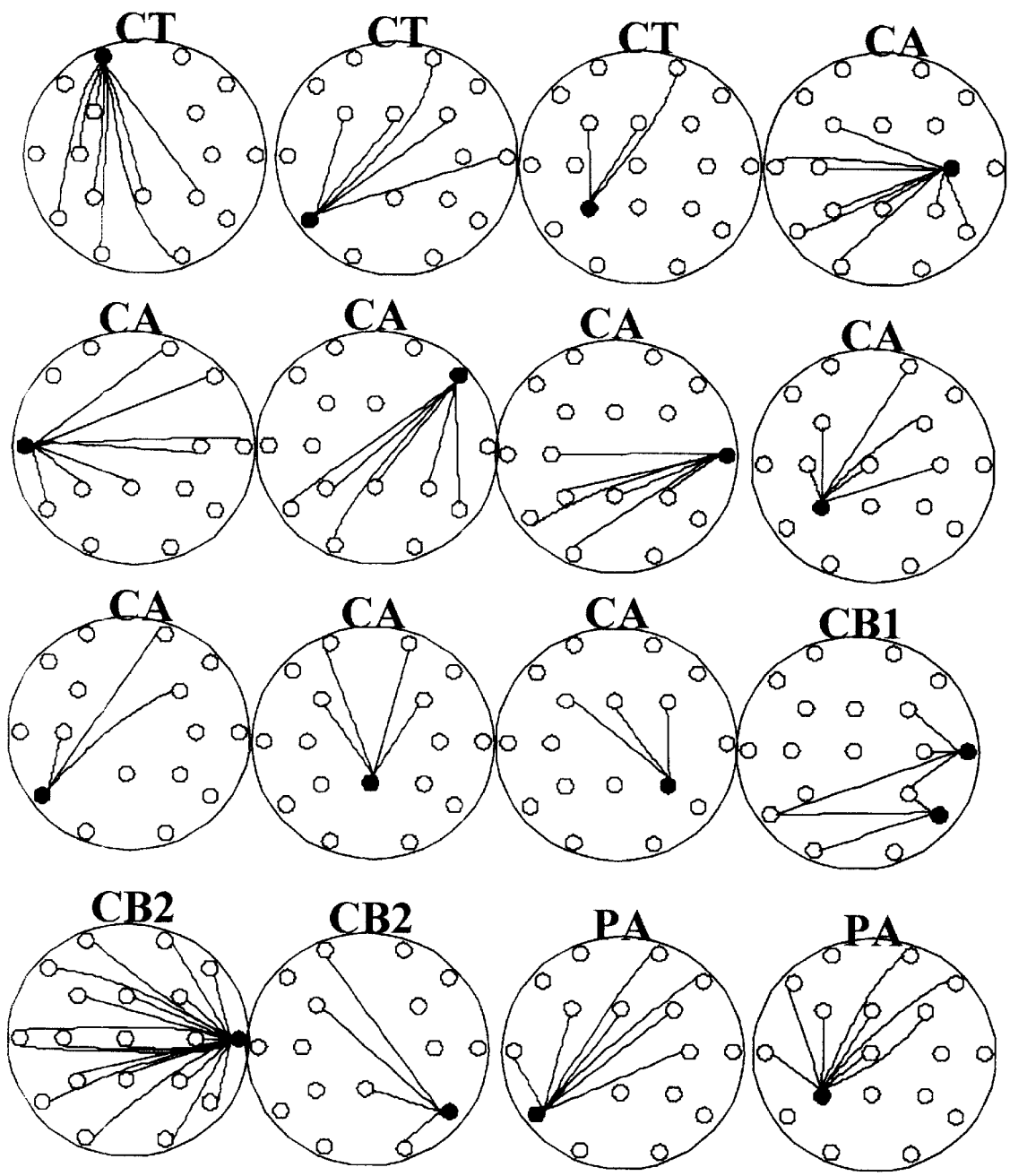
Figure 69A:
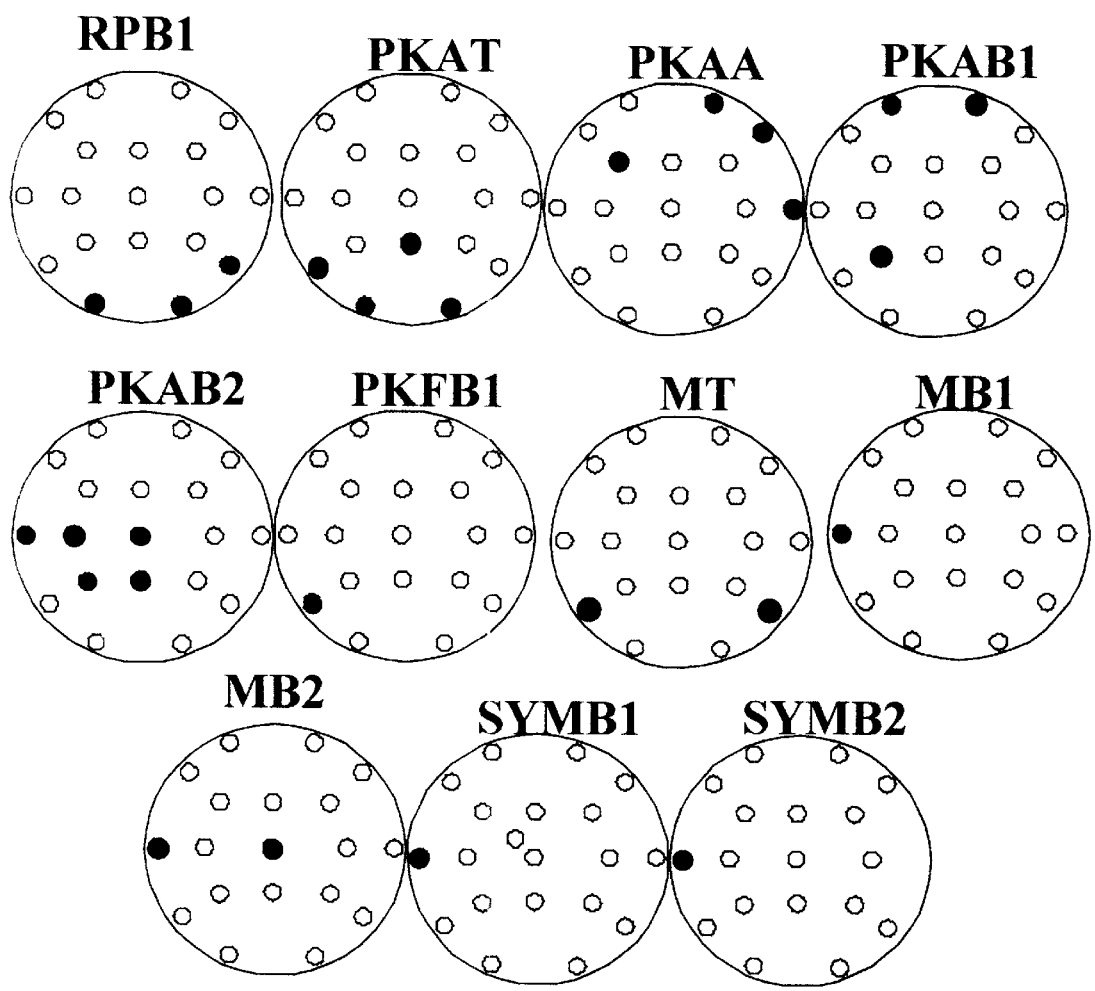
Figure 69B:
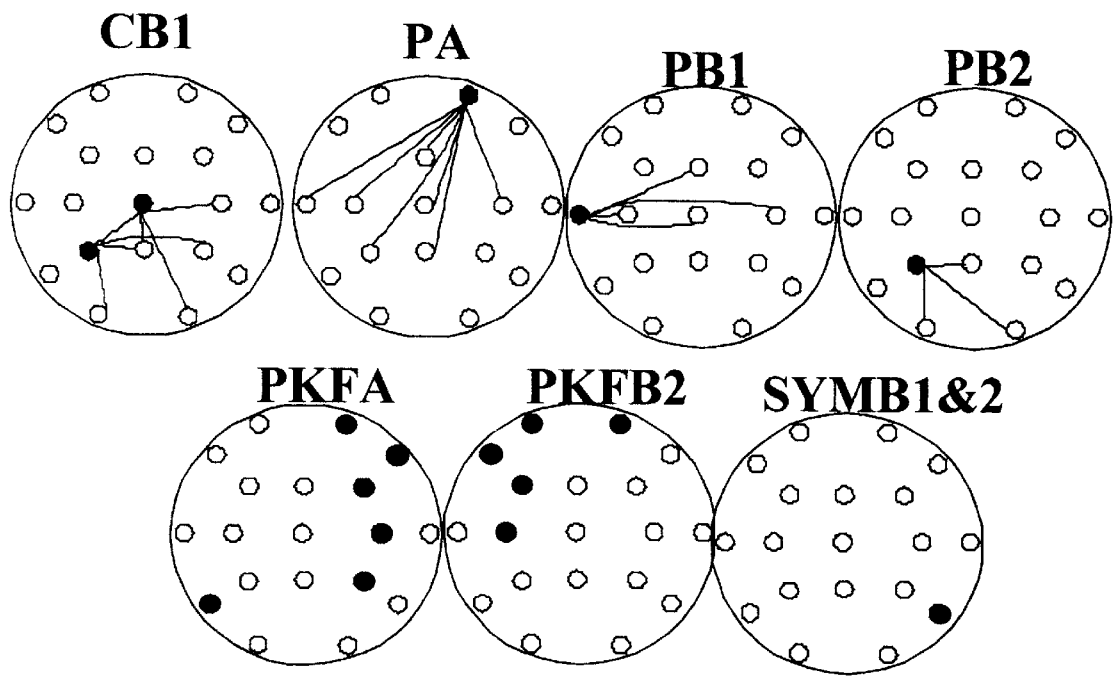
Figure 71A:
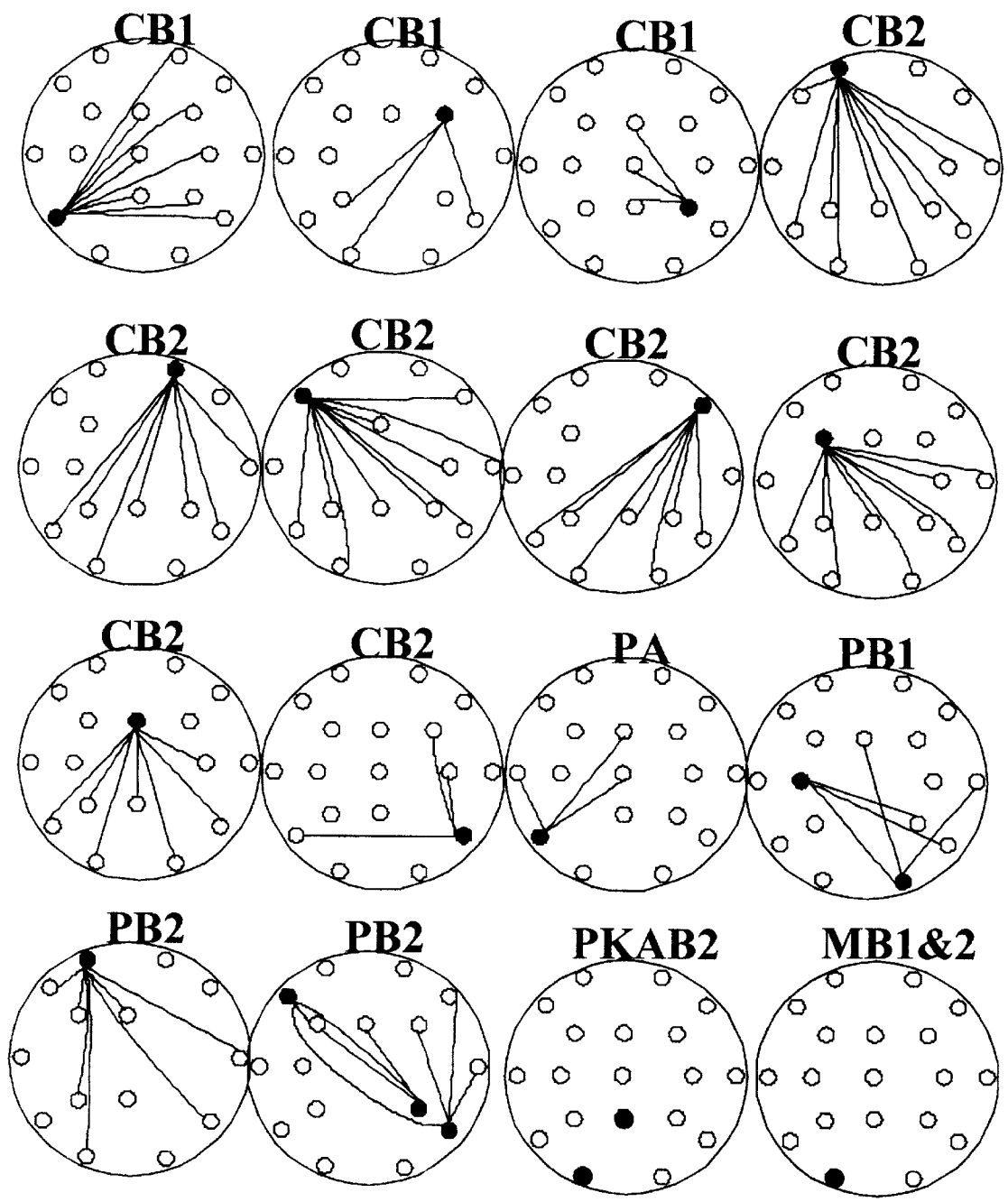
Figure 71B:
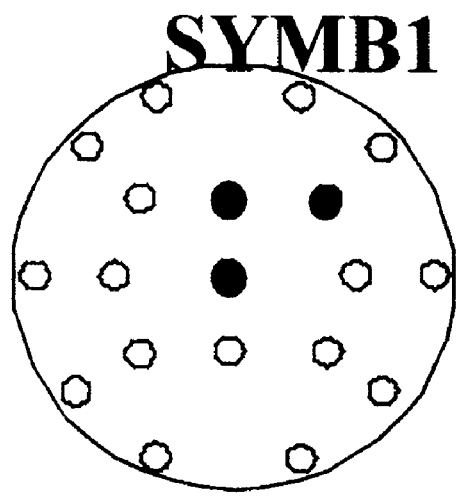
Figure 72A:
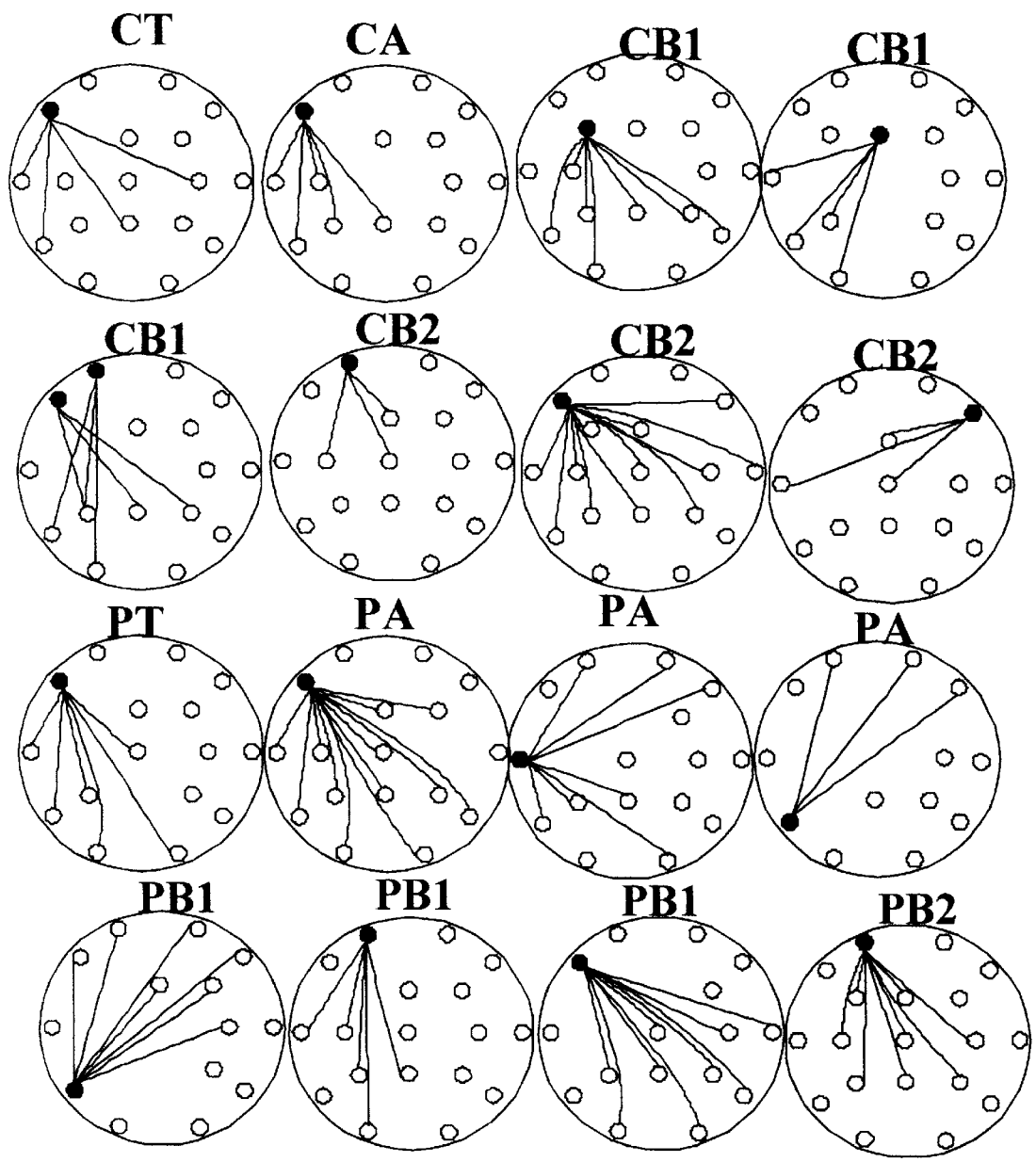
Figure 74A:
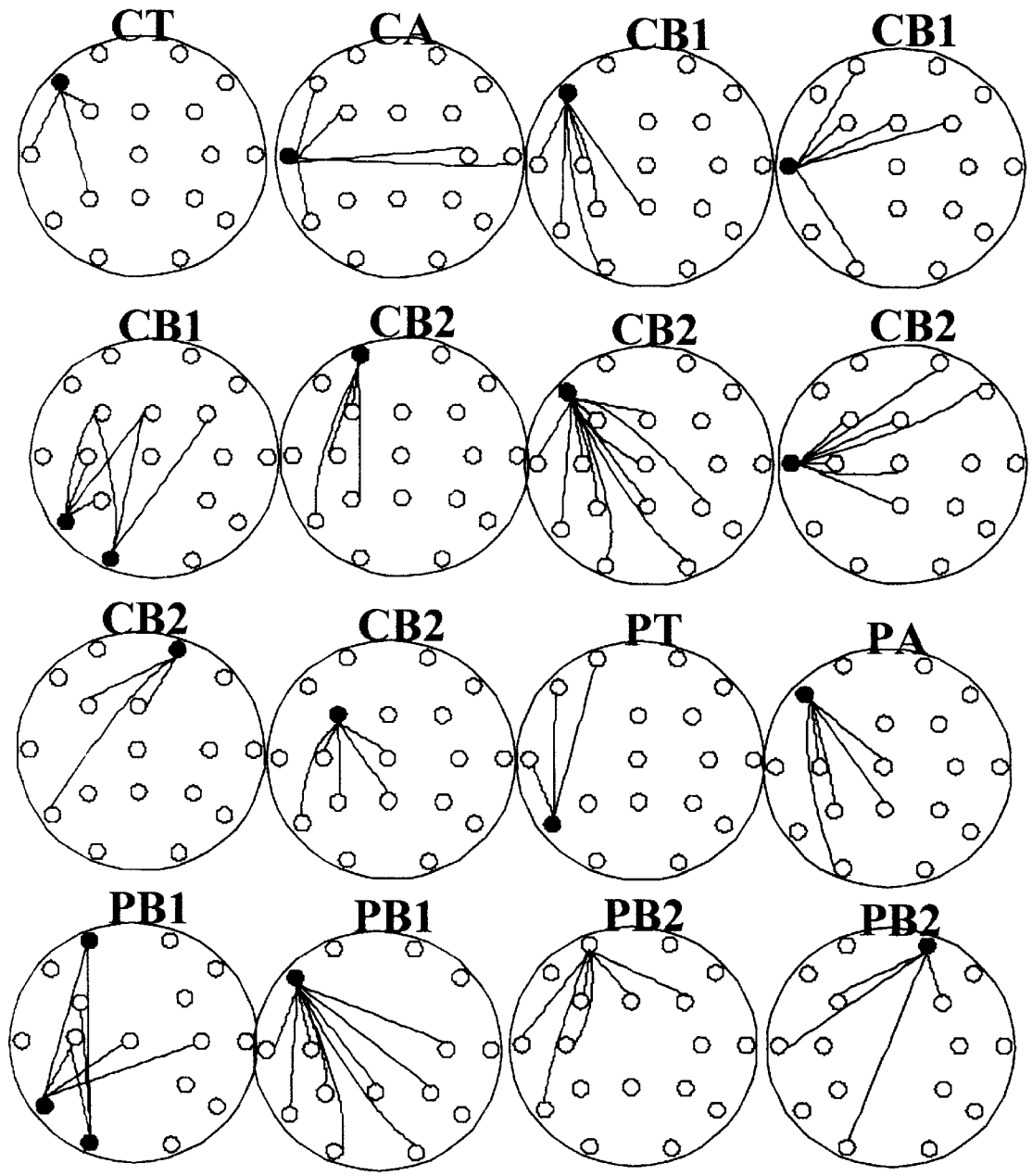
Figure 75A:
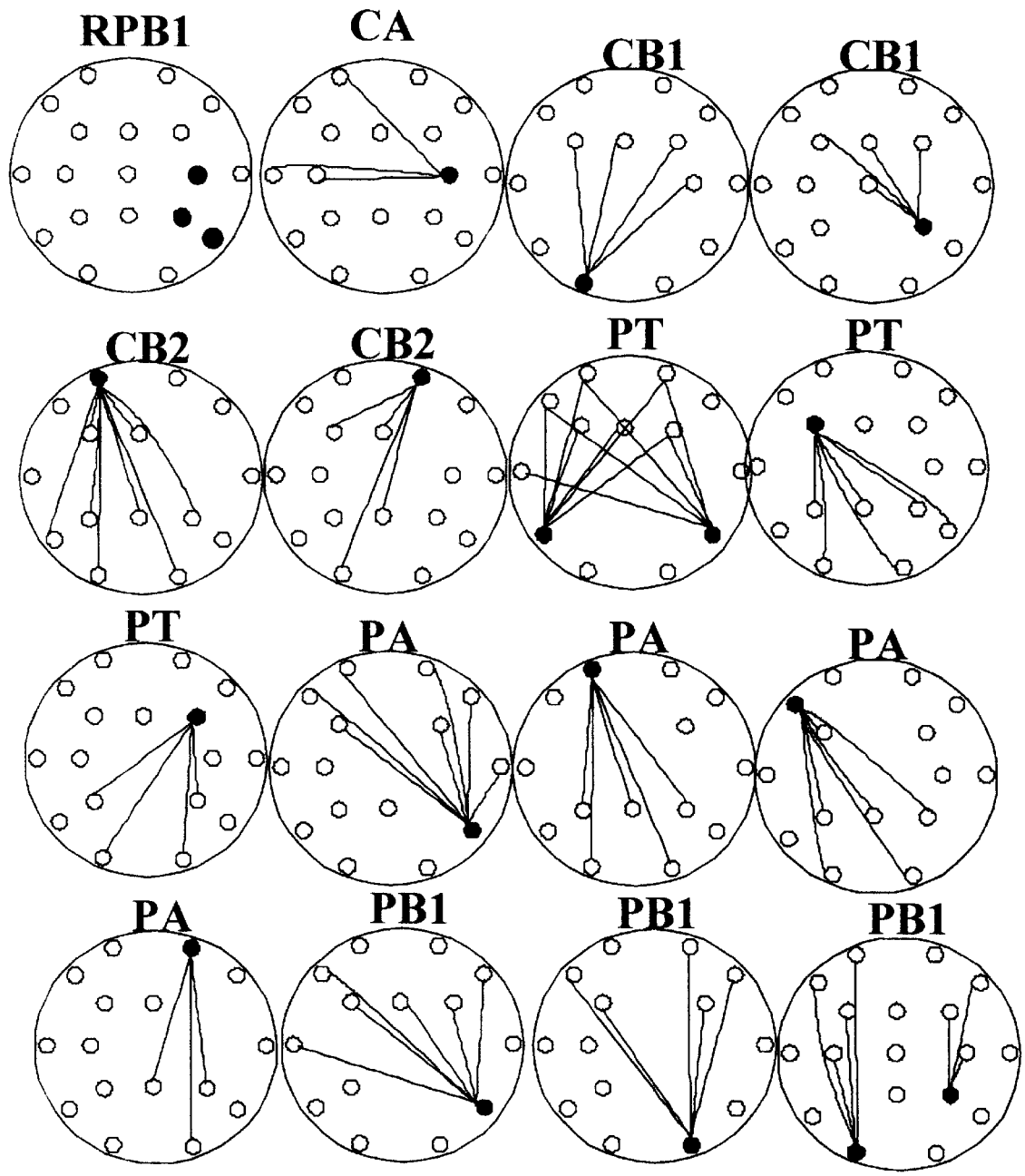
Figure 76A:
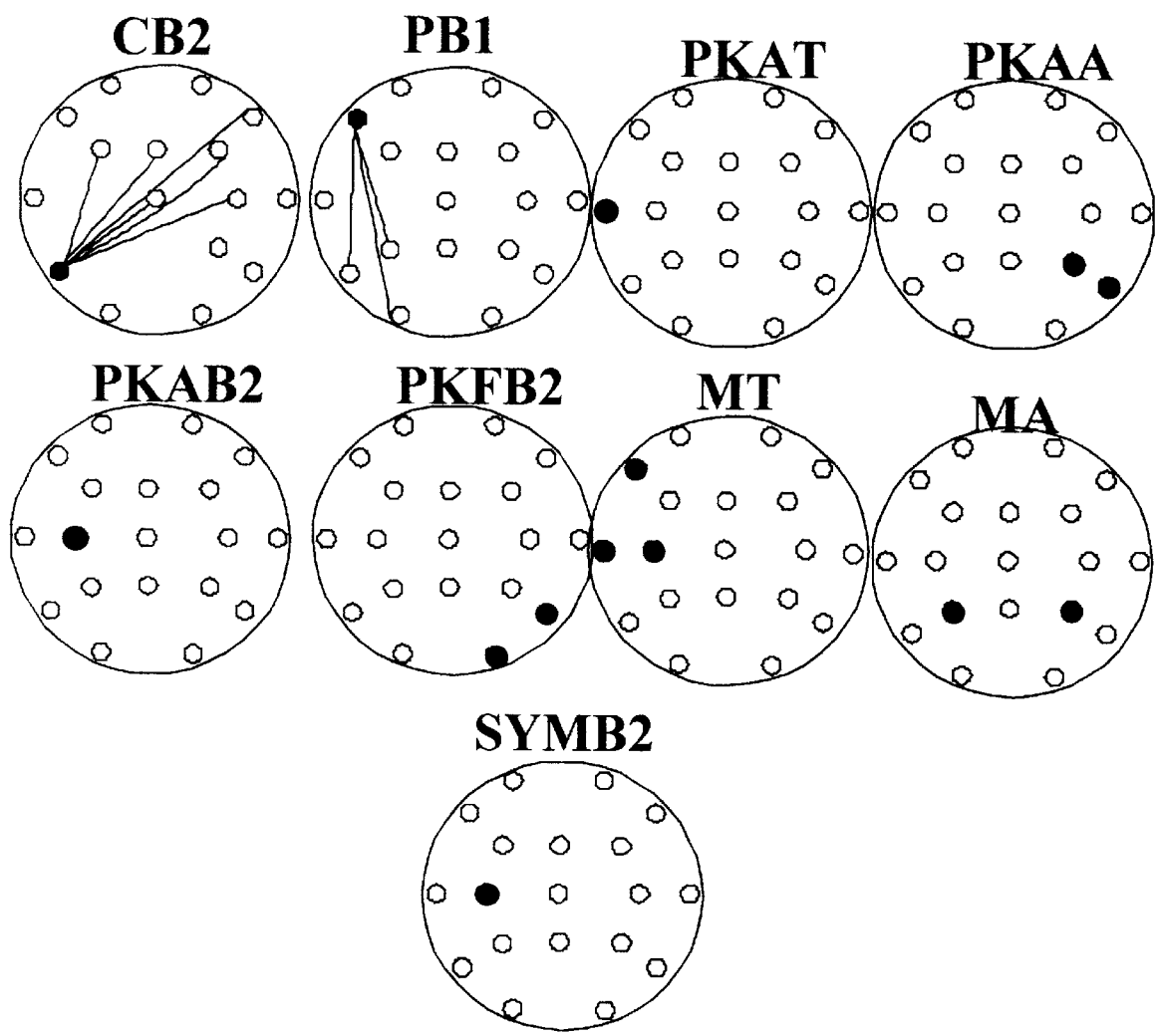
Figure 77A:
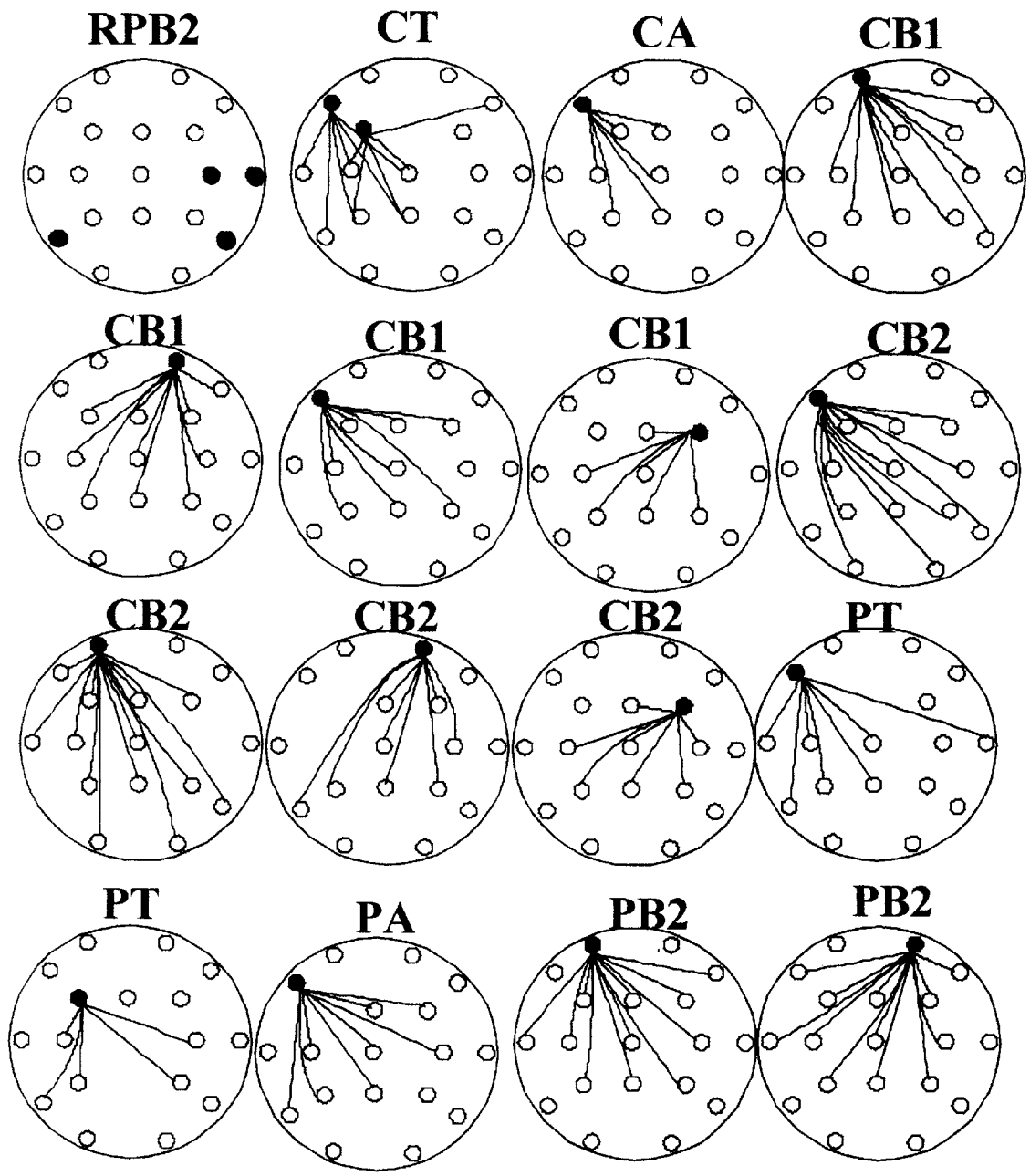
Figure 77B:
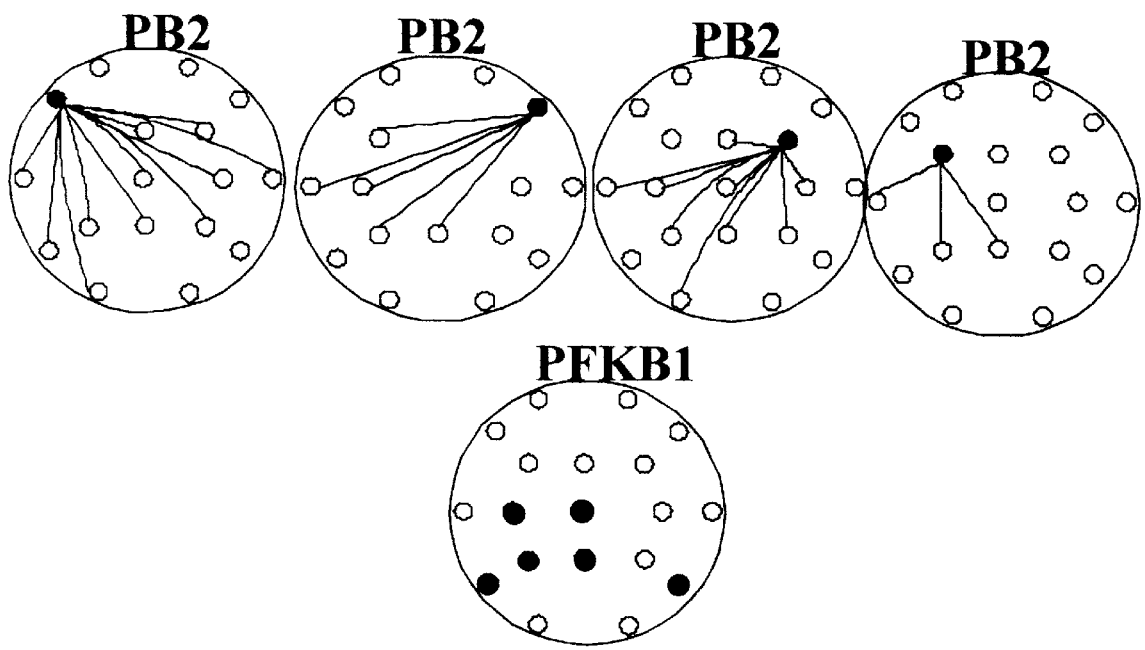
Figure 77C:
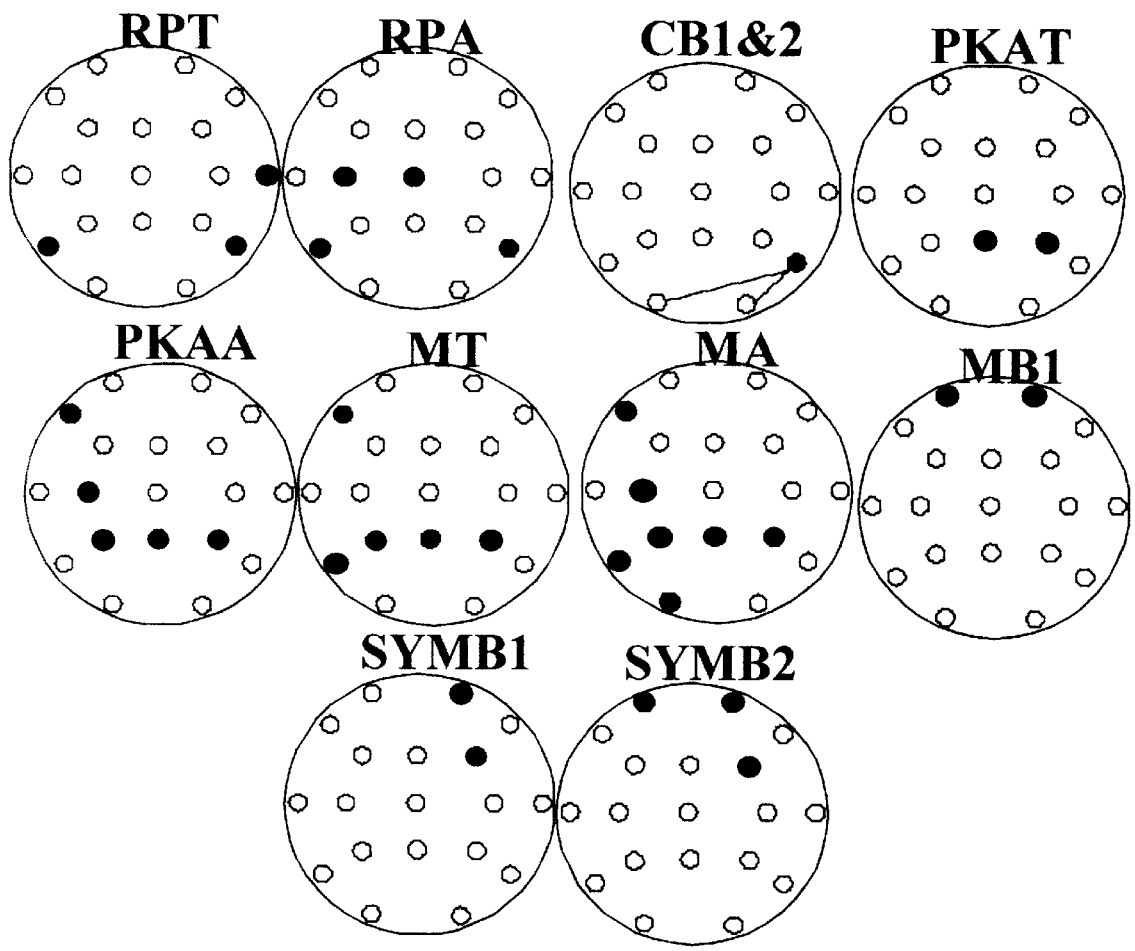
Figure 78A:
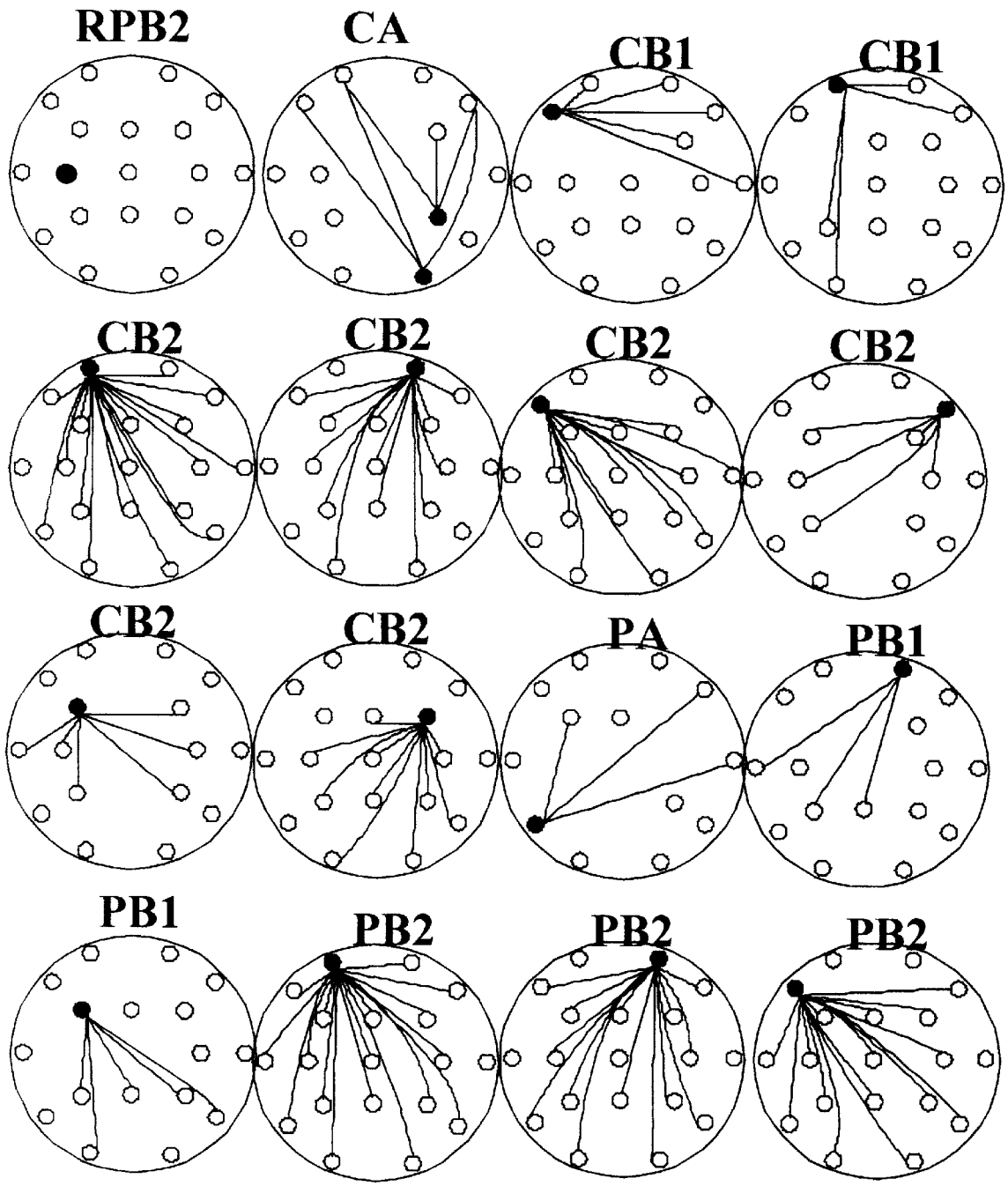
Figure 82A:
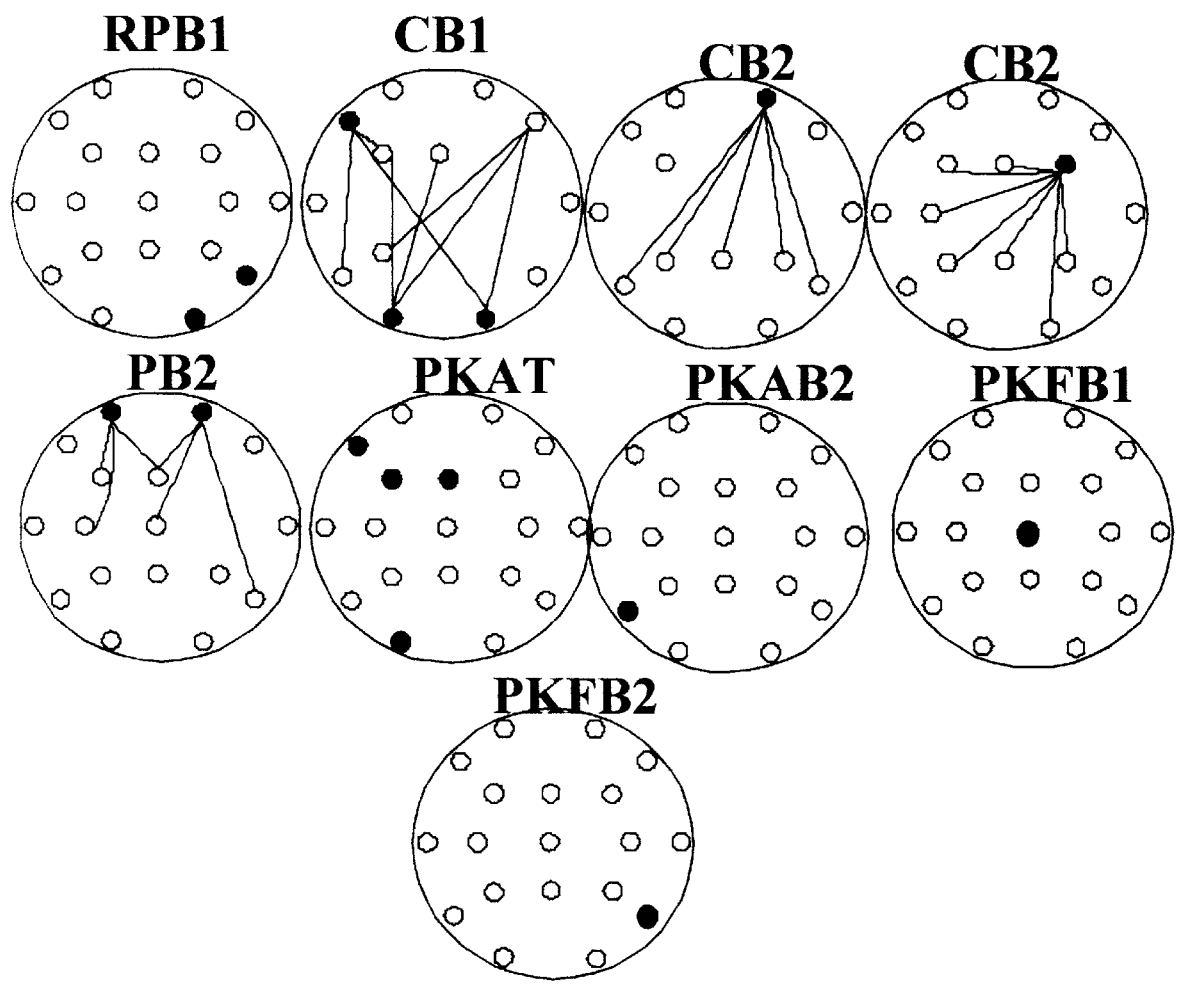
Figure 82B:
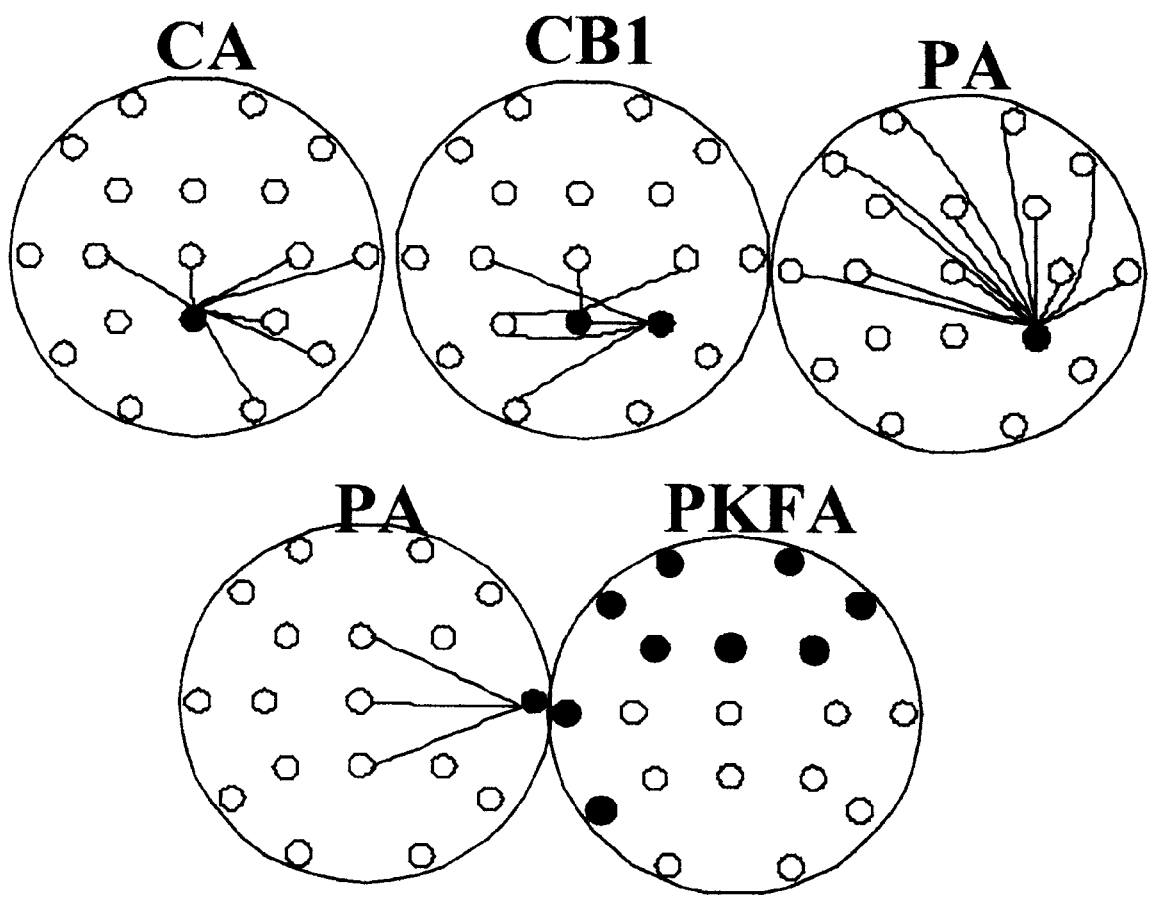
Figure 83A:
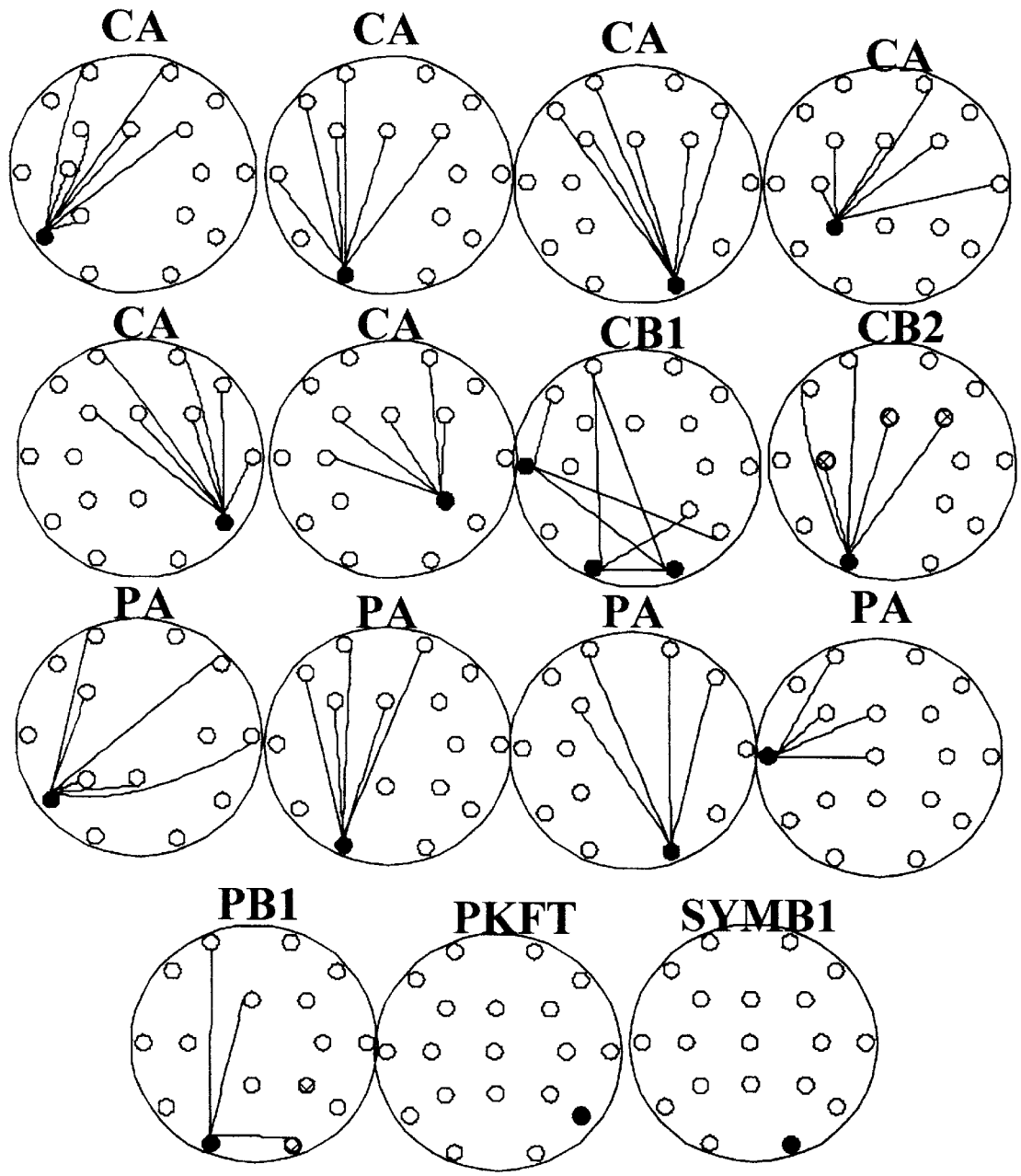
Figure 83B:
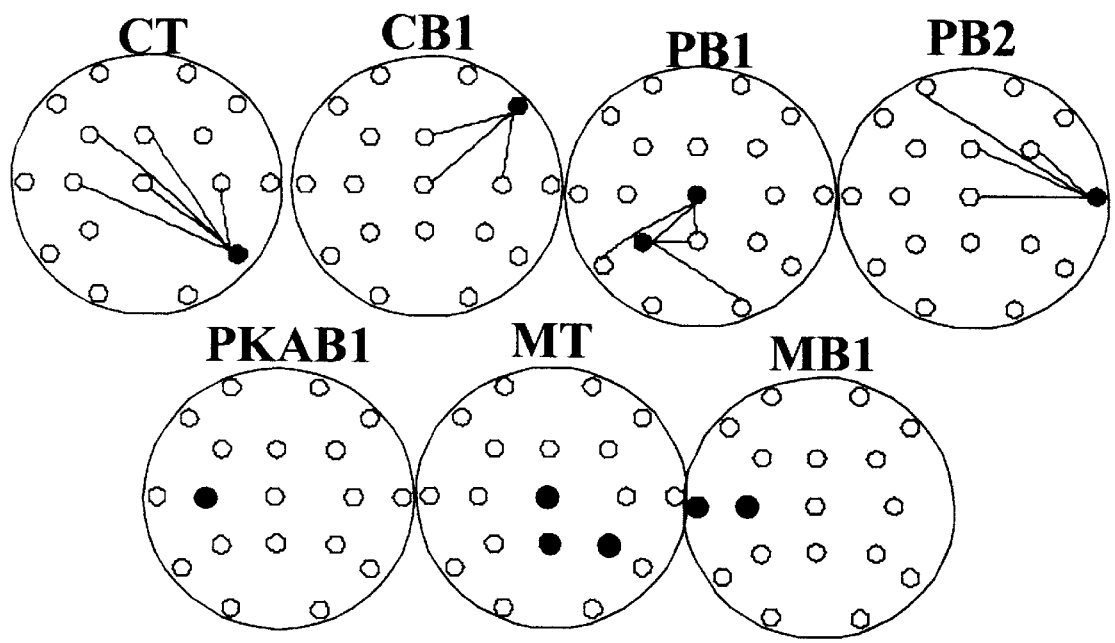
Figure 84A:
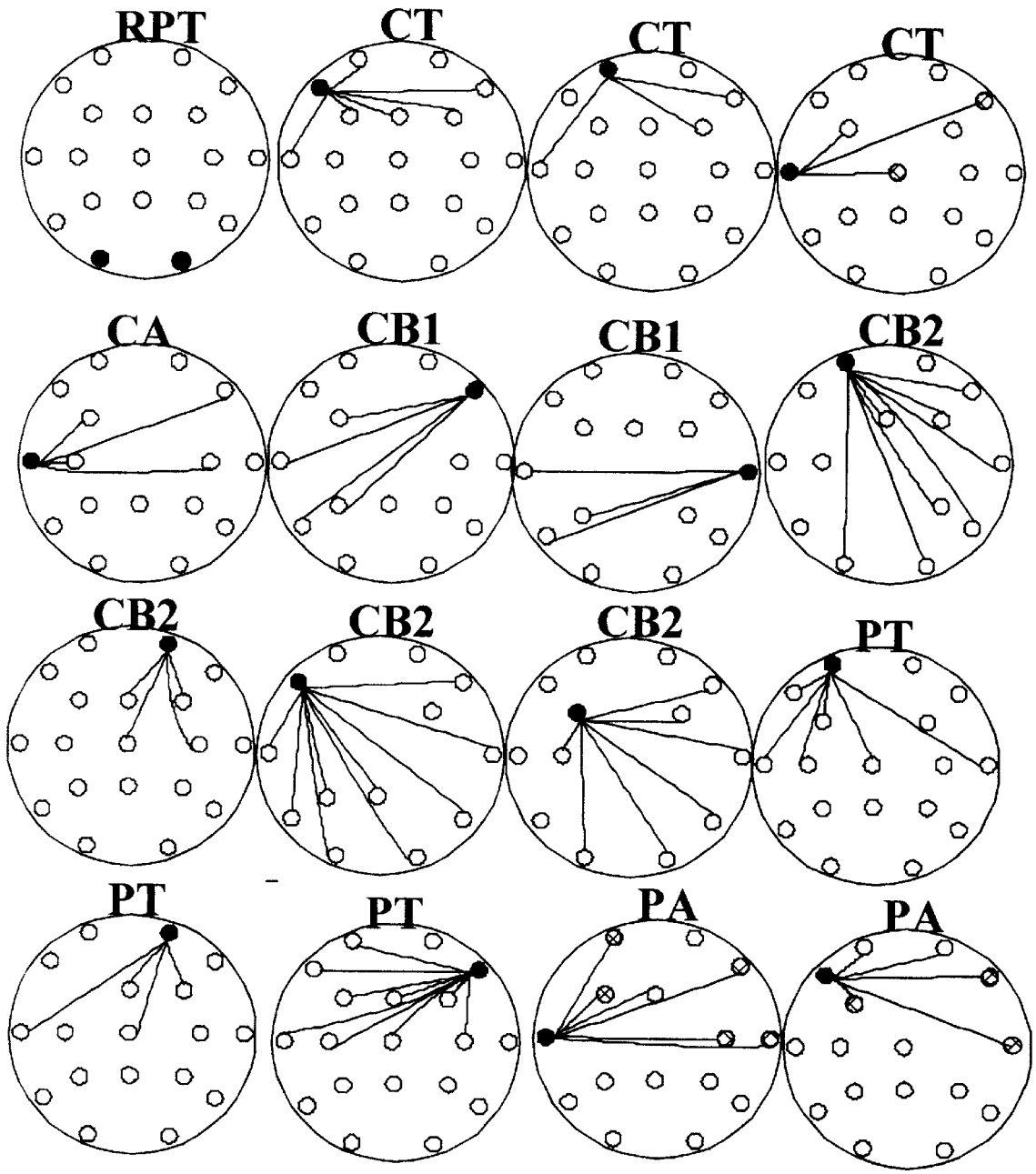
Figure 85A:
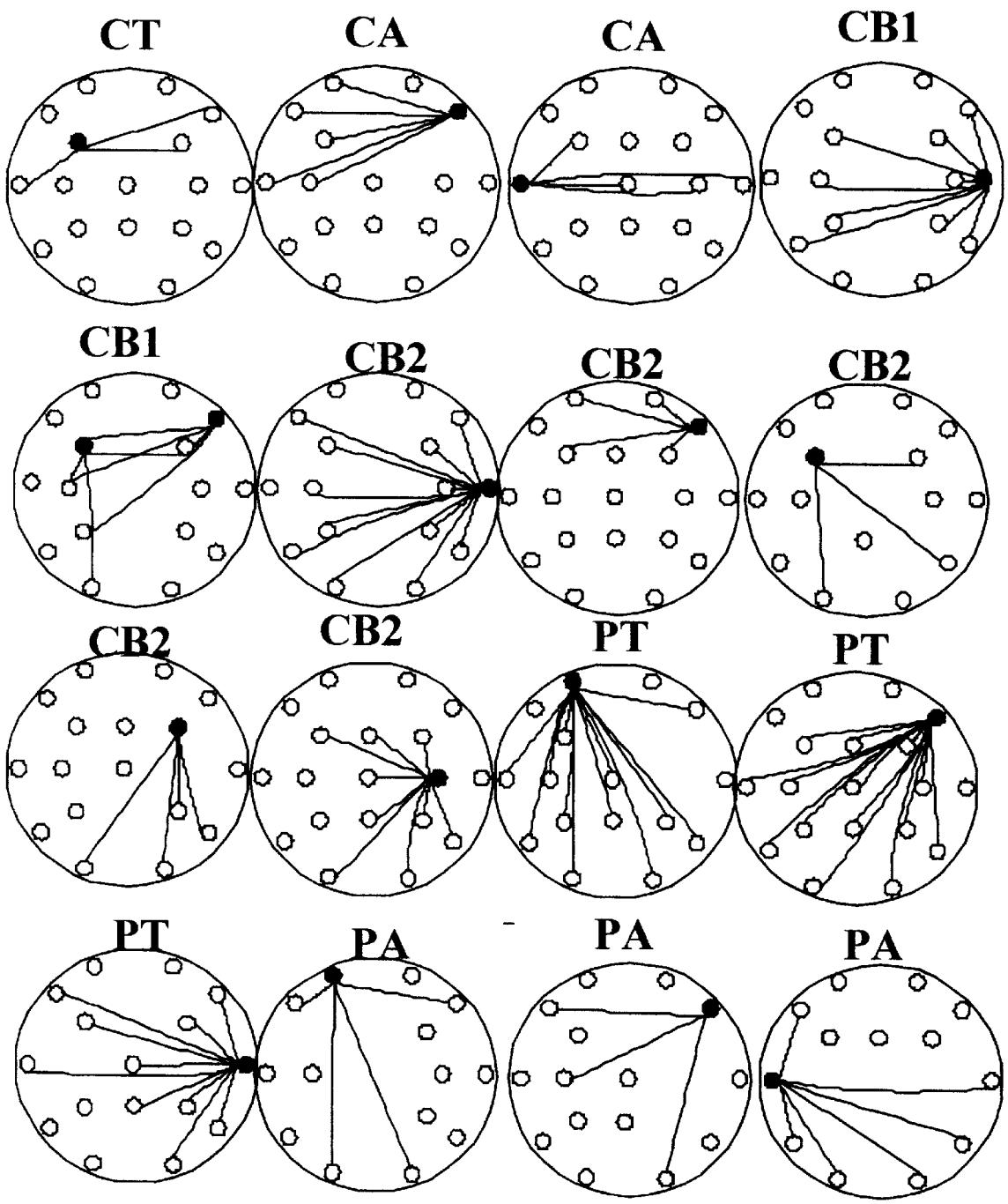
Figure 85B:
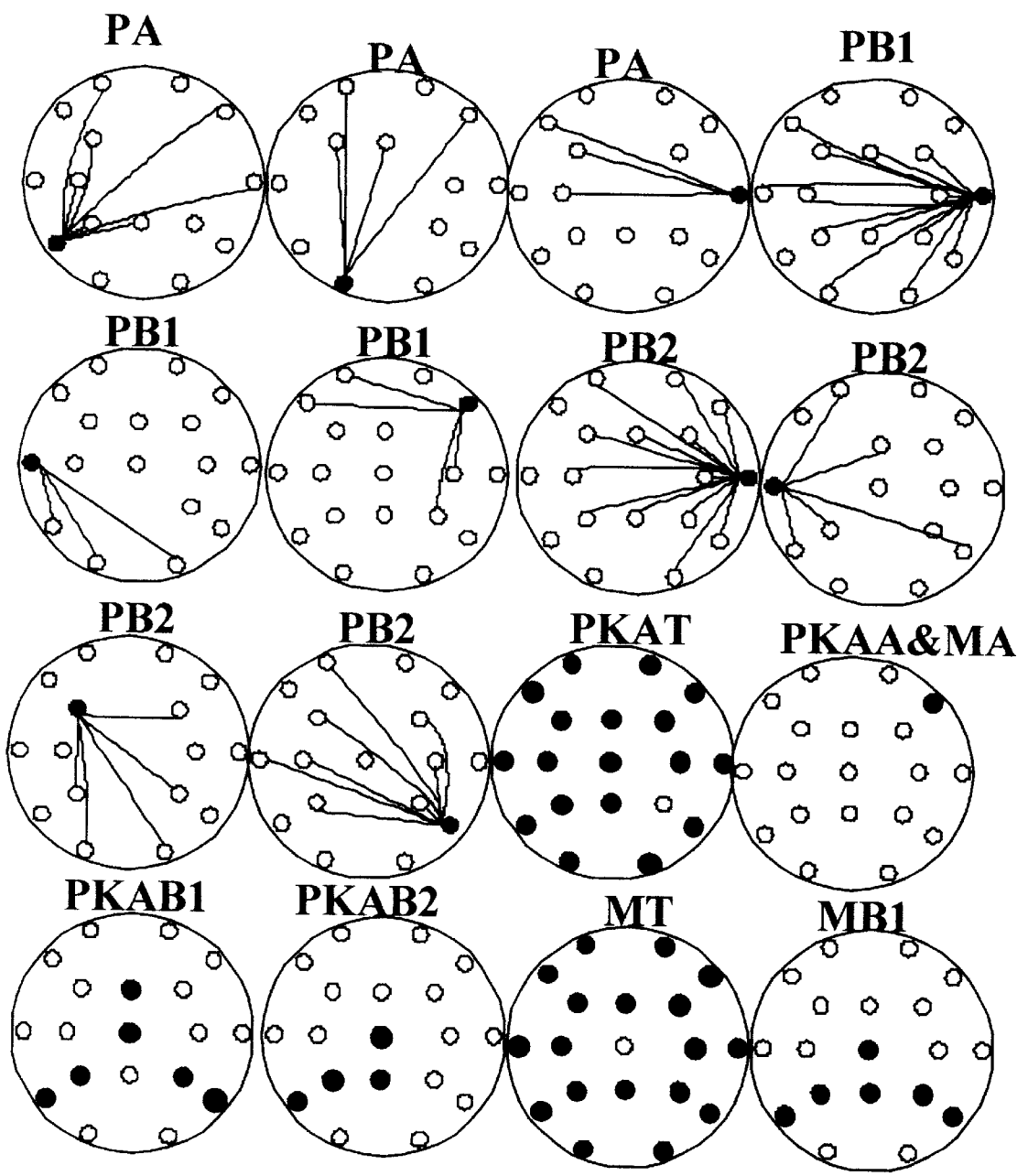
Figure 87A:
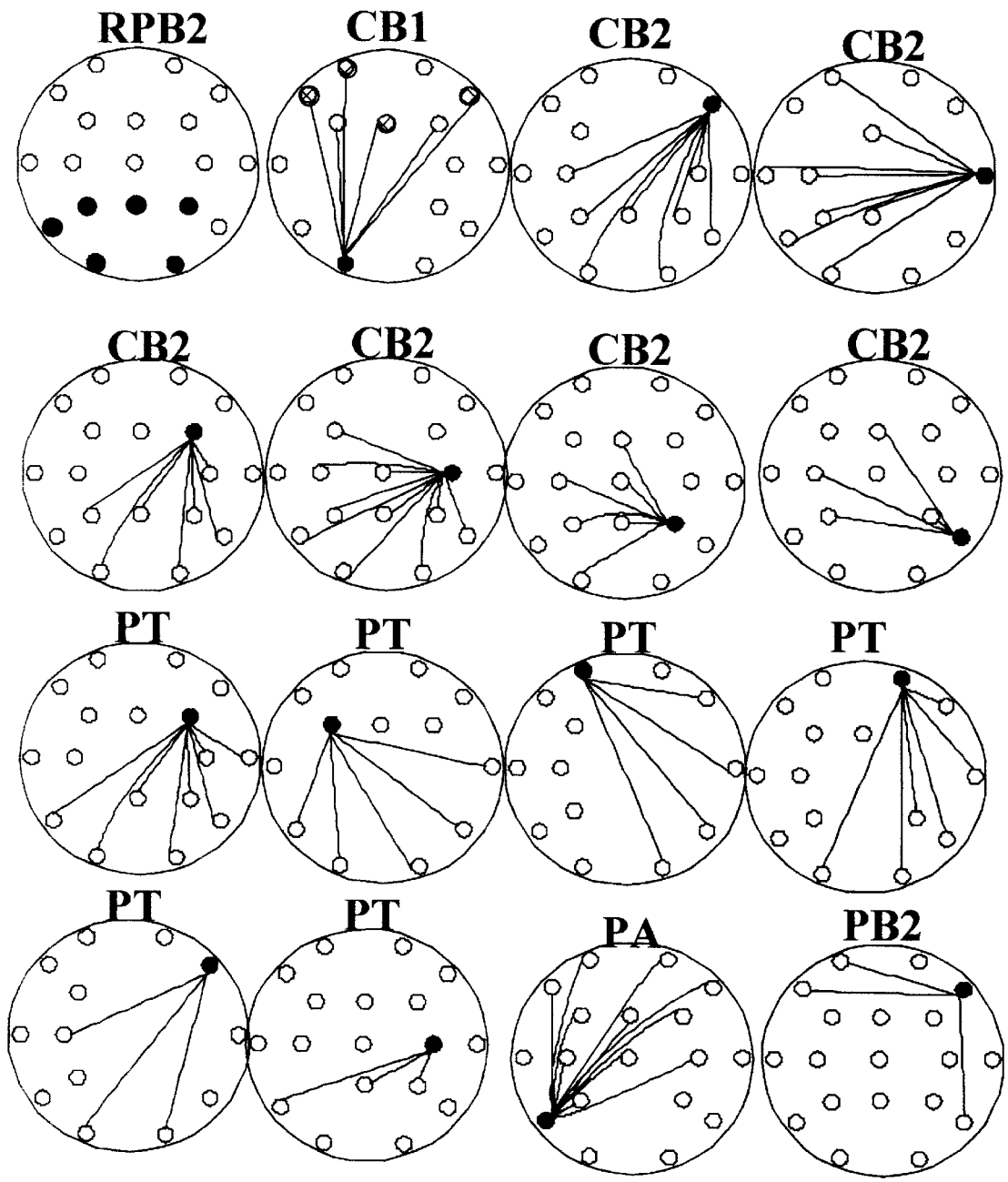

The FIGS. 15 and 16 (E #1 and #2) present the respective significant levels of activation for successful recall in terms of level of activation (FIG. 15) and degree of activation from the auditory attention task (FIG. 16). The lines represent the significant relationships between the variables and the total memory score (short and delayed recall). The Alpha projections from the T3 positions are the most significant contributor to performance for both level of activation and degree of activation. Frontal positions (coherence Alpha) are significant contributors to memory in terms of degree of activation from the auditory attention control condition, in addition the F3/F4 phase Beta1 projections. The stepwise multiple regression FIGS. 57 and 58 present the results of employment of these significant variables for both the level of activation and degree of activation analysis. The amount of variance that can be accounted for by these respective variables is 0.49 and 0.65 respectively.

The FIGS. 17 and 18 (F #1 and #2) present the significant levels of absolute activation and degree of activation from the subject's respective listening condition when the subject was quietly recalling (memory or recall) the paragraphs to himself. The correlations are between the variables and the total memory score. The T3 projection system, again, is the prime determinant of immediate recall in terms of level (Theta and Alpha). In terms of degree of activation from the listening condition, it is the relative power, magnitude, peak amplitude of Theta which is important as well as Theta (phase and coherence activity) emanating from the T5, Fz, Cz, & F7 position. This is reminiscent of the results of the Klimesch studies.

As to the function of Studying and recalling Korean figures, FIG. 19 represents the level of activation for the variables which had a significant correlation with total recall (immediate and delayed) during the 60 studying period the subjects were asked to study the figures. FIG. 20 represents the degree of activation from the visual attention comparison condition and the variables, which were significantly correlated with total memory. The frontal projection systems become important in the upper frequency bands in this difficult task (F7, F8 F3) as well as the T5 phase Alpha projection to the frontal positions. This may represent the subject's attempt to name aspects of the figures in terms from a visual attention condition, it is interesting to note right temporal and C4 projection system involvement.

Figure 21A:
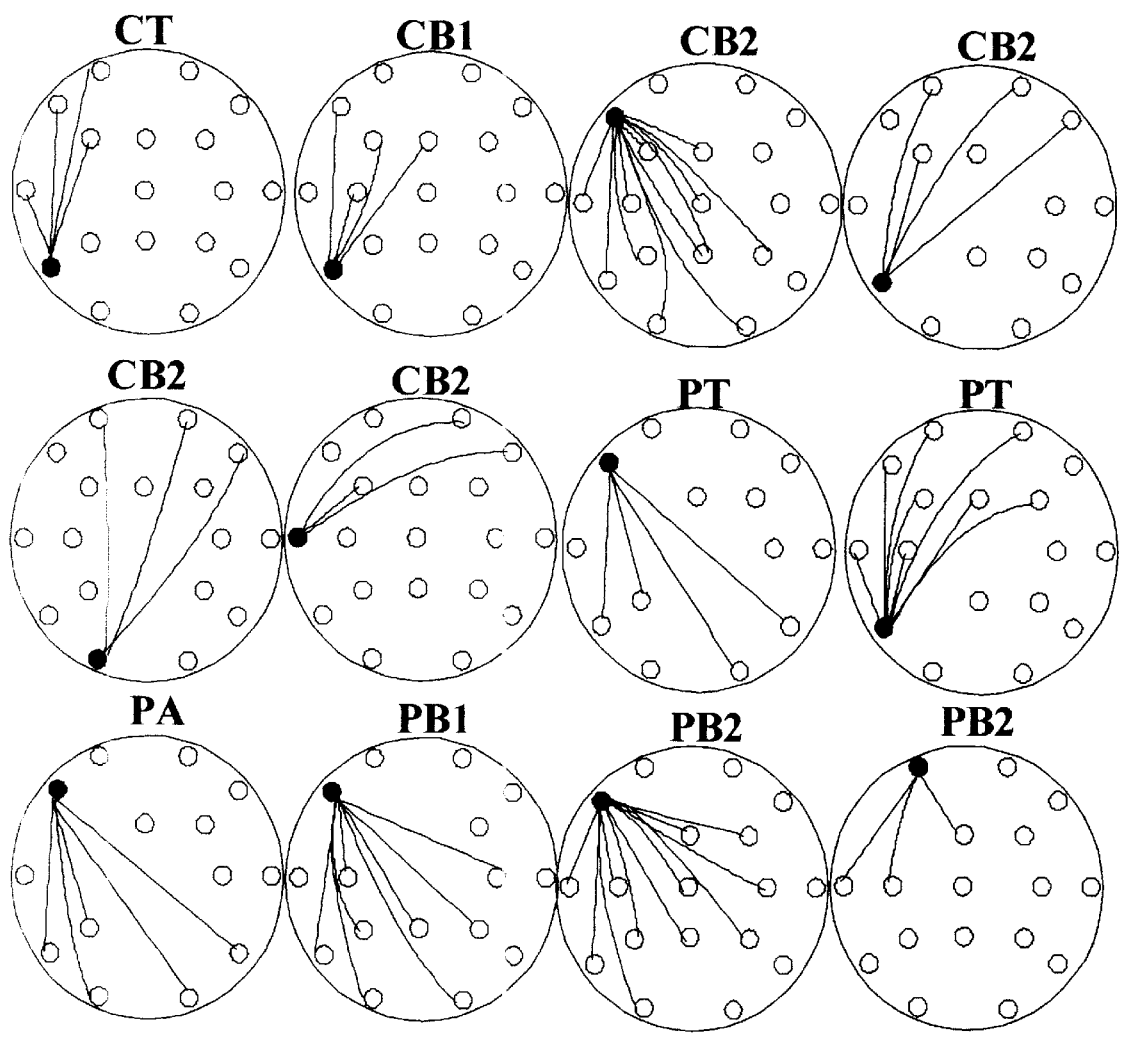
FIG. 21 represents the level of activation of the variables during the 30-second quiet recall period, which correlated with total memory.
Figure 21B:
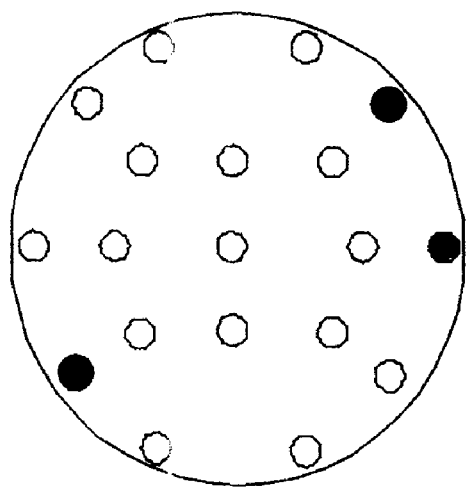
Figure 22:
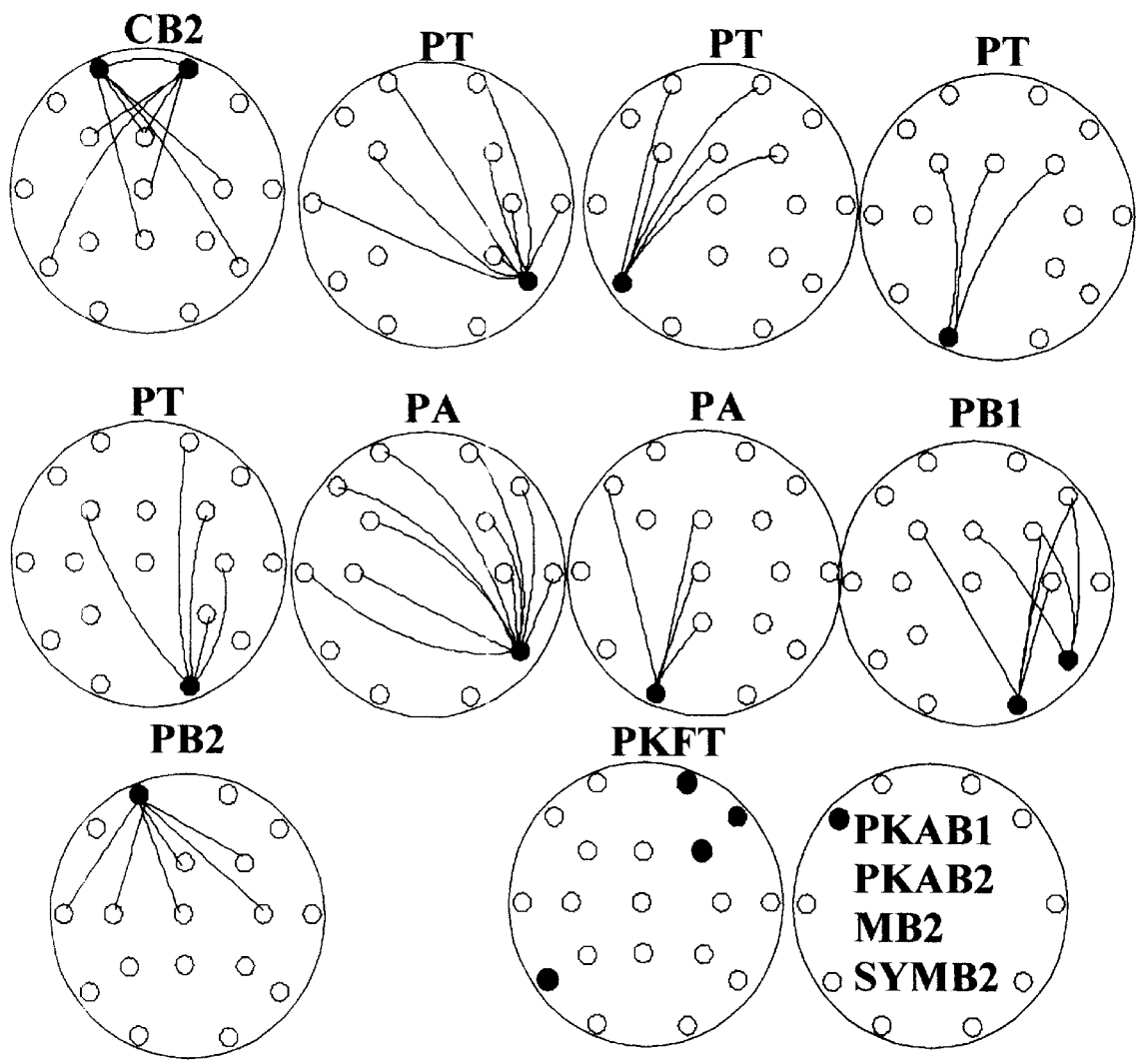
FIG. 22 represents the degree of activation (from eyes closed condition) of the variables which were significantly correlated with the memory score.

FIG. 21 (experiment coding H#1, #2) represents the level of activation of the variables during the 30-second quiet recall period, which correlated with total memory FIG. 22 represent the degree of activation (from eyes closed condition) of the variables which were significantly correlated with the memory score. Successful immediate recall of the Korean figures depended upon predominantly two locations (F7& T5) in terms of coherences of Theta Beta1 & Beta2 and phase activity in the Theta to Beta2 range. Even though this was the most visually oriented task, the predominant responsible projection systems involved the left hemisphere. Many of the subjects verbalized a verbal strategy in memorizing the figures. Interestingly however, the degree of activation from eyes closed comparisons resulted in more projections from T6,O1 & O2, which is more in line with the visual nature of the figures.

The following theory is the explanation of how the electro-psychophysiology of the mind works in memory situations. The theory will make references to the figures supplied in the Figures section.

The analysis will proceed from a backward framework. The theory starts with the assumption that both the level of the variable and the degree of activation of the variable are relevant to understanding the functioning of the mind. It further argues that there are three important systems involved in effective memory. The first system in the activity at time of input which involves the primary cortical entrance of information. In terms of auditory information it is the left temporal lobe (T3) and its ability to send signals to predominantly the frontal regions. More visually oriented information employs the T4 position (Faces, Reading) or moves posteriorly from the T3 position to the T5, O1 and O2 positions. The second system is the long distance frontal to posterior projection system which predominantly involves Beta frequency ranges. This is the system that sets up the hologram in the posterior portion of the head. The third system is the posterior projection system, which is involved predominantly in immediately recall situations and involves the sending of information to the frontal areas.

Starting with FIGS. 42 and 43 (experiment coding S#1, 2—delayed recall of word lists) information is being transferred from the T3-T5 positions predominantly in terms of the Alpha frequency and appear to create a hologram image in the frontal lobes. The activation variables also reflect the posterior area (in particular left posterior) sending Alpha and Beta1 frequencies to the frontal area. Frontal activity is evident in the Beta1 and Beta2 band in terms of connectivity to the posterior regions. Conclusion #1 is that the posterior (and T3) regions are the holders of the information and recreate the information by predominantly projecting to the frontal areas. The frontal projectors predominant purpose is either to stimulate the signals or create its own posterior hologram.

In the case of paragraphs as shown in FIGS. 44 and 45 (experiment coding T#1&2), it is again the temporal positions (T3 & T4) projecting to the frontal areas. In this case, however, there is a greater emphasis upon the projection system from the frontal areas in terms of coherence Beta2 (F1,F2,F7, F8). With the degree of activation variables, the pattern is repeated—high degree of coherence Beta2 activity originating from the front of the head. Thus, again, the frontal projectors appear to stimulate a hologram in the posterior portion of the head with a coherent beam.

In the case of names as shown in FIGS. 47 and 48 (experiment coding V#1,2) it is the T3 for level and T4 for degree of activation which determines recall ability. The frontal projection again project to the posterior portions of the head in terms of Beta activity.

In the case of reading it is the T3 position (level) to the frontal areas and the right frontal Beta projections to the posterior regions. In the case of the degree of activations it is the frontal projectors in terms of Beta and Theta activity. As in the words example, there are posterior projections from the left posterior in terms of Alpha which project predominantly to the frontal areas.

In terms of location of objects as shown in FIG. 51 (experiment coding X#1) it is again the left posterior (and T3) sending projections to the frontal areas. Degree of activation variables were not calculated for this task.

Therefore the long term recall of information involve long distance projection from the posterior portion (including T3 & T4) portion of the head combined with long distance frontal projection activity to the posterior portion of the head. It appears, therefore, that there are two projection systems responsible for memory functioning (anterior and posterior). The function of the anterior projection system is either 1—to stimulate the message from the posterior, 2—create its own hologram of the information of 3—provide a posterior hologram while the posterior projections create an anterior hologram. While logically one could argue that the posterior projection systems is stimulating the frontal areas, it is more consistent with other knowledge in the field is that the information is in the posterior portion of the head. The conclusion that long term information is held predominantly in the posterior portion of the head is consistent with our present knowledge from Neuropsychology. The posterior portion is the location of the information.

In examining the word lists (FIG. 10) the left temporal (T3) level is critical to success in terms of its role in sending, information to the frontal areas. Yet simultaneously it is the F7 position (Beta activity) which is signaling the posterior portion. FIG. 11 offers an additional clue as to how the operation works. This presents the one second period of time while the subject processes the word. In this Figure T3 no longer is relevant, as it is the F7 and F8 projection system to the posterior portion which is critical to success. Thus the information originally supplied to the frontal lobes is now being activity placed into long tern memory. FIG. 12 further argument. FIG. 12 present the activity during presentation and processing of the words and correlation with successful recall one half hour or more later. The figures indicate both the importance of the T3 Alpha generator and the frontal Beta generators (experiment coding F7 & F8). The silent recall of word lists (FIGS. 13 and 14—experiment coding D#1-2) reflect the three projection systems in action. It is the frontal projectors FIG. 13, in particular F7, with 5 projectors in different bands and relationships) combined with the temporal (T3) and some posterior projectors from the left posterior which produce success in recall. Of particular note in this example is the interference of activation variables (Beta1) on successful recall. Degree of activation variables point more strongly to the posterior projection system (left posterior—phase alpha). Of particular note in this example FIG. 14 is the activity of the right temporal position and coherence Beta2. While the input stage did not reflect any significant activity from the right temporal position, its relevance during recall is reflected in the significant correlations emanating from this position. There are two possible reasons for its involvement at this stage. 1—The band width was too broadly defined, thus hiding the power of a particular band among other bands which have little or negative relationships to success and 2—the projection system operates independently from input and serves as a stimulant to activity. This T4 system becomes relevant in the reading situation, where a similar pattern is observed—i.e. no relevance at input, but significance at recall time.

The input and recall of paragraphs (see FIGS. 15, 16, 17 and 18—experiment coding E#1-2, F#1-2) mirrors the theory, as the projections from the left temporal lobe are critical at the input stage. They serve possibly both to stimulate degree of activation variables from the frontal region to the posterior region (setting up of long term memory) and as a holographic image for the frontal lobe. Immediate silent recall, however, depends upon the same projection areas, but focuses on a lower band (Theta). Degree of activation variables (Figure F#2) point to the importance of the rear projection system. Of particular note in this example is the activity of the T4 position. While the level of activation variables at input indicated T4 as a negative influence on memory, at time of recall the same band (phase Beta2) from T4 becomes a positive influence. As with the previous example, word lists, the T4 position offers an intriguing problem.

The studying of Korean figures are shown FIGS. 19 and 20 (experiment coding G#1 & #2) present the input focus to a more posterior location (T5) than the previous purely auditory input which prompted T3 as the primary location of the input signal. The O1-T3 path has been demonstrated in research to contain the visual information pathway, with the O1 as the predominant visual receiving center. The lower pathway (O1-T3) has been empirically demonstrated to be involved in the naming of objects. When many of the subjects were faced with the Korean figures, they reported the use of naming the figures (according to the letters they looked like) to aid in memory. This activity calls into operation the T5 generator. The frontal projection system is operating from the F7 & F8 positions. The degree of activation variables point to the right temporal/central focus of activity predominantly focusing on the posterior portion of the head. The pattern, again, is similar to the auditory input tasks, where the primary receptive area sends signals to the frontal area, which then project back to the posterior generating a hologram in the posterior region. In the immediate recall task for the Korean figures, the T5 location again projects anteriorly which is accompanied by posterior projections. Degree of activation variables, as in other tasks, reflect predominant activity in the posterior regions (along the occipital-temporal pathways) projecting frontally.

Figure 26:
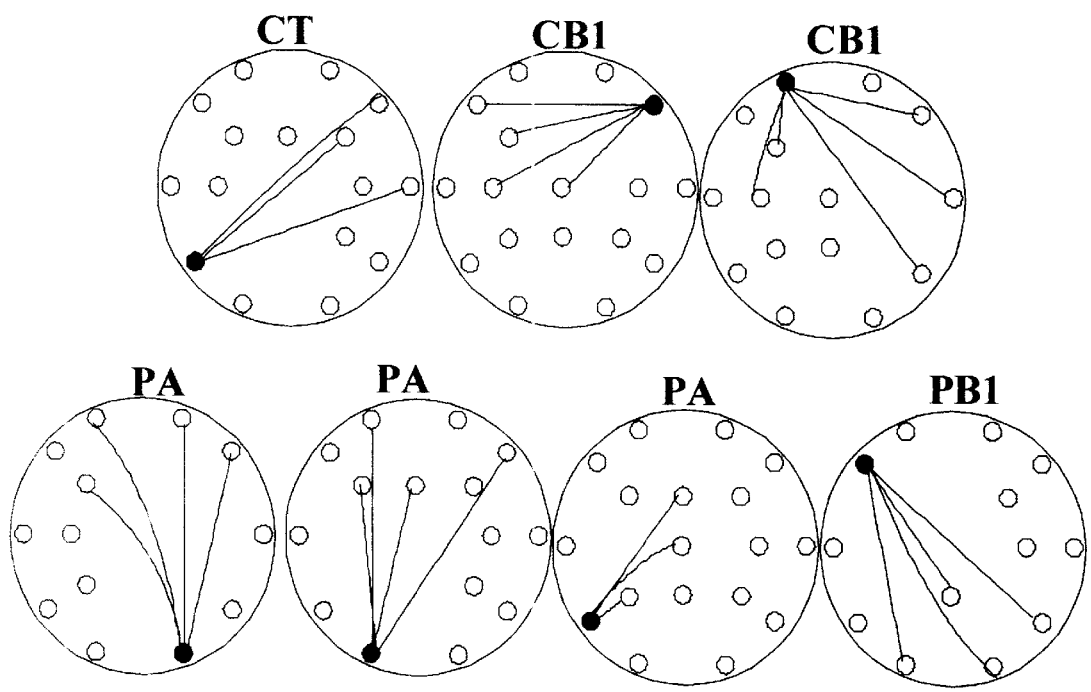
FIG. 26 presents the variable whose degree of activation from the eyes closed condition correlated significantly with total recall.

In the studying of names for faces as shown by FIGS. 25 and 26 (experiment coding J#1,#2) both temporal positions become involved in terms of frontal projections. The degree of activation variables in this example focus on the high frequency projections from the frontal areas. The immediate recall of names involves all three projection systems, temporal areas of T3 & T4, posterior (T5) and frontal (F7) in terms of absolute level of the variables. In terms of degree of activation variables the occipital and occipital-temporal (T5) pathways are the predominant posterior projection sources, while the frontal projection system focuses on F7, F8 and F1.

In the reading situation as shown by FIGS. 27 and 28 (experiment coding K#1,#2) the temporal projectors originate in T3 and T5, while the frontal originated from the left frontal area in terms of F3 and F7. Degree of activation variables focus on the posterior projection systems. The reading tasks both a subvocal auditory and visual task, thus the employment of almost the entire occipital-temporal pathway from O1-T3 and O2 makes conceptual sense. The immediate silent recall of the reading material involves predominantly right frontal projectors as well as T3 and T4 (absolute level, see FIGS. 29 and 30). The degree of activation variables heavily involves the temporal areas (especially T4) as well as right frontal projectors (4 of 5 frontal projection systems).

The role of subvocal speech and visualization during cognitive tasks requires addressing to fully understand the results. As analysis of the norms Figures demonstrate that there is are distinct patterns of activations during the tasks and it is predominantly in the upper beta ranges where the significance resides. The empirical fact (from this data) that these levels of activation have very little to do with successful memory requires elaboration. The subjects were all normal subjects. As indicated in the review of the literature there are clinical conditions (learning disabilities, etc.) where these variables are significantly lower than normals and do appear to have an effect of cognitive abilities. The restricted range of subjects in this study (all normals) rendered these variables not relevant to effective memory or cognitive performance, by and large. An analysis of 47 subjects was undertaken for the task of subvocal or silent speech. The norms (not presented) indicate no specific connectivity pattern. There was a significant (0.10 alpha) level of activation averaged across all subjects in terms of the activation at T3 (relative power of Beta2), peak amplitudes of Beta2 at T3, C4, T5, P3,P4, O1 and O2, and magnitudes of Beta2 at all locations except F2,F3,F4 and Fz. Symmetry values reflected a T3 and T4 focus of activity in terms of Beta1 and Beta2.

Thus throughout all the memory tasks, the general pattern remains the same. The input projection system is dependent upon the type of input with auditory information focused upon the T3 location and more visually oriented tasks employing the T5-O1-O2 T4 locations as a source for the projectors. The input projections are predominantly to the frontal lobes, which respond with projections back to the posterior region for future long term recall.

FIG. 23 (experiment code I#1) presents the significant correlations between the total recall (short and delayed) of the names of the faces and the period (15 seconds per association). FIG. 24 (I#2) presents the variables whose degree of activation variables, it was F7, FP1, FP2, F3, F4, & F8 projection system from coherence Theta to phase Beta2 which was relevant, in addition to both the T3 & T4 projection systems. The degree of activation variables focused on the FP1 & F7 locations.

FIG. 25 (experiment codes J#1, J#2) presents the significant variable whose level of activation correlated with total recall during the 30-second silent recall condition. FIG. 26 presents the variable whose degree of activation from the eyes closed condition correlated significantly with total recall. The level of activation variables indicated T3, T5 and F7 as the critical locations in terms of coherence Theta and phase Beta1. The degree of activation variables indicated a more posterior orientation as T5, O1 & O2 became important in addition to FP1, F7 & F8.

FIG. 27 presents the significant correlations between the total recall of the reading material and the level of activation of variables during the silent reading task. FIG. 28 compares the degree of activation from the visual attention condition and recall ability. Level of activation variables focused on T3, T5, F3 and F7 in terms of coherences in Alpha and Beta1. The degree of activation variables reflect a more posterior orientation to the projectors with O1, O2, & T5 (Alpha) becoming critical in successful reading. This is the third more visually oriented task (Korean, Faces) where the degree of activation variables originate in the posterior locations, the site of the occipital lobes. The shift from the left temporal (in the auditory input tasks) to the posterior locations (visually oriented tasks) reflects the nature of the input and further validates the results due to their consistency with known anatomical functions. As with auditory input, it is coherence Alpha to the frontal lobes which is the crucial band and relationship.

Figure 30A:
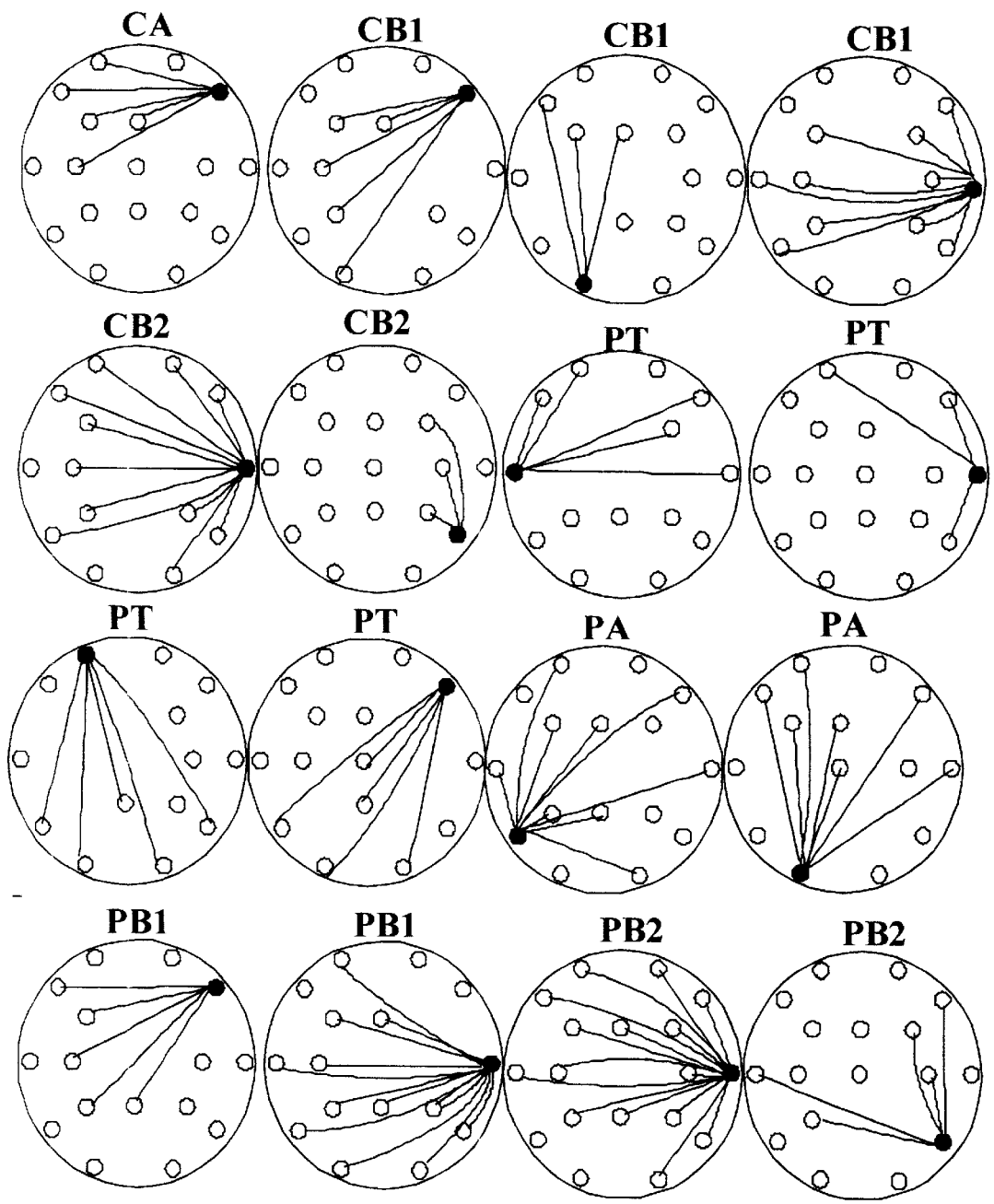
FIG. 30 presents the relationship between the degree of activation from the eyes closed condition and total recall.
Figure 30B:
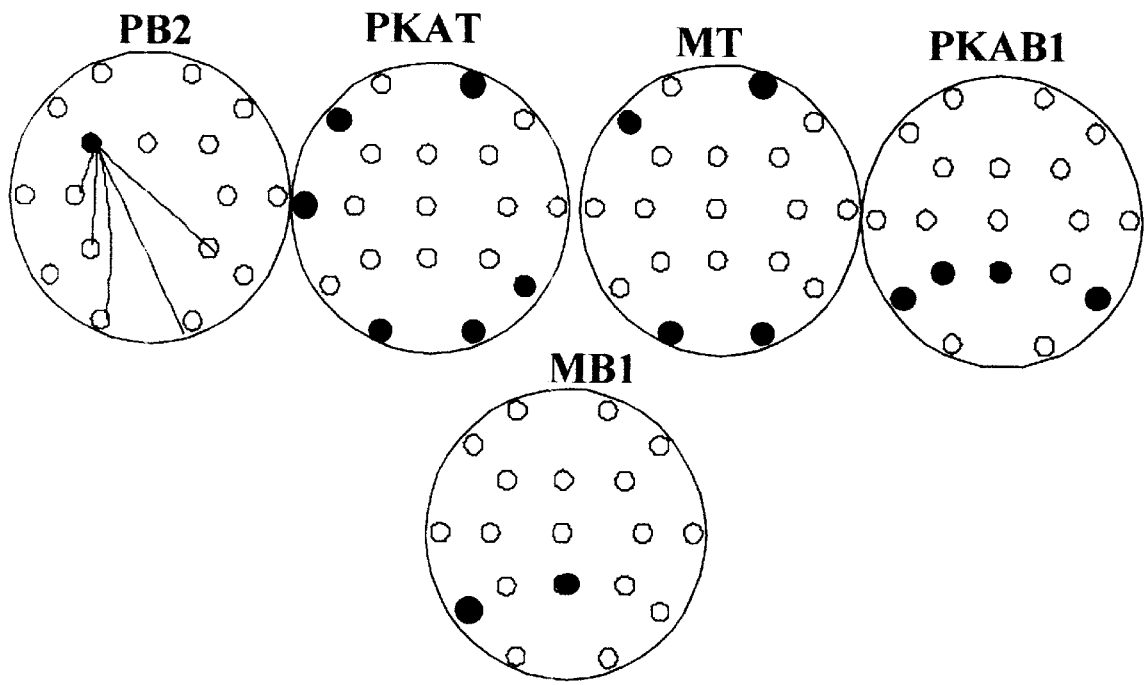

FIG. 29 presents the correlations between the absolute level of the variable during the silent recall period and total recall ability. FIG. 30 presents the relationship between the degree of activation from the eyes closed condition and total recall. In terms of level of activation it is predominantly frontal generators, with F8 involved in 5 of the 7 frontal projectors and T3 responsible for 2 of the 3 temporal projection systems (Phase Theta and Alpha). Similar to the immediate recall of auditory material, there is an important activation of the Theta band (frontally in terms of peak amplitudes and magnitudes. The degree of activation variables indicated 4 of the 5 frontal generators coming from F8, while 5 of the 6 temporal generators coming from T4(in the beta bands). Additional posterior generators included T5, O1& T6. The predominant recall focus was from the right frontal temporal areas, which accounted for 9 of the 17 generators. The dominant involvement of T4 in the recall phase with minimal indication of significance in the input stage presents an interpretive challenge, which cannot be understood at this point in the research.

Raven's—This figure presents the summed data for 9 of the eleven Raven's matrices (N=628). All the performances of all 9 tasks for all subjects were placed in one spreadsheet and a correlational analysis was conducted between the variables and success on the task. The figures represent the absolute degree of activation. The Raven's Matrices is generally considered the best non-verbal, culture free test of intelligence that is available. This aspect of the research is thus examining the operational definition of intelligence in action, which is of more theoretical validity to our understanding of intelligence. This is the first attempt to explore the electrophysiology of effective problem solving with such a large sample and with as pure a measure of intelligence as has been constructed to date. The results indicating the powerful role of the frontal generators (especially in the upper beta bands from the F7 and F8 position) is perfectly consistent with our previous understanding of intelligence as heavily involved in frontal lobe functioning. Of particular interest to note is the relative importance of posterior activation variables (peak frequency Beta1, peak amplitude of Alpha and Beta2). It is, as if, the frontal lobes are acting upon the posterior part of the head and, when successful, increasing the activity of these parameters. To put it simply, intelligence in action is revealed as the frontal lobes projecting to the posterior and the posterior activating.

Figure 33A:
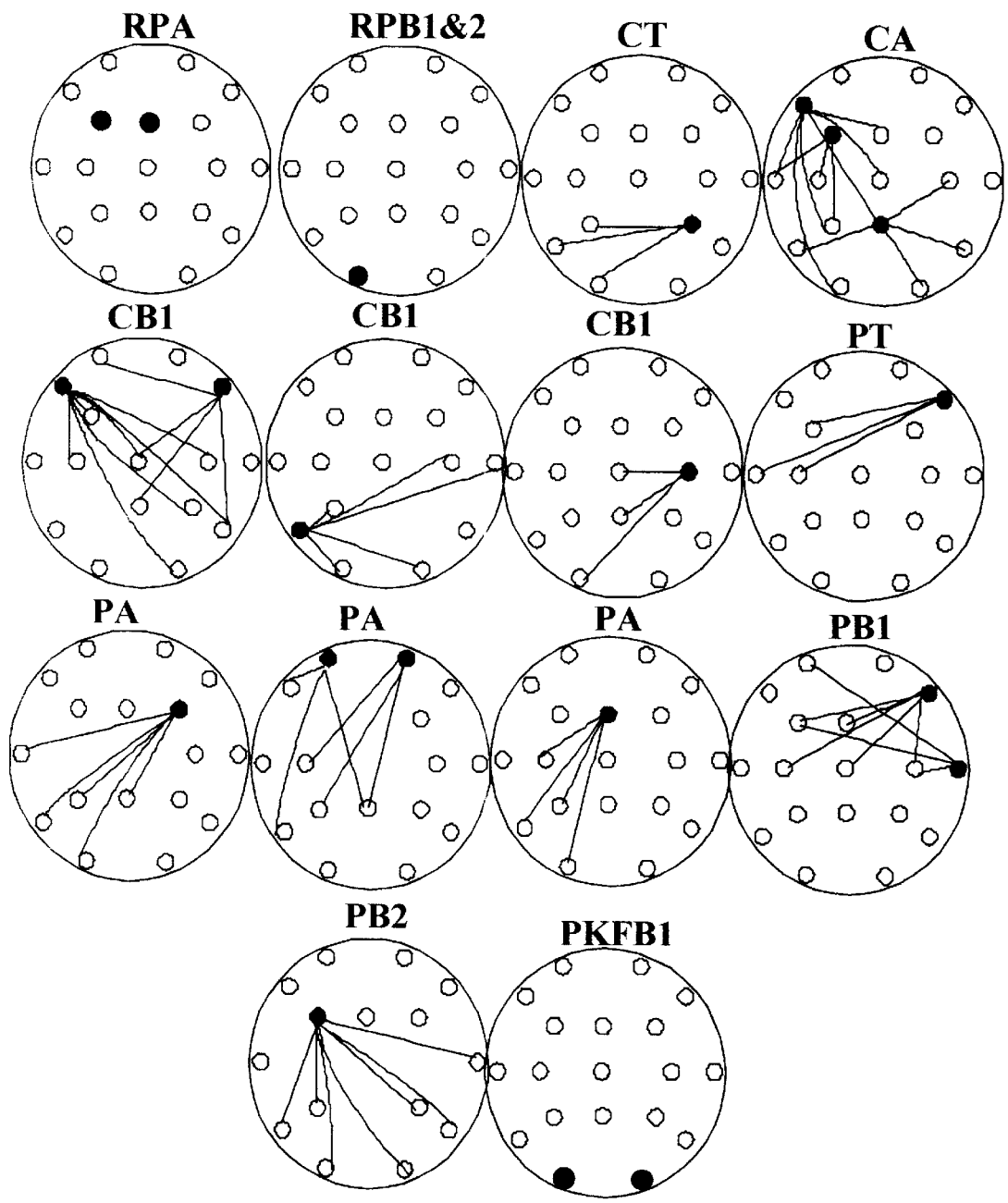
FIG. 33 presents the relationship between the degree of activation from the silent hearing of words condition to the internal spelling of words.
Figure 33B:
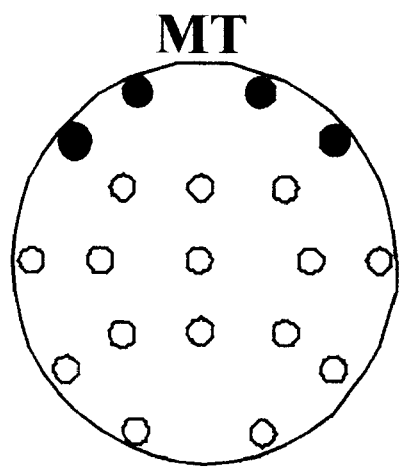

FIG. 32 presents the variable whose absolute level correlated with success the spelling task. FIG. 33 presents the relationship between the degree of activation from the silent hearing of words condition to the internal spelling of words.

The small sample size, due to changing of the word lists during the experiment, renders these results tentative. The best speller in the sample, however, had powerful projections from the T5 location ill the coherence Alpha range.

Figure 34A:
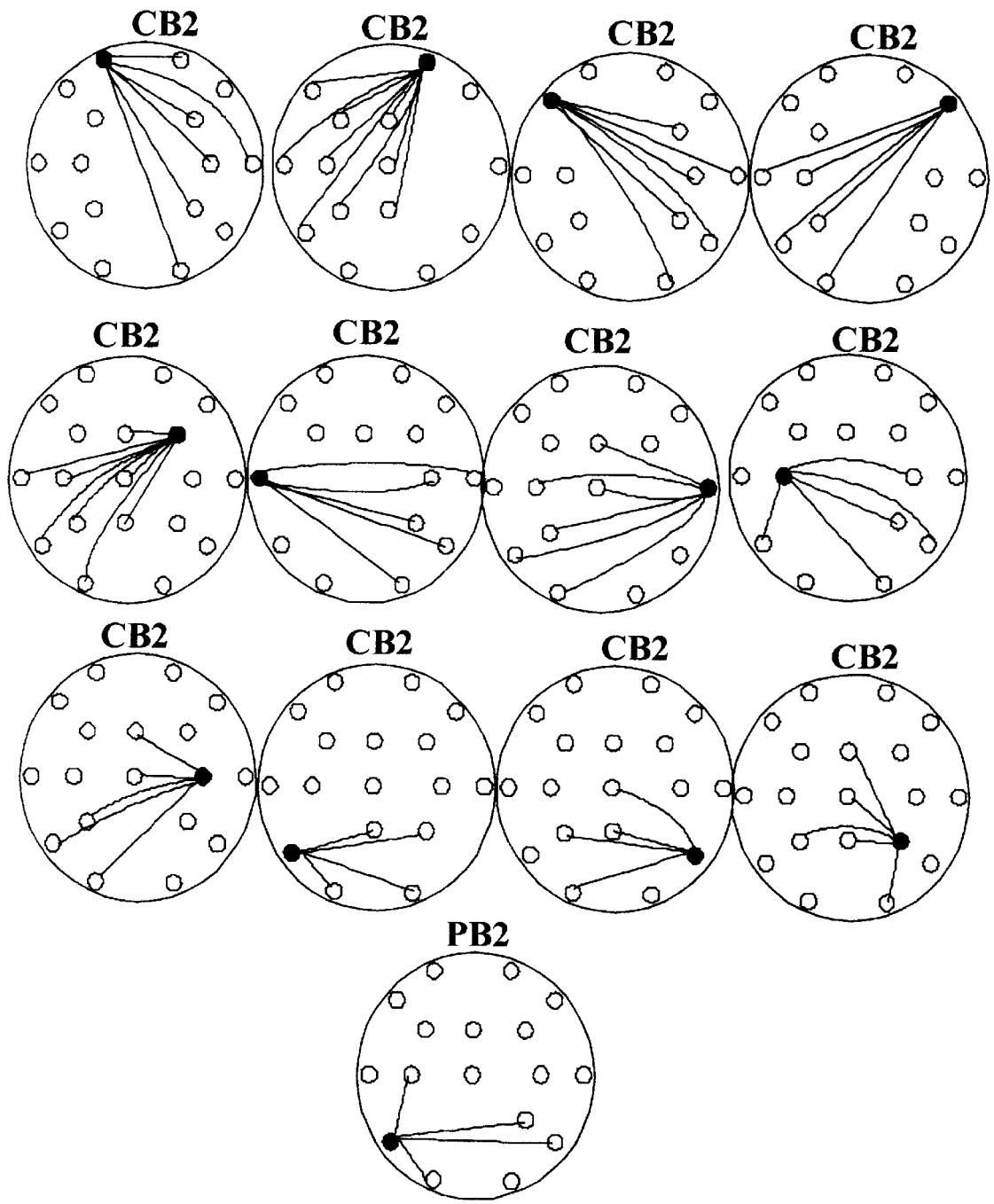
FIG. 34 presents the significant correlations between the absolute level of a variable and the degree of success on the 11 multiplication problems presented.
Figure 34B:
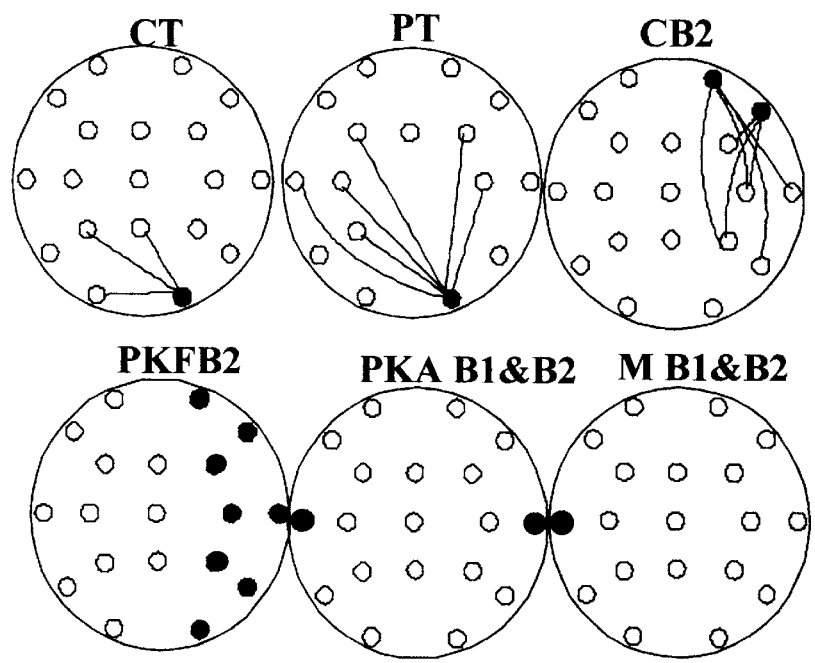
Figure 35A:
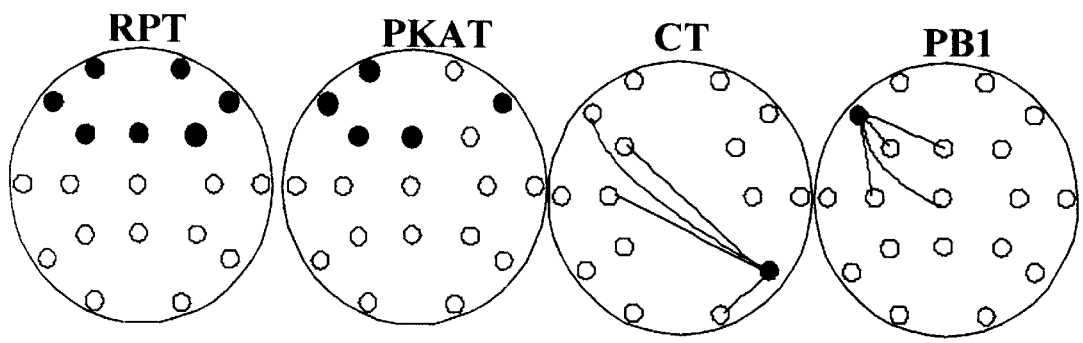
FIG. 35 presents the relationship between the degree of activation of a variable from the silent hearing of numbers and accuracy in calculation.
Figure 35B:
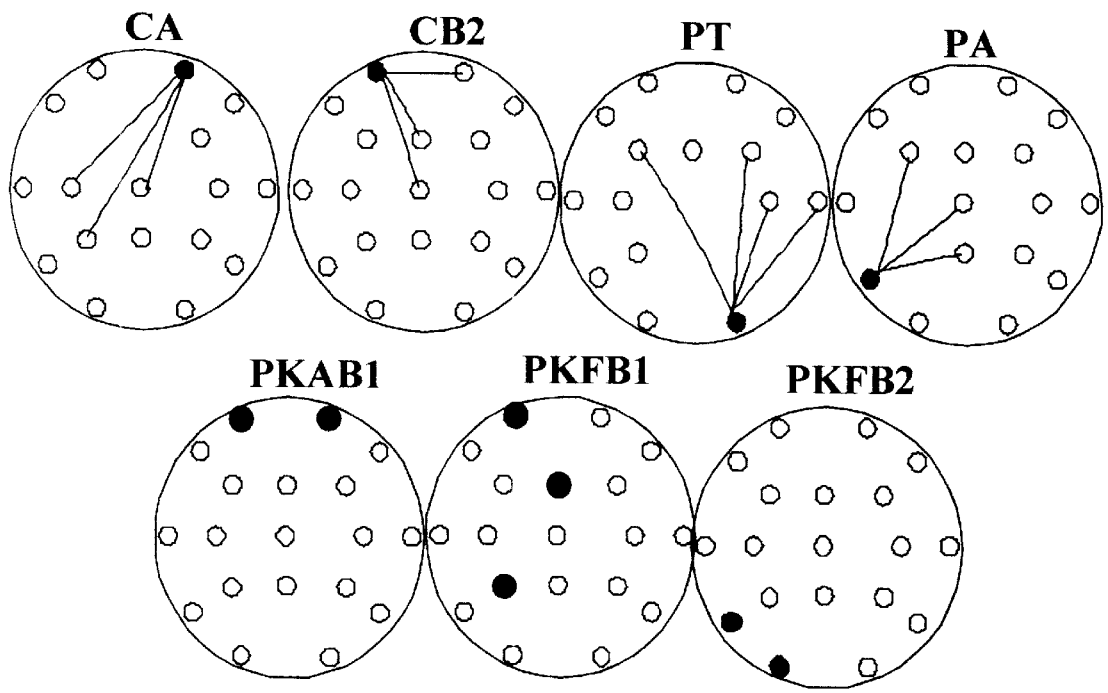

FIG. 34 presents the significant correlations between the absolute level of a variable and the decree of success on the multiplication problems presented. FIG. 35 presents the relationship between the degree of activation of a variable from the silent hearing of numbers and accuracy in calculation. The dominant frequency in this situation is the coherence Beta2 activity from the frontal and temporal lobes. The degrees of activation variables indicated the importance of the Theta activity in the frontal lobes and coherence of Theta from T6. It should be noted that this task is predominantly one of long term recall and not necessarily calculation ability, as the task involved single digits (i.e. 7×9=?). Subjects were only allowed 1–2 seconds to find the answer internally before another problem was presented, thus allowing little time for calculation.

Figure 36A:
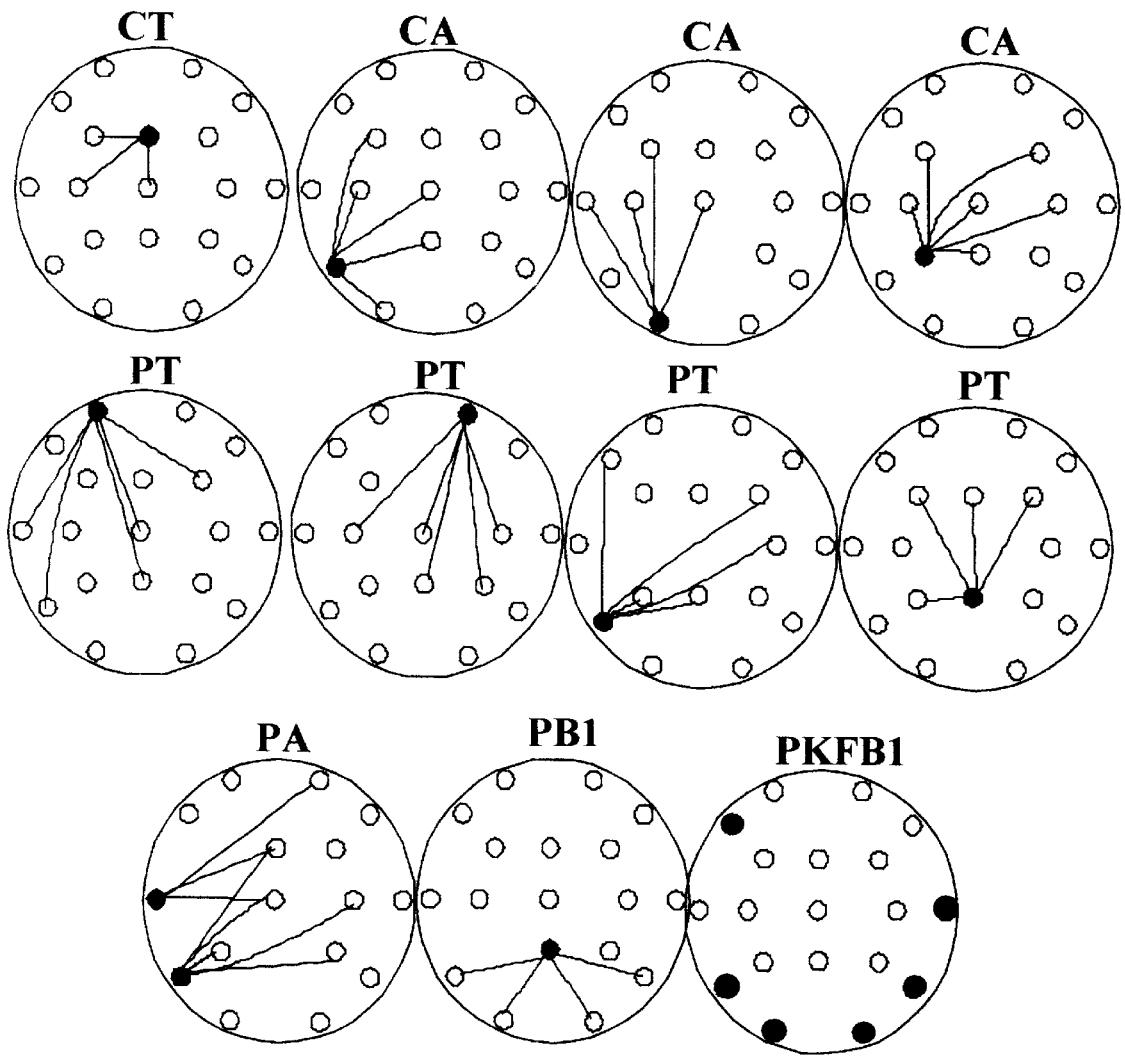
FIG. 36 presents the significant relationships betwveen the level of activation of a variable and the accuracy score for the 6 problems presented.
Figure 36B:
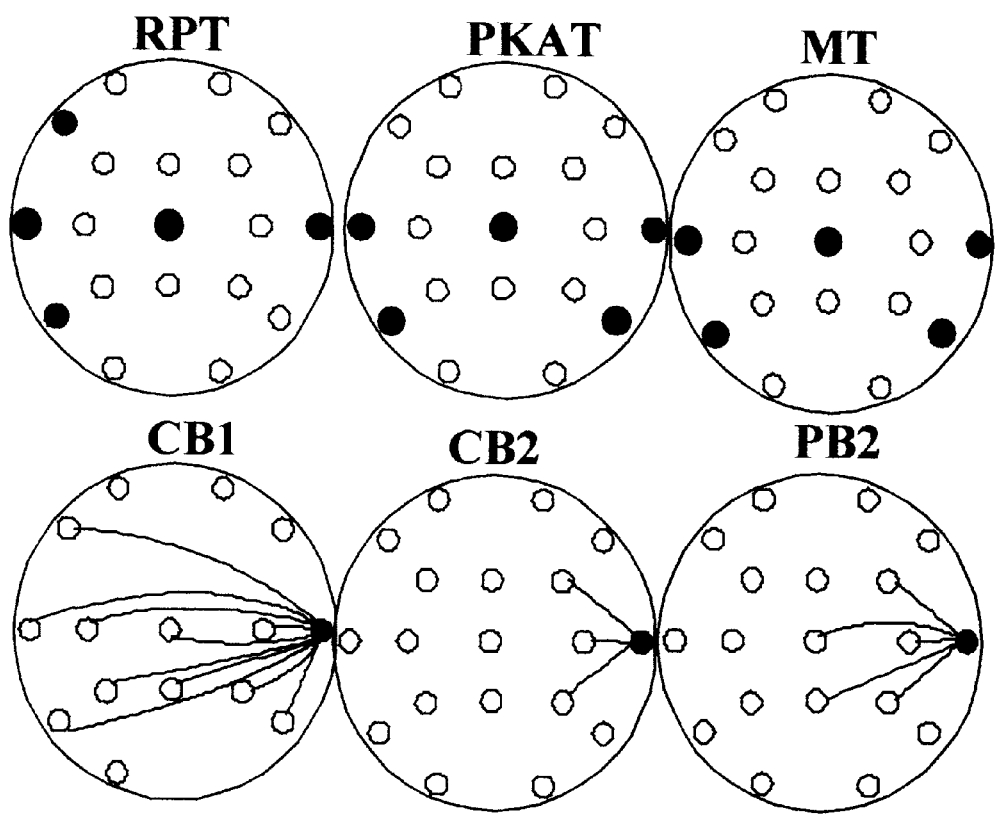
Figure 37A:
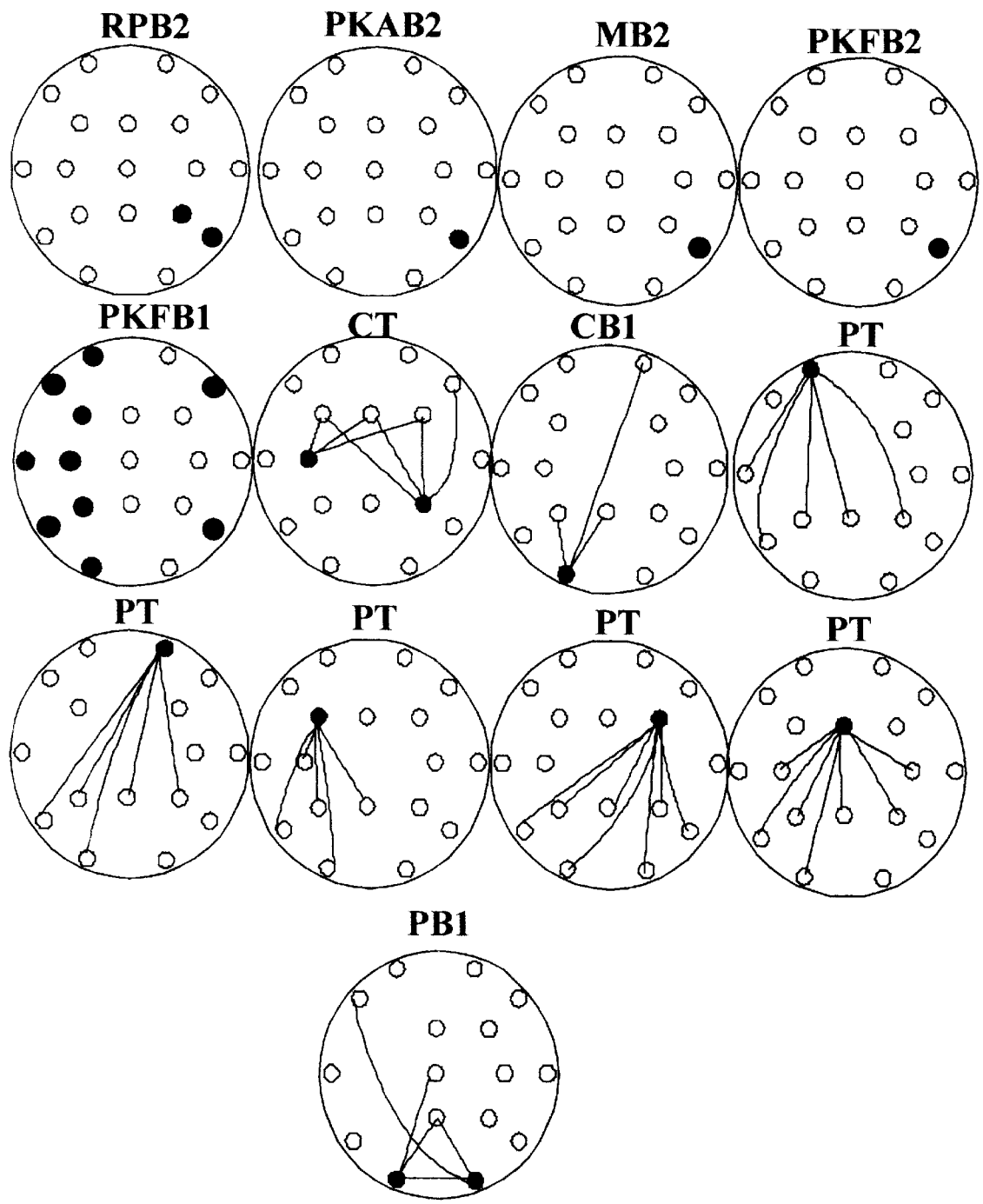
FIG. 37 presents the significant relationships between the degree of activation from the silent hearing of numbers and accuracy of calculation.
Figure 37B:
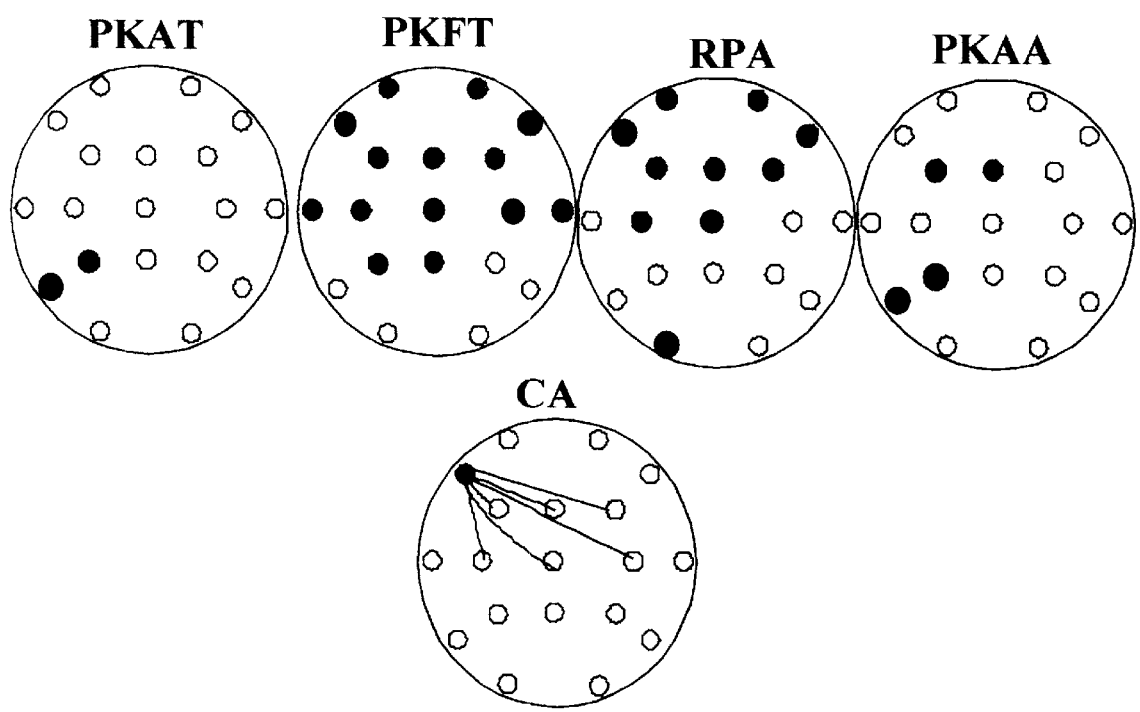

FIG. 36 presents the significant relationships between the level of activation of a variable and the accuracy score for the 6 problems presented. FIG. 37 presents the significant relationships between the degree of activation from the silent hearing of numbers and accuracy of calculation. The lower frequency ranges (Theta and Alpha, phase and coherence) dominated the projection systems responsible for success in this task, with 8 of the 10 coming from the posterior areas. Of interest to note in this task, is the appearance of the frequency Beta1 as an important contributor. Only rarely in these procedures were the activation variables of any significance. The degree of activation variables again supported the peak frequency of Beta1 (predominantly left hemisphere) as an important variable with the projection system now coming mainly from the frontal regions in terms of phase Theta activity. Of additional interest to note is the focus on the right posterior (in particular, T6, in the Beta2 band width) as an important contributor to success. Previous research has implicated the right posterior's involvement in spatial addition tasks. In this result, there were 5 activation variables which centered on that position.

Figure 39:
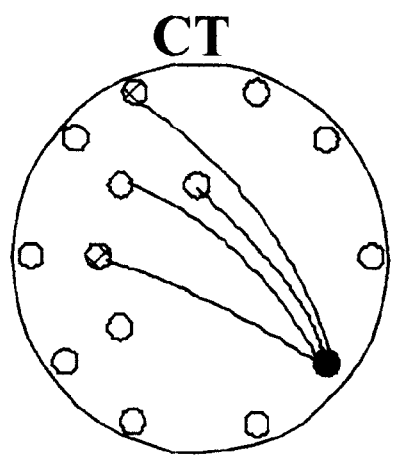
FIG. 39 presents the comparison between visual attention and silent reading of nonsense words.

FIG. 38 presents the relationship between successful silent reading of nonsense words (as measured by accuracy during reading outloud) and degree of activation of the variables displayed. The analysis of the relationship between degree of activation over visual attention did not yielded data only indicting negative relationships. The level of activation variables focused on the Theta and Alpha ranges (phase and coherences) and were approximately equal in terms of frontal and posterior generator involvement. FIG. 39 presents the comparison between visual attention and silent reading of nonsense words.

Figure 40A:
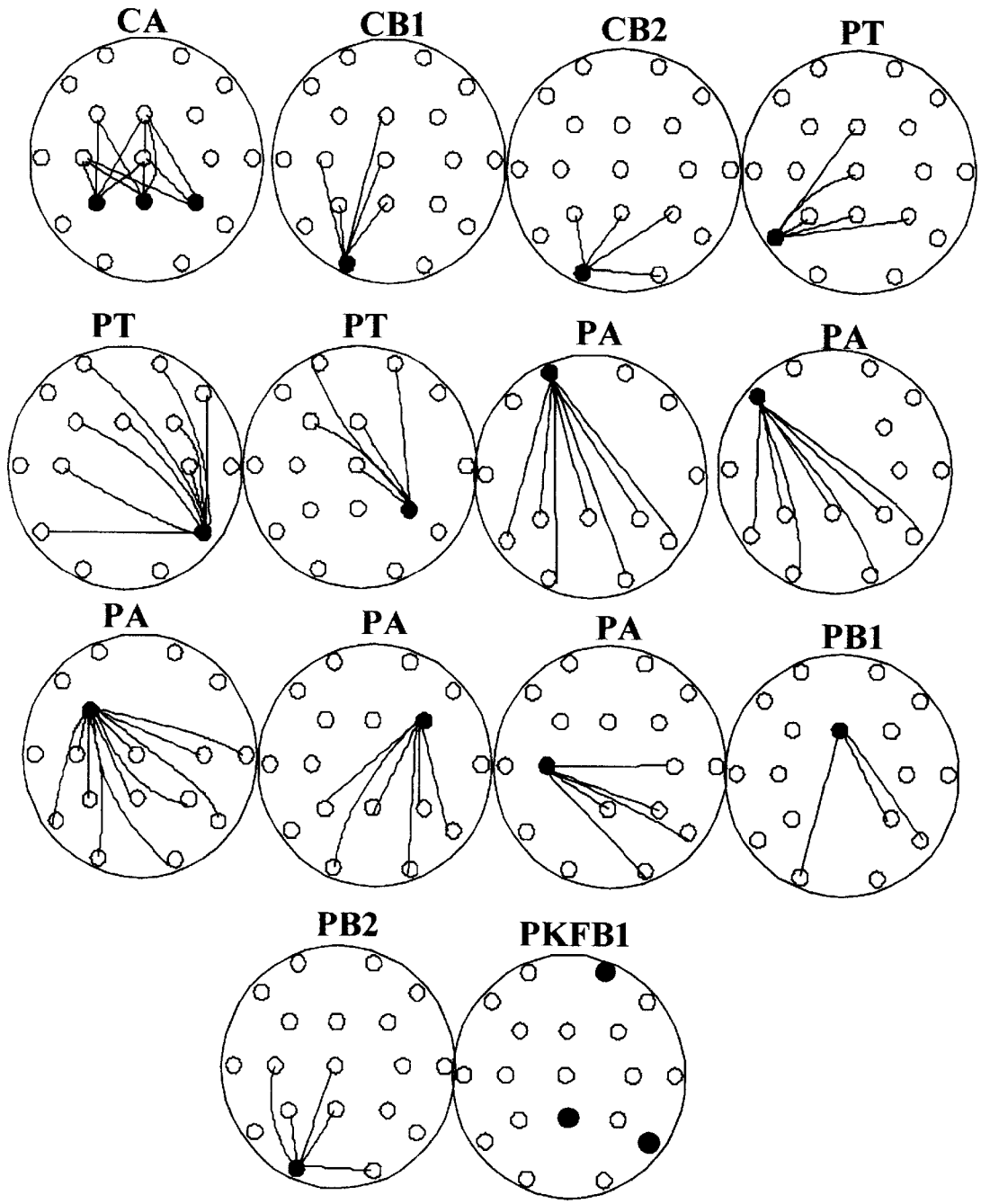
FIG. 40 presents the level of activation of a variable and success at reading the nonsense words.
Figure 40B:
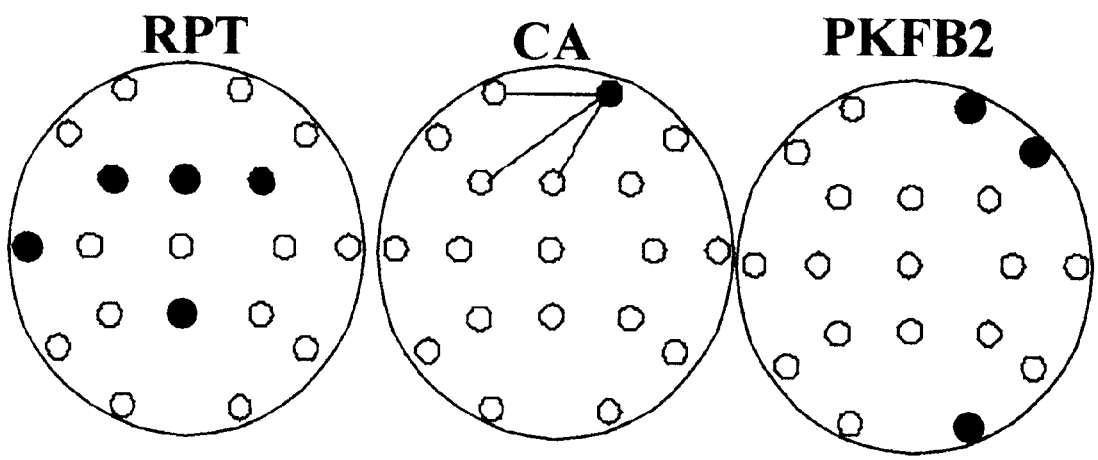

FIG. 40 presents the level of activation of a variable and success at reading the nonsense words. FIG. 41 presents the relationships between the degree of activation over the visual attention condition and accuracy in pronunciation. The level of activation variables focused upon posterior projections from the occipital-related positions (T5, O1, O2, T6) with 5 projections and the frontal generators predominantly emanating from the left frontal region (3 of 4 from frontal regions). The degree of activation variables focused on the posterior locations, especially O1 which had 3 systems and T4 which had 2 systems. This is similar to the reading and other visual tasks where the degree of activation variables focused on the posterior projection system.

FIG. 42 (experiment codes S#1, S#2) present the relationship between absolute level of a variable and degree of success in terms of delayed recall (not including the short term recall score). FIG. 43 presents the significant relationships between the degree of activation from the eyes closed condition and delayed recall ability. The level of activation variables focused on the T3 and T5 locations predominantly in terms of Alpha (phase and coherence). The degree of activation variables focused on a combination of frontal and posterior projection systems.

FIG. 44 presents the relationship between level of activation during the quiet recall period and subsequent recall outloud in terms of long term memory performance. FIG. 45 presents the relationship between the degree of activation from the eyes closed condition and long term recall. The level of activation variables focused upon the frontal projectors with F7, FP1, FP2, and F8 being central along with the temporal projectors (T3 & T4) in terms of coherence Alpha and phase Theta. The degree of activation variables had 6 projections from the frontal region in the beta bands (in particular coherence Beta2). There were three projection systems in the posterior region which involved T6.

FIG. 46 presents the significant relationship between the absolute level of a variable and successful recall of the Korean figures. The level of activation variables did not yield a strong pattern to the results, while the degree of activation indicated strong T3 involvement in terms of Theta and Alpha activity (phase and coherence).

FIG. 47 present the significant relationships between the level of a variable and successful recall of the names of the faces presented in the beginning of the experimental procedure. The presence of only one occipital projection system (O2, coherence Beta2) in a strong visual task and the interference of right posterior activation, where previous research has indicated involvement in face recognition is of some theoretical importance due to the conflict in findings. FIG. 48 presents the comparison between immediate recall of names and delayed recall. The purpose of this analysis was to determine the effect of time on recall approach. The correlations represent the greater the degree of change being associated with greater recall ability.

FIG. 49 presents the significant relationships between the absolute level of a variable and subsequent recall ability. FIG. 50 presents the significant relationships between the degree of activation from the eyes closed condition and recall ability. For the coherence Alpha figure, the level of significance was lowered to 0.10 and the number of variables required for significance raised to four. As in the immediate recall of reading material, the right frontal (F8 and F2) becomes important, while the T3 coherence and phase Alpha variables, again, contribute to success in terms of level of activation. The degree of activation variables indicate a roughly equal balance between posterior and frontal projection systems with the posterior dominated by phase Alpha from T5 and O1. The frontal generators focused upon the right frontal with 6 of the 8 frontal projections coming from the right frontal.

FIG. 51 presents the significant relationships between the level of a variable and subsequent successful recall of the object's location in the room. As in previous examples, it was the left temporal positions (T3 & T5) as well as other left posterior locations (P3 & O1) in the coherence Alpha range which were critical for recall. This was the first time that the activation variables in the Alpha range became important for recall (predominantly in the frontal region).

FIG. 52 presents the significant relationships between successful recall of intentions and the level of a variable. Only the level of peak frequency at T5 and Cz offered any useful information regarding recall of a "to do" list.

Figure 53:
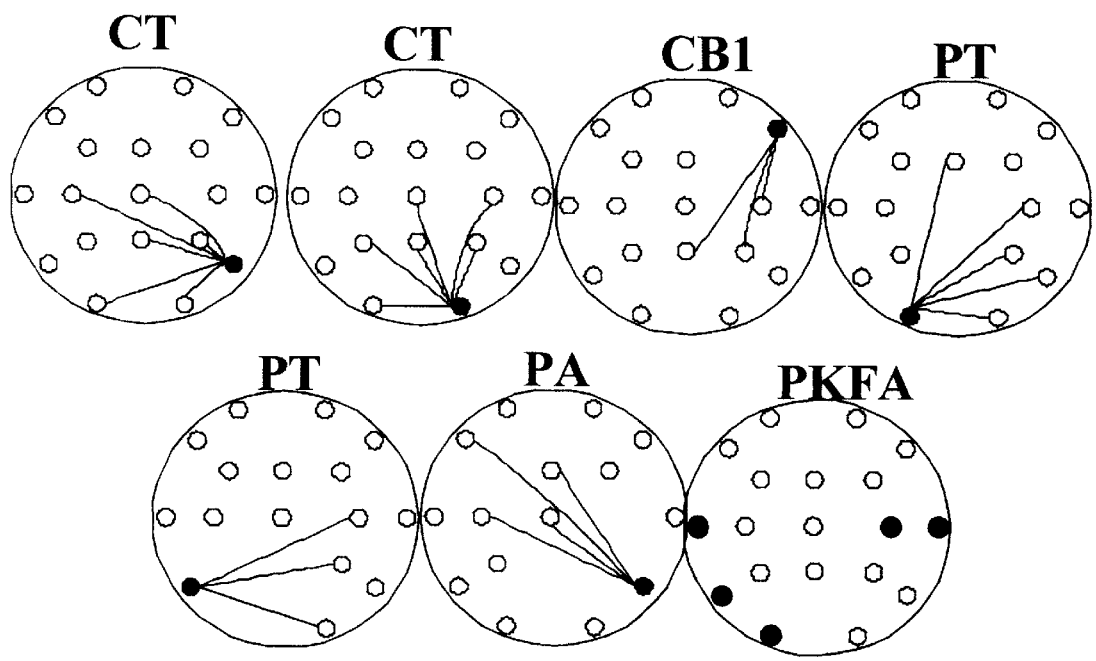
FIG. 53 presents the results of the level of activation with respect to the autobiographical questioning. The results only reflect negative influences on recall.
Figure 54A:
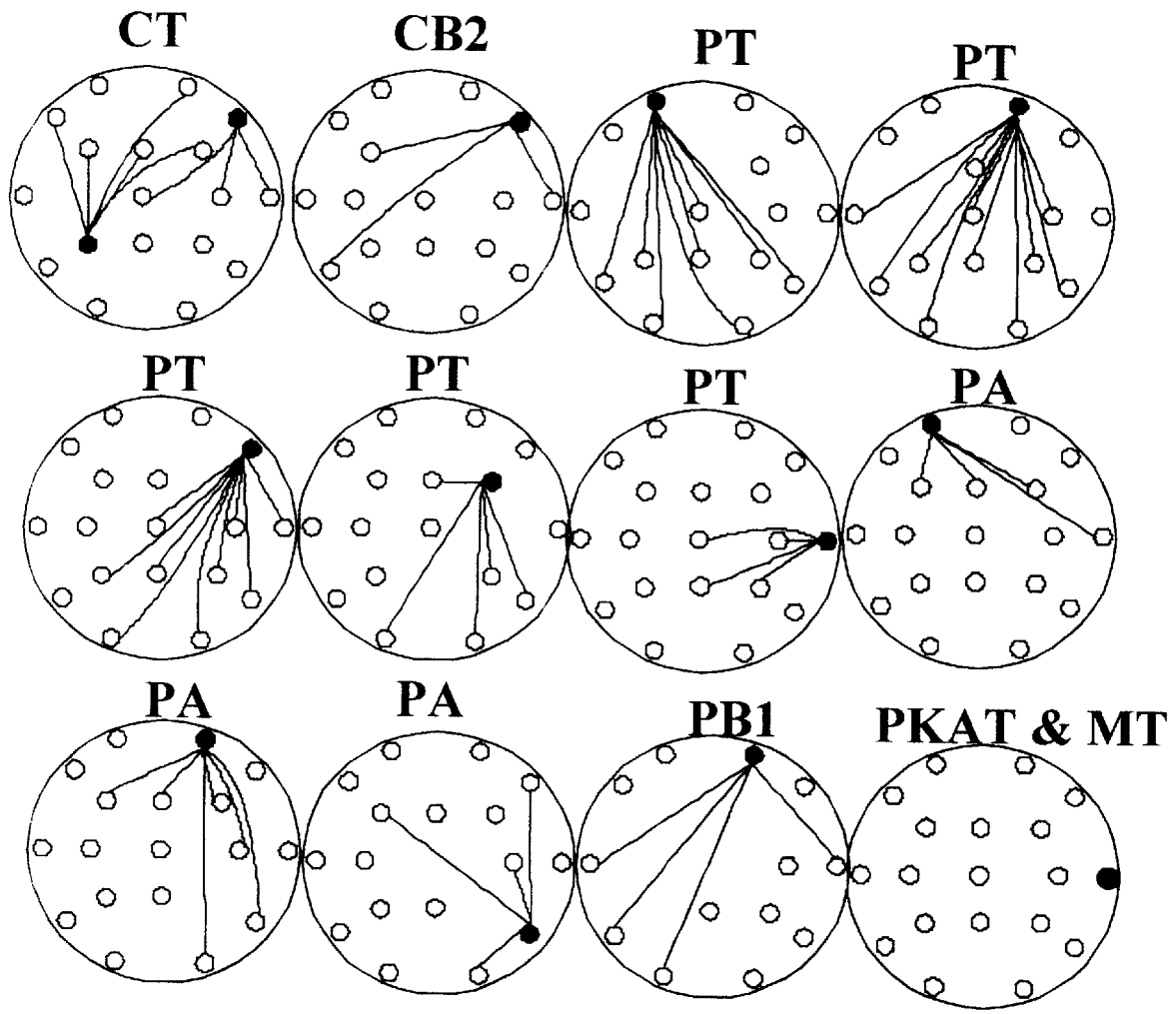
FIG. 54 shows the significant correlations with degree of activation from the eyes closed condition. The strongest effect is from the frontal Theta phase generators in terms of effectiveness of recall.
Figure 54B:
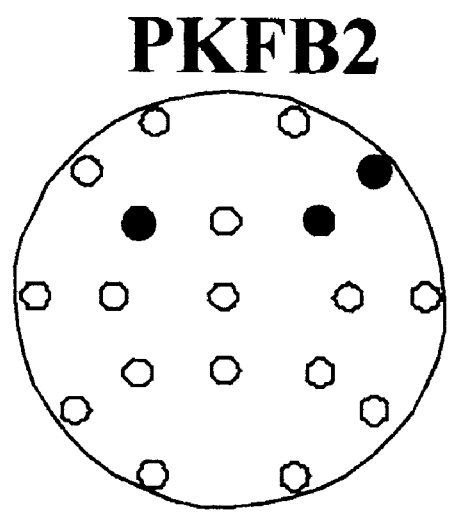

FIG. 53 presents the results of the level of activation with respect to the autobiographical questioning. The results only reflect negative influences on recall. FIG. 54 shows the significant correlations with degree of activation from the eyes closed condition. The strongest effect is from the frontal Theta phase generators in terms of effectiveness of recall.

Figure 55:
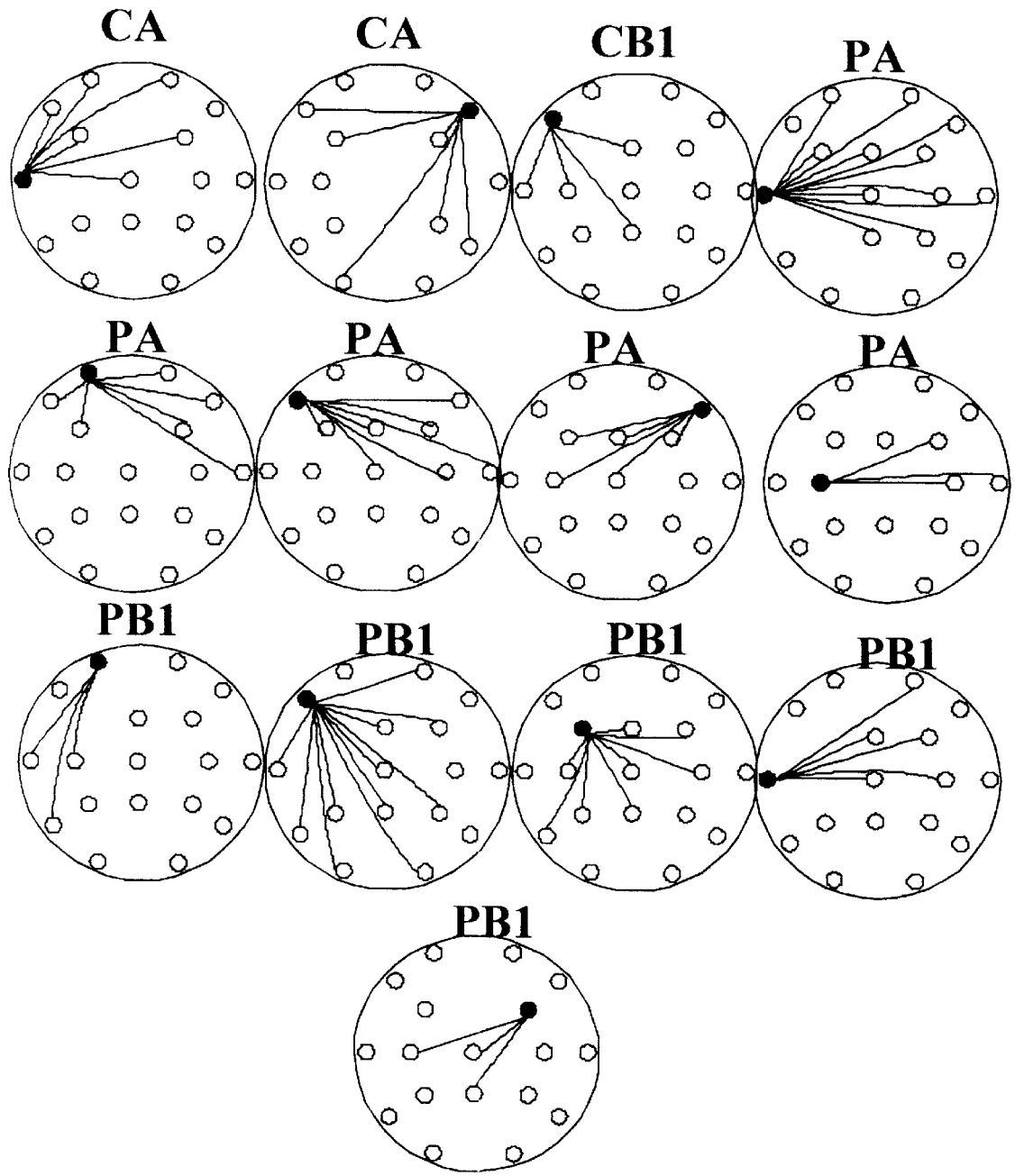
FIG. 55 presents the level of activation variables which correlated with earlier childhood memories.
Figure 56:
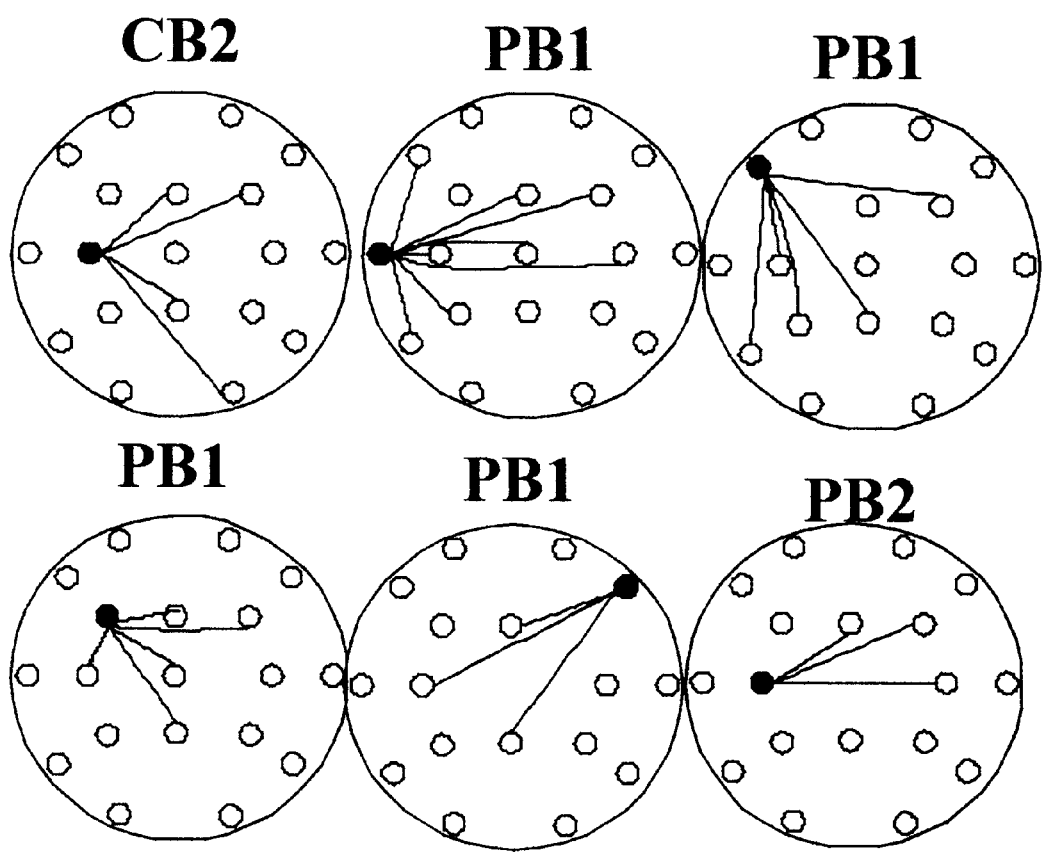
FIG. 56 presents the degree of activation variables and their relationship to earliest memory.

FIG. 55 presents the level of activation variables which correlated with earlier childhood memories. The higher the variable the earlier the childhood memory. The correlation between the age of the subject and the age of the memory recalled was non-significant and negative. FIG. 56 presents the degree of activation variables and their relationship to earliest memory. The data relied upon the subject's estimation of his age at the time of the incident they recalled. The results of the level of activation analysis reflected 3 generators from the T3 position and 9 from the frontal areas. The degree of activation measure reflected 1 from the T3 position and 3 from the frontal lobes.

FIGS. 179 to 194 present the results of the analysis of the activation of bands from the respective comparison conditions (norms). They are presented to compare to previous research regarding degree of activation and to relate other contributing factors to the results, such as visualization, subvocal speech. They do not present relationships to successful performance or recall. They present what happens to the brain when engaged in various tasks (as compared to a relevant alternative states of mind). Significant differences were those in which the T value exceeded 2 across a group of 45–50 normal subjects over the age of 14. The T value was chosen as it represents for each subject the degree of activation from the comparison and incorporates the sample size in its analysis. Not all comparisons were conducted. As can be discerned from the figures, there is a clear pattern across almost all tasks. Locations, in which there was evident a much higher T value than the other positions, are indicated in red. The symmetry figures employ a red line for indication of significance. The color red is chosen for display purposes and not to indicate any particular degree of relative significance. The symmetry measure is determined by summing the symmetry measure of a particular location to every other location in the head.

As can be discerned from the analysis of these figures, the general pattern is activation in the higher frequency range (32–64 Hz) in terms of amplitude, relative power and magnitude. There is no common pattern of activation of the coherence figures except for studying names, reading silently, and reading nonsense words outloud. Reading outloud produced a similar pattern to reading nonsense outloud. This analysis was not presented in the figures.

It was undertaken ascertain if there was a particular frequency in the Theta and Alpha ranges would could account for their importance in the results. Klimesch had pursued an individual analysis of frequency ranges by dividing Alpha into lower and upper frequency ranges to discern differences. Twelve subjects with differing levels of performance on the auditory memory tasks and reading were selected. Their raw data was re-analyzed in 1 frequency Hertz ranges from 5 to 13 Hertz in addition to three narrow beta bands, 19–21 Hertz, 29–31 Hertz and 39–31 Hertz. The results are presented in the Section entitled Alpha figures. The figures employ the same selection criteria as was employed in the previous analysis. The figures that are mostly presented are those in which a strong pattern resulted from the analysis and for which the previous analysis indicated significance in that frequency range and location. Thus if T3 Coherence relationships were significant with the larger group of subjects, it was that relationship which was examined in single frequency hertz ranges. Several patterns, however, were so strong that they are also presented. These patterns are indicated with 3 asterisks. As can be discerned from the figures, there are indications that a single frequency range can be critical and other indications that the significant relationships are spread over several single Hertz ranges.

ANALYSIS OF ONE SUBJECT RECORDED UP TO THE 128 HERTZ RANGE

One subject undertook the experiment with the sampling rate increased to 512, allowing analysis of the frequency range up to 128 Hz. The range from 64 Hertz to 128 Hertz was divided into two ranges, 64 to 96 (Beta3) and 96 to 128 (Beta4). The purpose of this analysis was to gain further understanding of the brain's electrical activity Unfortunately, unbeknownst to the experimenter until after the procedure was completed, four of the channels became malfunctioning. These four locations (FP2, F4, C4 and P4) were eliminated from the analysis. The subject's overall responses to the tasks indicated that she was one of the best overall subjects in the experiment, rendering the data relevant for further understanding of brain functioning.

As the analysis of the listening to paragraphs yielded a strong effect of coherence and phase Alpha from the left and right temporal lobe (T3, T4), an analysis of this subjects patterning of response to the listening to paragraphs condition was undertaken. The figures HF (Frequency) #1 display the significant pattern of responding. Only those increases, which had a significance level of, less than 0.05 are presented and for which there were at least three connections with this level of significance. An analysis of the other coherence and phase generators revealed a similar pattern for the frontal generators (FP1,F7, F8, & F3) across all bands with the left (FP1 & F7) being the strongest overall pattern. Of particular note is that these frontal and temporal generators were clearly the dominant pattern with very little increase over auditory attention values for the rest of the possible connections. Thus, in this case, a highly focused mind is one, which employs specific locations across all bands and deactivates the other connections. In specific the locations are the temporal lobes and the frontal locations (in particular the left frontal for verbal tasks). This subjects pattern of responding (highly focused use of particular locations across a wide variety of bands) was evident on almost all the tasks employed. She also was in the highest range of scores on almost all of the tasks. This pattern was seen also in another subject (who had one of the highest scores on the paragraph.

Another pattern of note in this subject is the increased activation (i.e. relative power, absolute power, & magnitude) in the upper bands under the listening condition. The main analysis of the pattern of results did not indicate a strong effect of these parameters on memory functioning. This subject actually showed a decrease in these variables (from the auditory attention condition) in the Beta1 and Beta2 bands yet demonstrated a dramatic increase in the upper bands (beta3 and beta4). This result may indicate that the problem with the main analysis is that the lack availability of the upper bands for analysis may have biased the results towards no effect of these level of activations. If the upper bands have been collected for all the subjects, there is a strong possibility that these activation patterns would be significant for memory, as they were for this subject. Some of the other good memory performers also showed a tendency for the Beta1 and Beta2 bands to decrease along these activation patterns.

The FIGS. 88–124 (coded CA#1 to CR#1 in the studies) present the results of the analysis of the children under the age of 13 who were involved in the experimental procedure. For many of the figures only the positive relationships are presented, as there were too many numerous negative relationships (especially in terms of the coherence and phase variables) to be useful. On occasion, for demonstration purposes, some of the negative findings are included. Significance at the 0.01 level is indicated by the hatch pattern in the circle. Only for the spelling condition are the ages up to age 14 included, as these subjects were exposed to the same spelling words. Although children up to the age of 14 read the same reading material, inclusion of the subjects between ages 13 and 14 changed the results significantly. In order to preserve the nature of children's responses, it was decided to leave this group out of the analysis (ages 13 to 14). Apparently there is a fundamental change in the functioning of the child after age 13, that a researcher cannot consider such a subject a child anymore. This is in line Piaget's theory of mental development, as well.

The Neurotherapy research (biofeedback of the QEEG signal) has successfully demonstrated that the C3 and Cz positions are important in terms of the frequency range of 13–12 Hertz for cognitive change to occur. This research demonstrates why that feedback protocol is effective, as reflected in FIG. 88, FIG. 89 and FIG. 91. The figures indicate the importance of the relative power of Beta1 figures for the posterior portion of the head, not necessarily the positions which have been employed in the rehabilitation setting. A factor analysis (principle components) of the relative power of Beta1 revealed four factors which accounted for 87% of the variance. The two major factors were a frontally located factor which extended back to the C3-Cz-C4 and a posterior factor (T5-P3-Pz-T6O1-O2). Thus the majority of the rehabilitation efforts have not focused on the important locations in terms of memory.

Figure 88A:
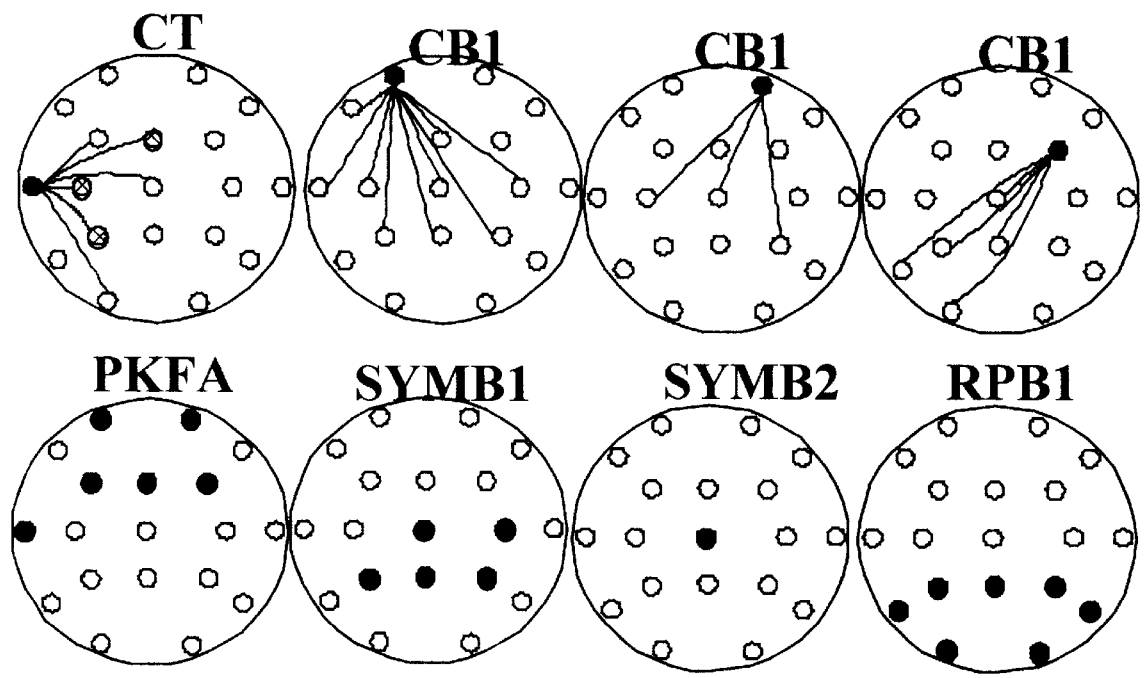
Figure 88B:
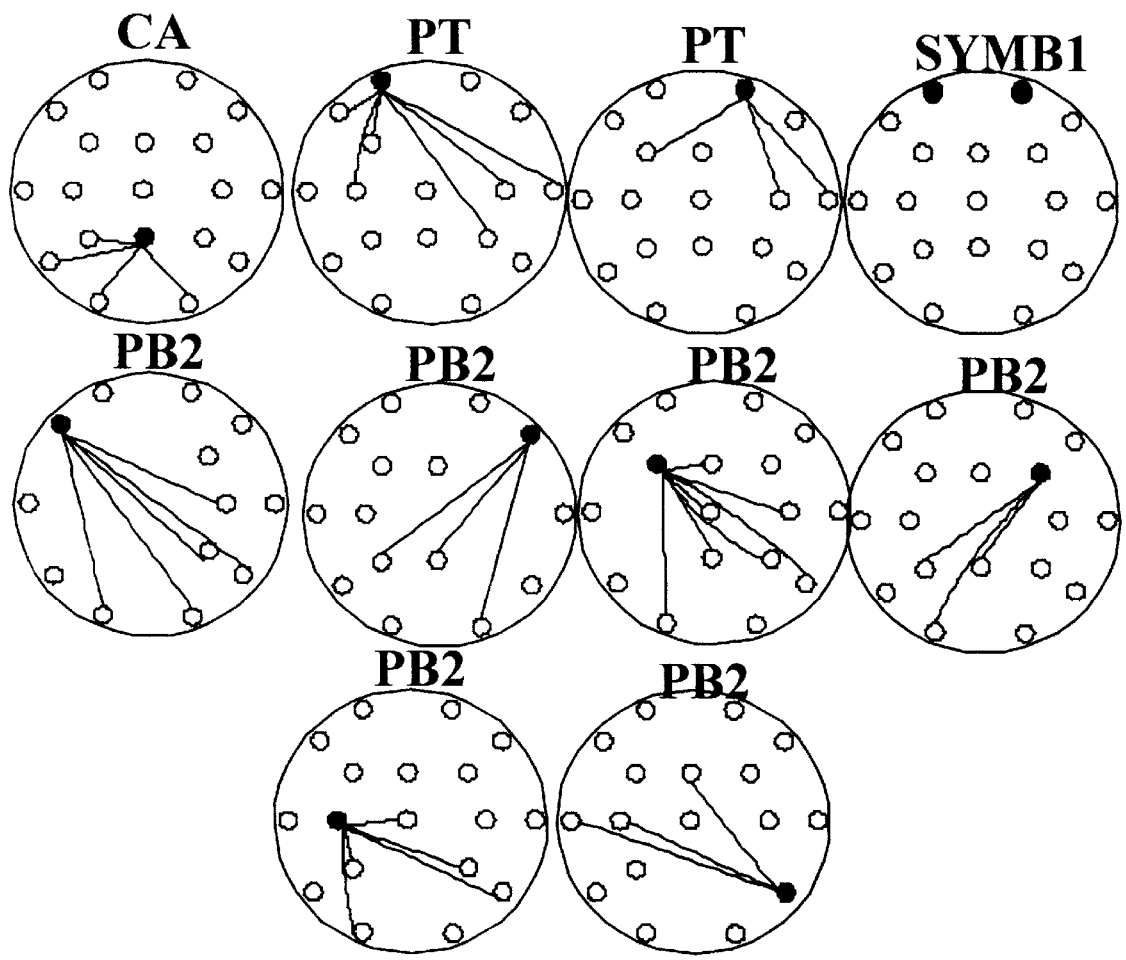
Figure 89B:
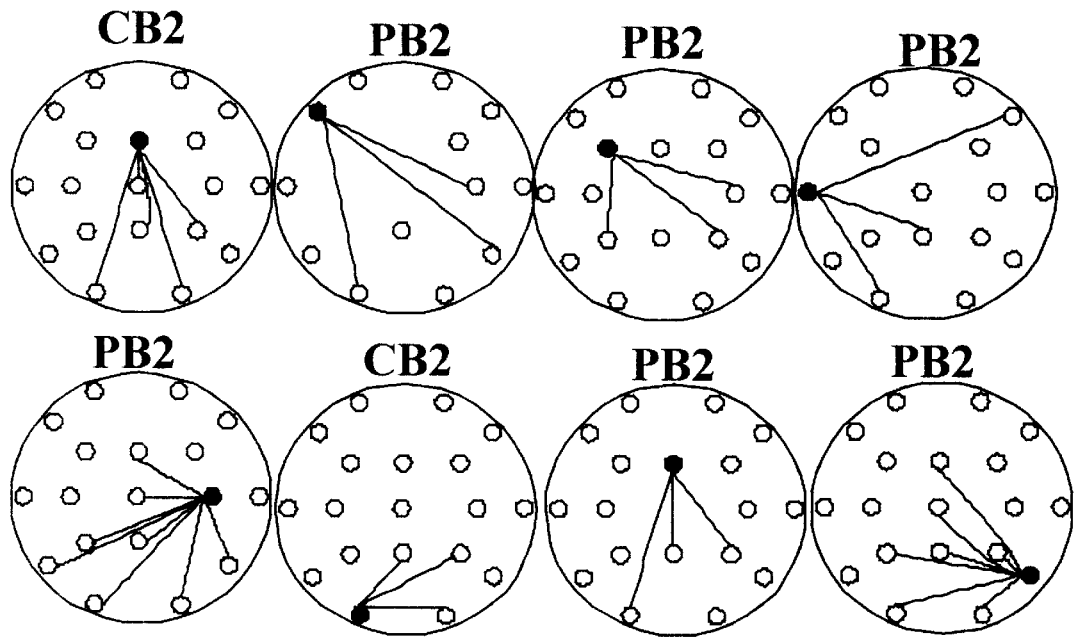
Figure 90A:
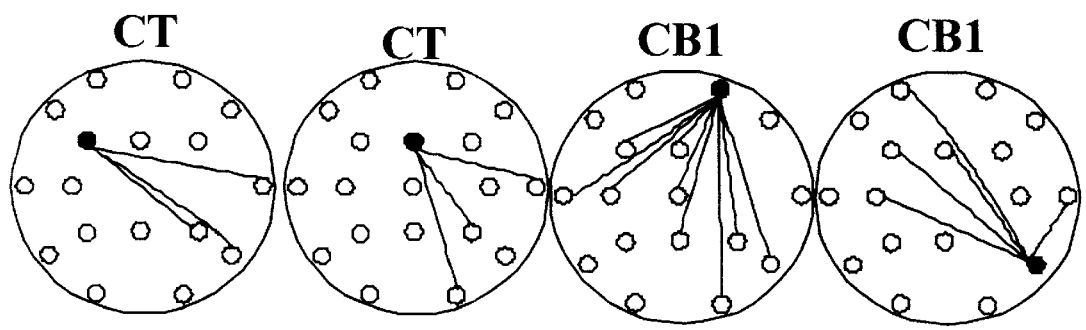
Figure 90B:
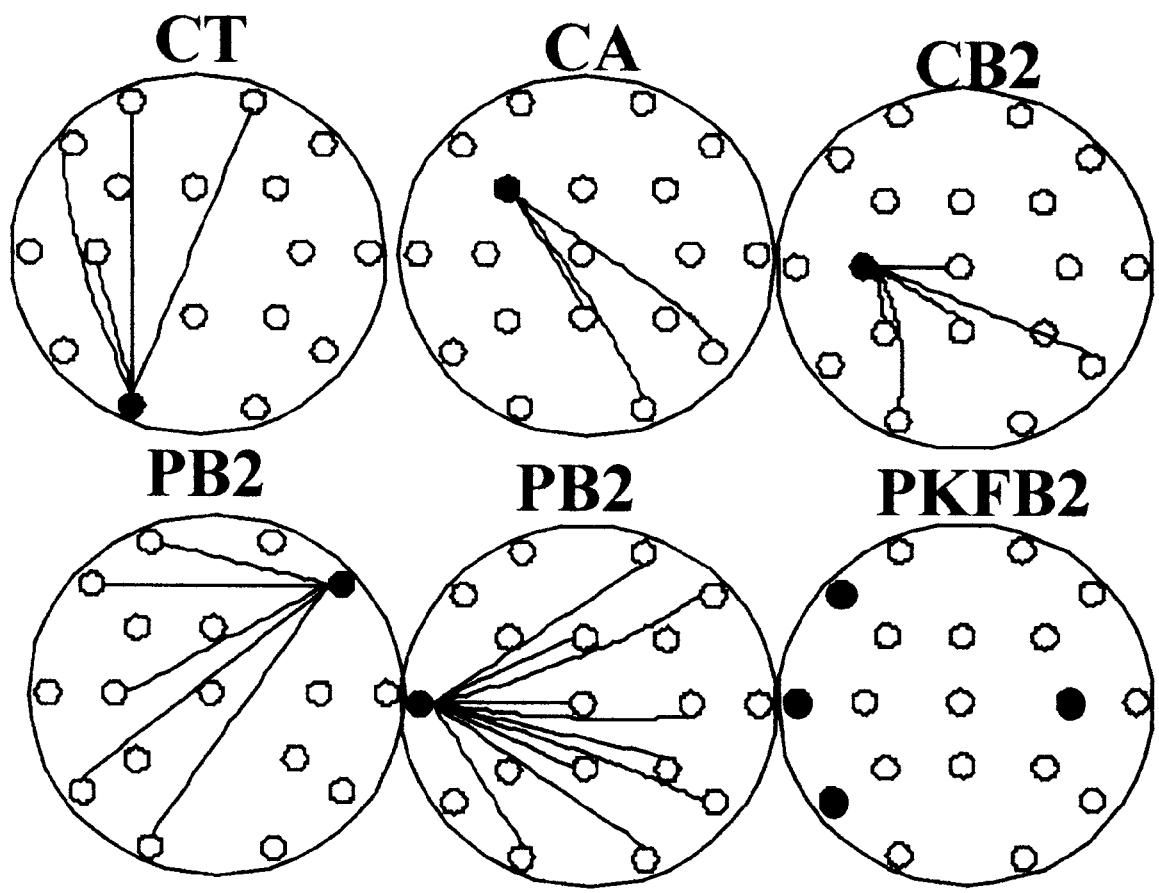
Figure 91A:
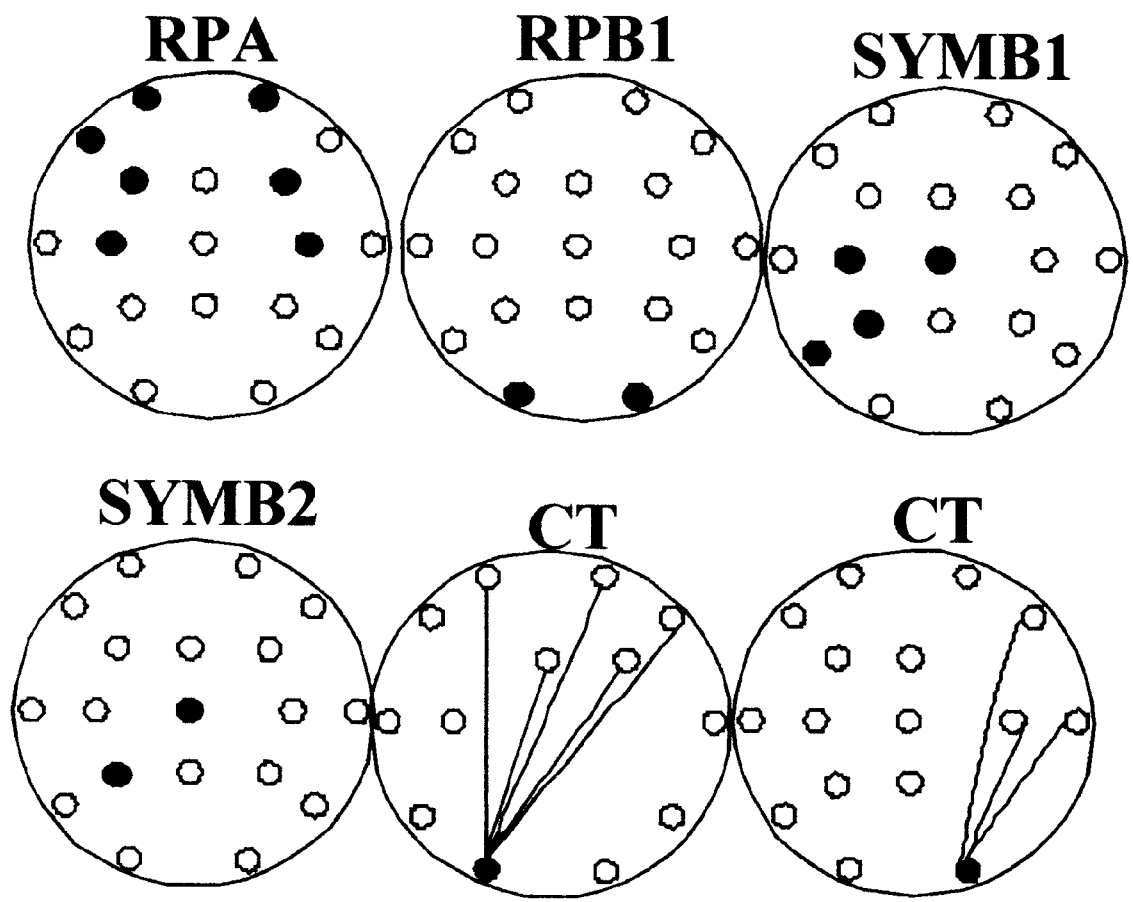
Figure 91B:
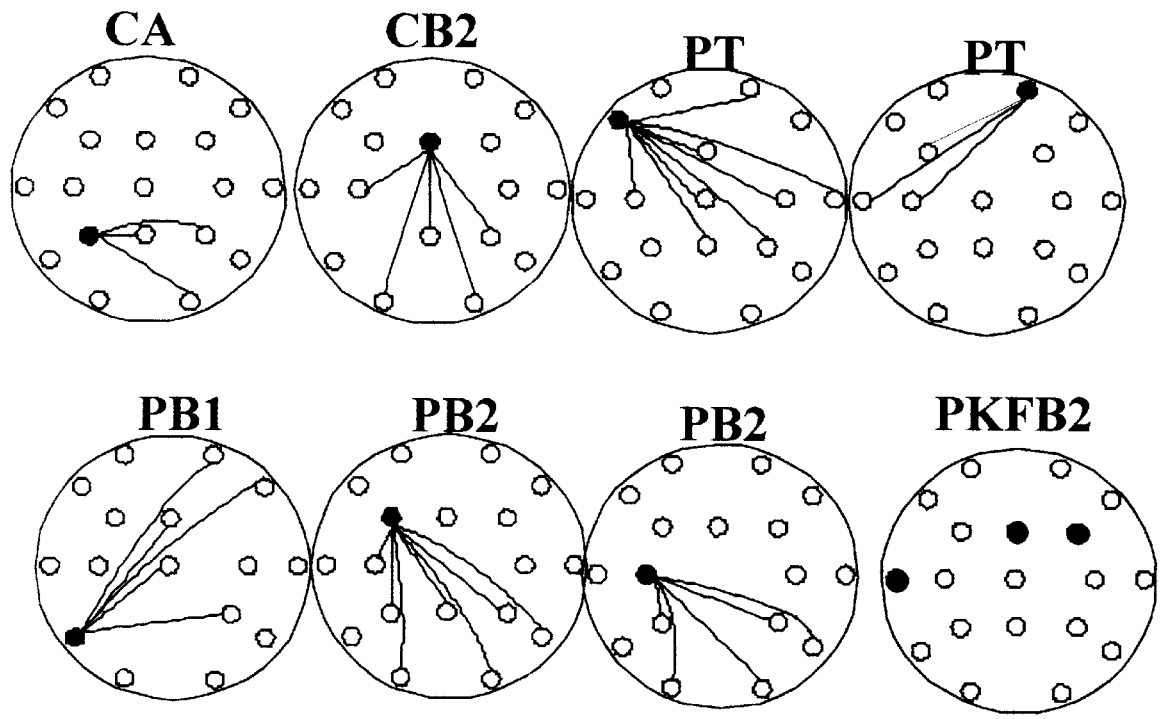
Figure 92A:
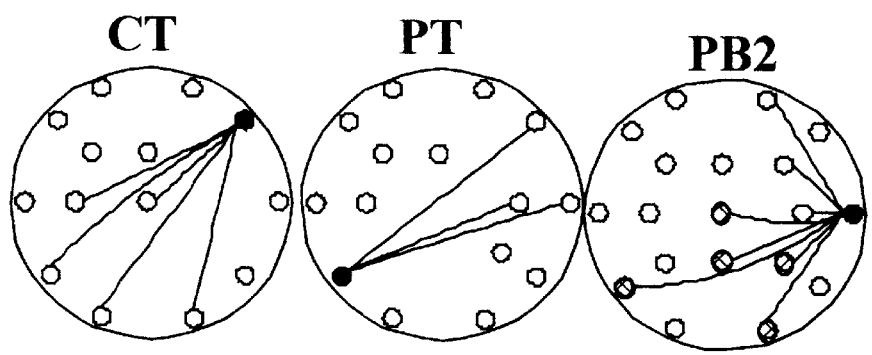
Figure 92B:
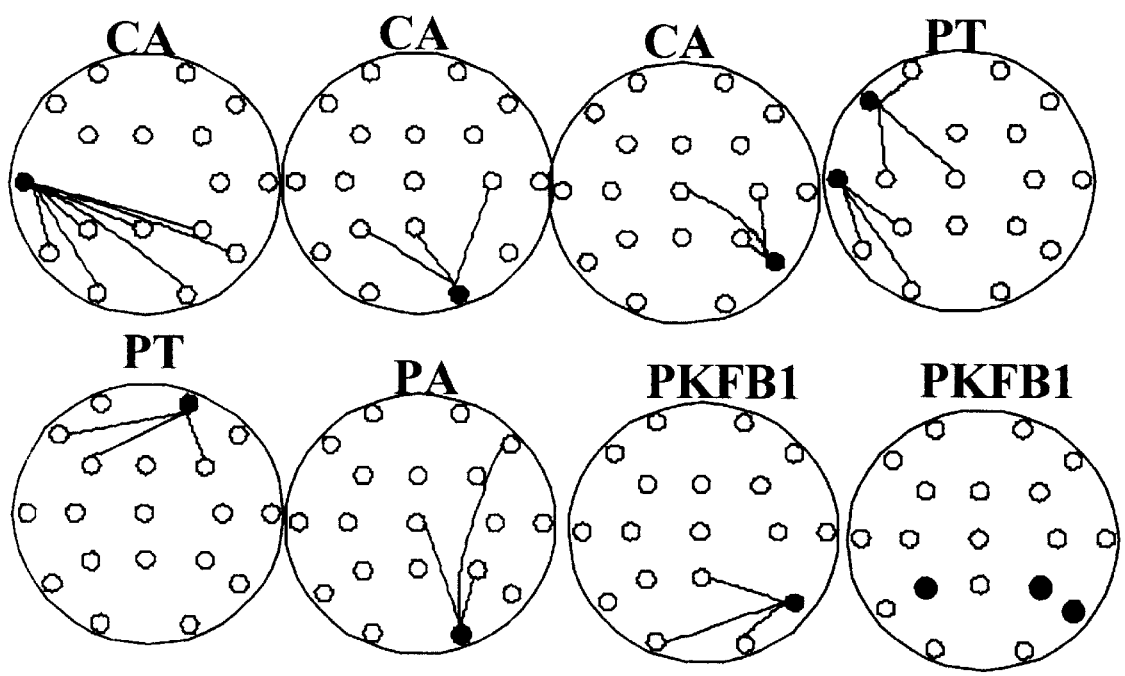

FIG. 88 (Hearing Words from a Word List—experiment coding CA#1-5) presents the variables, which were important for memory during the initial presentation of the words in the word list task. FIG. 89 presents those variables, which were important for the one-second intervening processing period. FIG. 90 presents the variables, which predicted recall ability under the delayed recall condition. FIG. 90 presents those variables (levels of activation) which accurately predicted recall under the quiet 30-second recall condition in between each word list. FIG. 92 presents those variables whose degree of activation from the eyes closed condition predicted recall.

Figure 93A:
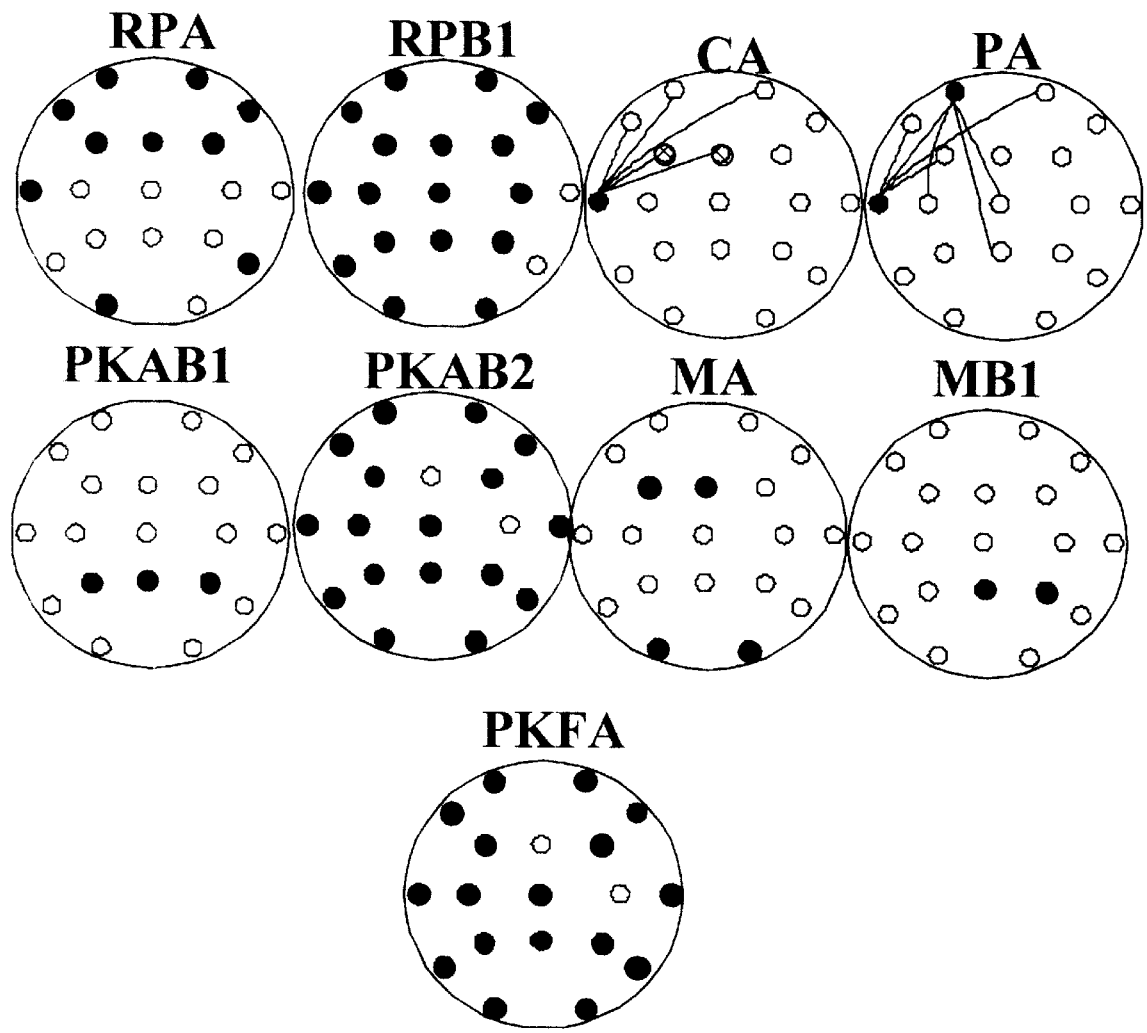
Figure 93B:
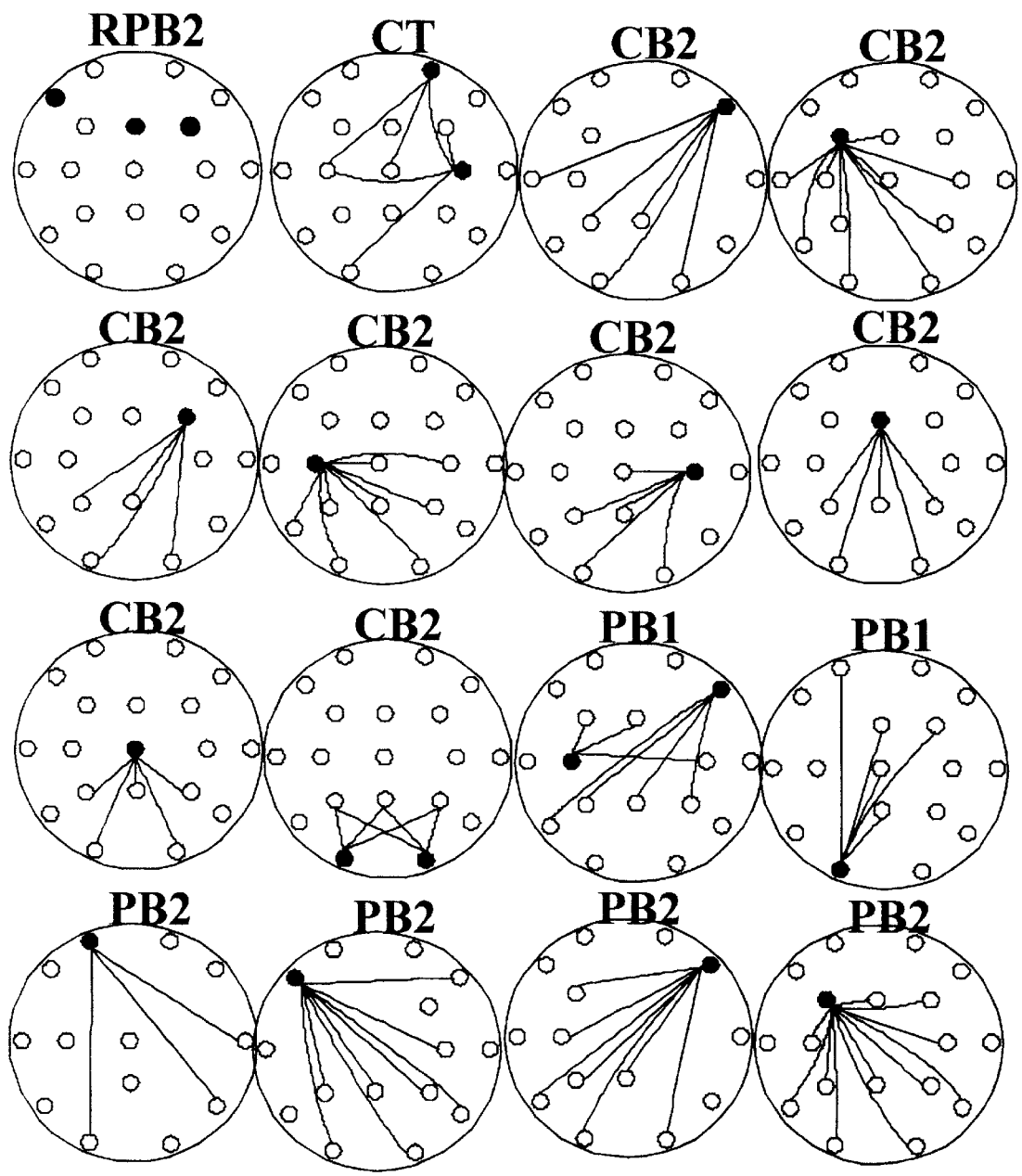
Figure 93C:
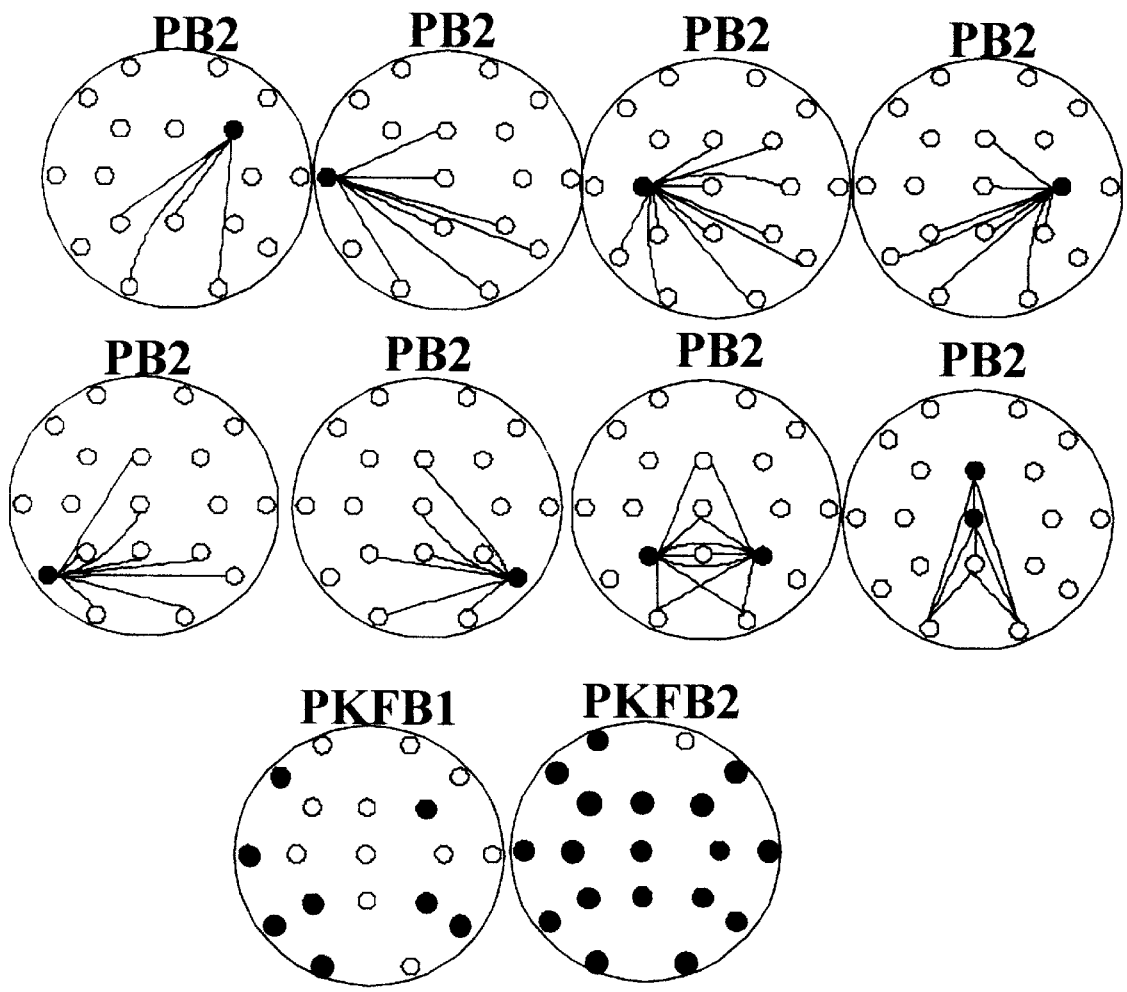
Figure 95:
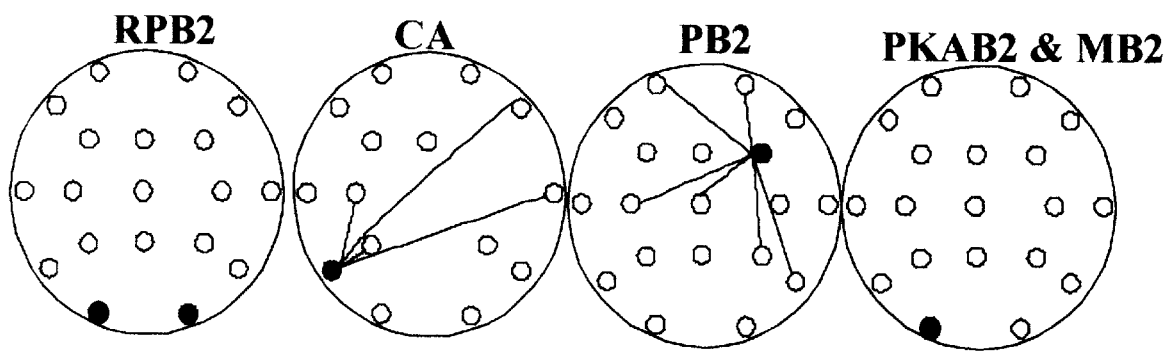
Figure 96:
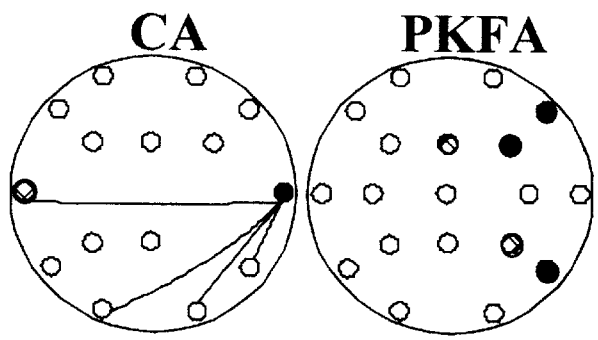

FIG. 93 (Recall of Paragraphs—experiment coding variables whose absolute level of activation predicted recall. FIG. 94 shows those variables whose degree of activation from the auditory attention condition predicted recall. FIG. 95 presents those variables whose level of activation under the immediate silent recall condition predicted recall. FIG. 96 shows those variables whose degree of activation from the eyes closed condition predicted recall.

Figure 98:
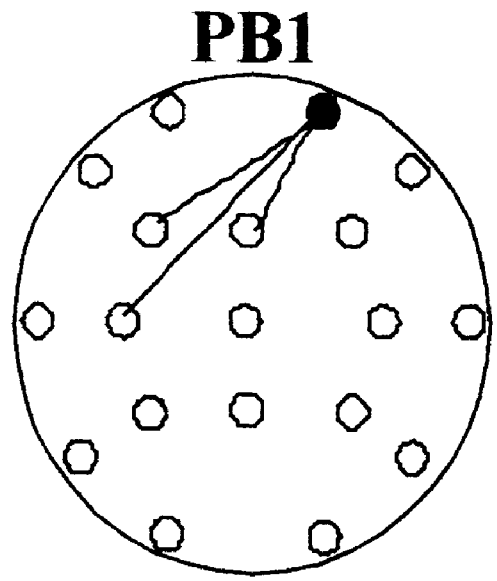
Figure 99A:
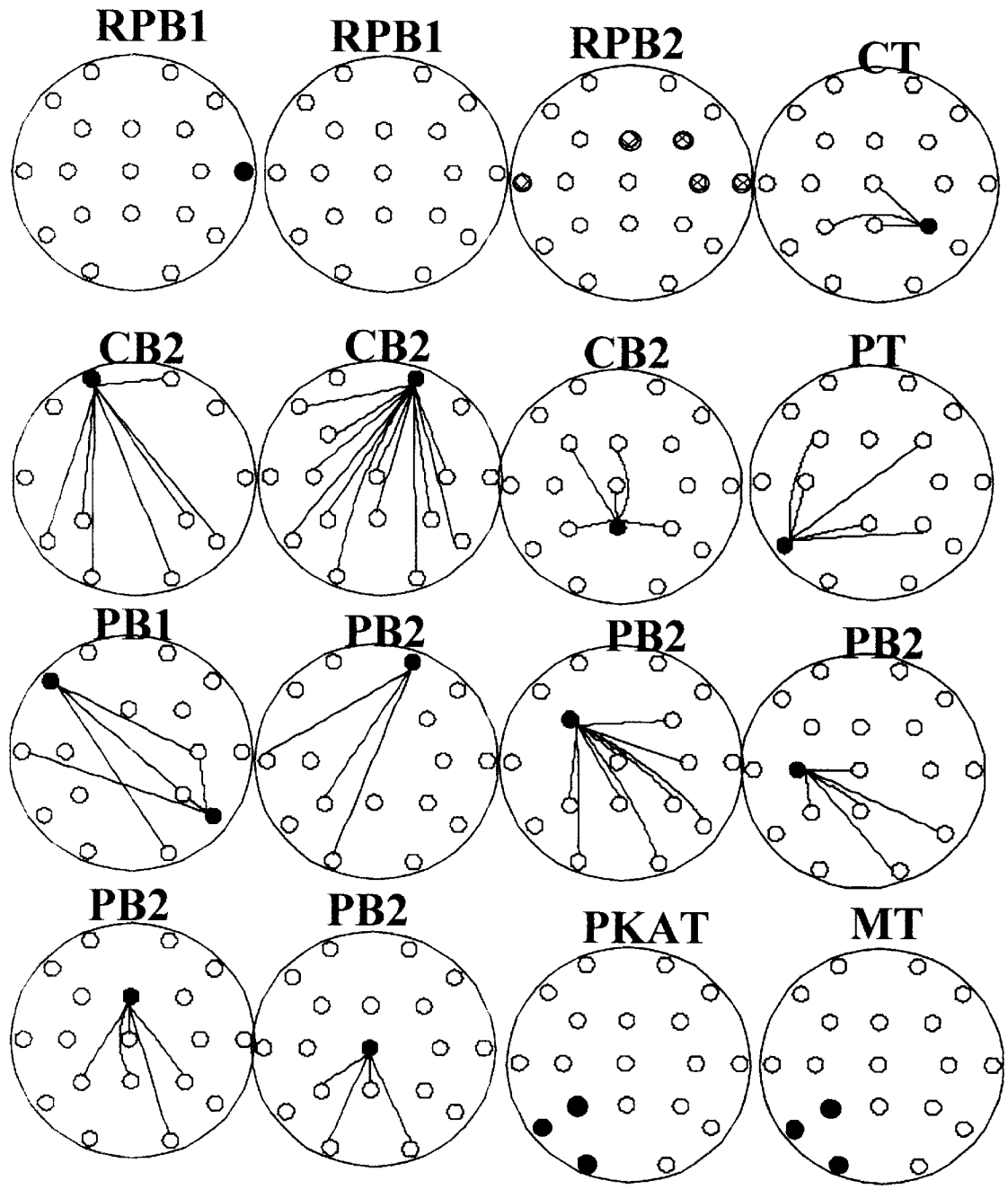
Figure 101:
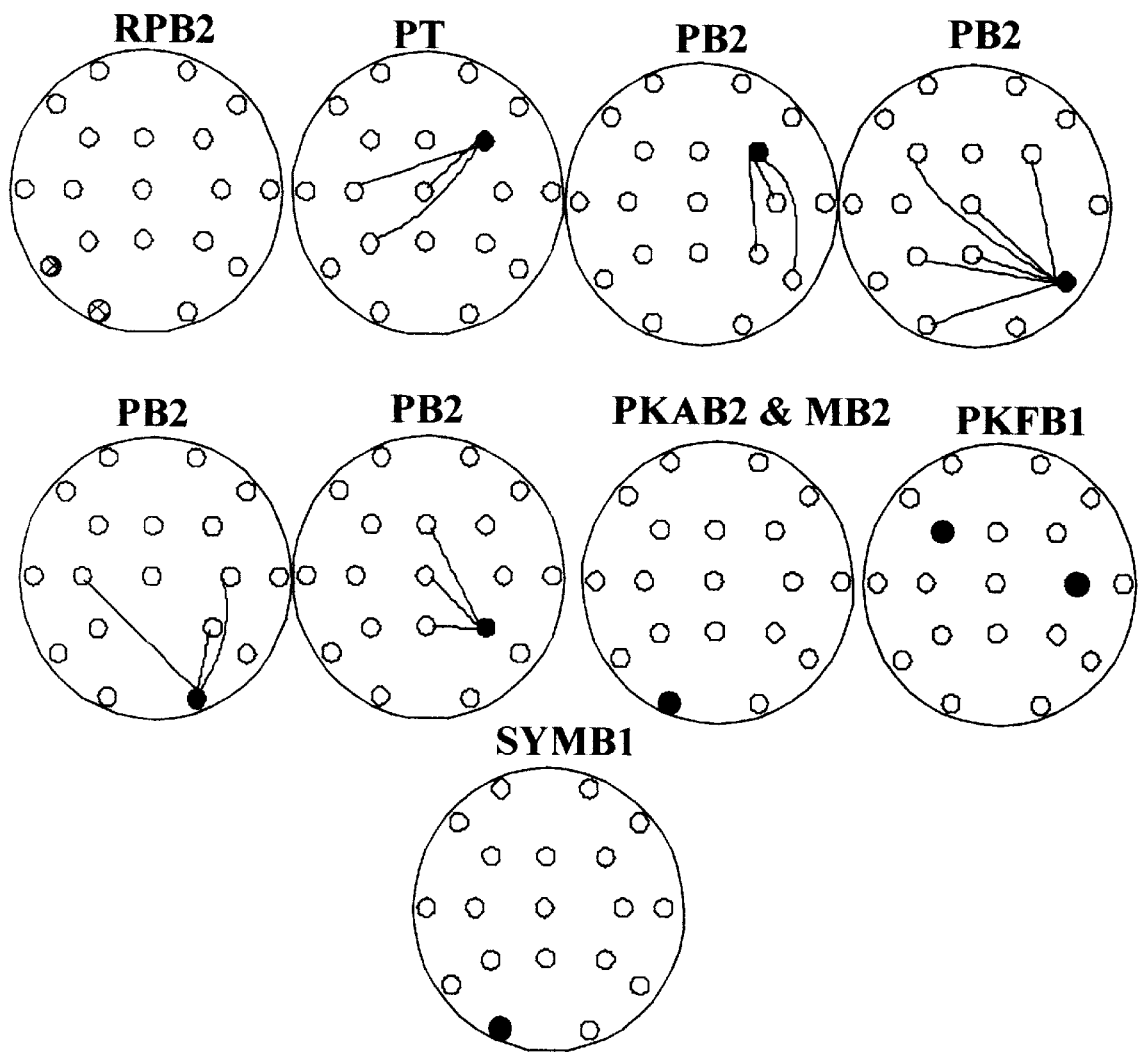
Figure 103A:
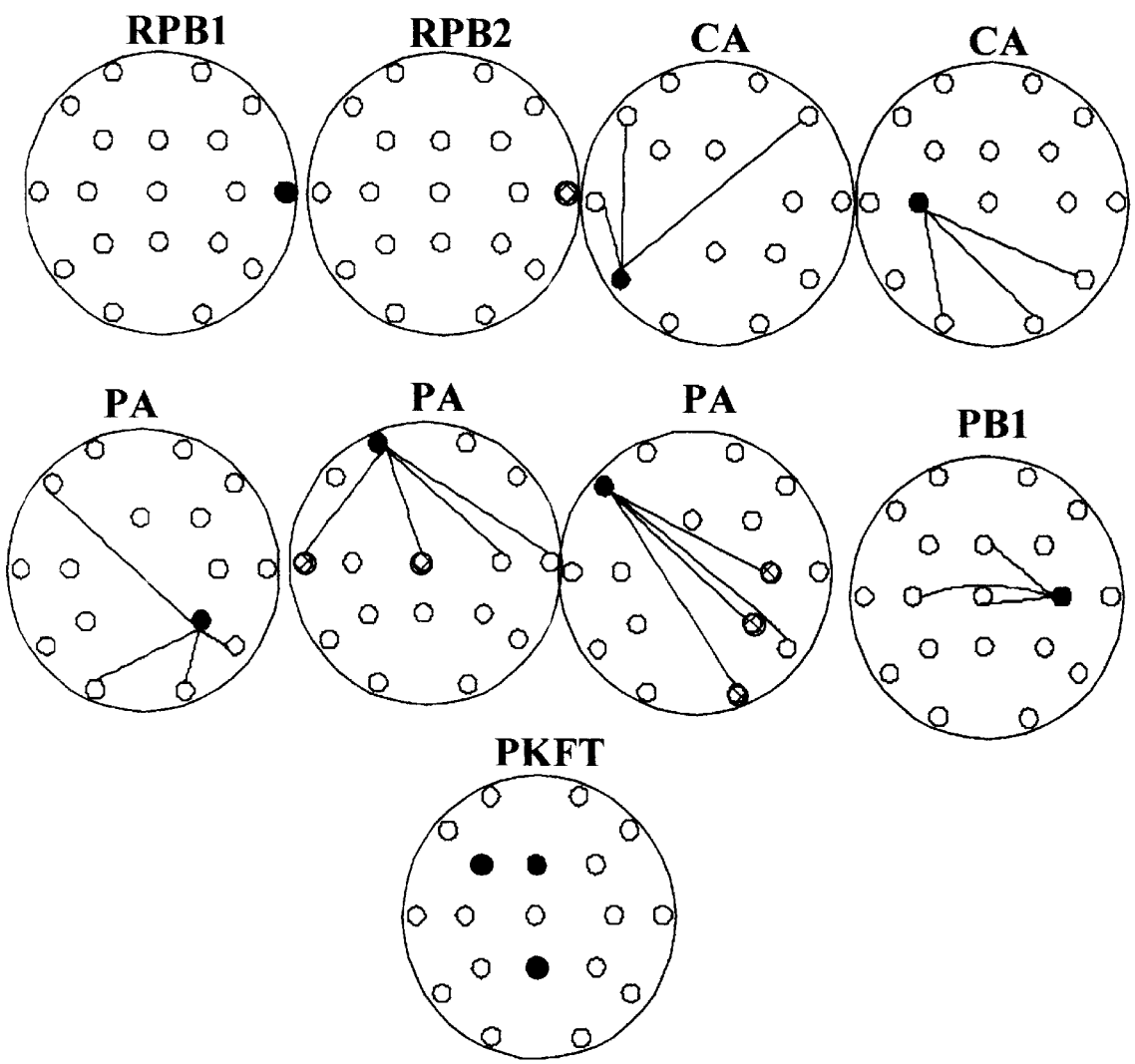
Figure 103B:
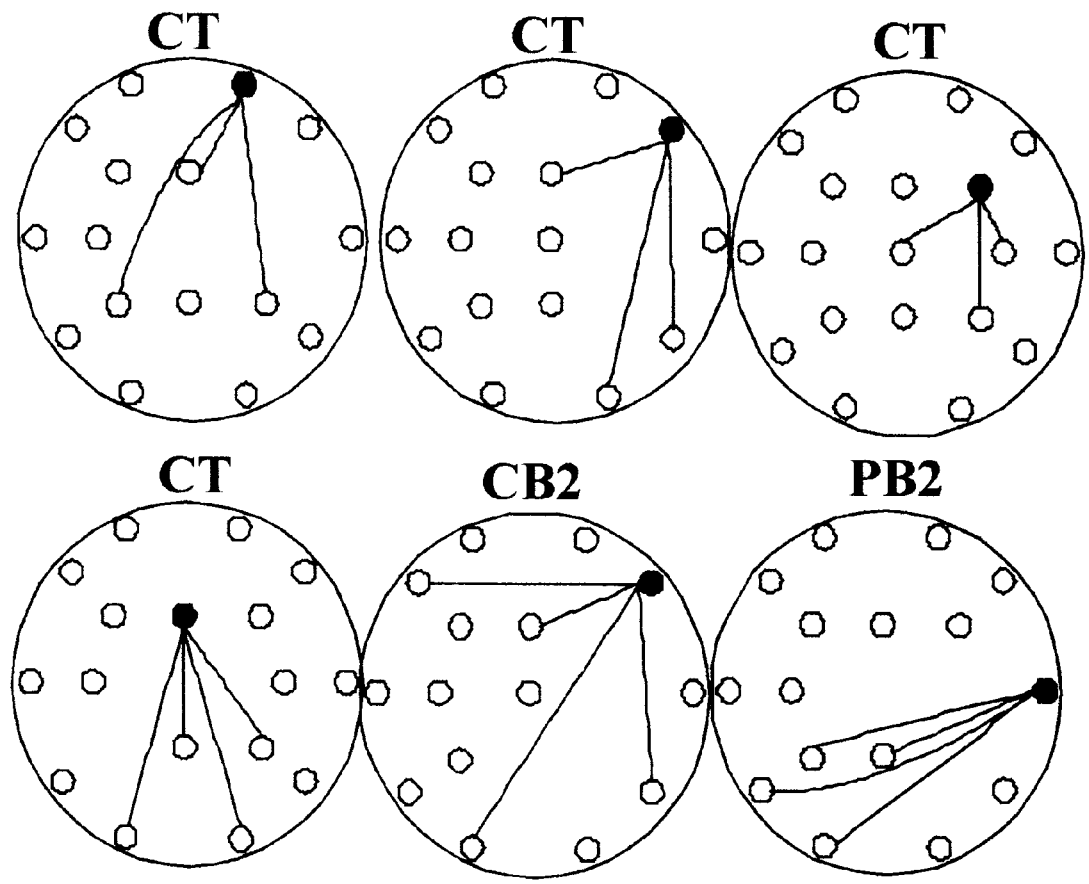

FIG. 97 presents the variables that were important for recall in terms of the degree of activation from the visual attention condition. There was no pattern that distinguished success in terms of absolute level during the studying condition. FIG. 98 presents the variables during the quiet recall of Korean characters were important. These variables are the degree of activation from eyes closed condition, as again there was not distinct pattern in terms of absolute level during quiet recall.

Figure 104:
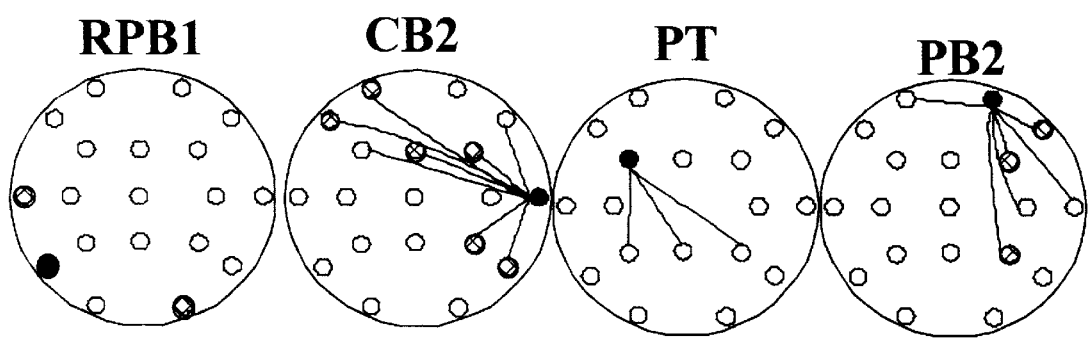
Figure 105:
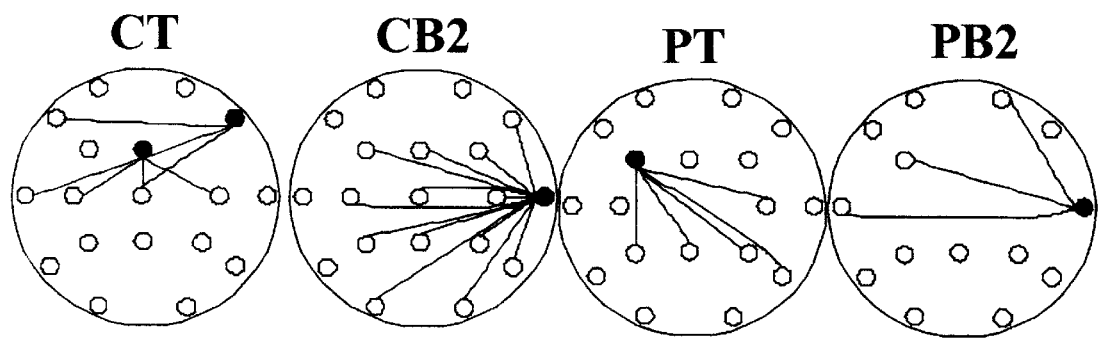
Figure 107:
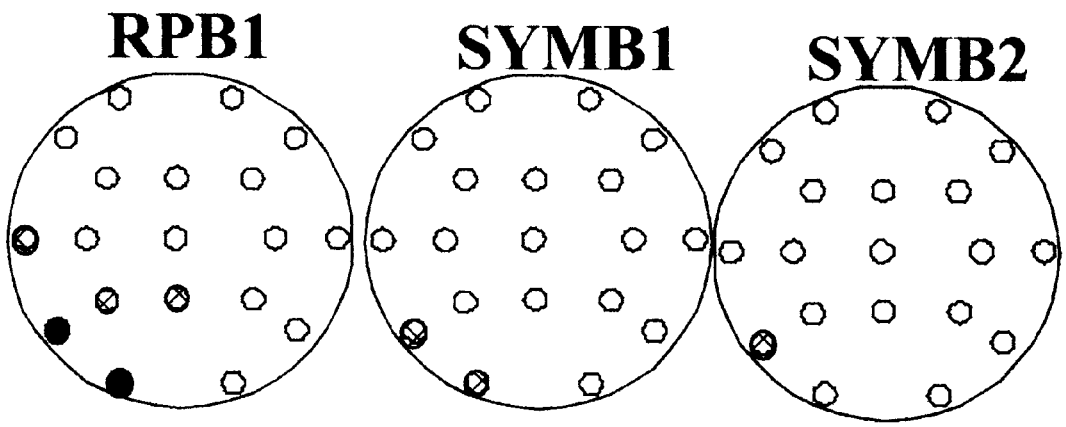
Figure 108:
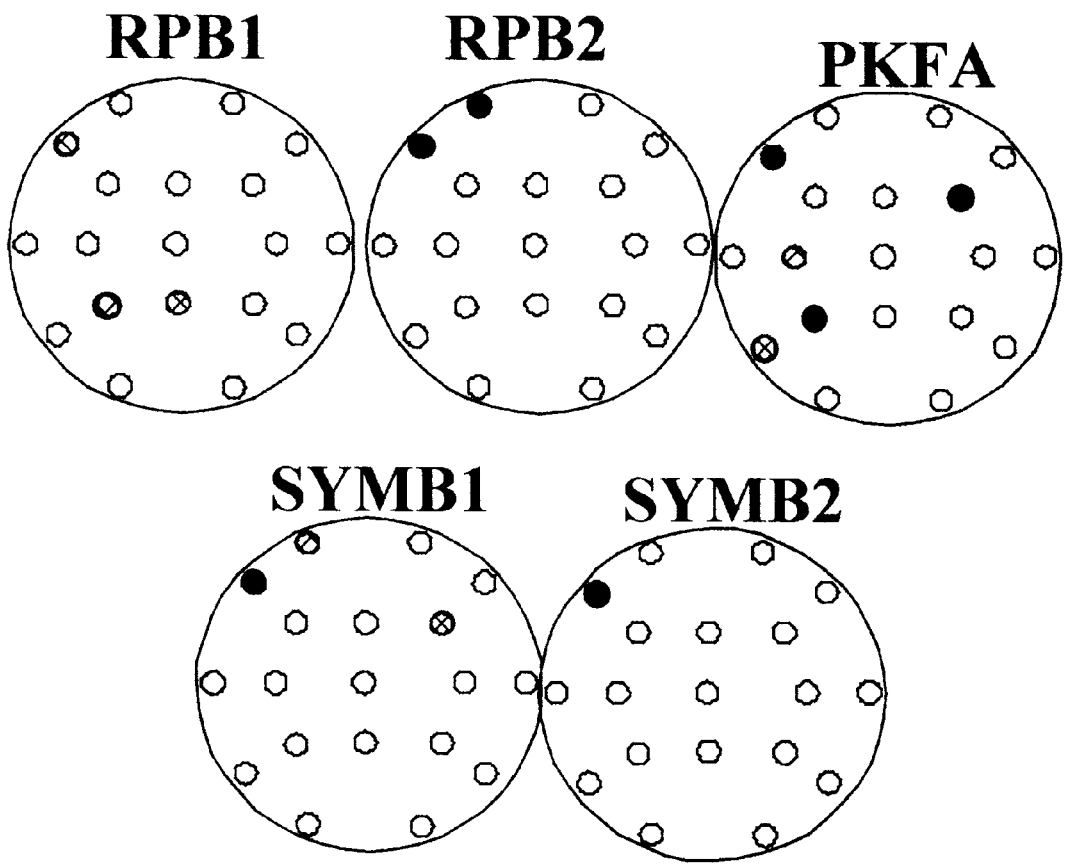
Figure 109:
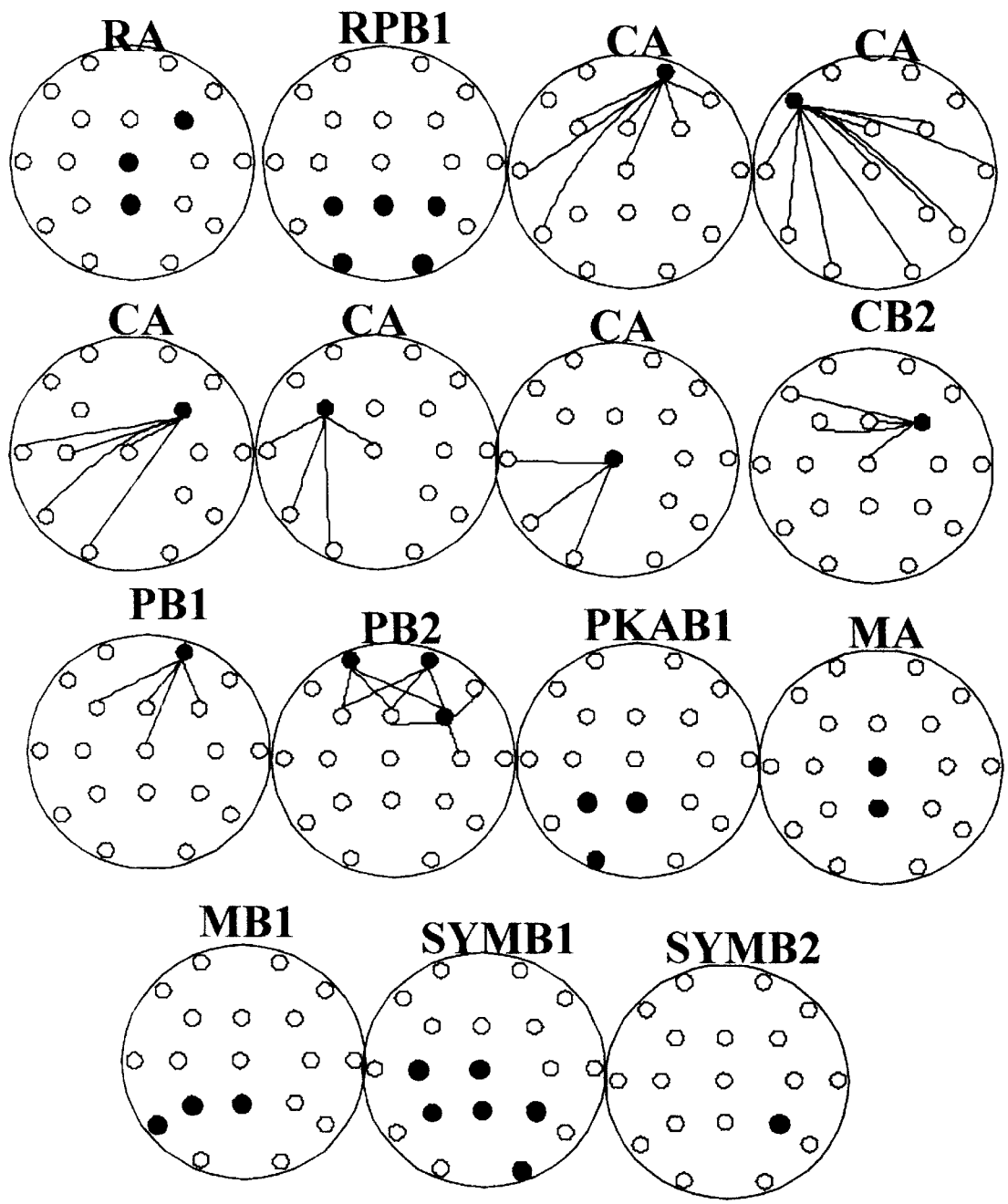
Figure 110:
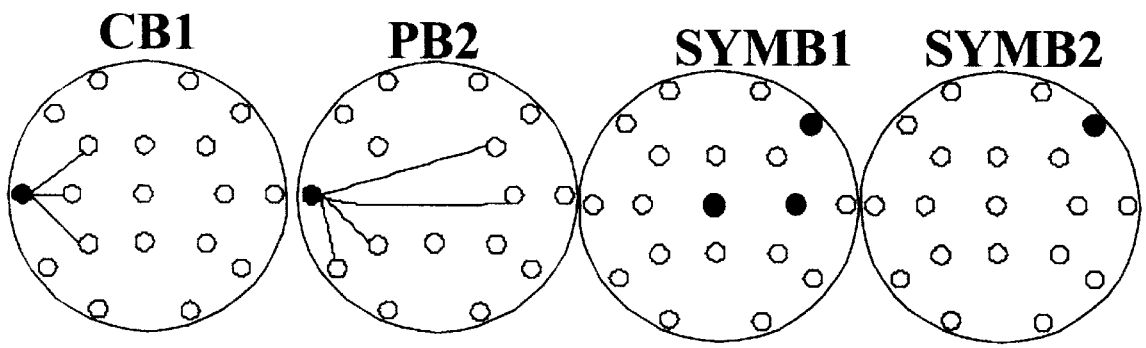
Figure 111:
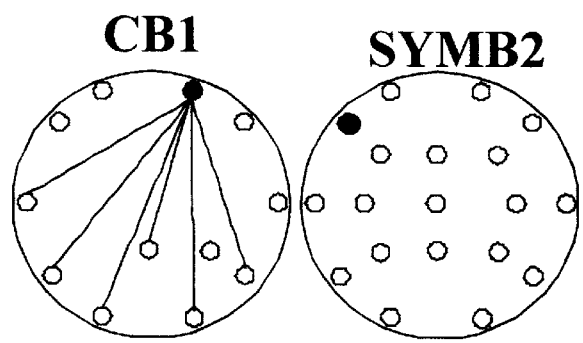
Figure 112:
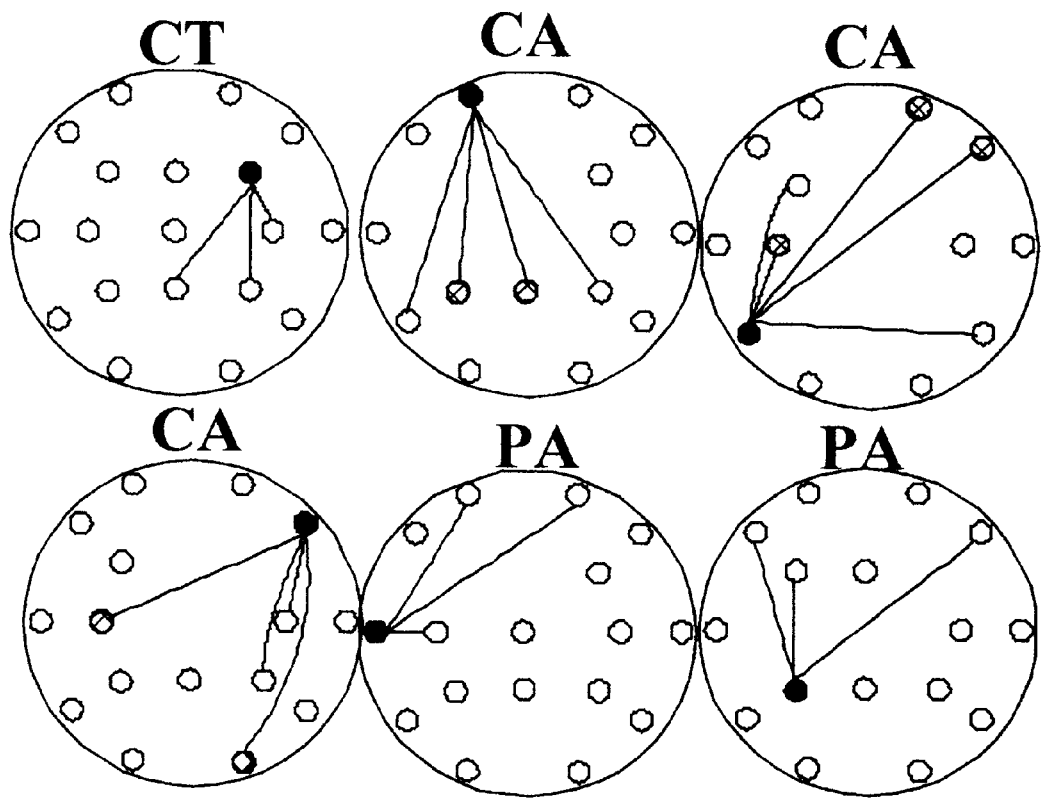
Figure 113:
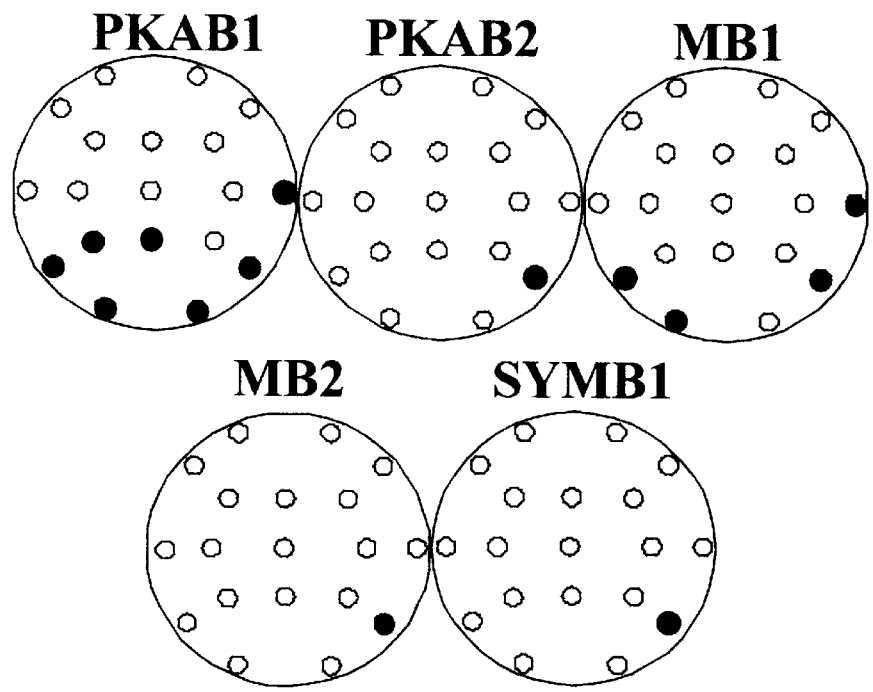
Figure 114:
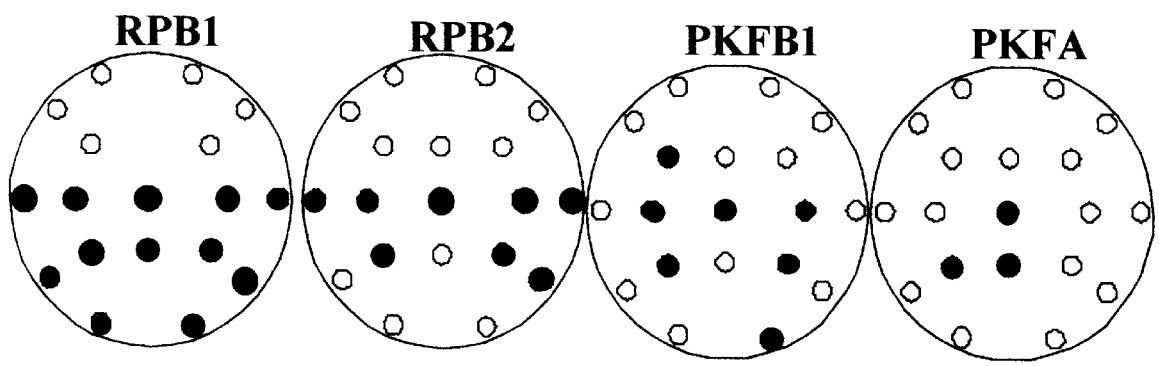
Figure 115:
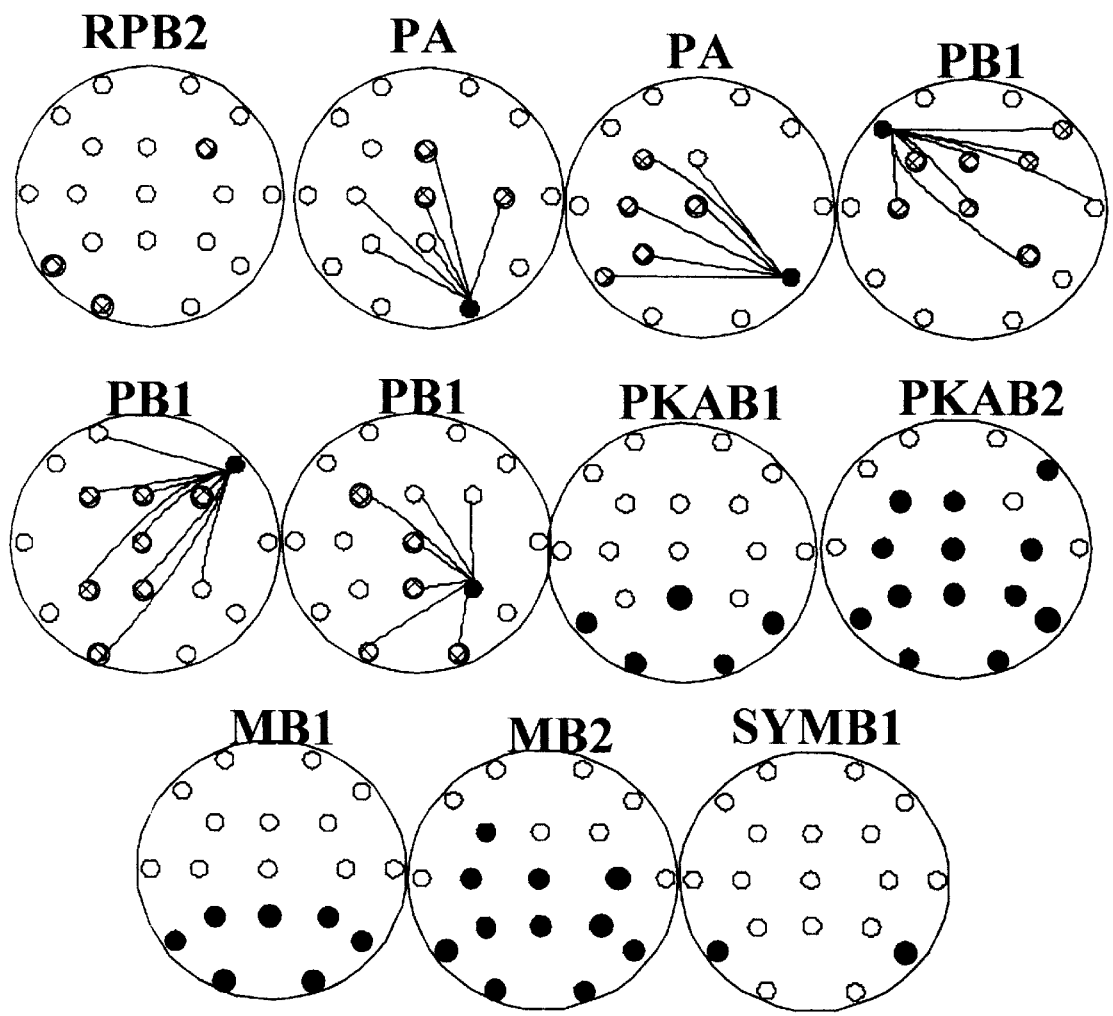
Figure 116:
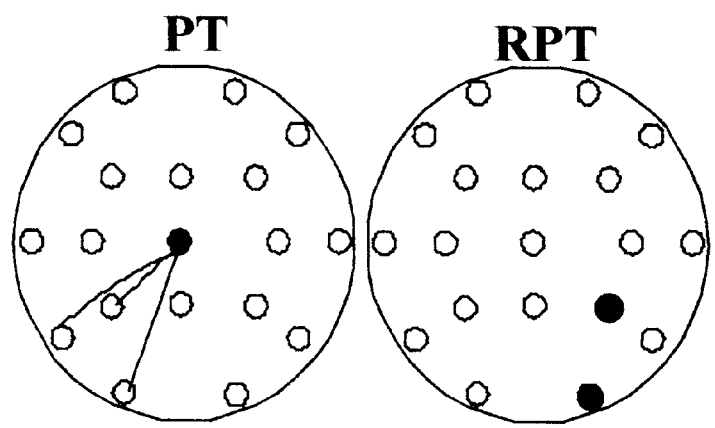
Figure 156:
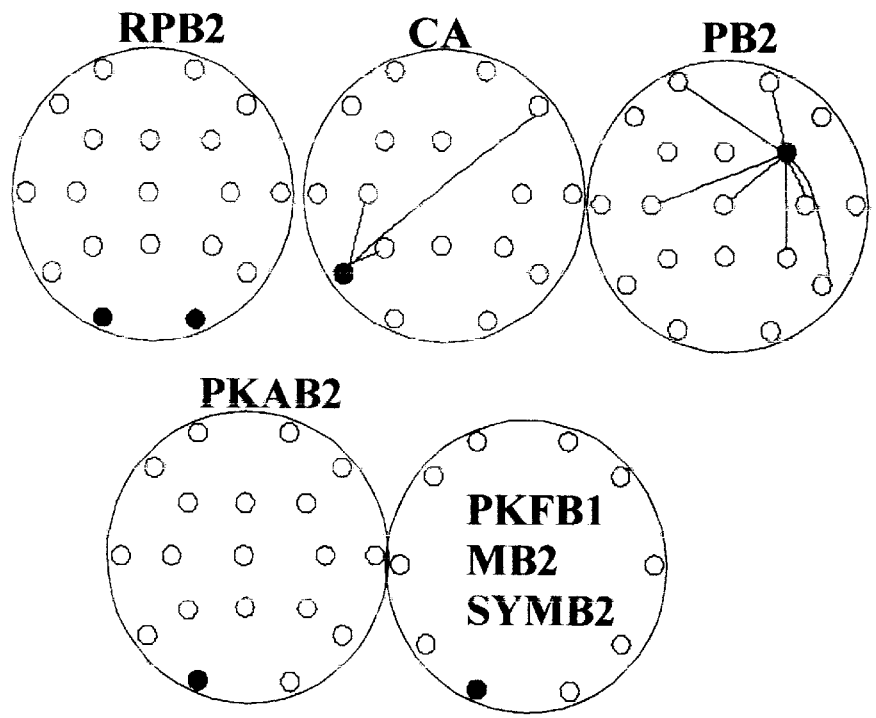
Figure 157:
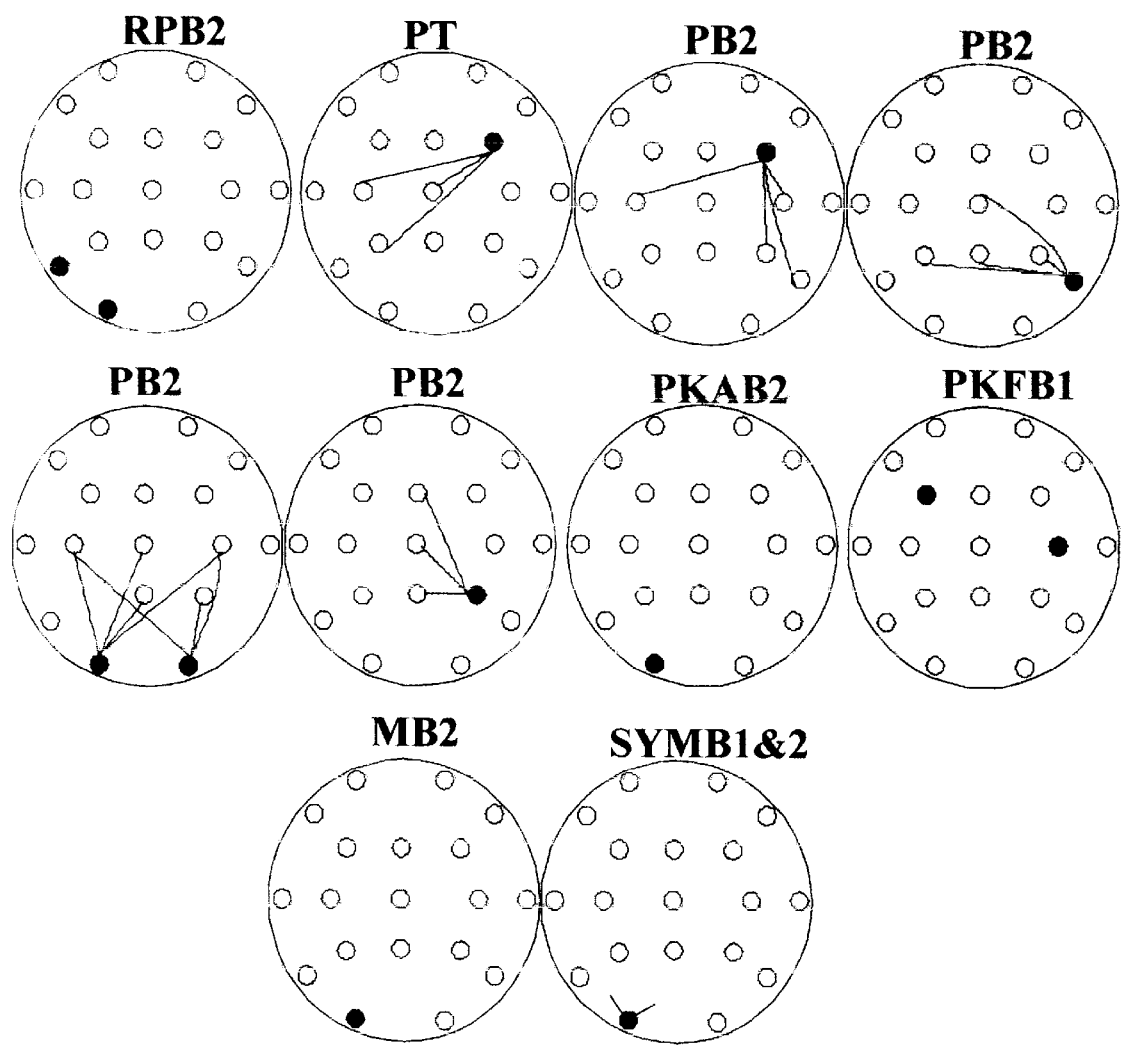

FIG. 156 presents those variables whose level of activation at the time of studying the names of faces were important. FIG. 157 presents those variables whose degree of activation from the visual attention condition predicted recall ability. FIG. 104 presents the variables whose level of activation, during the 30-second quiet recall period for the names of faces, predicted subsequent recall. FIG. 157 presents the degree of activation from eyes closed analysis and recall for the same period of time.

Figure 158A:
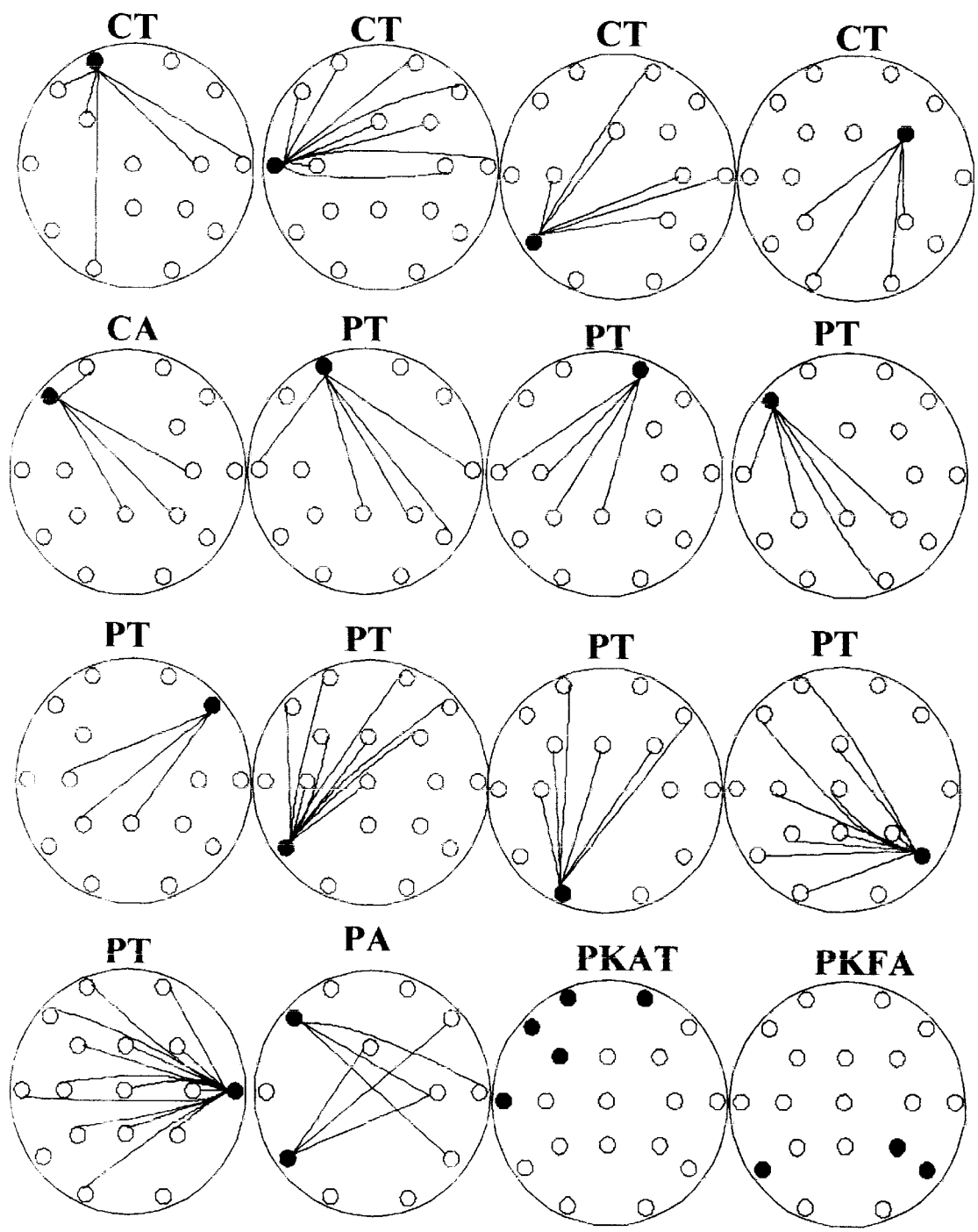
Figure 158B:
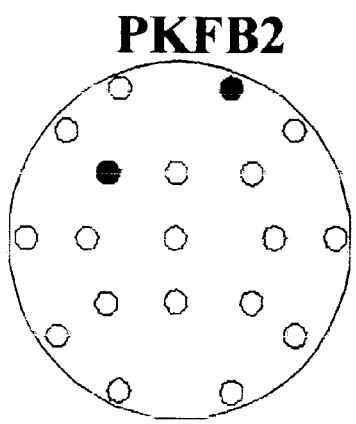
Figure 159:
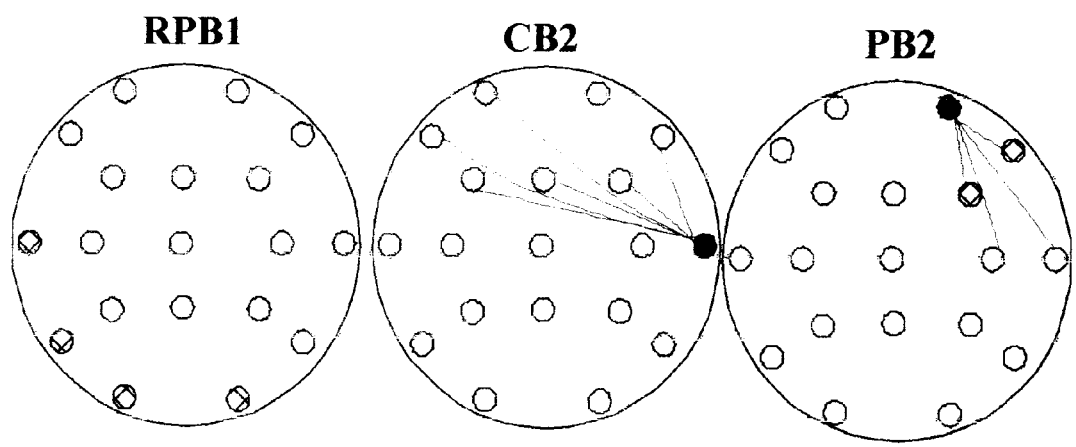
Figure 160:
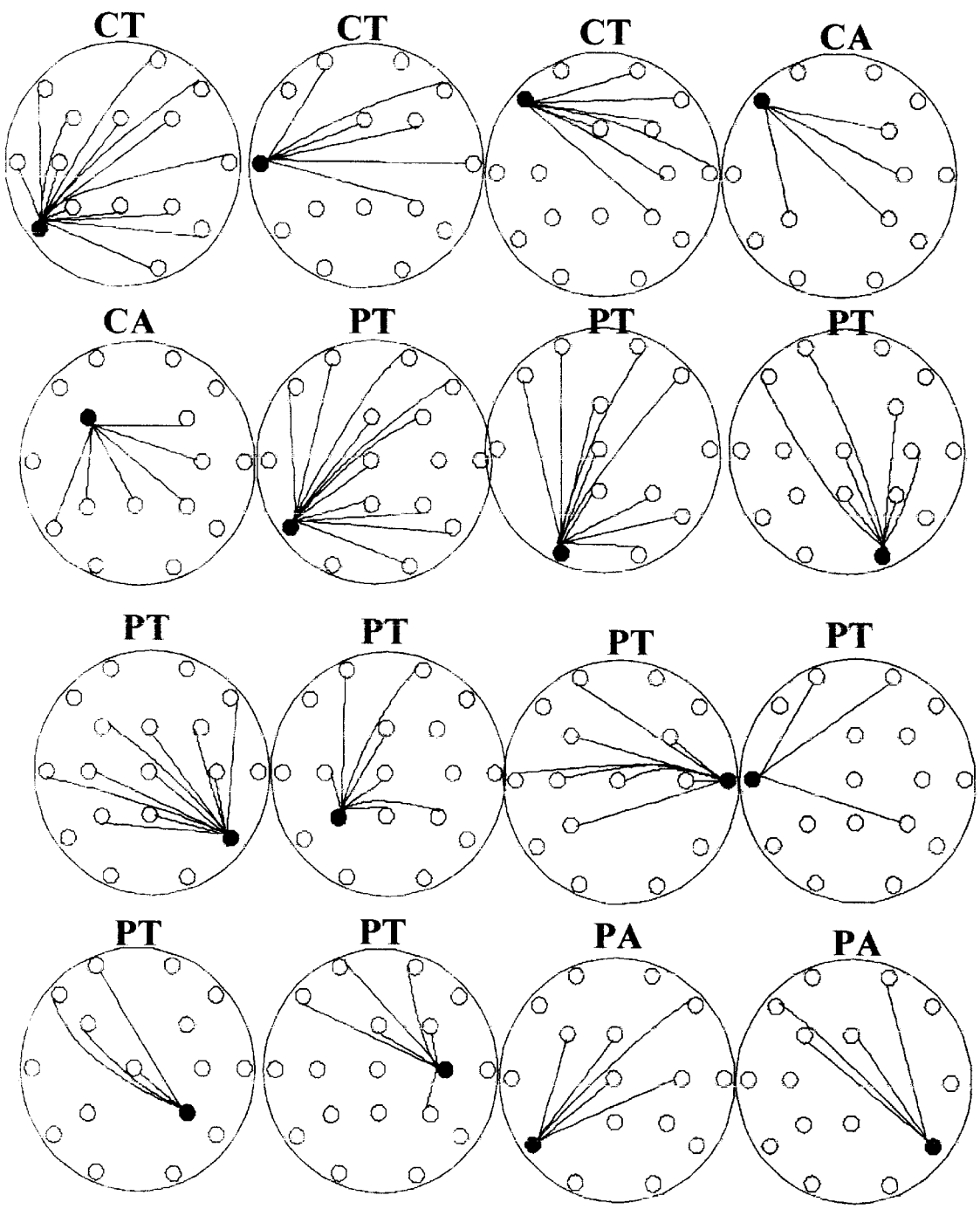

FIG. 158 (experiment coding CF#1,2,4) presents the variables whose level of activation during the quiet reading period predicted subsequent recall. FIG. 159 also presents the degree of activation from visual attention during the silent reading and the variables who subsequently had a positive correlation to recall. FIG. 159 presents those variables whose level of activation during the quiet recall period predicted recall, while FIG. 160 presents the degree of activation from eyes closed variables which were important for recall.

Figure 161:
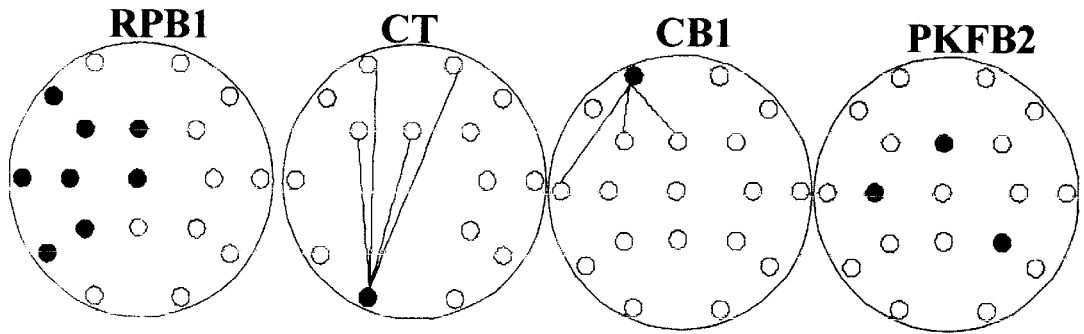

FIG. 161 presents those variables that were positively and significantly related to effective problem solving (Raven's Matrices). The method was the same as in the adult analysis. The performance for all the 9 matrices were placed in a single file and success or failure across every task was analyzed.

Figure 162:
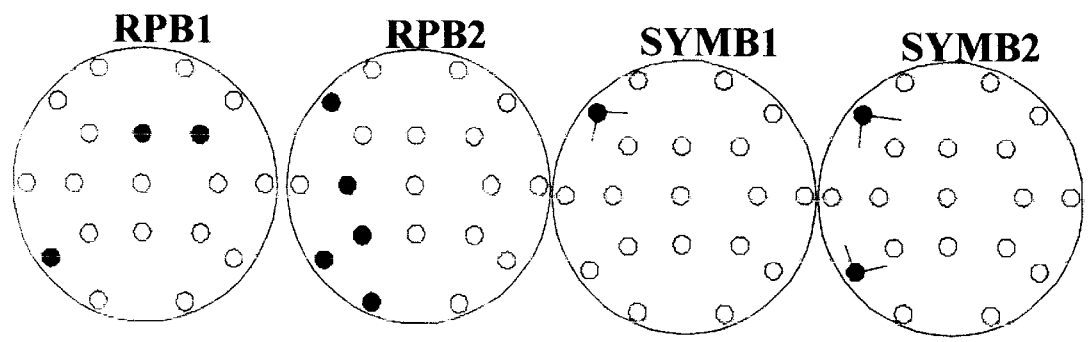

FIG. 162 (experiment coding CH#1-2) presents the variables whose level of activation during the spelling task positively correlated with subsequent success. FIG. 162 presents the variables whose degree of activation from hearing word silently condition successfully predicted spelling ability.

Figure 163:
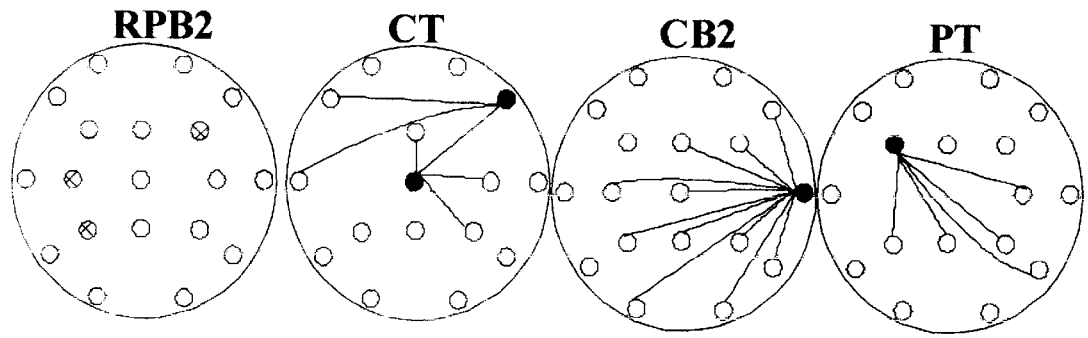

FIG. 163 (experiment coding CI#1-2) presents the variables whose level of activation during the silent multiplication period predicted subsequent ability FIG. 163 presents the variables whose degree of activation from the hearing silent numbers condition predicted success multiplication tables.

Figure 164:
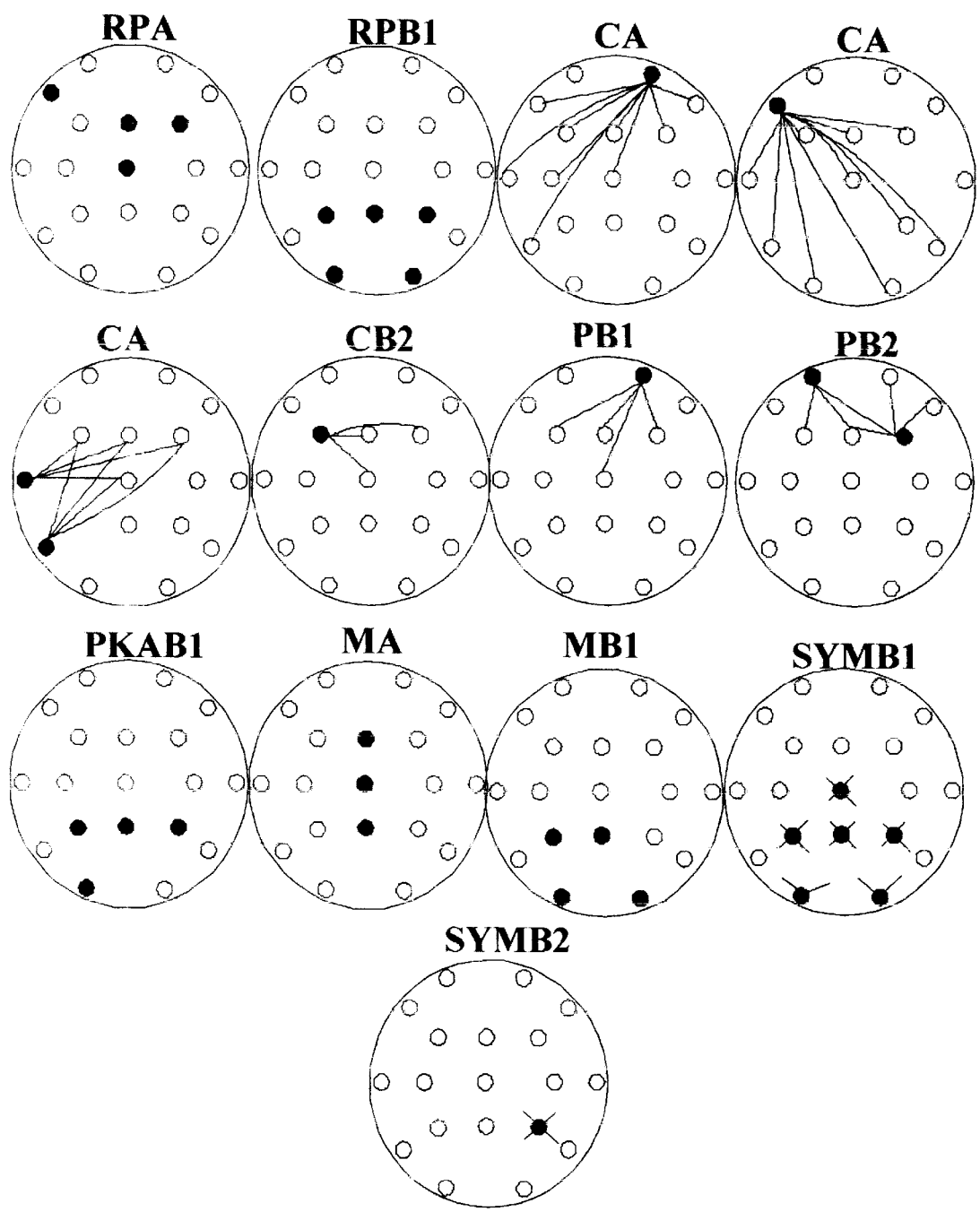

FIG. 164 (experiment coding CJ#1—Spatial Addition of Two Digit Numbers) presents the variables whose degree of activation from the silent hearing of numbers condition predicted subsequent addition ability. There was no significant pattern for level of activation.

Figure 165:
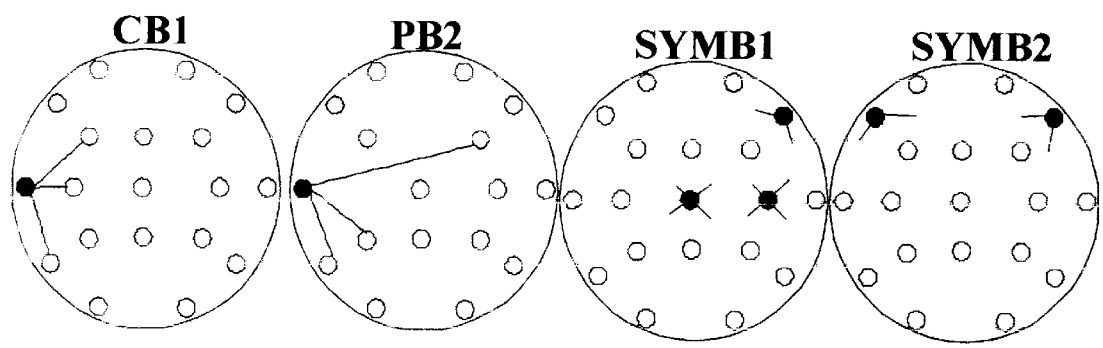

FIG. 165 (Sounding out Nonsense Words Silently and Outloud—experiment coding CK#1-4) presents those variables whose level of activation during the silent reading of nonsense words predicted subsequent ability in the outloud condition. FIG. 165 presents the variables whose degree of activation from the visual attention condition predicted subsequent ability in the outloud condition. FIG. 165 presents the level of activation during the outloud condition which predicted reading ability.

Figure 166:
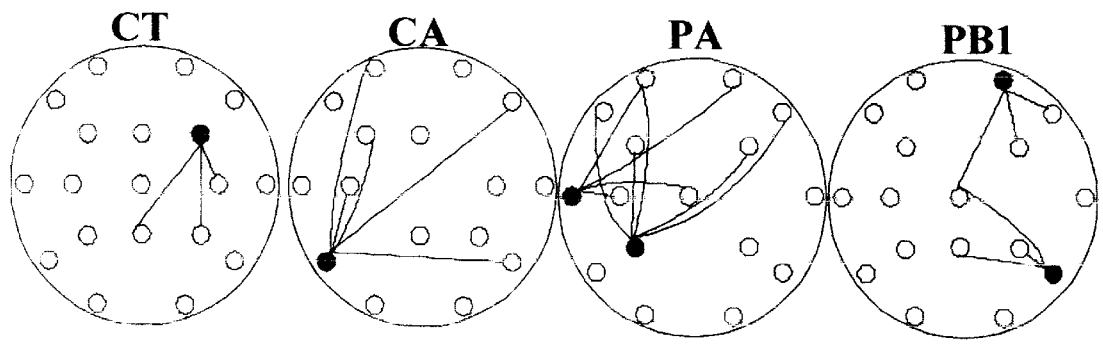
Figure 167:
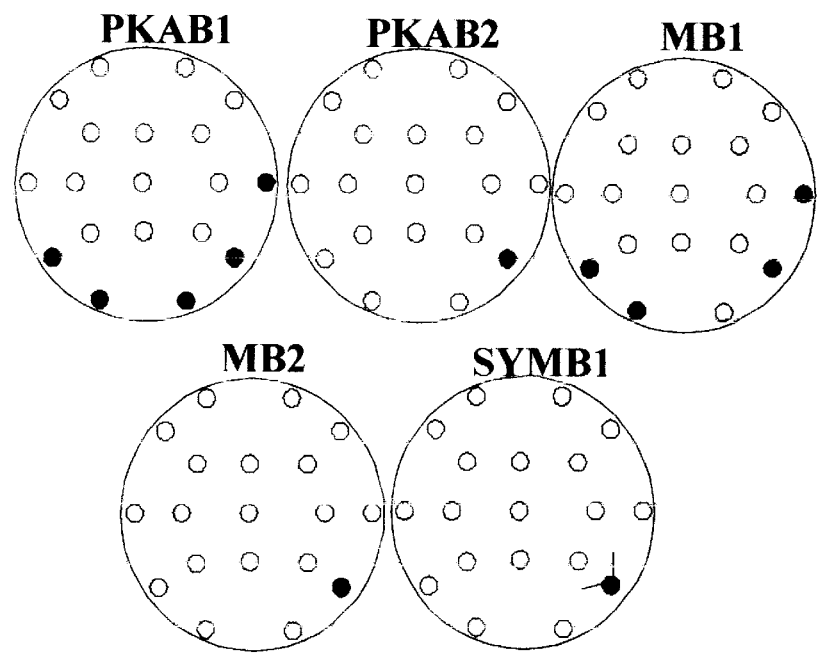
Figure 168:
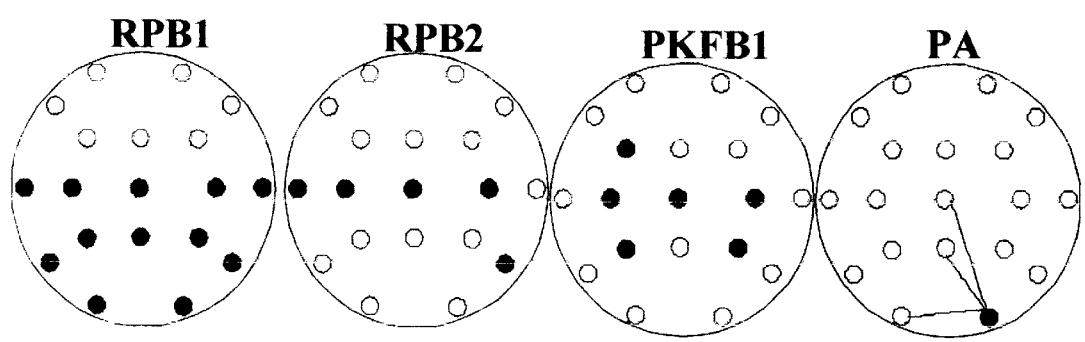
Figure 169:
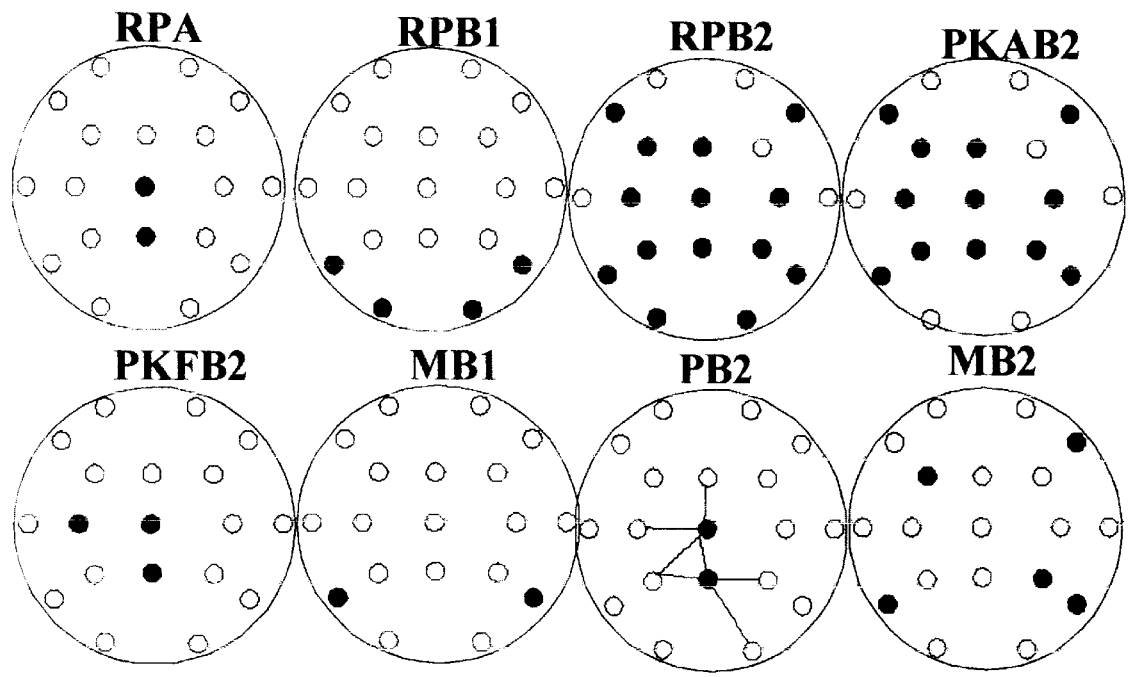
Figure 170:
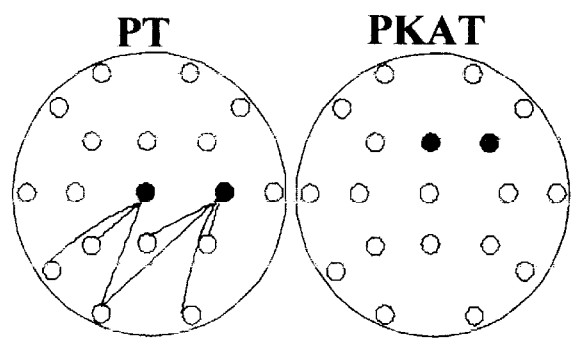
Figure 171:
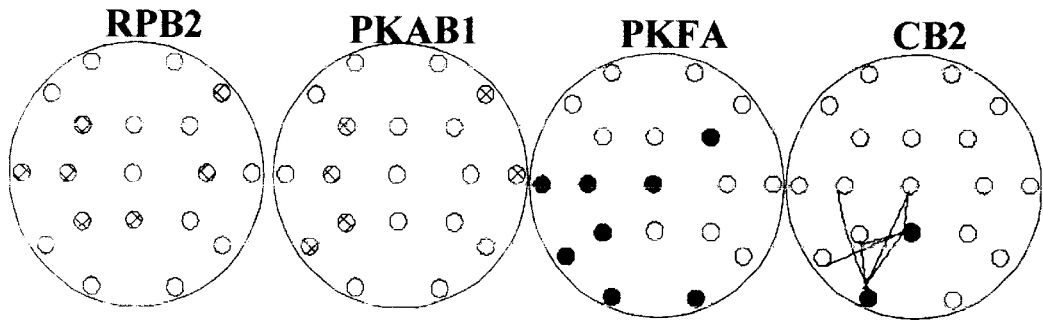
Figure 172:
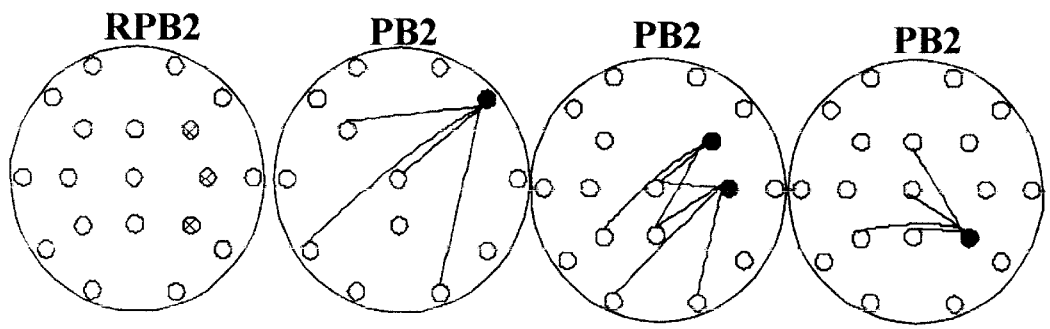
Figure 173:
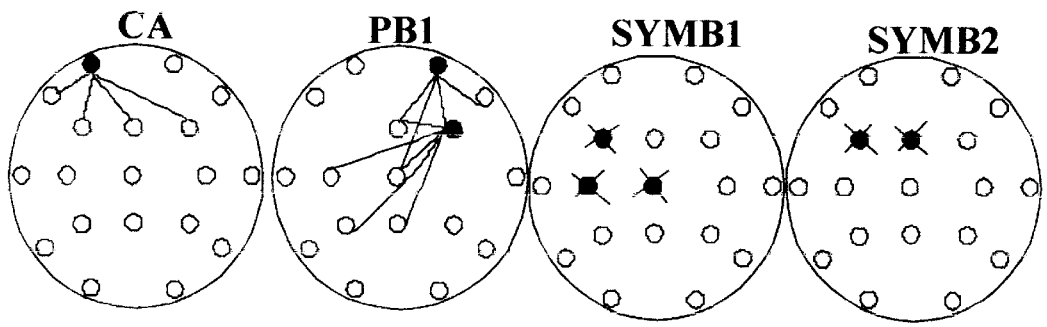
Figure 174:
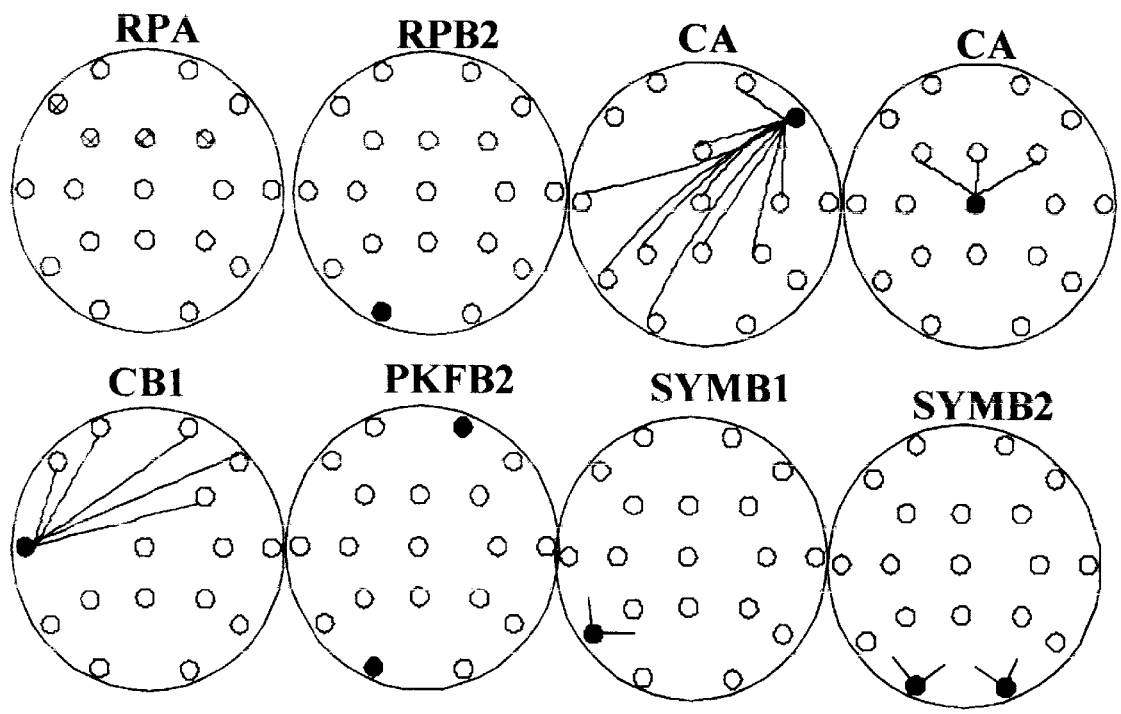
Figure 175:
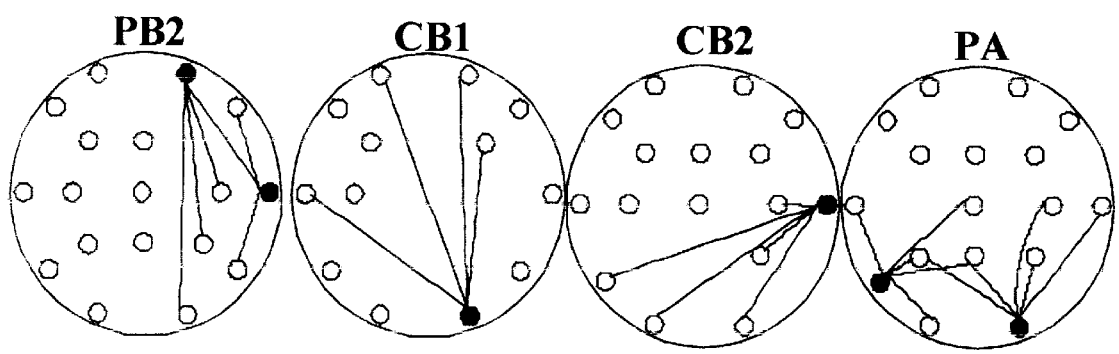
Figure 176:
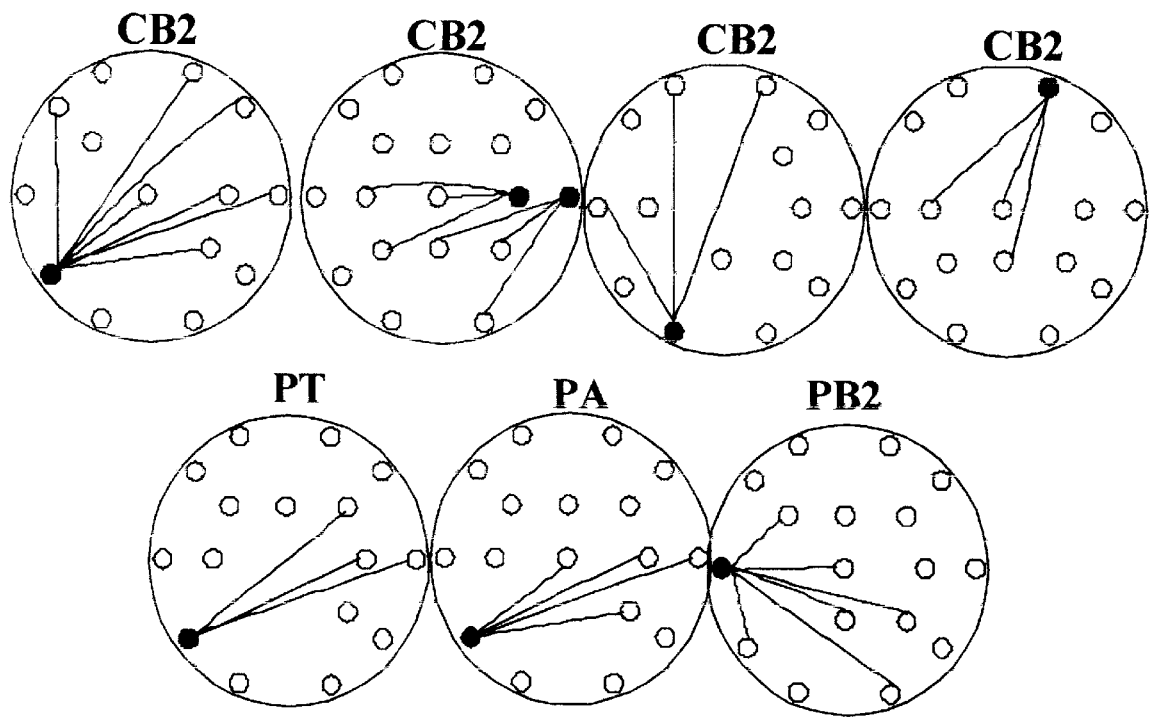
Figure 177:
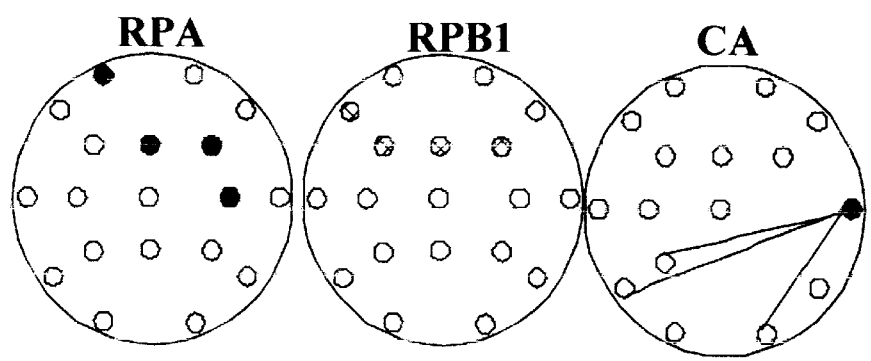
Figure 178:
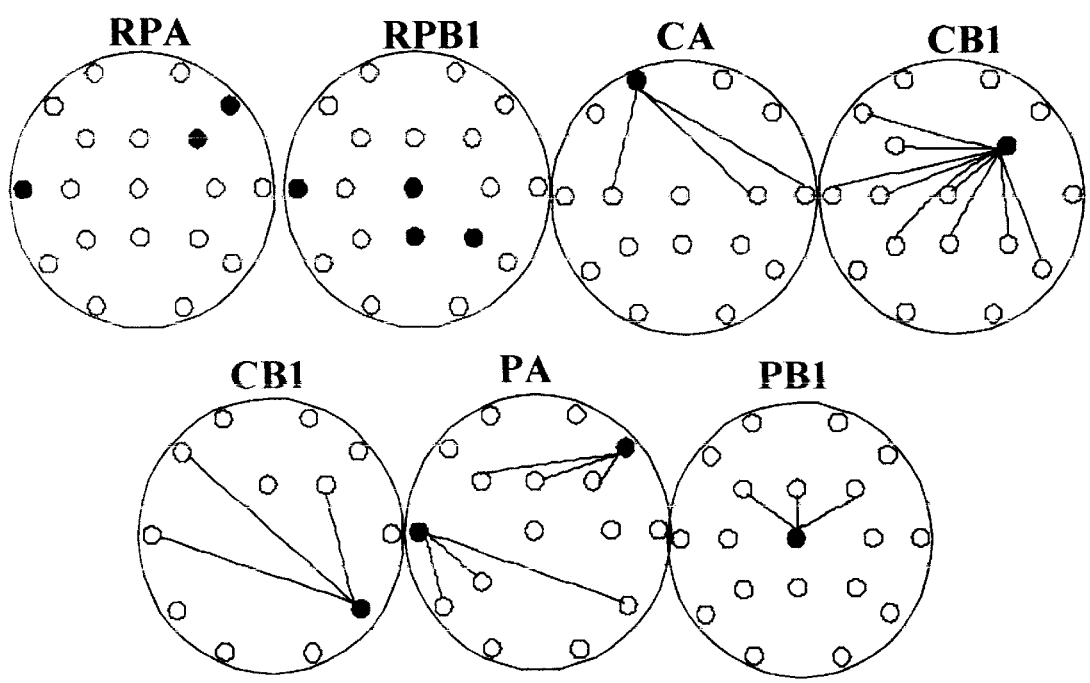
Figure 179:
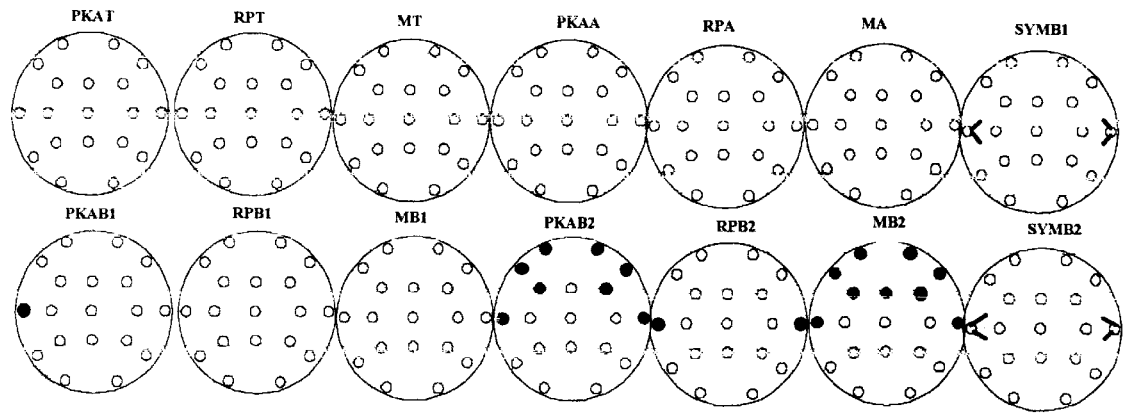
FIGS. 179 to 196 present norms: Results of the analysis of the activation of bands from the respective comparison conditions.
Figure 180:
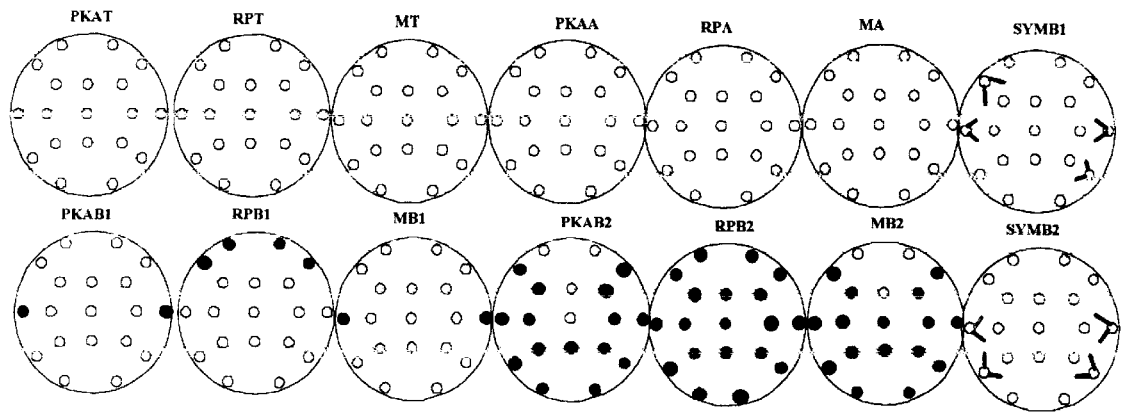
Figure 181:
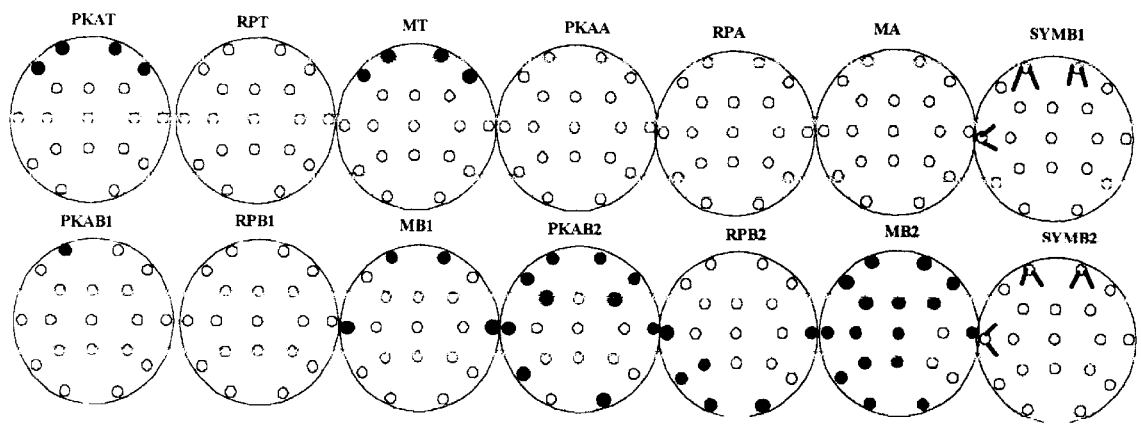
Figure 182:
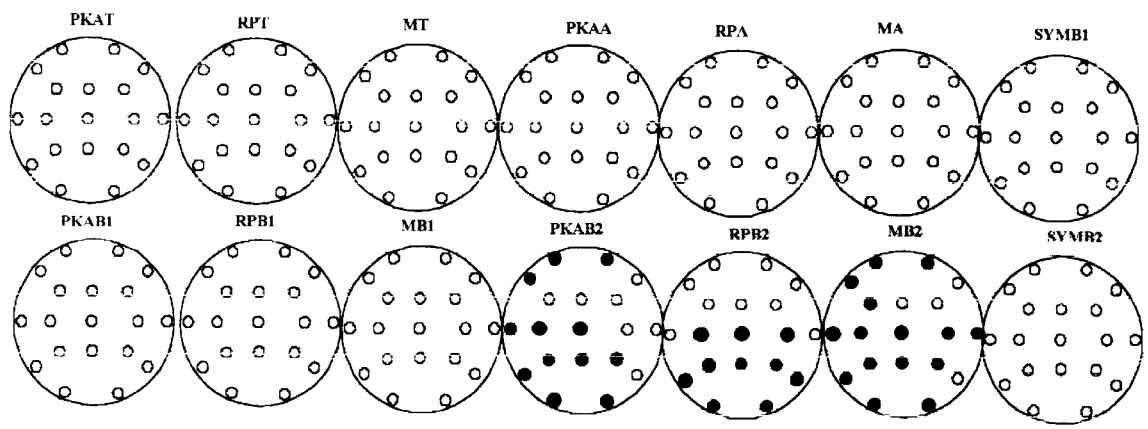
Figure 183:
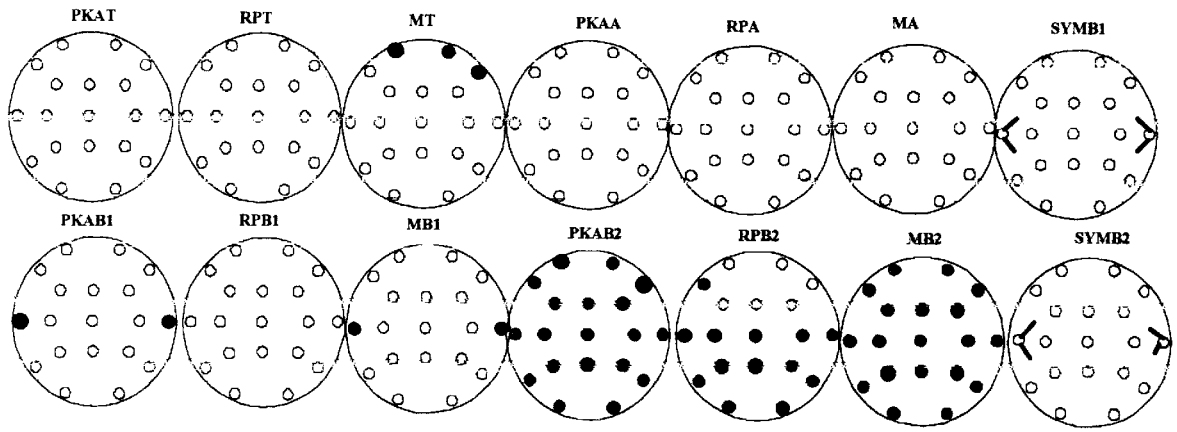
Figure 184:
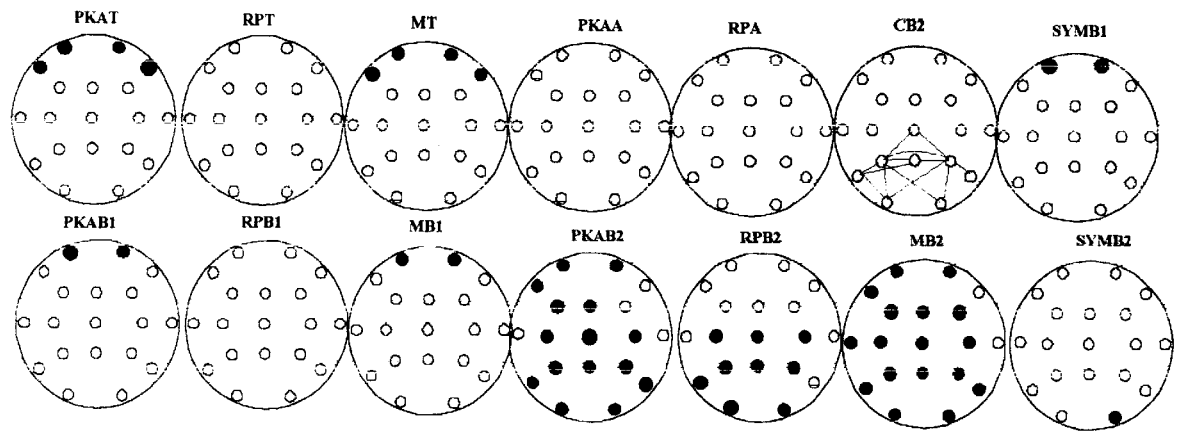
Figure 185:
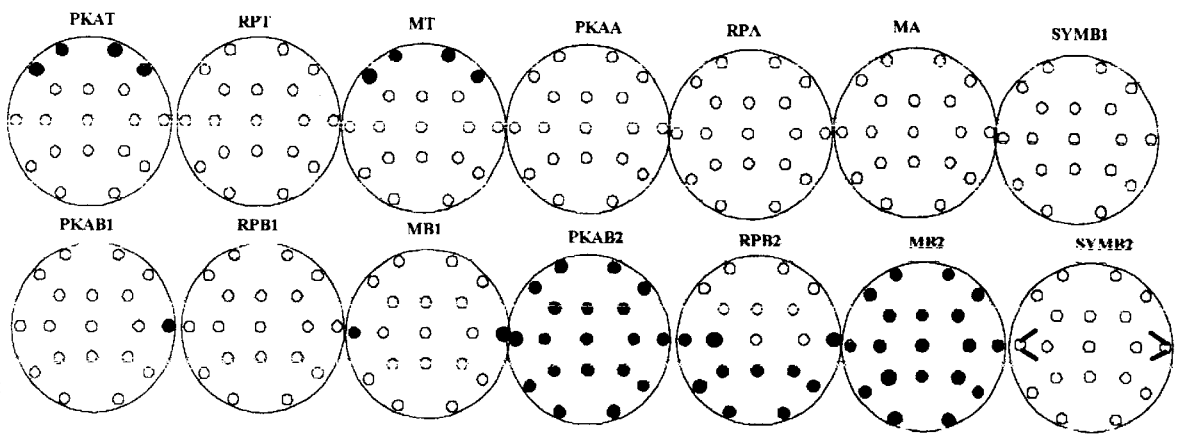
Figure 186:
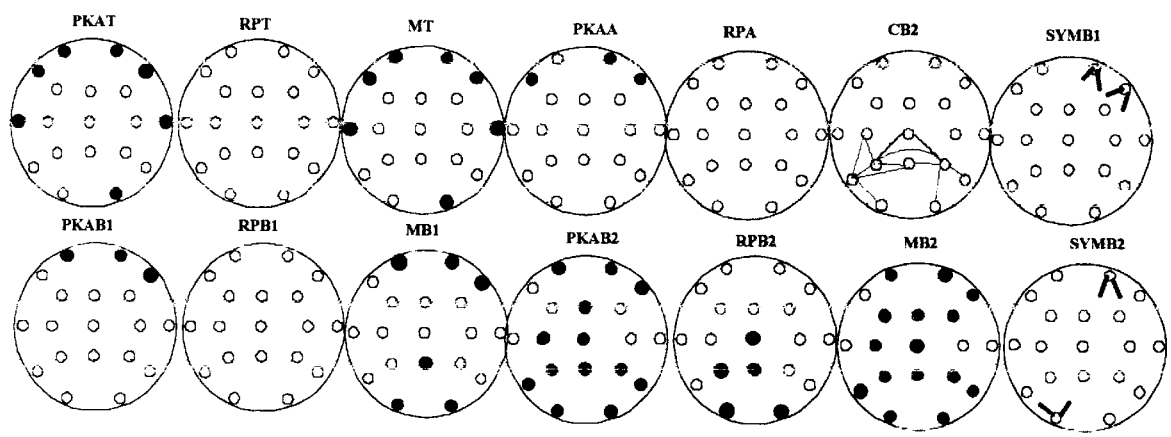
Figure 187:
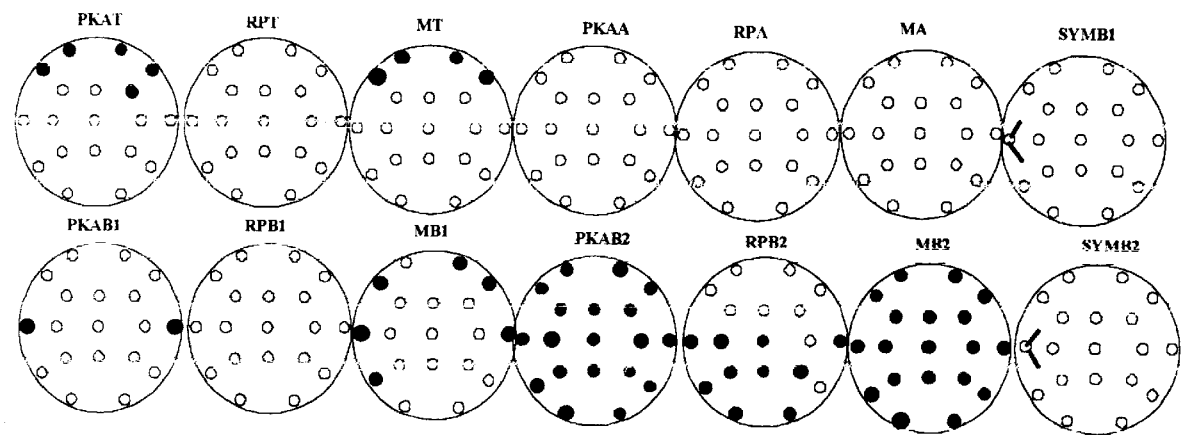
Figure 188:
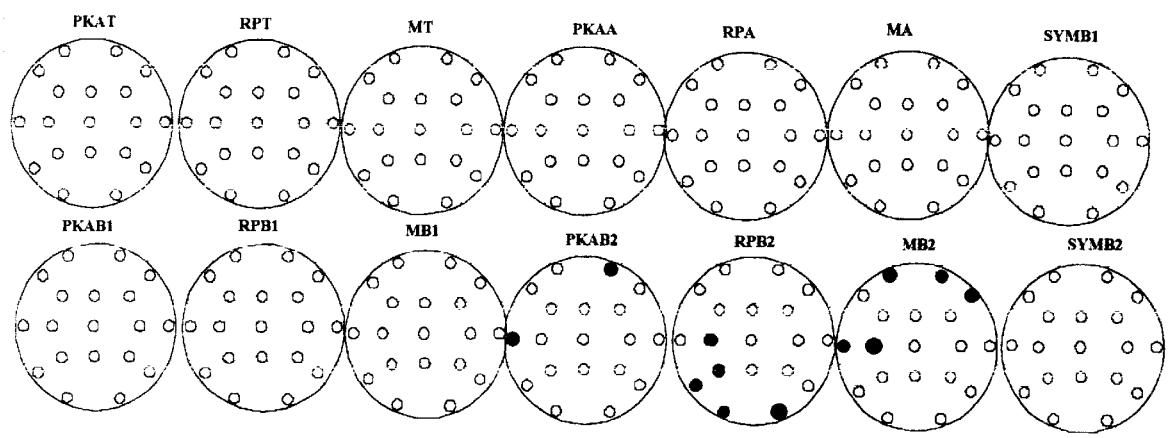
Figure 189:
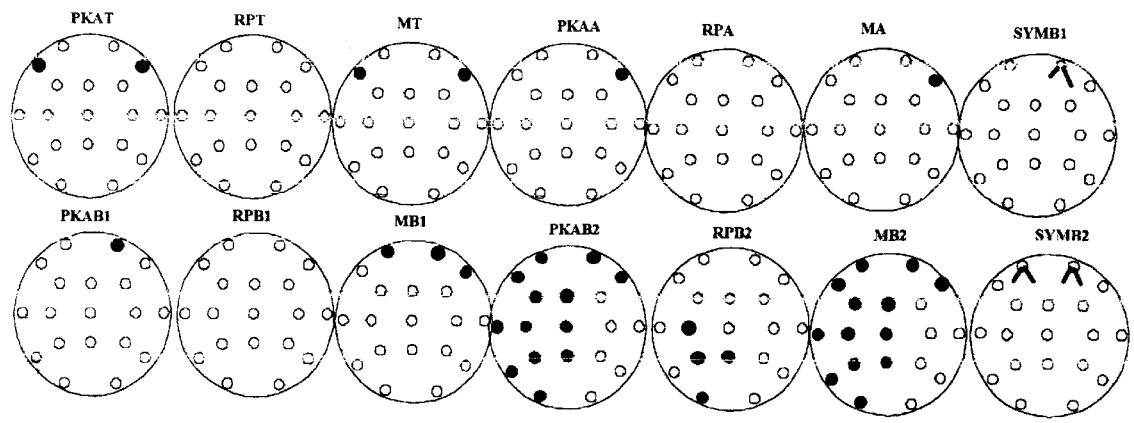
Figure 190:
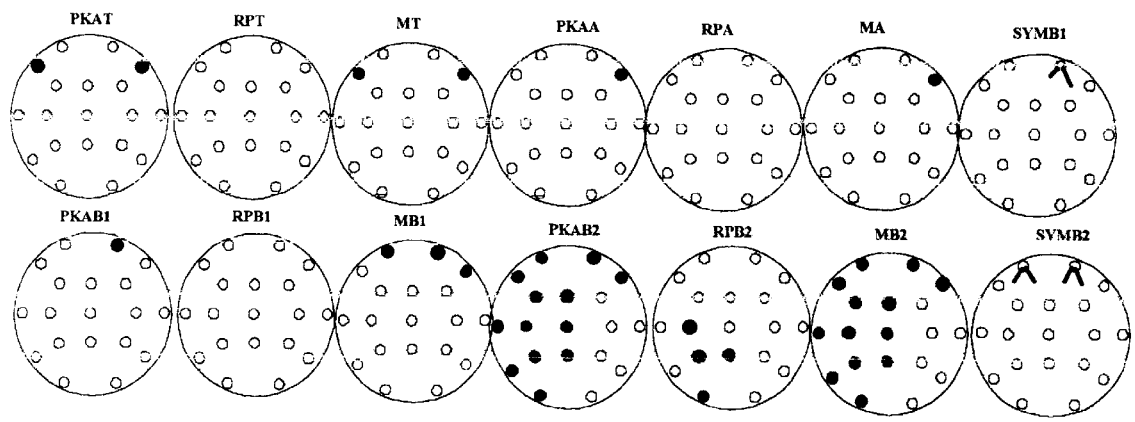
Figure 191:
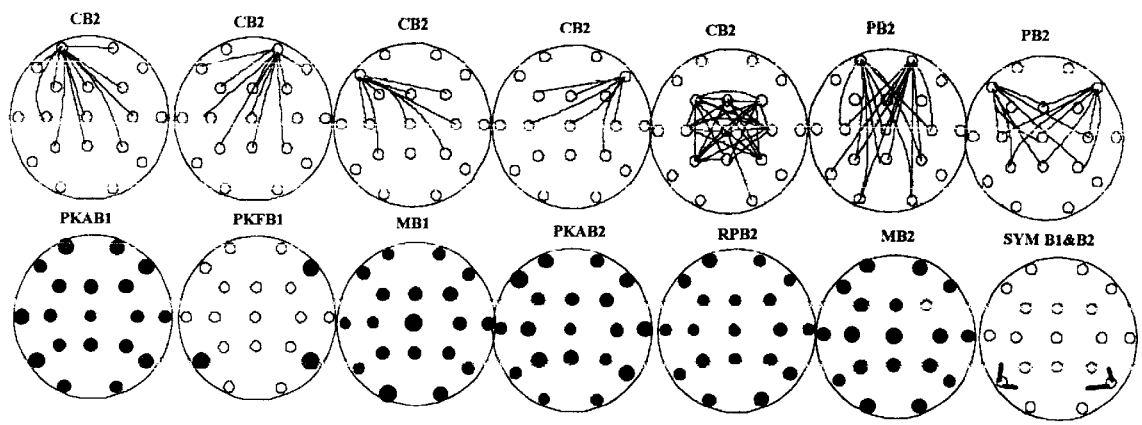
Figure 192:
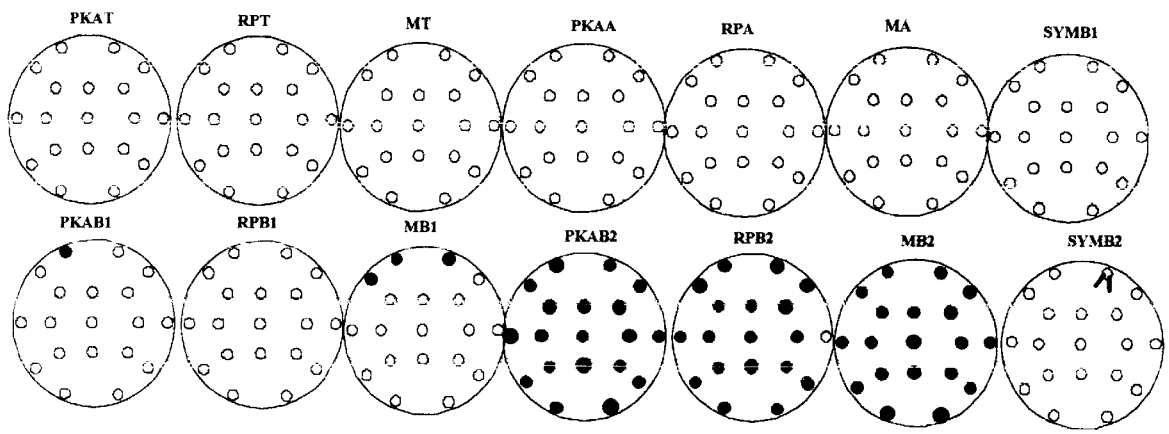
Figure 193:
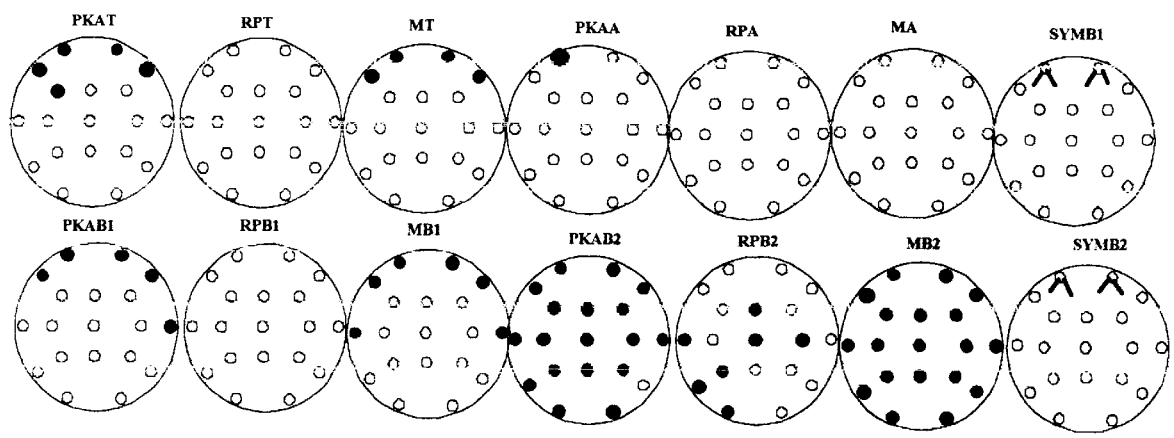
Figure 194:
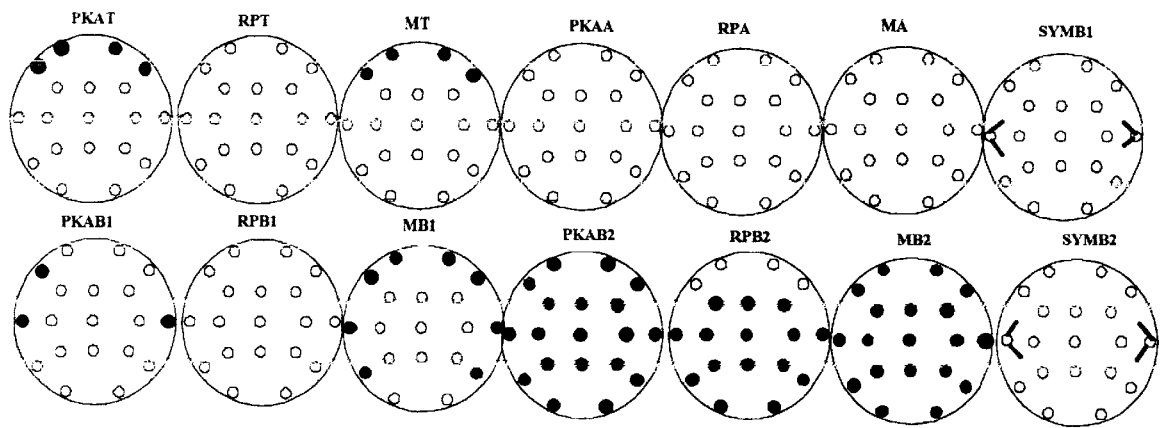
Figure 195:
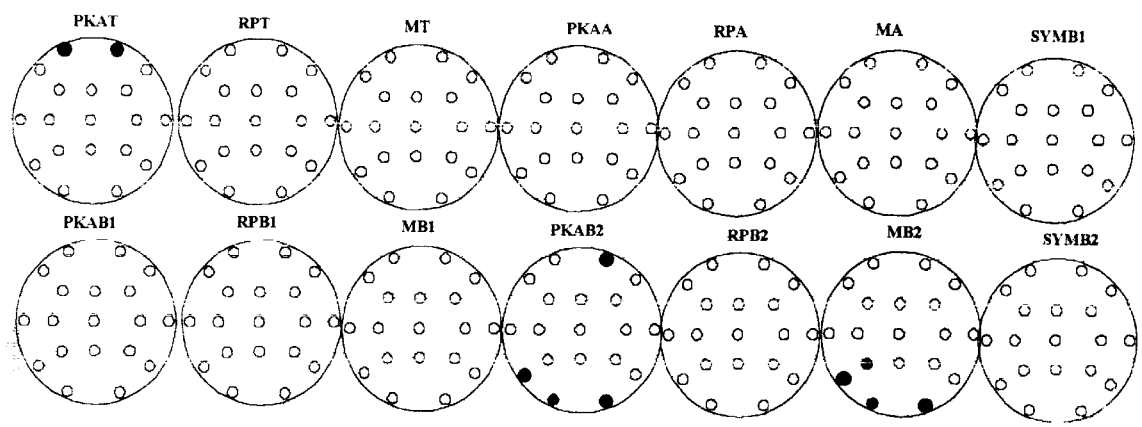
Figure 196:
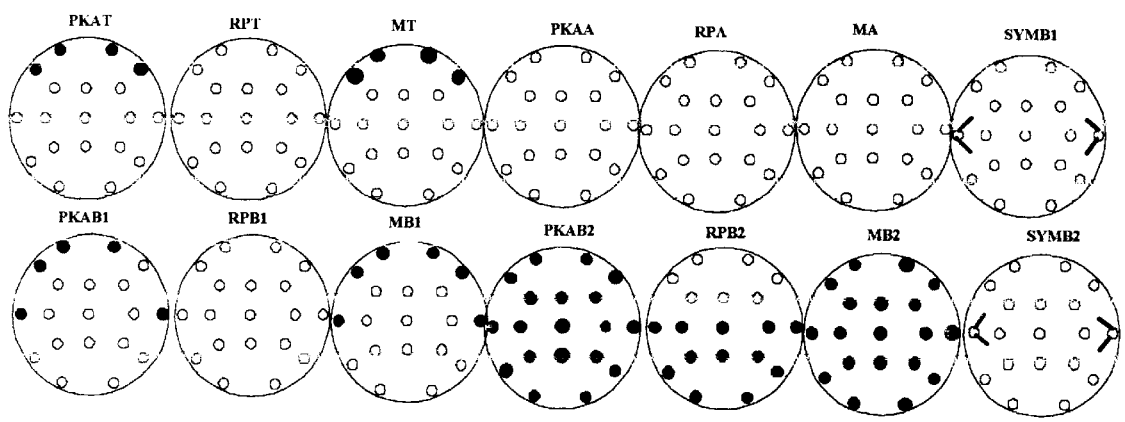

FIG. 166 relates "Delayed Recall of Word Lists" tasks (experiment coding CL#1). There was no significant pattern for level of activation and success at delayed recall. FIG. 166 presents the degree of activation from eyes closed and the variables, which related to success.

Figure 117:
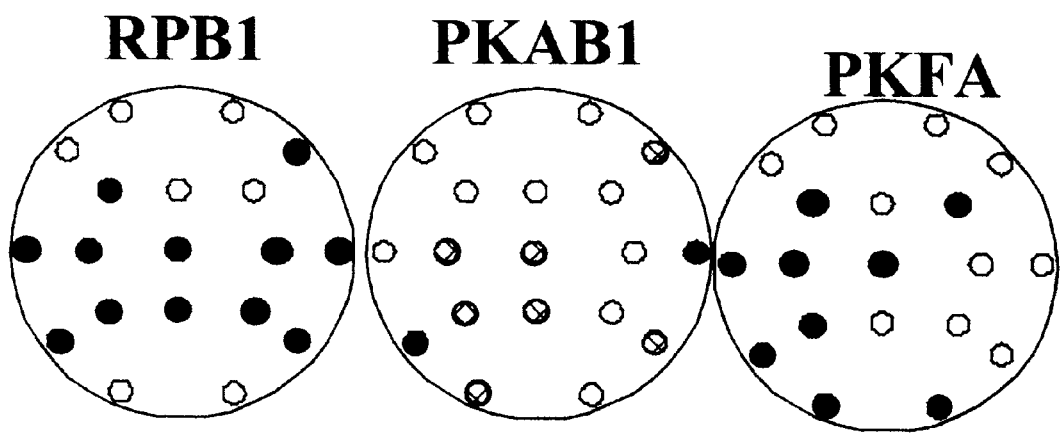
Figure 118:
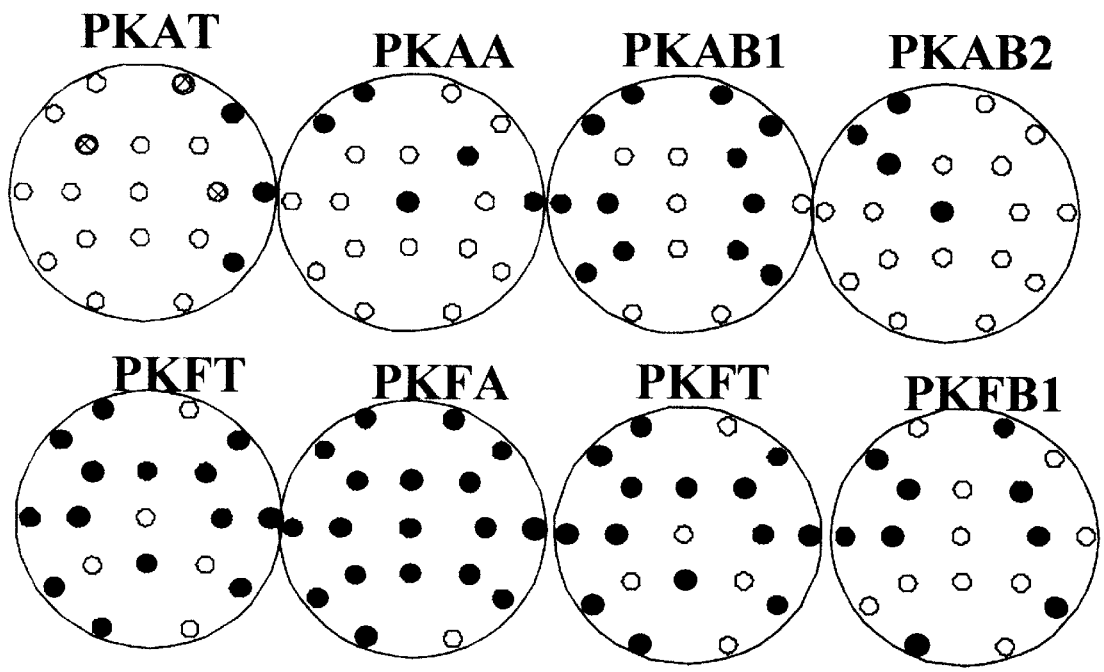

FIG. 117 presents the variables whose level of activation during the silent recall of paragraphs predicted success. FIG. 118 present the degree of activation from the respective eyes closed condition. Those variables, which correlated with subsequent success, are presented.

Figure 119:
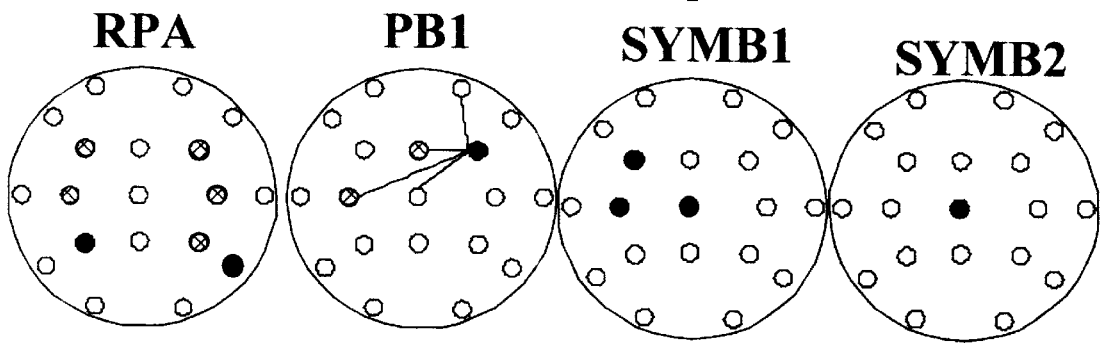

FIG. 119 presents the results of the relationship between the level of activation of success at recalling Korean figures. FIG. 119 presents the variables whose level of activation predicted subsequent recall ability.

Figure 120:
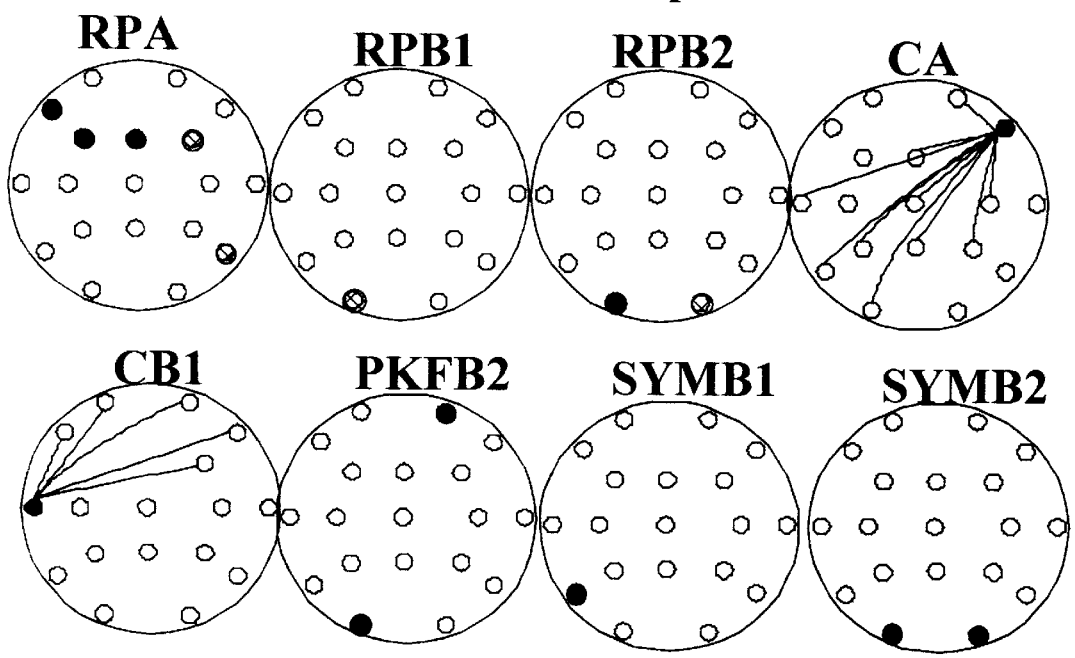
Figure 121:
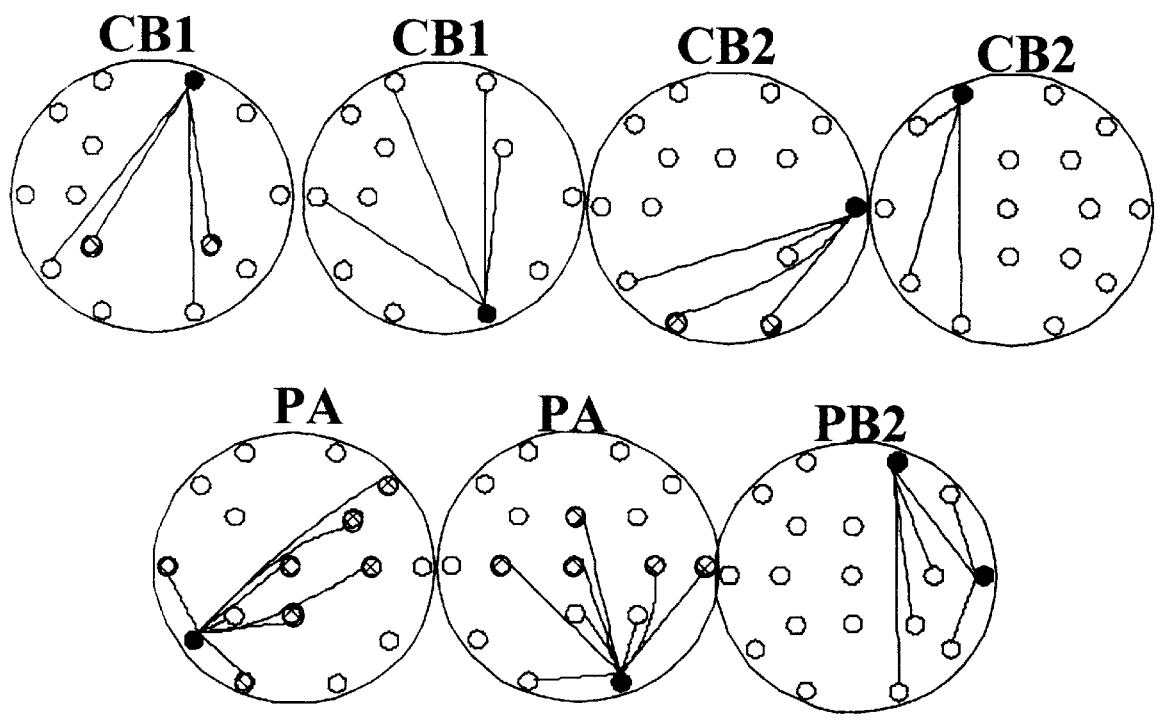
Figure 122:
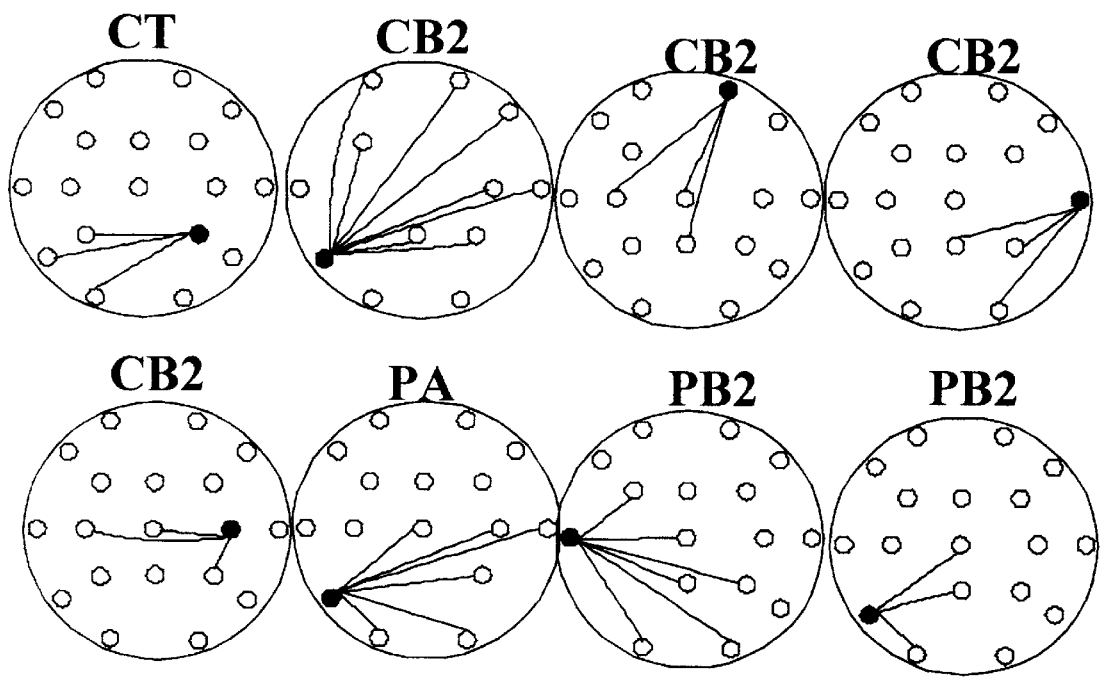

FIG. 120 presents the results for those variables whose level of activation during the silent recall of reading material predicted subsequent recall ability. FIG. 121 presents the results for the degree of activation from the eyes closed condition. Those variables which were positively correlated with subsequent recall ability are presented.

Figure 123:
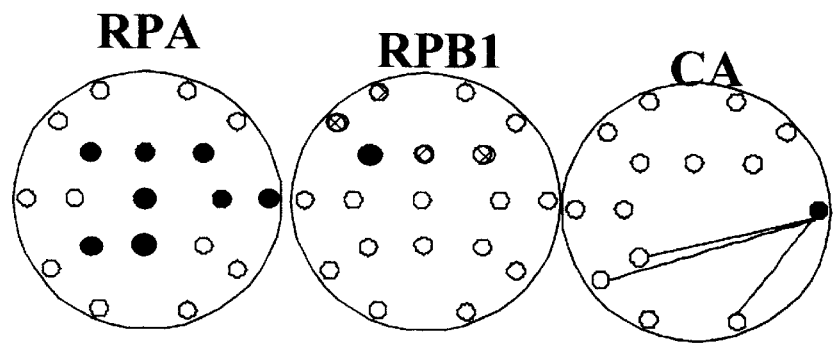

FIG. 123 (Delayed Recall of Location of Objects—experiment coding CQ#1) presents the variables whose level of activation during the silent recall condition predicted subsequent recall ability.

Figure 124:
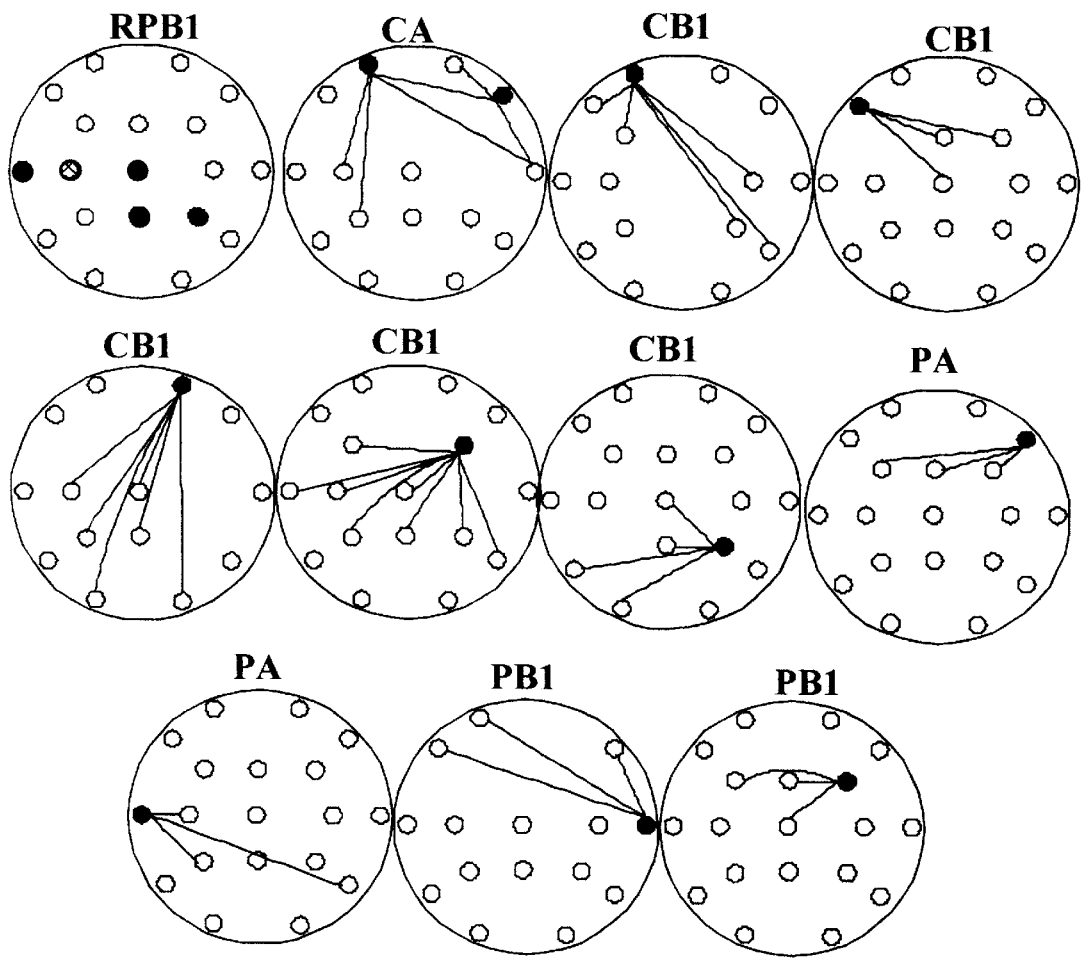
Figure 125A:
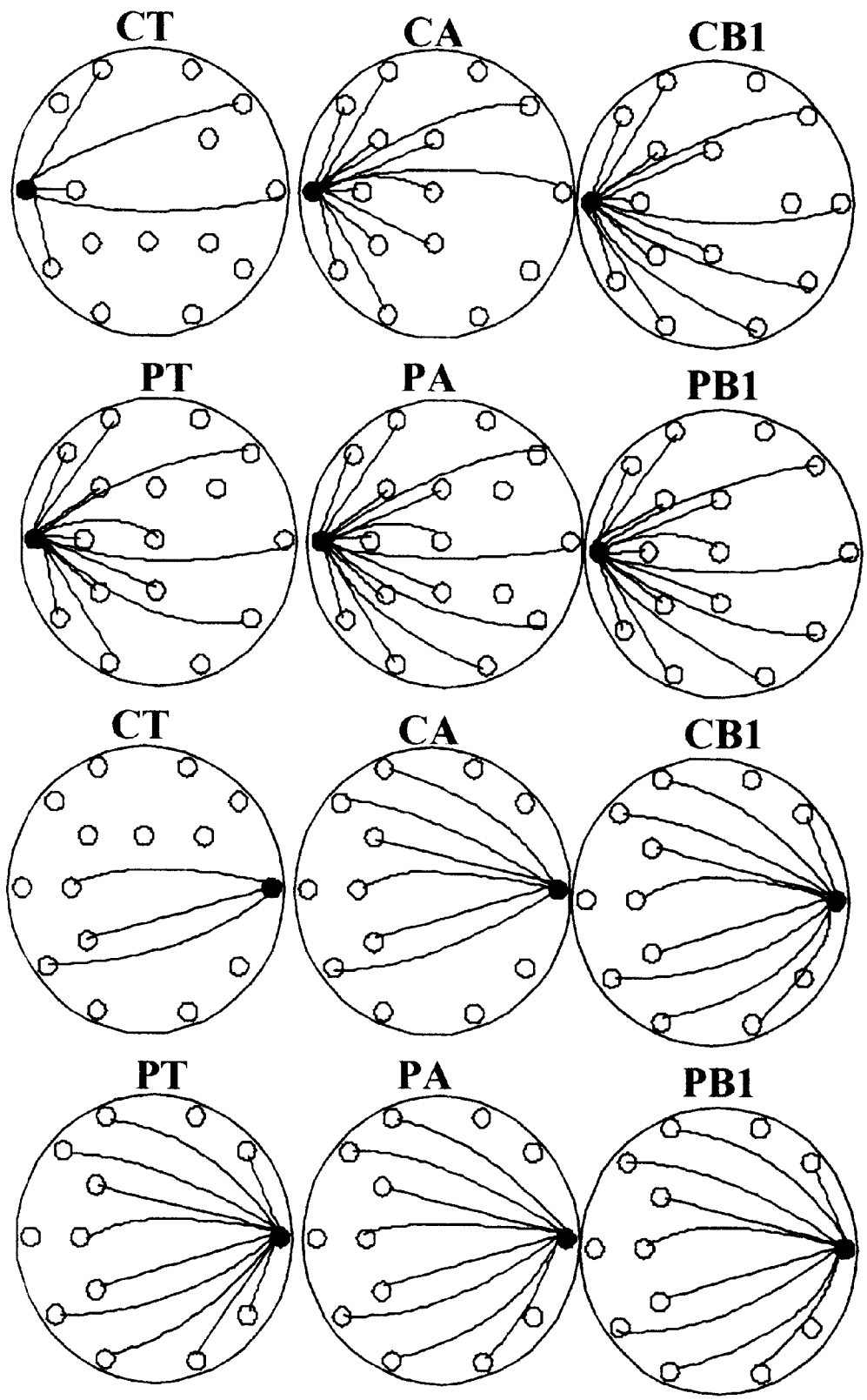
FIGS. 125 to 142 present high frequency analysis data and related data.
Figure 125B:
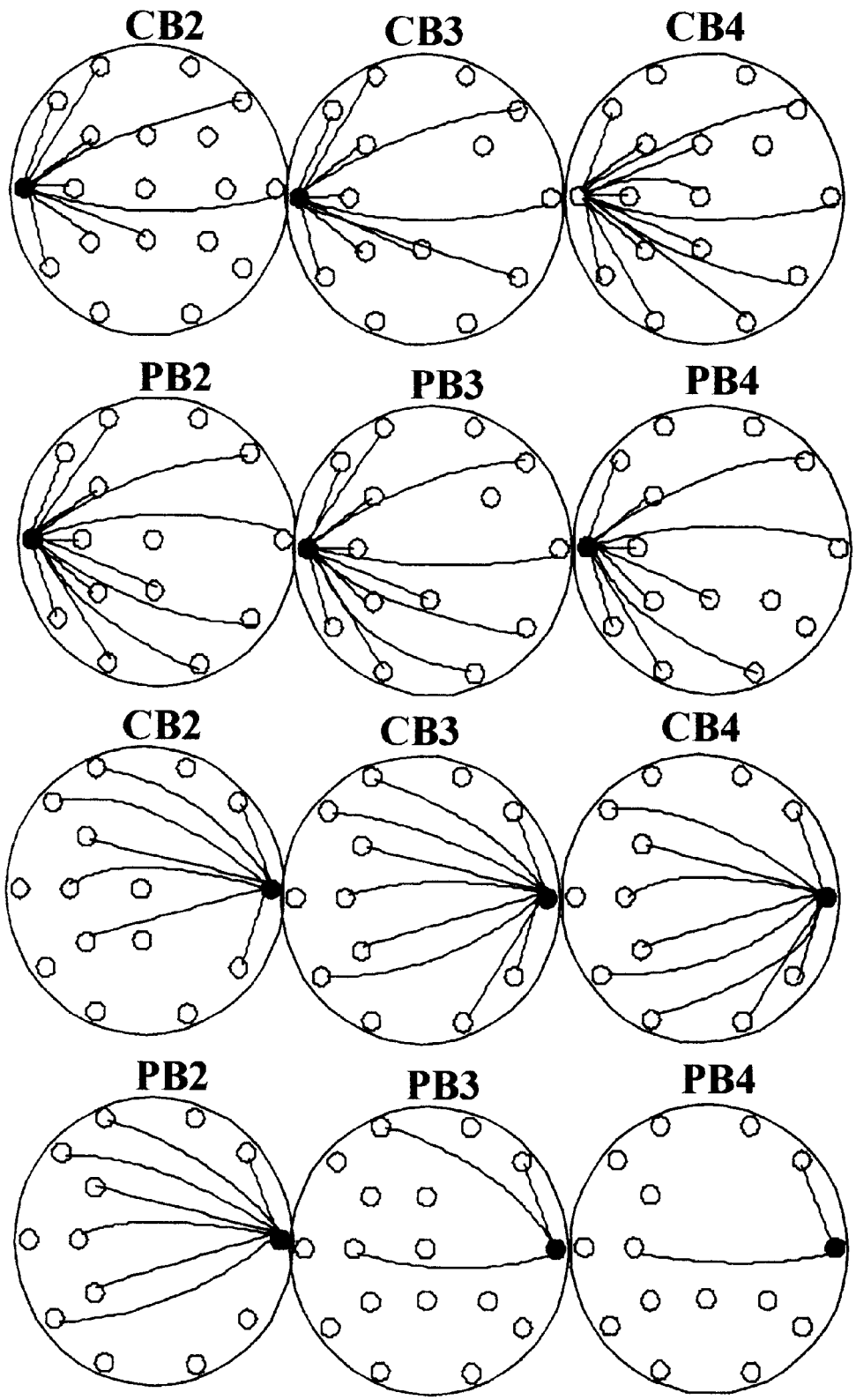
Figure 126:
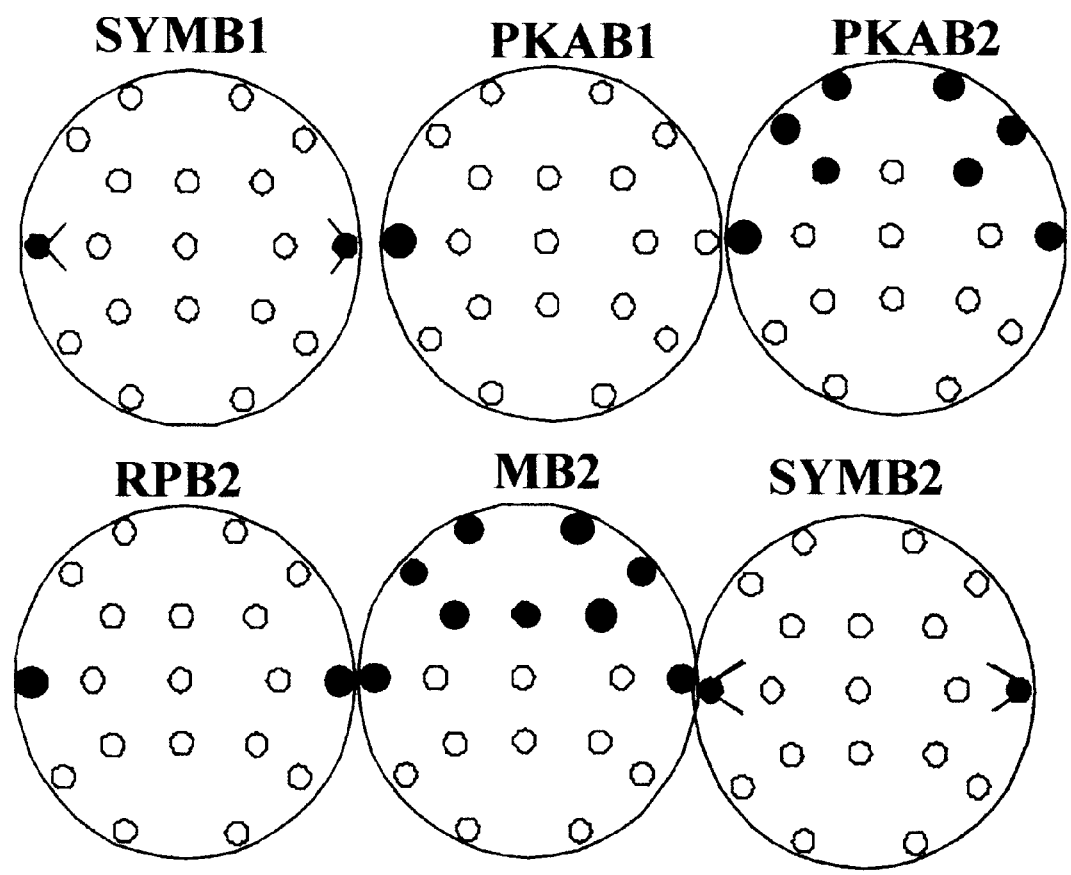
Figure 127:
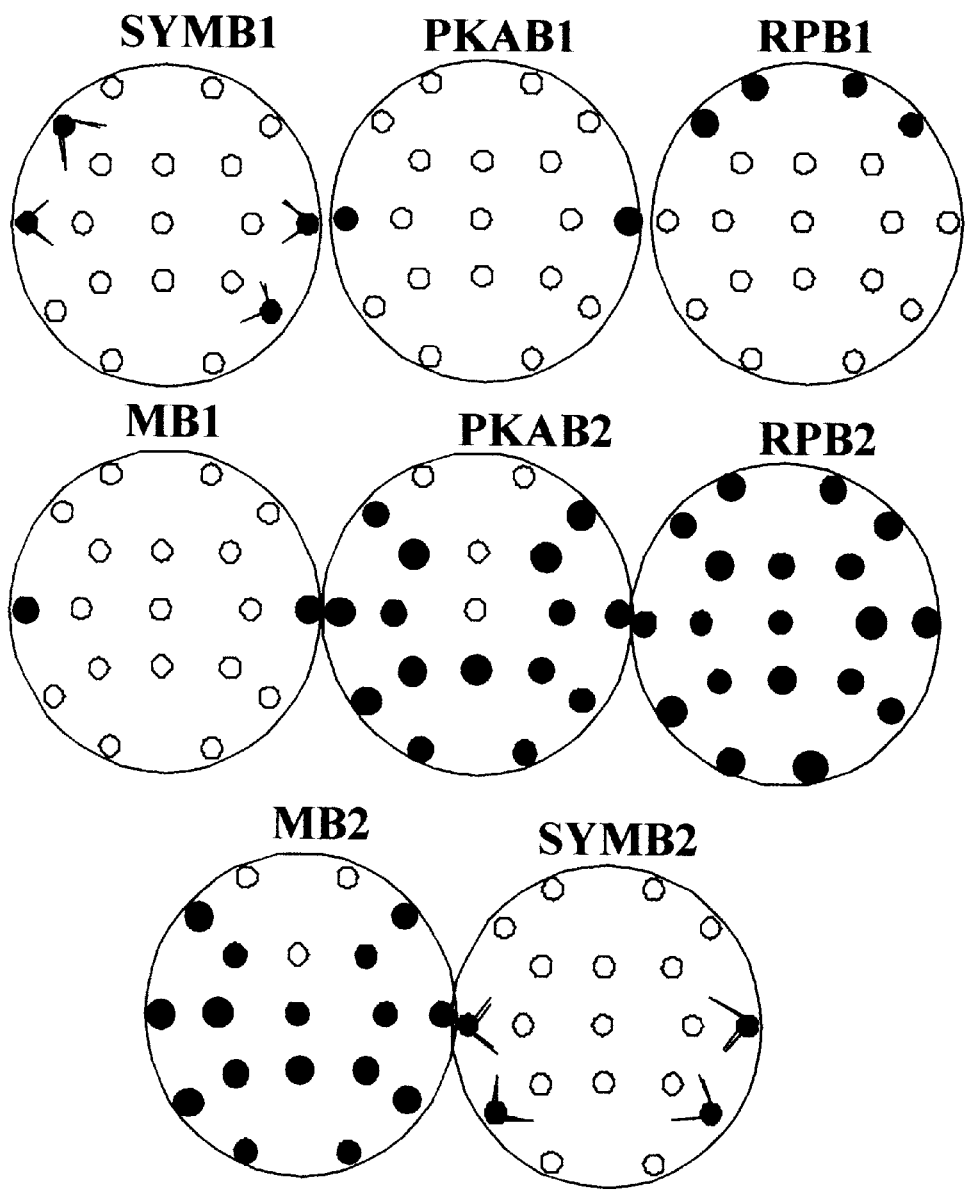
Figure 128:
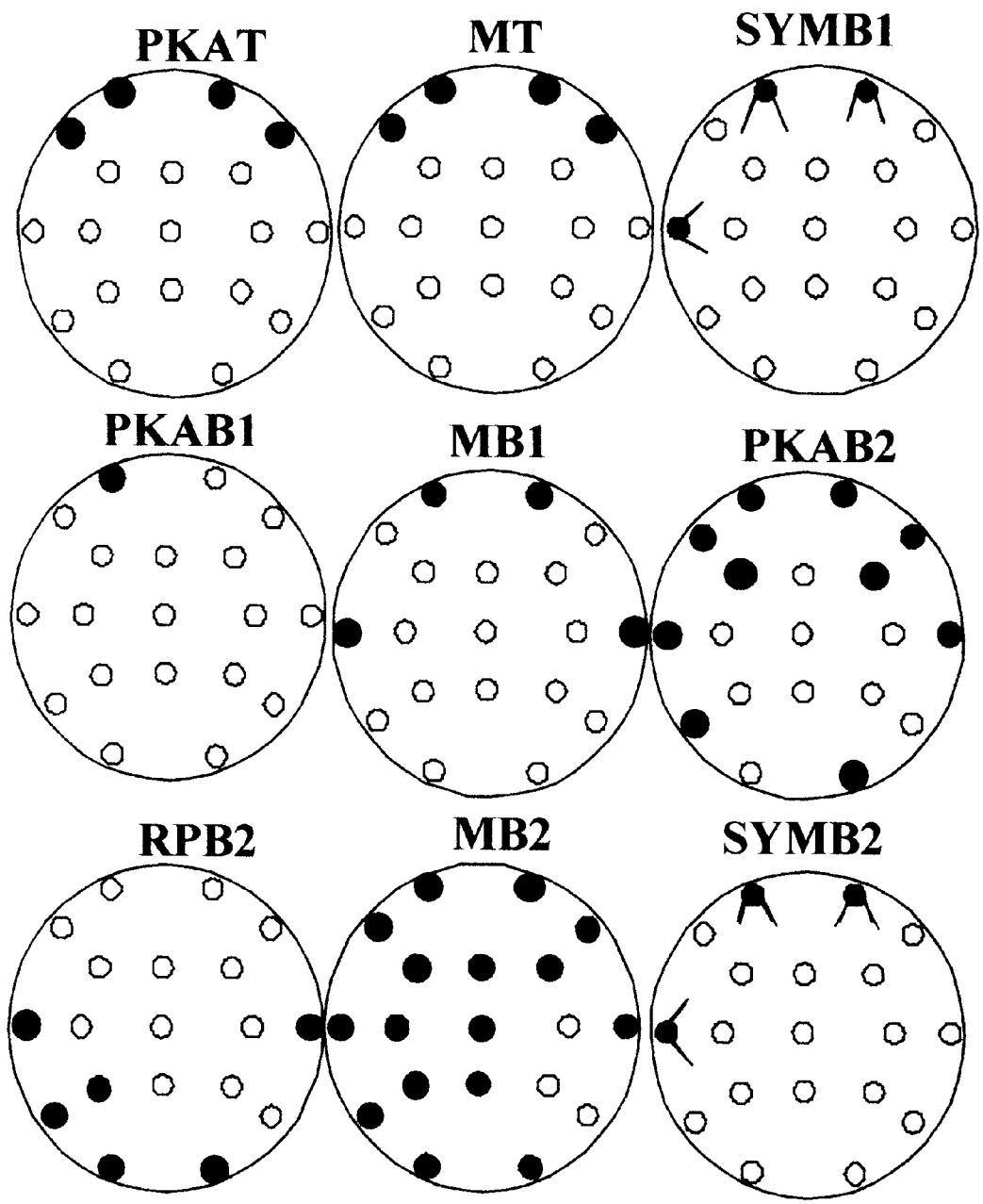
Figure 129:
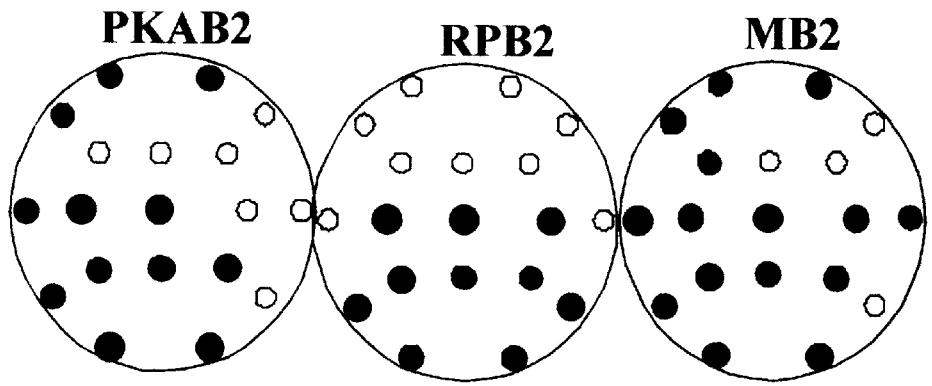
Figure 130:
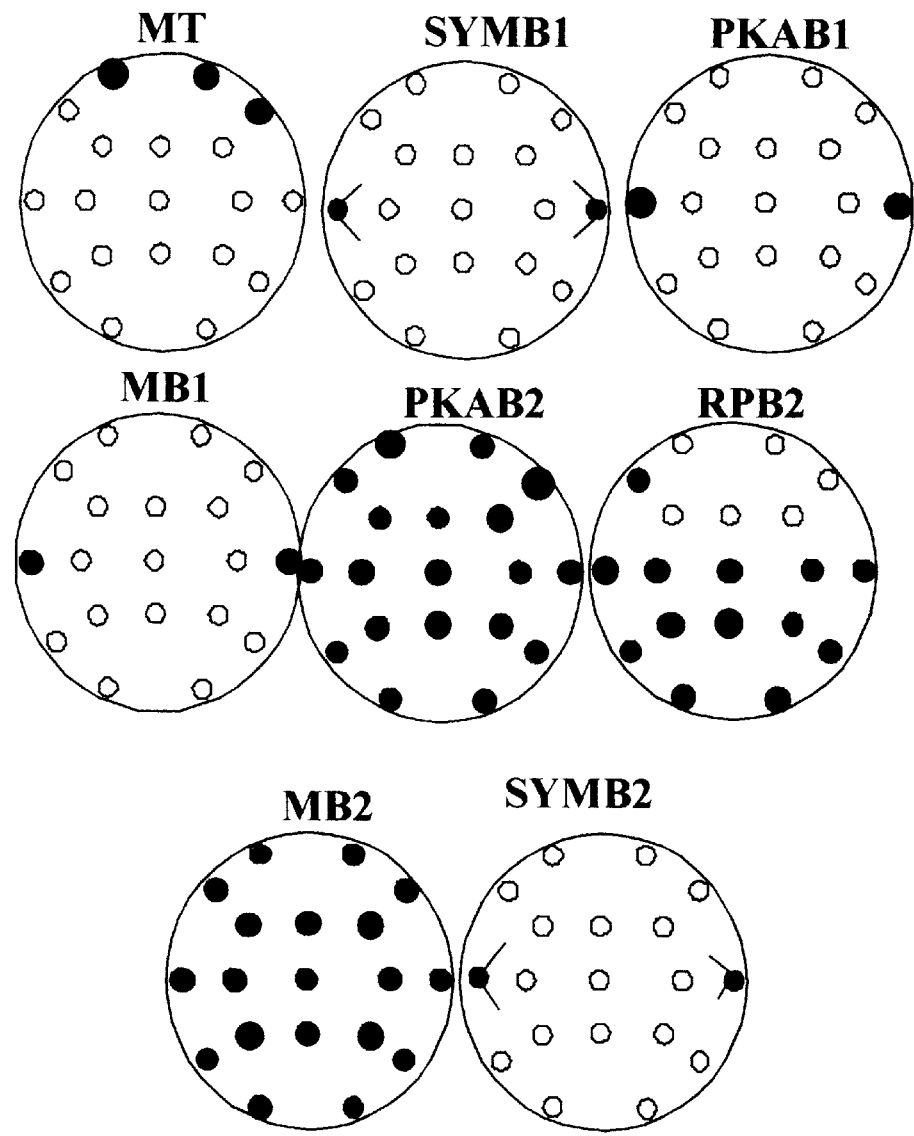
Figure 131:
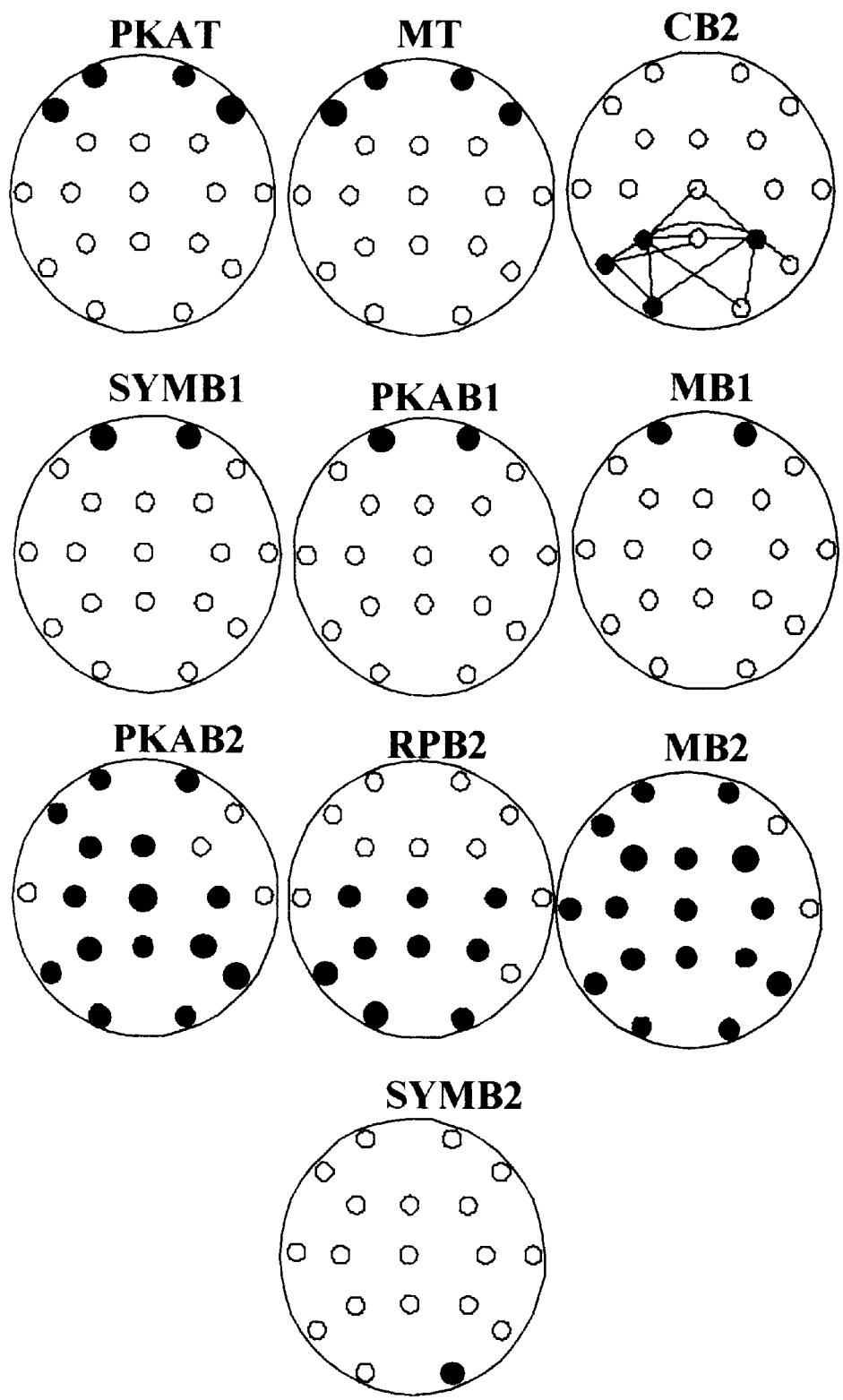
Figure 132:
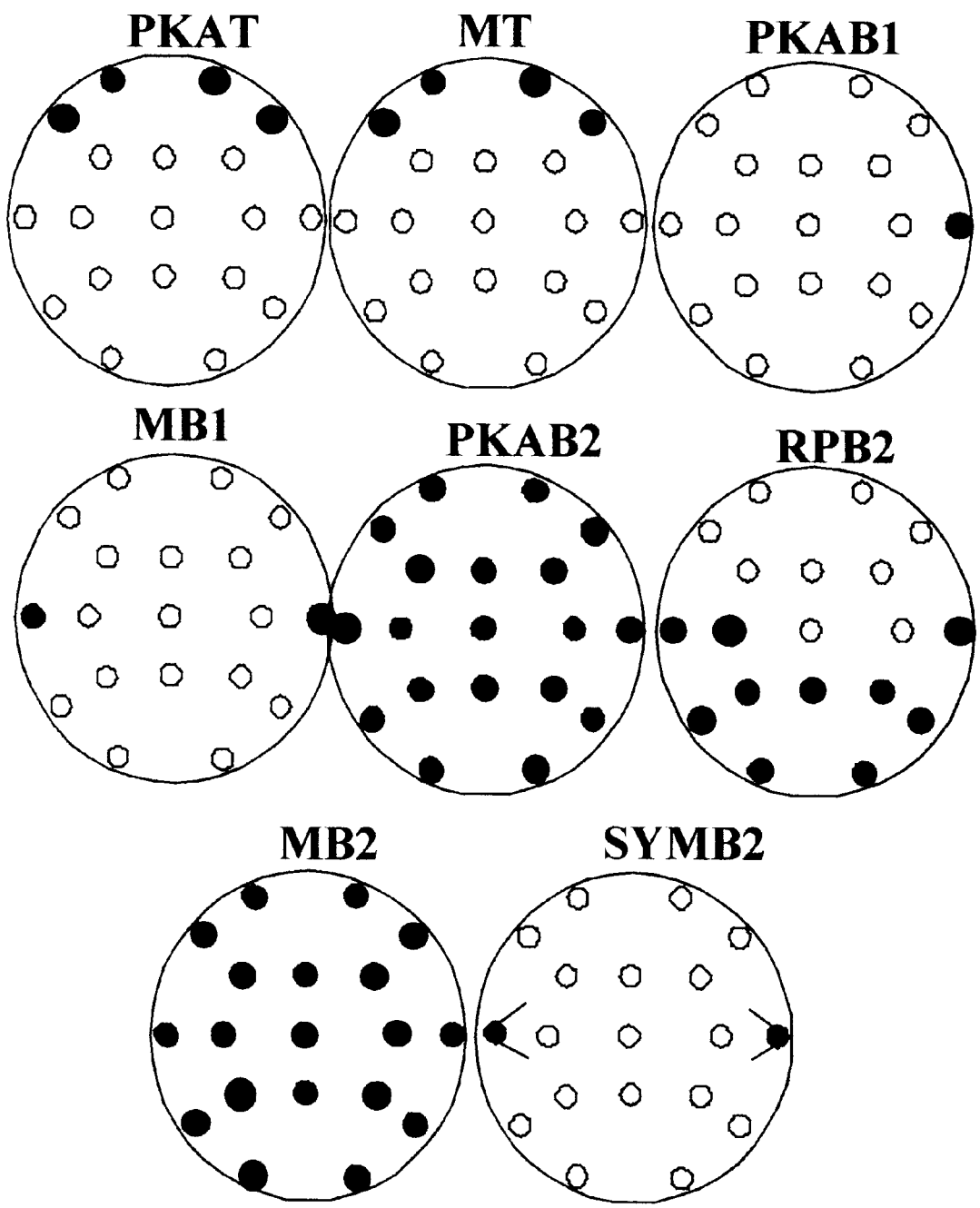
Figure 133:
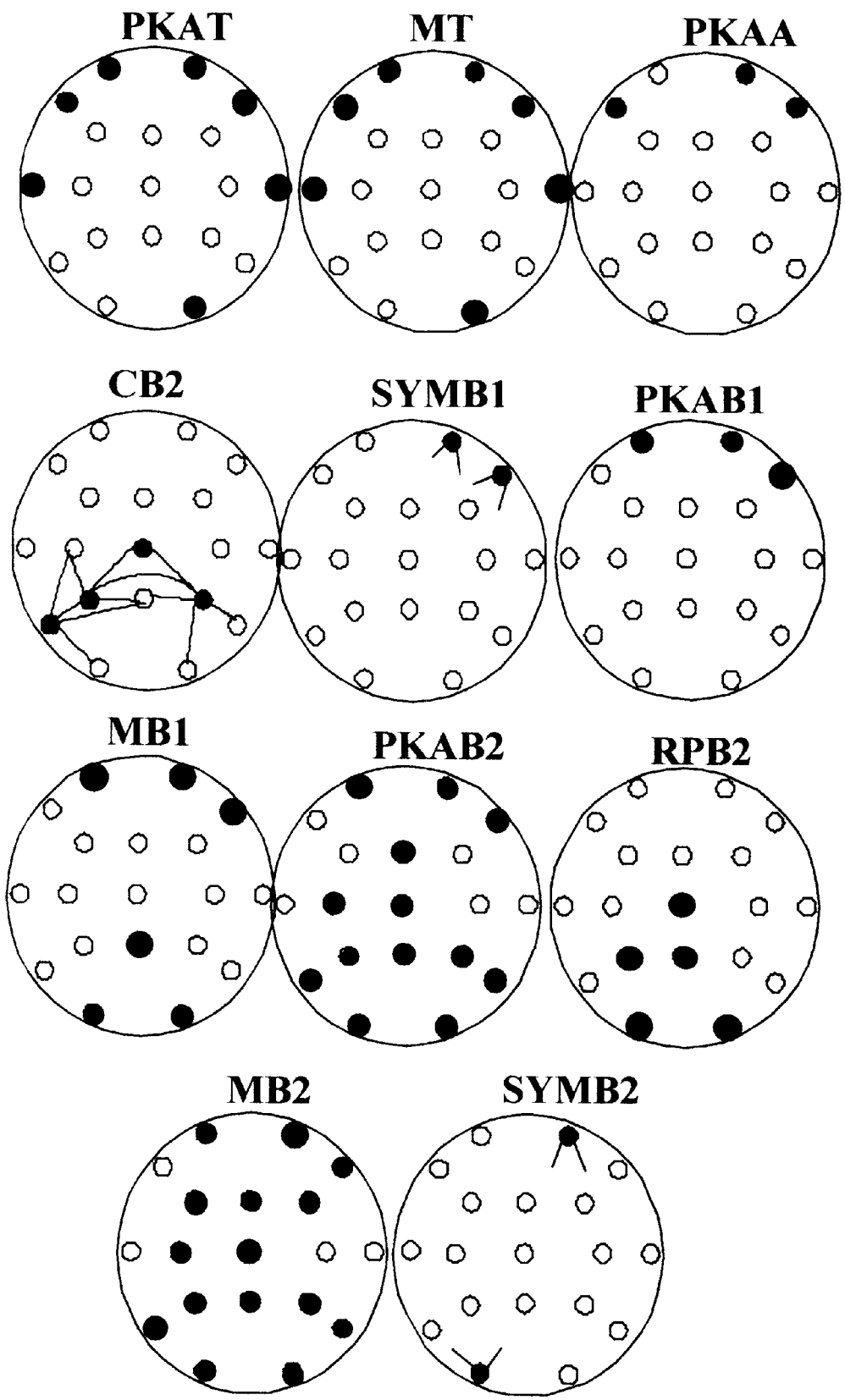
Figure 134:
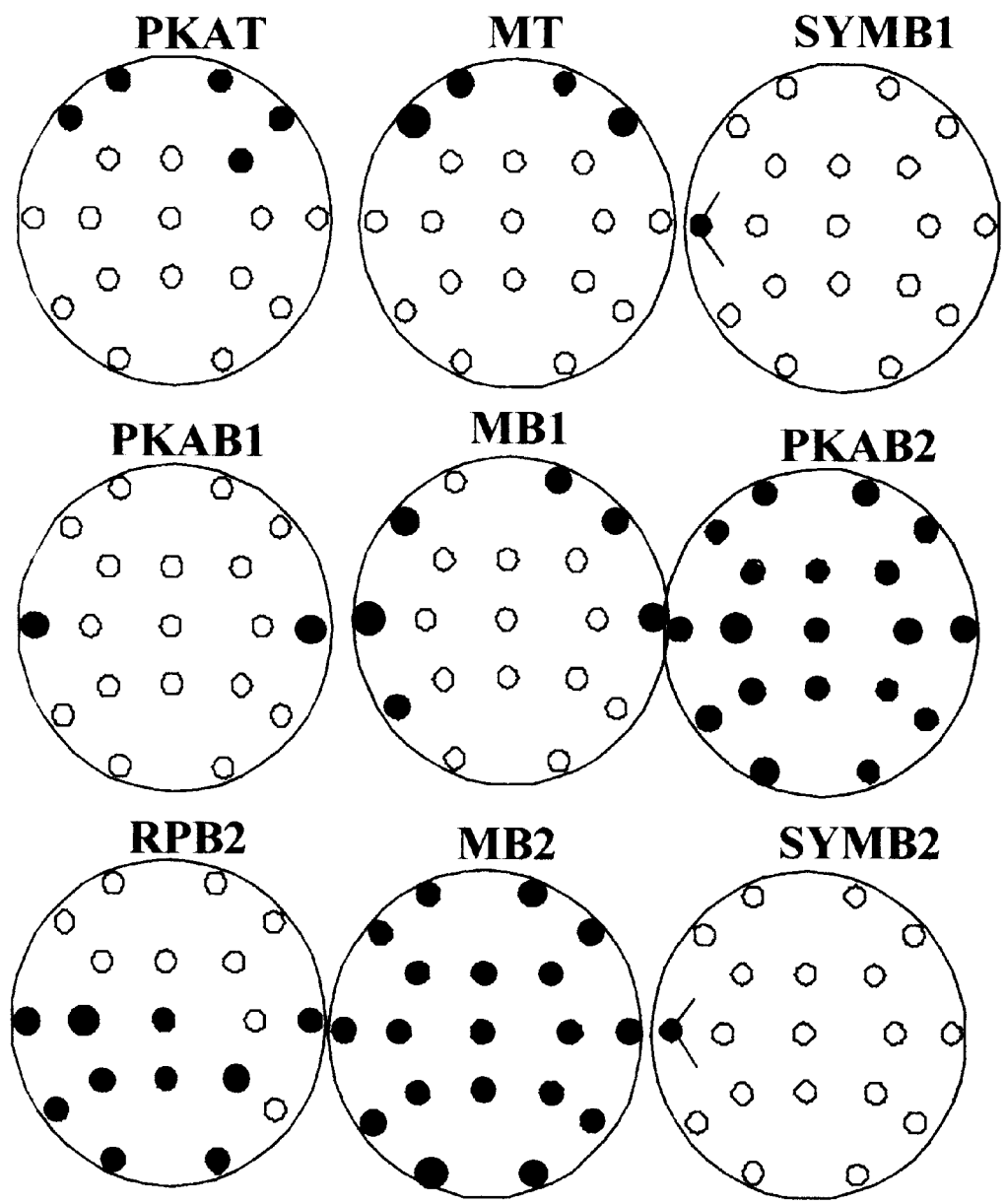
Figure 135:
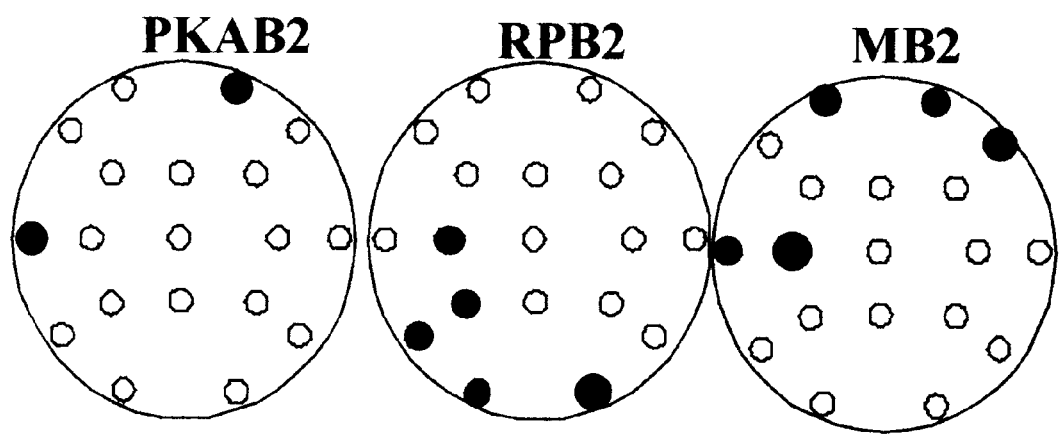
Figure 136:
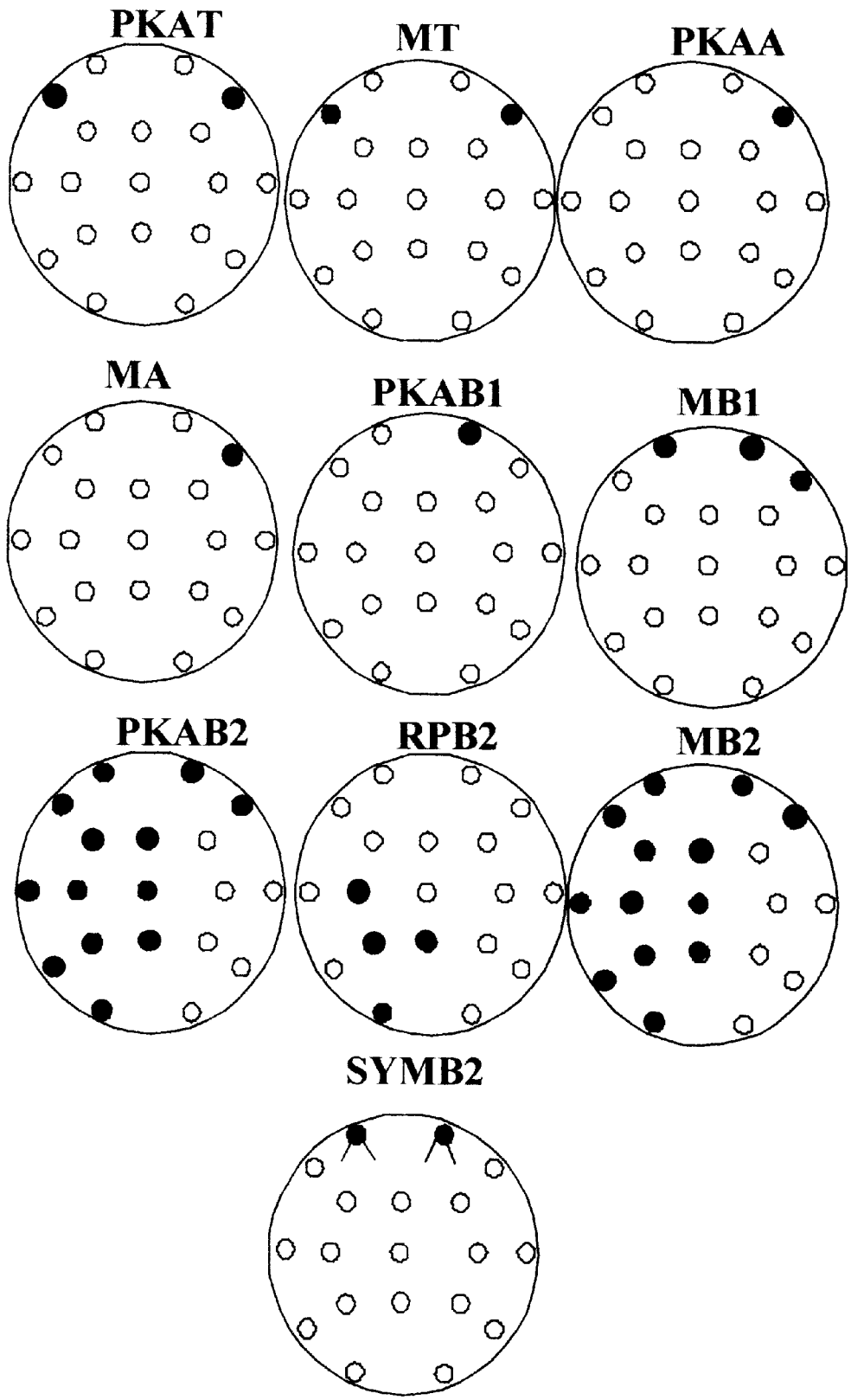
Figure 137A:
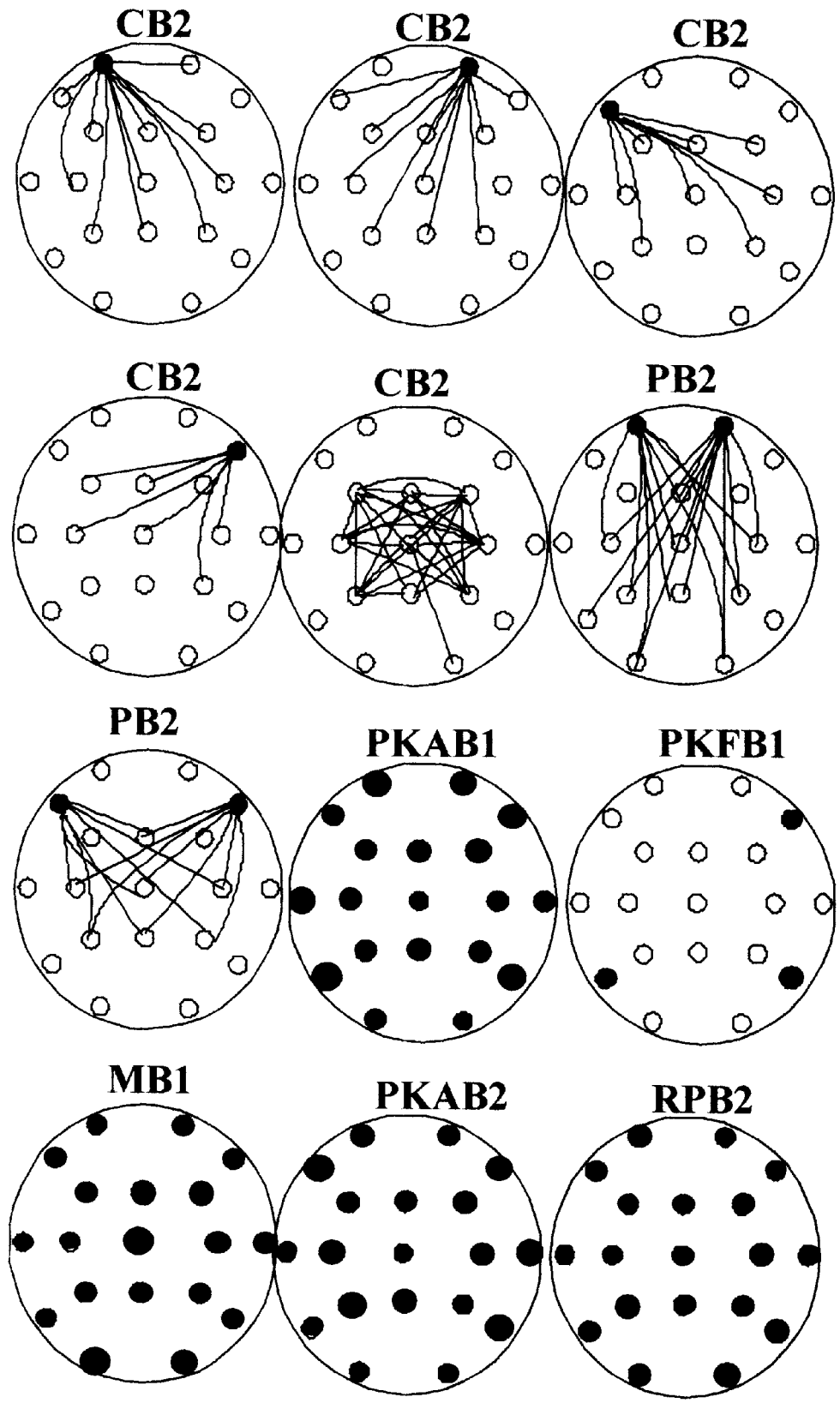
Figure 137B:
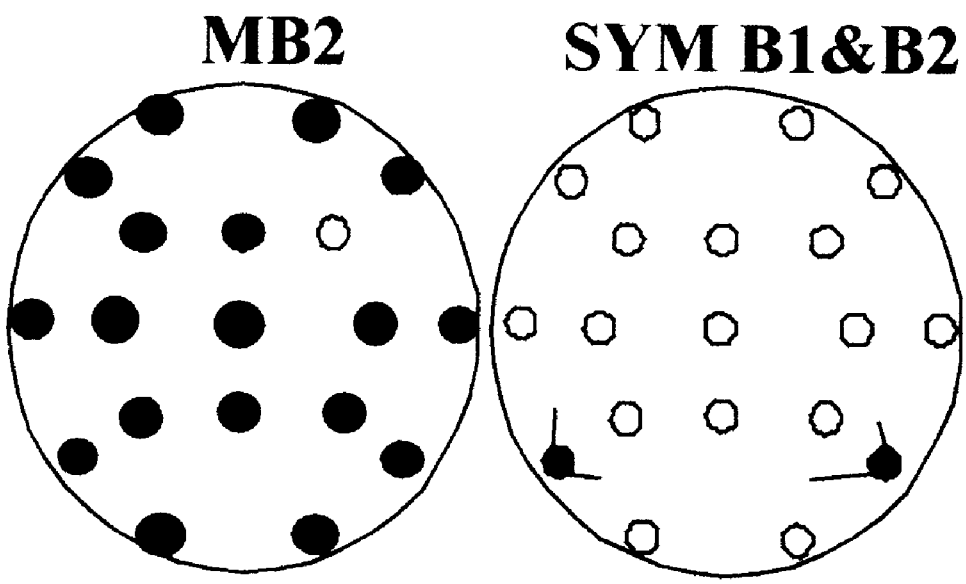
Figure 138:
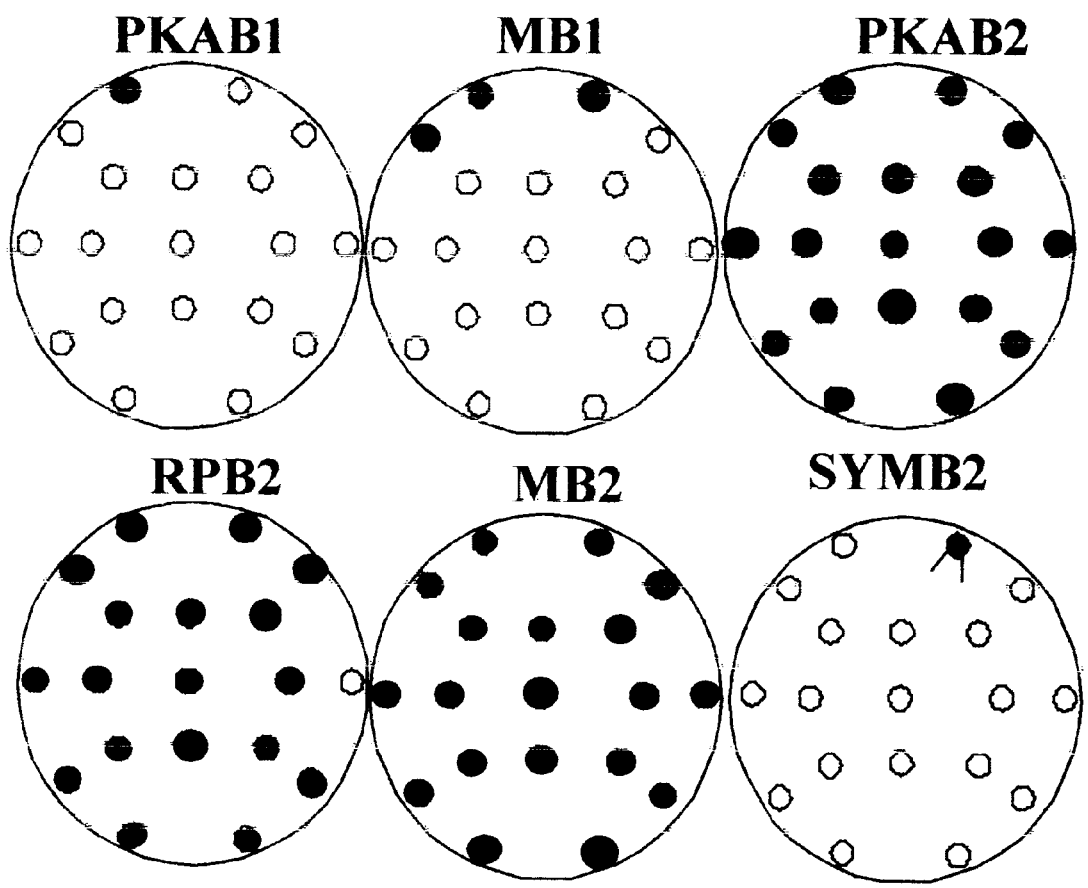
Figure 139:
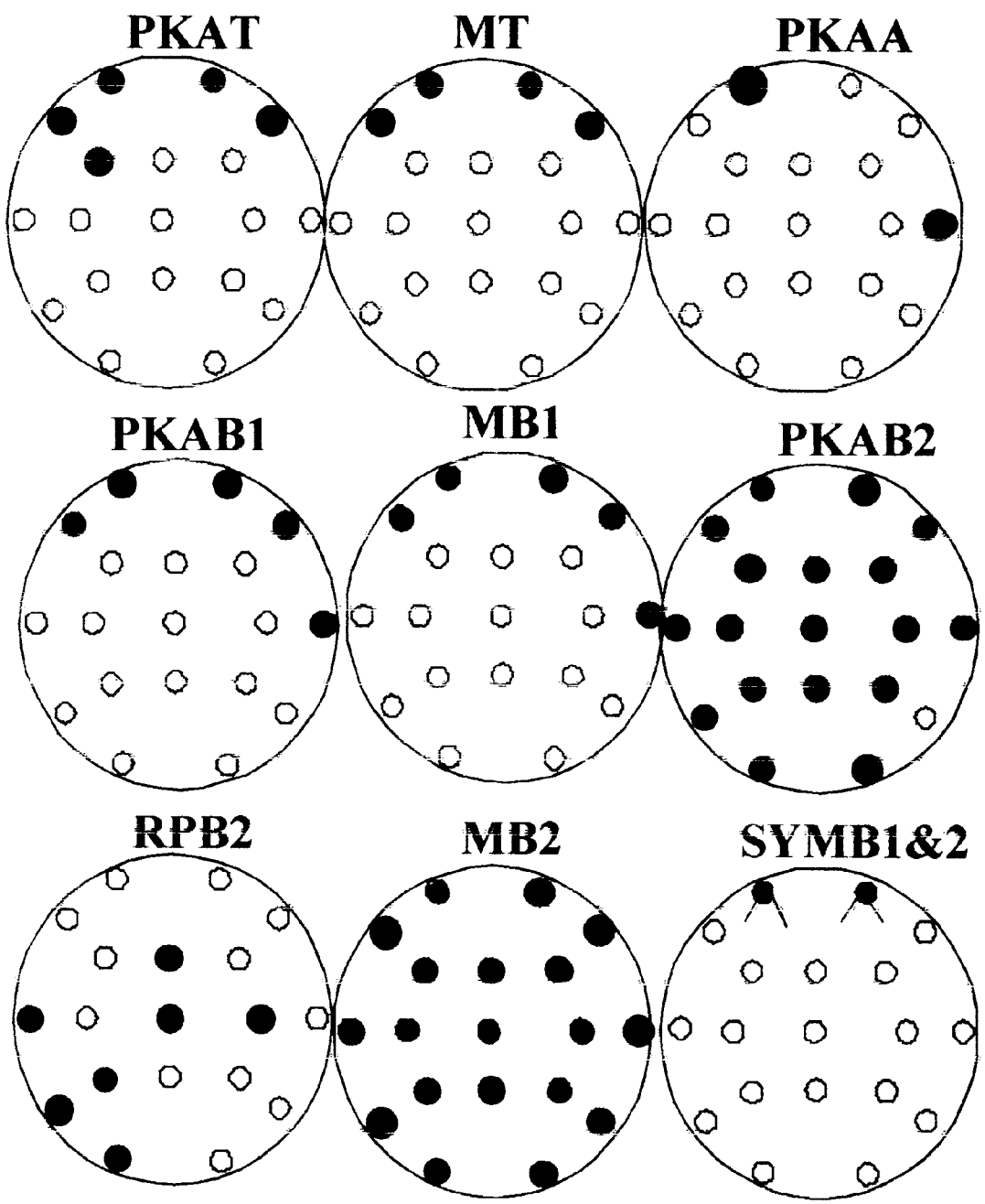
Figure 140:
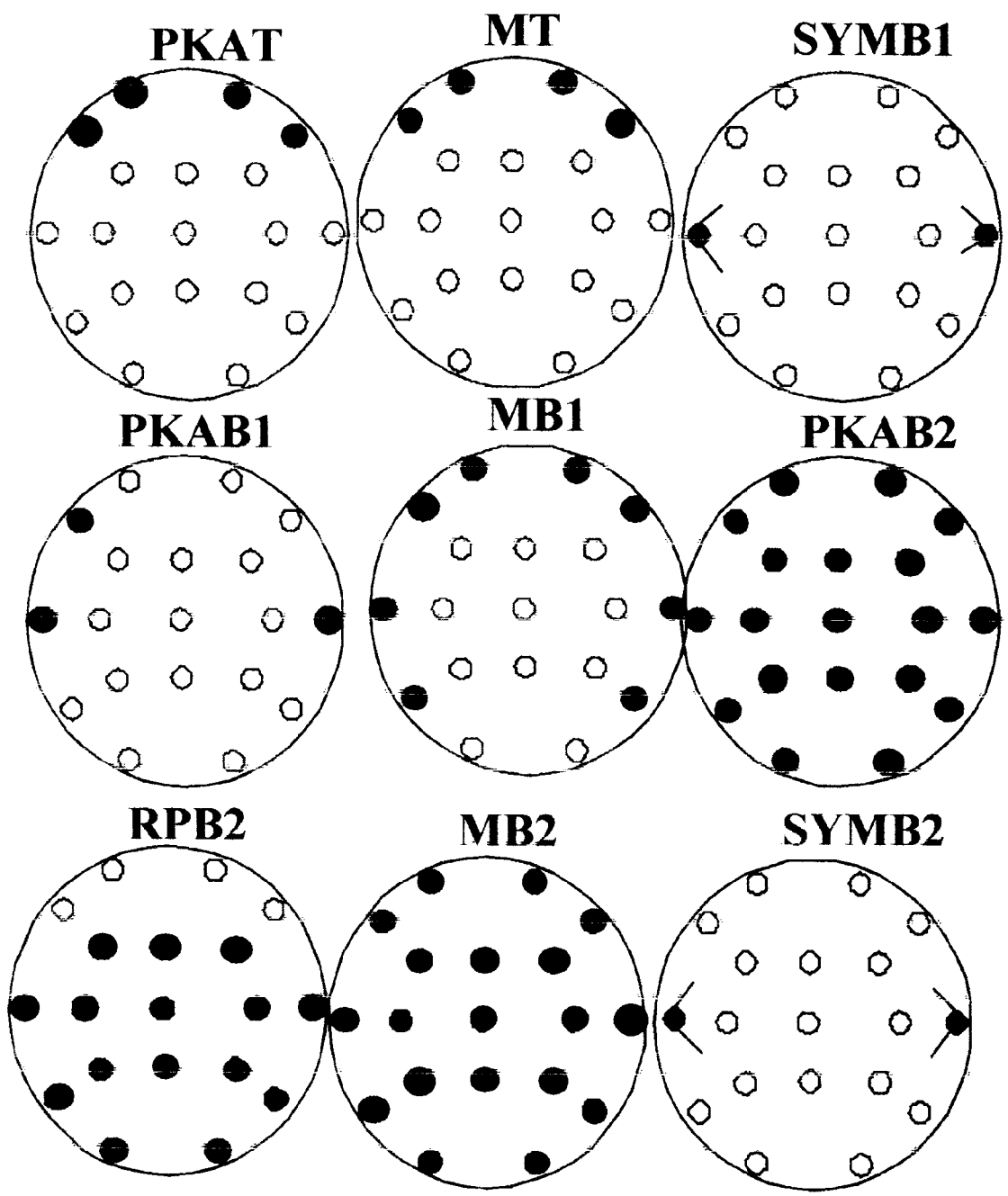
Figure 141:
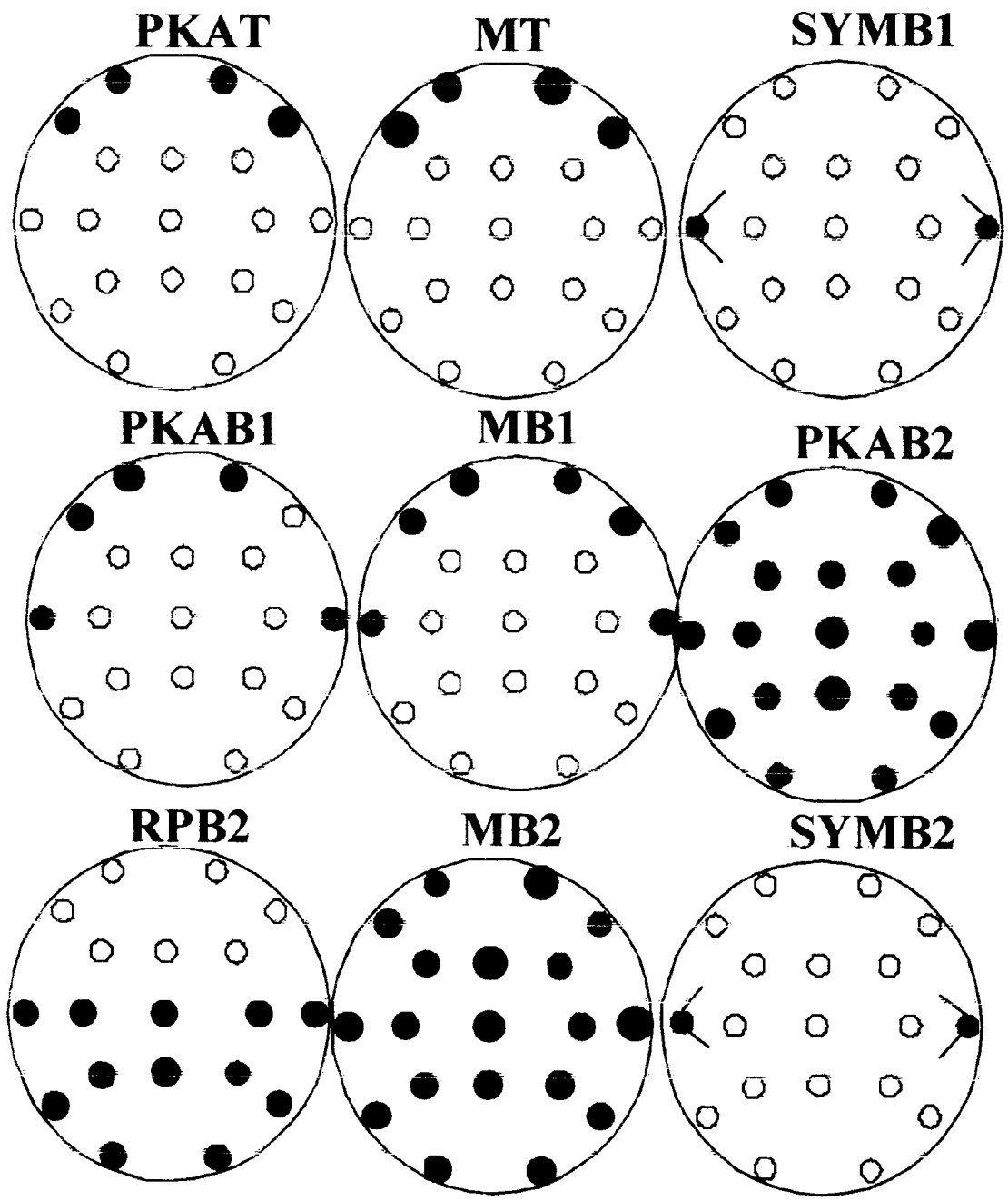
Figure 142:
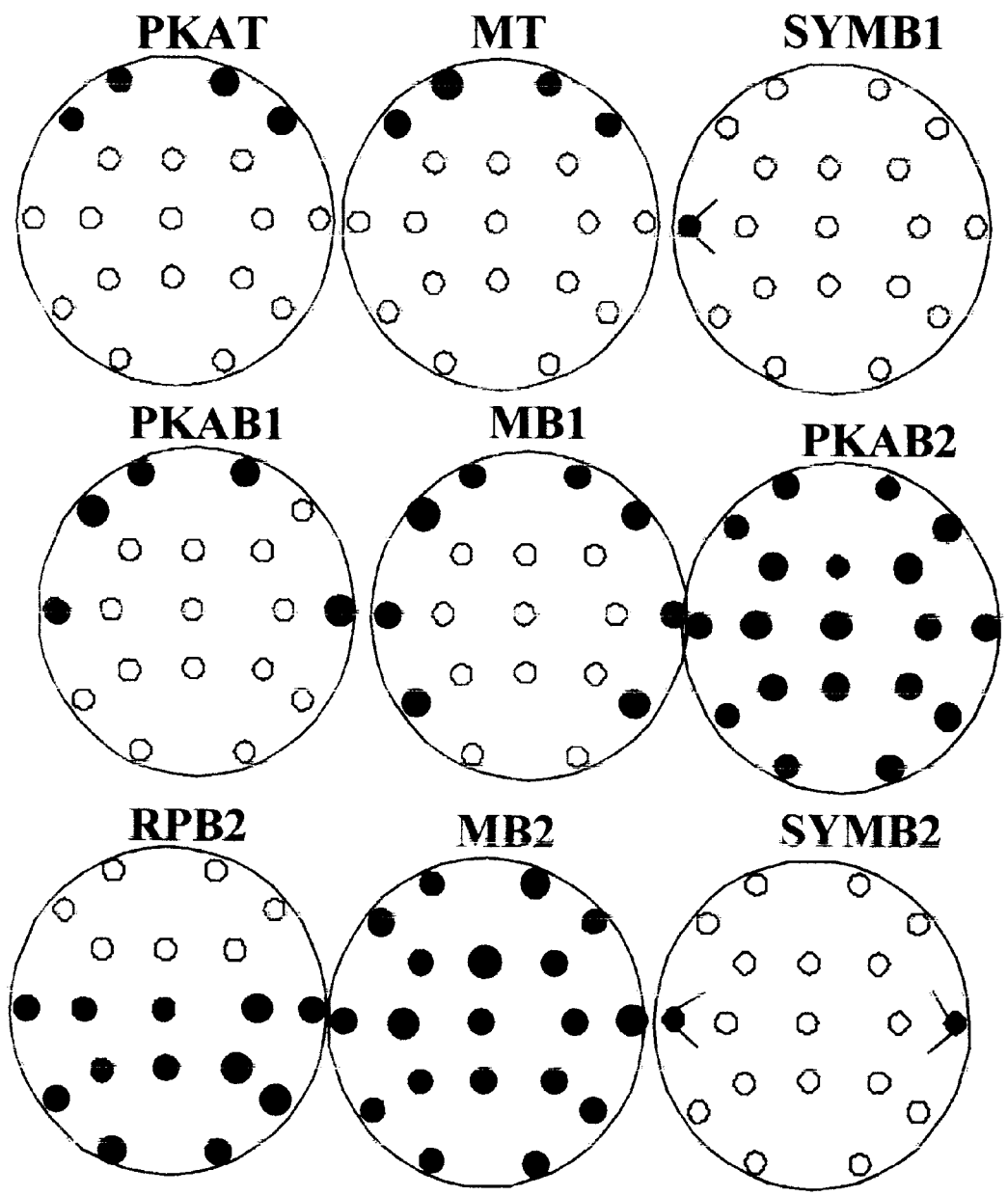
Figure 143:
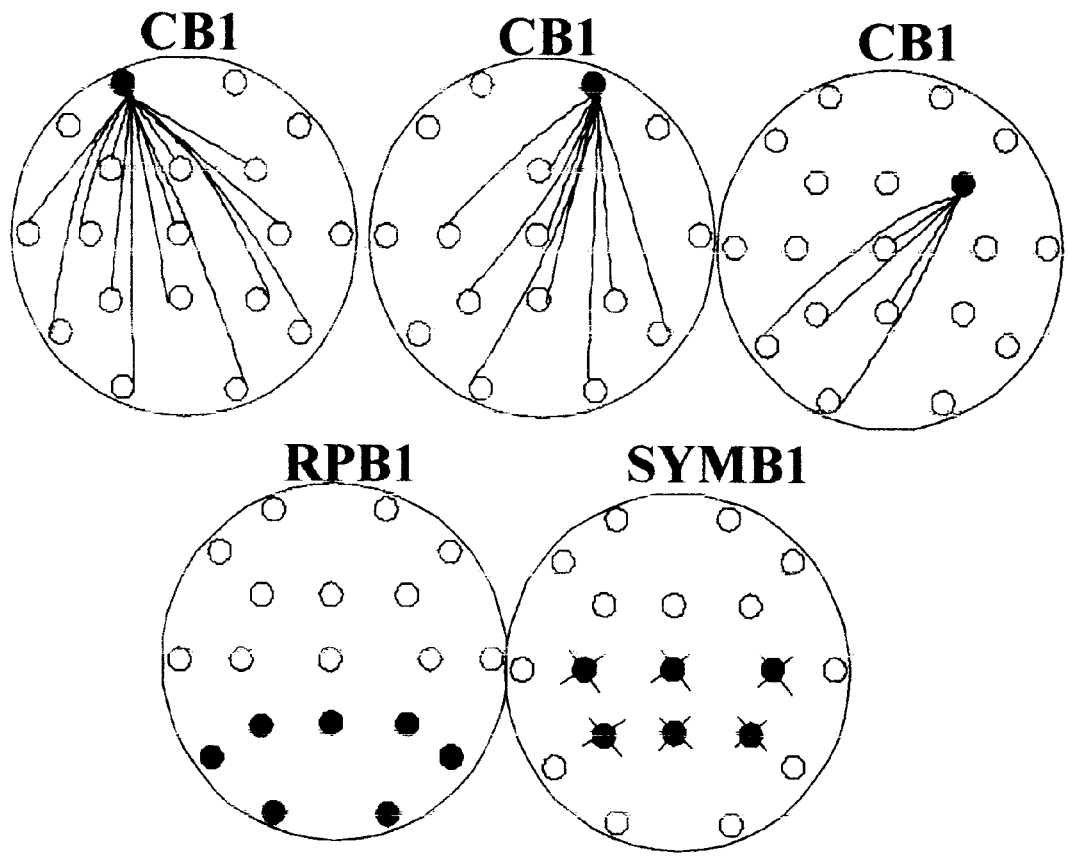
Figure 144:
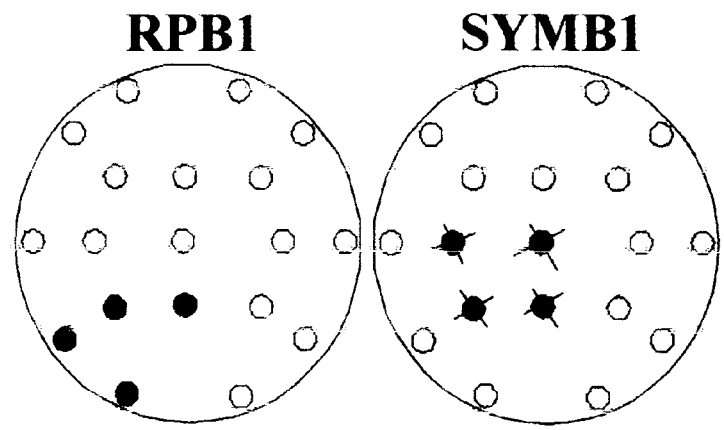
Figure 145:
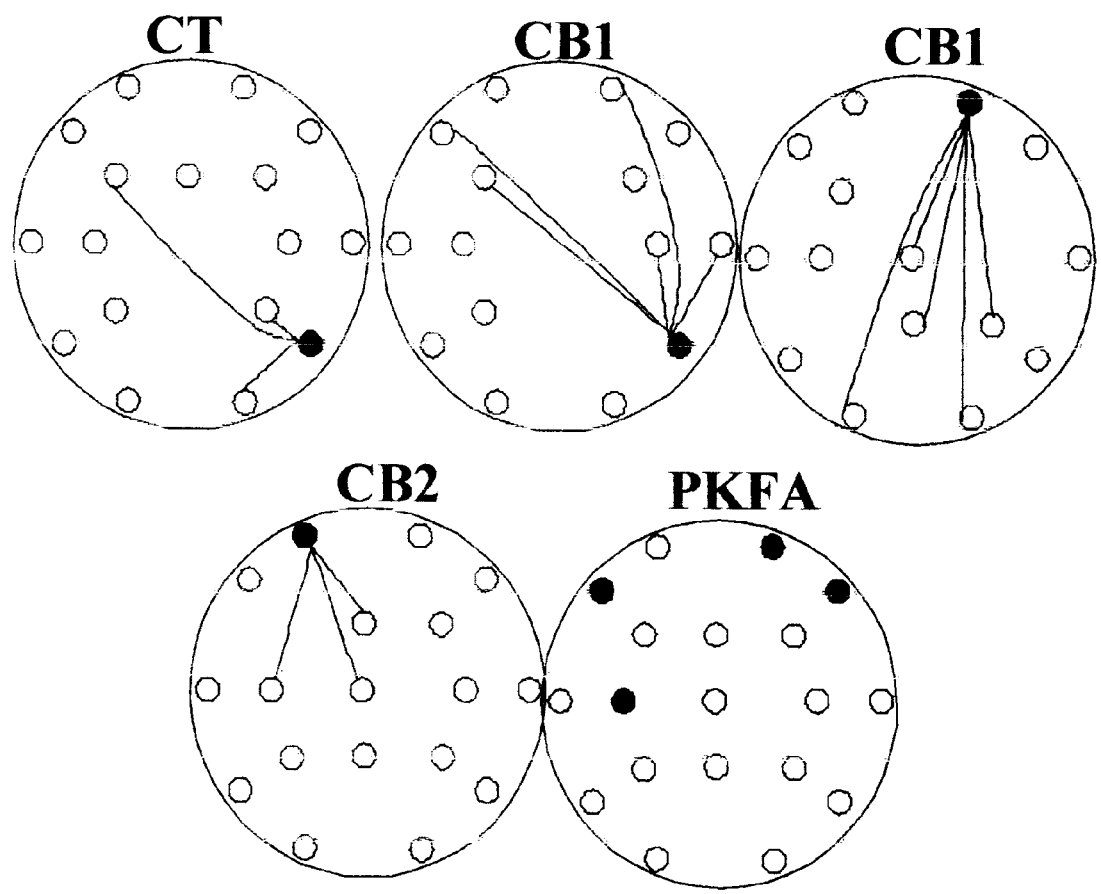
Figure 146:
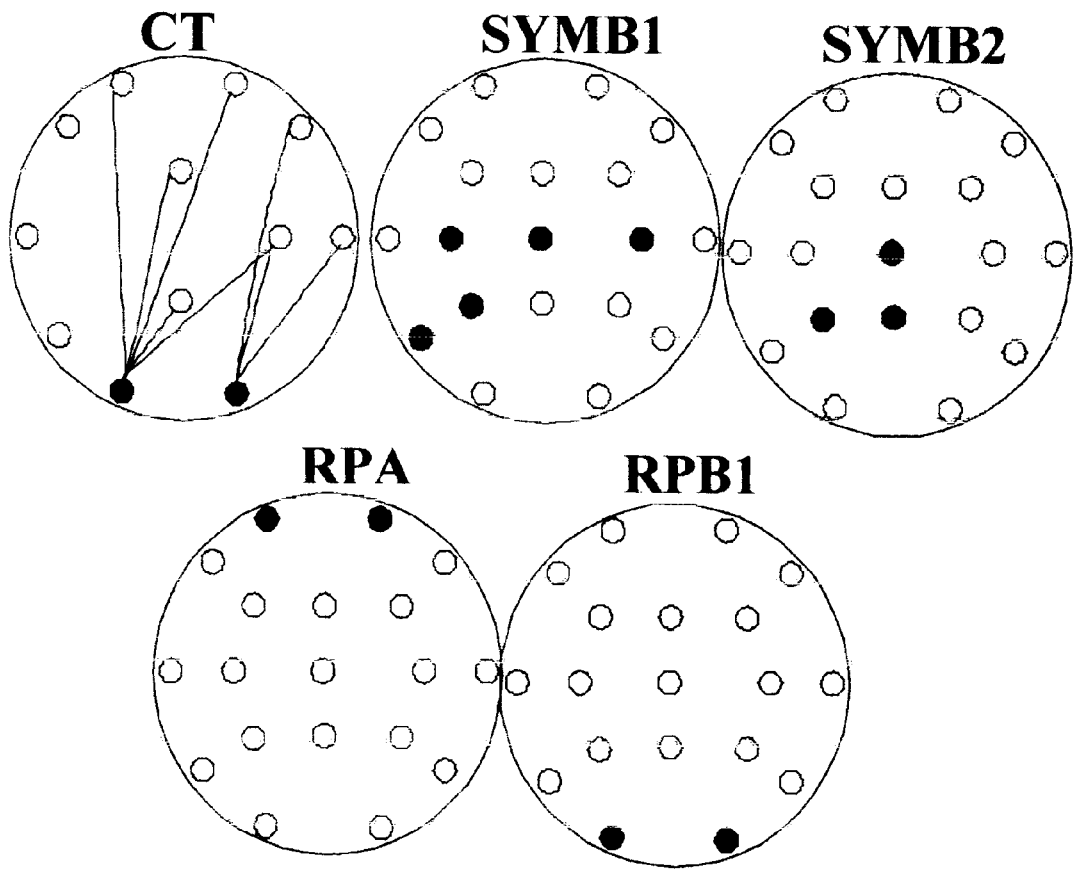
Figure 147:
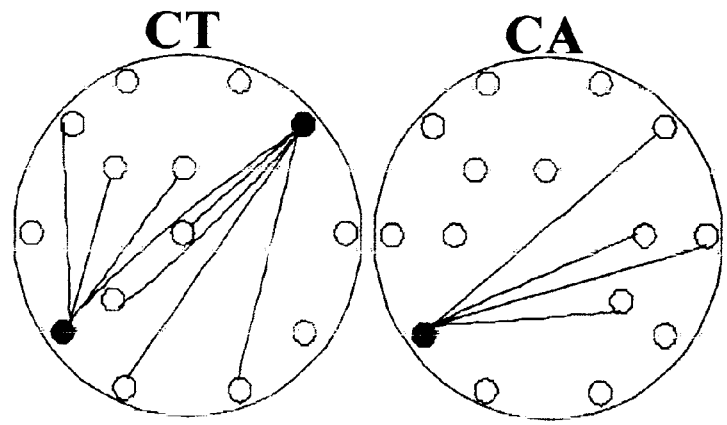
Figure 149:
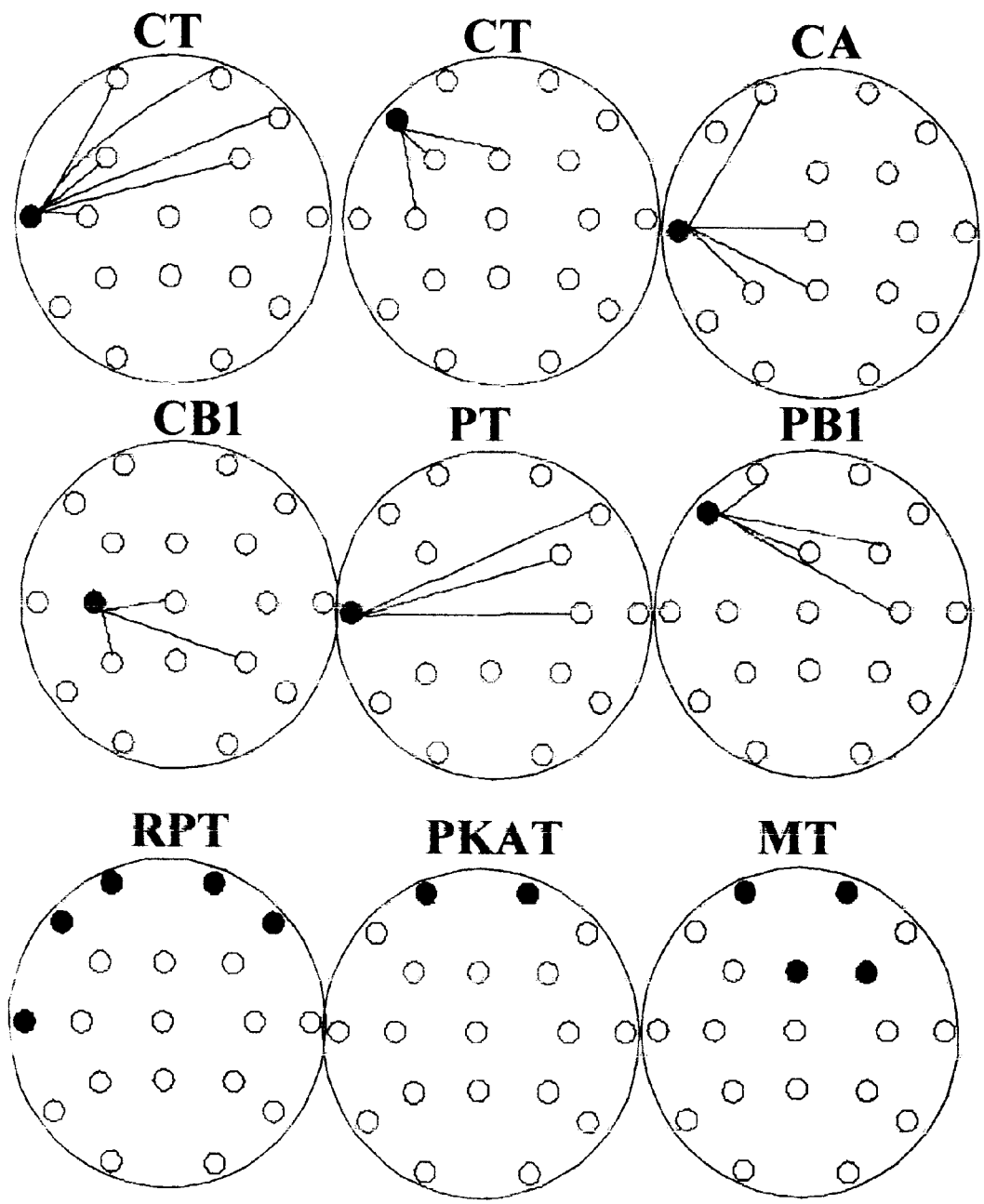
Figure 150:
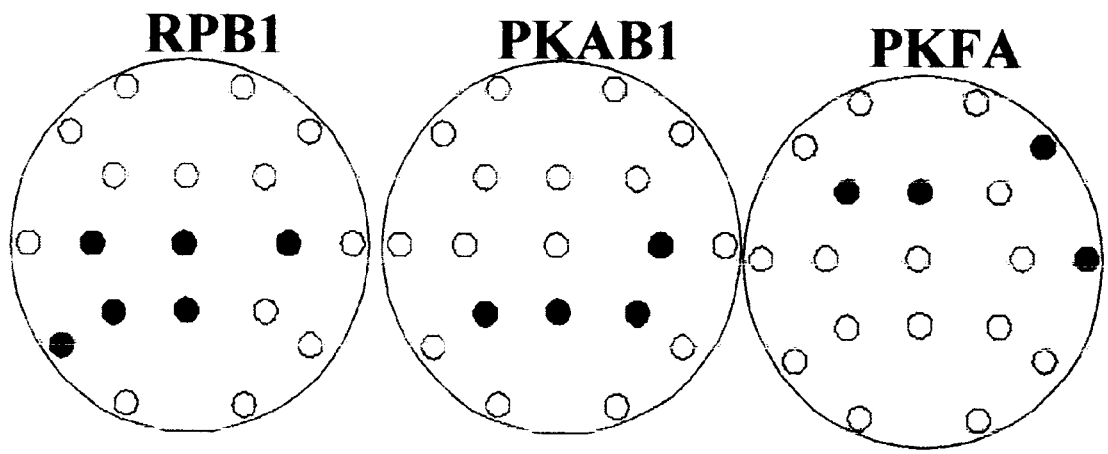
Figure 151:
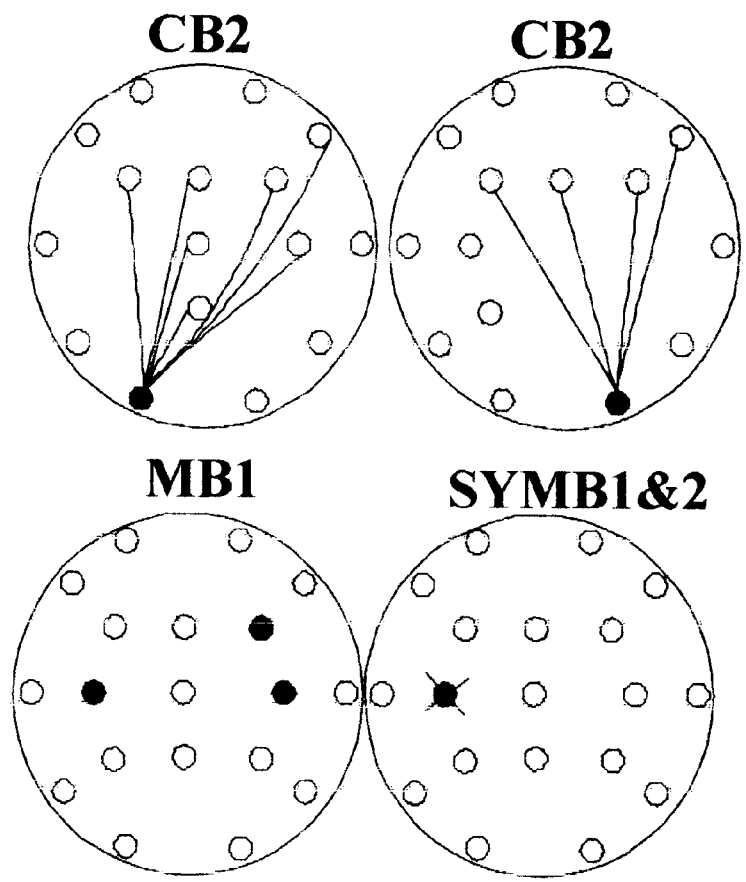
Figure 152:
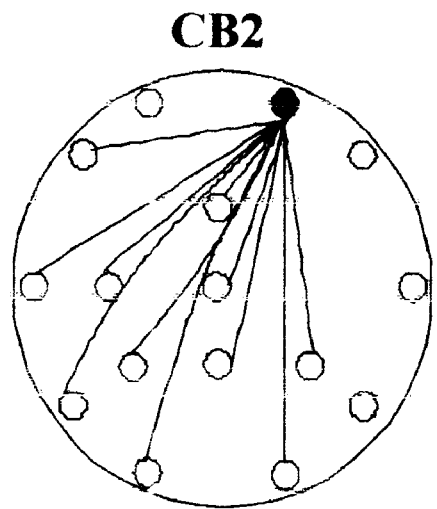
Figure 153:
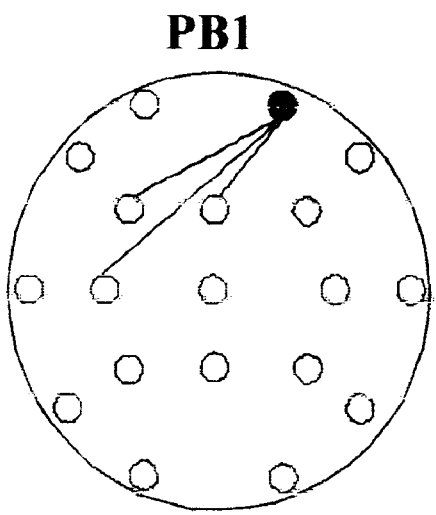
Figure 154:
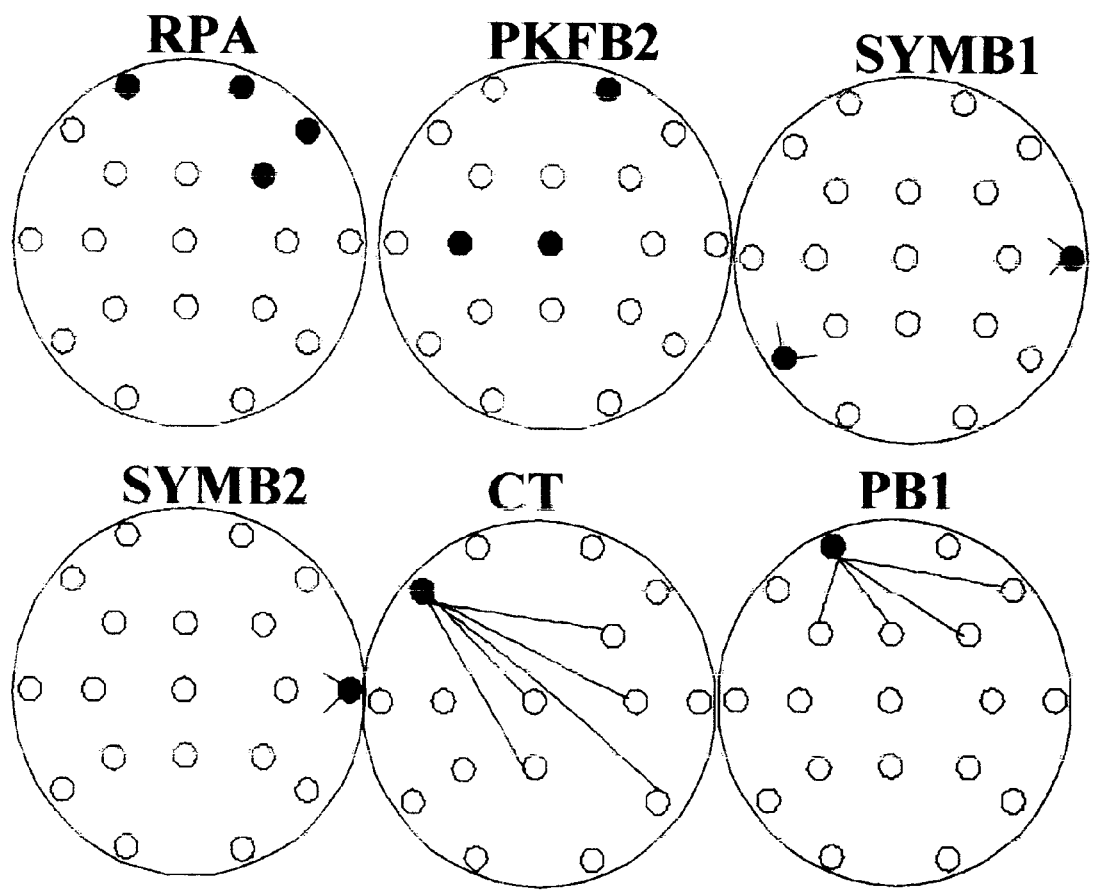
Figure 155A:
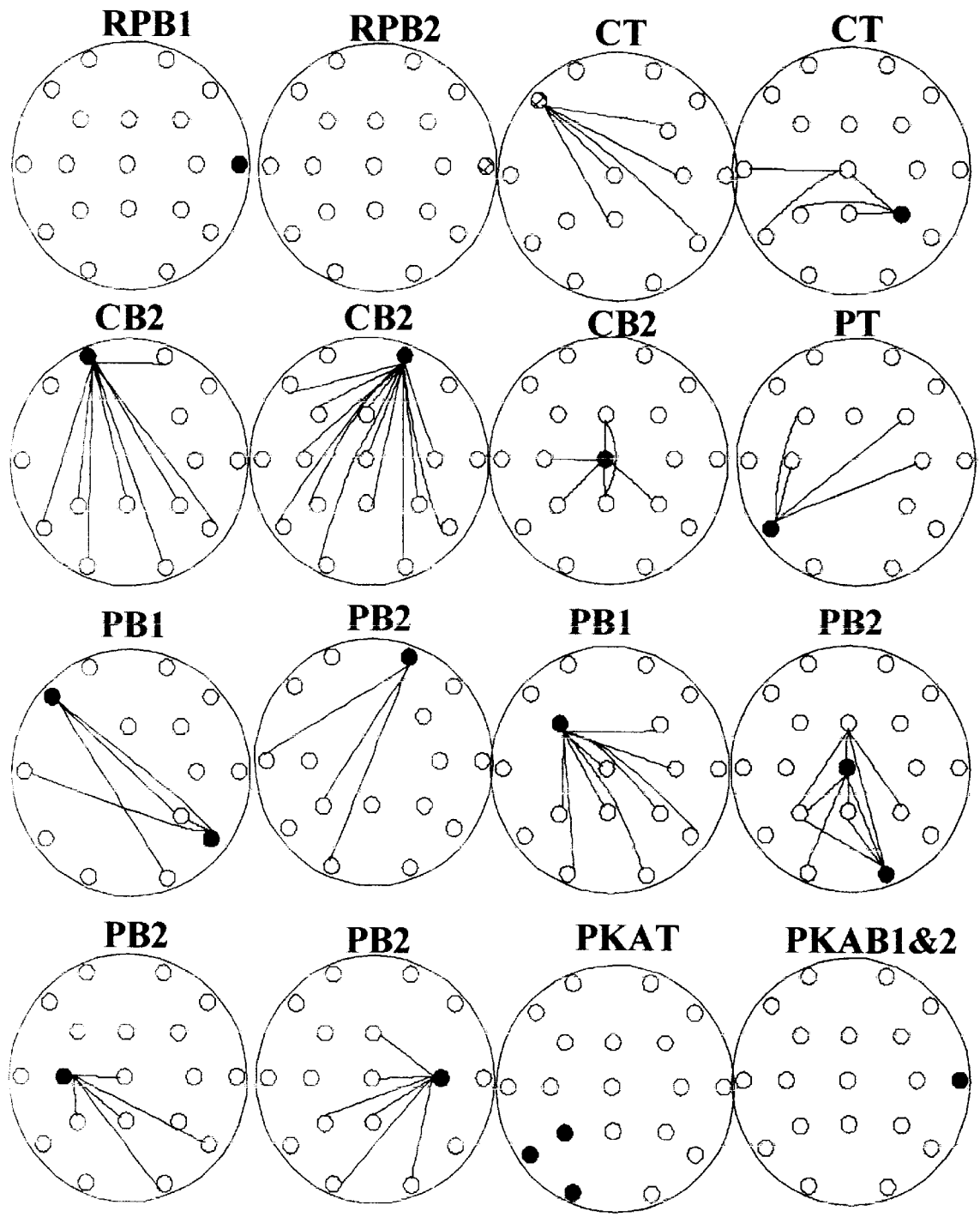
Figure 155B:
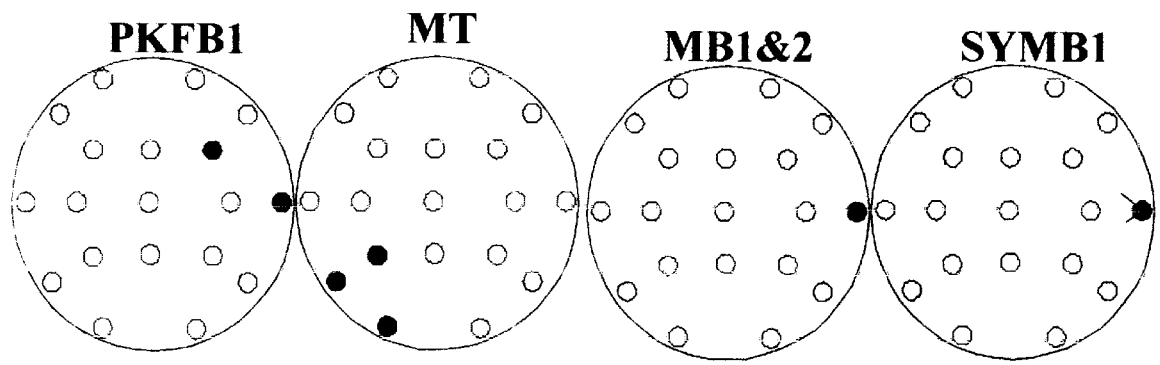

FIG. 124 (Delayed Recall of Intentions ("to do" list)—experiment coding CR#1) present the variables whose level of activation during the silent recall period predicted subsequent success in recall.

A similar analysis of a visualization task (subjects to visualize a beach) resulted in significant (0.10 or lower alpha level) activations in terms of relative power of Beta2 at T6 and P3, peak amplitudes of Beta2 at T4 and T6, magnitudes of Beta2 at T3, T4, C4, T6, P3, O1 and O2, and symmetry significant activations at T3 and T4 in terms of Beta1 and Beta2 and T5 in terms of Beta2 activity. There were no significant patterns of connectivity in the visualization task. Thus the results of the memory tasks cannot be understood in terms of subvocal speech or visualization.

Clinical conditions such a dementia, Alzheimer's and memory disorders can be diagnosed using the novel invention. Primarily it is the temporal lobes which are affected in these disorders and the memory system mostly affected is the short memory ability. Long term memory is the last to be affected. If the temporal lobes are unable to send their projections to the frontal lobes then no posterior projection system can be established and thus the information is lost, i.e. memory does not exist. However, as long term recall appears less dependent upon temporal lobe activity, there is adequate recall of information from childhood, etc. This is only affected, according to this data, if the frontal lobes are affected. The data indicated that the degree of activation variables which are relevant for recall are not of temporal lobe origin, but of frontal lobe origin (Theta) projecting to posterior portion of the head. See, FIGS. 55 and 56.

Hence, QEEG variables (5 activation, 2 relationship variables, 19 locations and 5 bands up to 64 Hertz) were collected under a variety of cognitive tasks and correlated with relevant performance measures to discover the relevant QEEG parameters of effective cognitive functioning. For one subject, all tasks were conducted under a sampling rate of 512, which allowed the Hertz range to be extended to 128. The tasks involved two auditory memory conditions (list learning and paragraph recall) and two more visually oriented tasks (recalling Korean figures, names of faces) under short-term recall and delayed recall conditions. As additional short and delayed recall condition included reading. Additional delayed recall conditions included memory for location and a "to do" list. Additional cognitive tasks included auditory and visual attention, non-verbal problem solving, hearing words, spelling, multiplication problems, two digit spatial addition problems, pronouncing nonsense words (silently and outloud), eyes closed, subvocalization patterns, visualization and autobiographical memory (earliest childhood memory and memory for facts during elementary school years). Recognition measures were taken only for the faces-names condition. There were 151 subjects evaluated, consisting of 38 head-injured subjects, 83 normals over the age of 13, and 30 children under the age of 13. Additional variables collected included years of education, time since accident, sex, handedness and Shipley Institute of Living measures of IQ, verbal and abstraction scores. The results indicated significant effects of the frontal, posterior and temporal phase and coherence generatators in terms of their relationship to effective memory and problem solving performance, with all ranges involved to some extant, dependent upon task and condition.

The electrophysiology of the brain employs a holographic type approach which varies by task and employs the location specific projectors in different frequencies for different tasks. The specifics of the brain's employment of these locations and frequencies for these tasks is what has been discovered.

Auditory input of information requires the projection of signals from the Theta to Beta1 frequencies (in terms of phase or coherence) from the temporal lobes (T3) and secondarily from the C3 position to the frontal (all F positions) and central regions (C3,Cz,C4). The more difficult the task is the higher the frequency employed. Simultaneously, frontal projections in terms of the Beta frequencies (coherence or phase) must project to the posterior/central portion of the head (predominantly left posterior). Posterior is defined as the following locations: T5, P3, Pz, T6, O1 & O2. Central positions are defined as C3, Cz and C4. Left posterior is defined as T5, P3 & O1.

Immediately following the input of information the effective processing of the information requires the continuation of the signal from the T3/C3 positions and the continuation of the frontal phase and coherence generators (predominantly F7 and F8) to the posterior/central portion of the brain. In addition the temporal position (T5) becomes an added projection system (Theta to Beta1, phase and coherence) to the posterior/central and frontal areas.

The immediate recall of auditory information involves T3 projections and secondarily C3 (Theta and Alpha coherence and phase) to the frontal regions. Frontal projections to the posterior/central regions need to occur in the Theta to Beta2 ranges (predominantly Alpha and Beta1(F7)). Posterior projections from left posterior (T5,Pz,P3 & O1, with T5 being the most important) to the entire head (but frontal regions in particular) in terms of the Theta and Alpha (coherence or phase) are the third element of effective recall. The fourth element involves the right temporal lobe generator (Beta2 coherence) to the whole head. Activations (amplitudes, magnitudes and peak frequencies) in the posterior and left temporal regions are also important contributors to effective short term recall. Activations of the frontal poles (Fp1 & Fp2) in terms of beta activity are contributing factors to effective recall.

Long term (30 minutes) recall of auditory information involves the T3 generator to the frontal areas (phase and coherence, Theta, Alpha & Beta1) to the frontal/central regions. The left posterior (T5,P3 & O1) projection systems must be in operation (Theta, Alpha, Beta1-phase and coherence) predominantly to the frontal/central portions of the head. The O2 and T6 locations are secondary contributors to the creation of the frontal/central hologram. The frontal projection (predominantly left frontal F7, Fp1 & F3, coherence and phase) systems are active in terms of the Beta ranges (especially Beta2 coherence and secondarily Theta) to the posterior/central regions. The right temporal (T4 and secondarily T6 phase) coherence Beta activity to the entire head is important for word lists but not paragraphs). Posterior activations (C3, P3, Cz, Pz, O1,P4) in terms of Beta activity (Peak amplitudes, magnitudes) are important contributors to effective delayed recall of auditory information.

As reading is an important issue by itself, it will be discussed apart from the other more visually oriented tasks such as Korean Figures and the recalling of Names.

Reading input requires projection systems from the T3, T5, O1, O2, P3, P4 & T6 positions in terms of Alpha coherence (and secondarily Beta activity-coherence and phase—from O1) to the frontal areas. Frontal projections to the posterior/central regions are required to be active in terms of Beta activity (phase and coherence).

Immediate recall of reading material involves temporal lobe (T3) projections to the frontal areas in terms of Theta, Alpha, Beta1&2-coherence and phase) and right temporal (T4) in terms of Beta1&2 to the whole head (coherence and phase) and secondarily Theta phase. Also relevant is Beta activity from the T6 position in terms of Beta2 phase.

Posterior projection systems to the frontal regions involve left posterior (T5, O1) Alpha phase Frontal projections in terms of Theta to Beta2 coherence and phase connections to the posterior regions are critical. Although the entire frontal projection system is relevant, the right frontal and lateral (F8, T4) are more important in the reading situation than in the auditory information situation. Activation issues focus on the posterior peak amplitudes and magnitudes of Beta 1&2.

Delayed recall of reading material depend upon the left temporal (T3) Theta and Alpha phase and coherence generators. Right hemisphere activity in the Beta2 bands projecting to the left hemisphere are relevant from the T4, C4, P4, T6 and right frontal (F8, F4, Fp2) positions (coherence activity). Additionally the right temporal (T4) projection system in terms of phase theta is secondarily important.

The posterior projection system involve Phase Alpha and Theta activity from the T5, O1 & O2 positions to the frontal region and secondarily coherence Beta1 from O1.

The frontal projection system predominantly involves the right frontal (F8, F4 & F2) Beta2 coherence and phase generators to the posterior regions, although Beta1 and Theta phase and coherence figures are secondarily important. Activation measures which are relevant include posterior magnitudes, symmetries and peak frequencies of beta activity.

As to visual information regarding "Memory for Names/Korean Figures" the input stage for more visually oriented situations involves predominantly the frontal lobe activity to the posterior region in terms Beta activity (phase and coherence). The left frontal positions (F7, F3,Fp1) employ, in addition, the lower frequencies (Theta and Alpha-coherence and phase). Temporal activity is significantly less than in the auditory input situations, but the T3 (phase Alpha to Beta2) positions is still participating as well as the T4 position in terms of phase Theta and coherence activity (Theta to Beta2). Posterior projection systems involves the T5 position in terms of phase activity (Alpha and Beta1) and O2 position in terms of coherence activity (Theta and Alpha).

Immediate recall of this type of information involve frontal activity in the beta ranges (coherence and phase) with again a tendency for the left frontal (F7) to also employ the lower frequencies (phase Alpha and Theta) as well. Temporal activity employs coherence activity from the T3 position in terms of Theta to Beta2 bands. Posterior involvement includes the four posterior positions (T5, O1, O2, T6) in terms of phase and coherence activity from Theta to Beta1) projecting to the frontal regions.

Delayed recall involves frontal generators in the Beta1 band predominantly (phase and coherence) but also coherence Beta2. The left frontal has an additional tendency to employ the lower frequencies (Theta, Alpha-coherence and phase). Temporal activity is evident in terms of T3 Theta to Beta1 bands to the frontal regions and T4 in terms of Theta activity (phase and coherence). Posterior involvement predominantly involves the T5 location in terms of coherence Alpha and coherence Beta2.

The predominant effective cognitive skill or problem solving approach involves the frontal phase an coherence generators from the frontal lobes in terms of Beta activity and posterior peak amplitudes of Alpha, Beta and peak frequencies of Beta1.

The effective parameters for spelling involve coherence activity from the posterior and temporal areas and T4 phase beta1 projections to the posterior region. In addition frontal projections to the posterior are in terms of Alpha, Theta and Beta1&2 (phase and coherence) activity. Posterior activations in the occipital regions are relevant in terms of Relative power of Beta1&2 and peak frequencies of Beta1.

Success with multiplication tables depends upon coherence Beta2 activity predominantly from the frontal areas, but also most of the posterior regions as well. Success on double digit addition depends upon frontal theta and alpha phase activity to the posterior regions, and also in terms of posterior Theta and Alpha (especially T5) activity (as well as T3 phase alpha). Posterior activations in terms of peak frequencies of Beta1 are important as well (especially the entire left hemisphere). Right posterior activation (especially T6) are important in terms of Beta2 activity (relative power, peak amplitudes, magnitudes and peak frequencies).

In terms silent reading, the frontal projections in terms of Theta and Alpha activity to the posterior regions. Temporal factors are not important in this task, but posterior projections (Theta, Alpha, Beta1-coherence and phase) from the right posterior as well as T5 are important for success. In terms of reading outloud, it is frontal phase Alpha projection system and the right posterior phase Theta (T6,P4) and left posterior coherence activity (Theta, Beta1&2) which are relevant to success. Right posterior activations in terms of peak frequencies of Beta1 from T6 and Pz are also contributory. Posterior coherence and phase Beta activity from O1 as well as T4 coherence Beta activity are important for success as the subject moves from the silent to outloud condition. In terms of recalling where objects are placed it is coherence Alpha activity from the left posterior T3 which are predominantly involved in success.

Effective memory for intentions is determined predominantly by right hemisphere (T4,T6) theta and Beta1 phase and coherence activity. The Norm figures indicate that the predominant normal response to tasks, whether the task is visual or auditory, involves the input, recall or delayed recall aspect of memory functioning, problem solving, etc. is the activation of the upper Beta frequency ranges in terms of amplitudes, magnitudes and relative power. These variables appear to have limited relationship to effective cognitive functioning in a normal population. Previous research has demonstrated that the inhibition of Theta activity and increased Beta1 type activity can have a beneficial effect on cognitive functioning and normalize brain functioning. The reason for the effect is demonstrated in the Child Figures, as the Beta1 band is one of the predominant effective Hertz ranges. Many of the research studies involving remediation addressed the clinical condition of Learning Disability, ADD, etc. If the task is to normalize the brain, however, and the brain's normal response is to activate predominantly the upper frequency ranges, then the main focus of the rehabilitation efforts have been misdirected If, for example, the central feature of auditory attention involves the frontal activation of the Beta2 frequency range and the temporal lobes, then the placement of the electrodes at Cz and C3 become inappropriate if the goal is to improve attentional ability in an Attention Deficit Disorder subject. The success of the rehabilitation efforts to date, therefore, have to be attributed to a generalization effect, as factor analysis of the beta frequencies generally reflect a two or three factor solution, i.e. frontal, temporal and posterior (not presented in data). Analysis of the Beta1 frequency band indicates that the C3, Cz, and C4 position load on the frontal factor. Thus the rehabilitation efforts have affected the anterior activation factor in the auditory attention condition in the lower frequencies and posterior factor in the upper frequencies.

The attainment of normal activation patterns is important for normalization and cognitive skills, as excessive Theta activity is a hindrance to cognitive skills, and the development of appropriate Beta activity is relevant to cognitive skills. The research of this patient, however, indicates that within normal activation levels there are distinct patterns that can further delineate effective cognitive functioning. A further development fact evident in this research is that the development of these activation patterns involves a movement towards decreasing the peak amplitudes and magnitudes of the bands and an increase in the relative power figures.

Different tasks may be employed but considered within the scope of the method of the invention. For example, a different pattern of activation/connections would constitute a different means to obtain the same function of the method. One such example would be to improve a blind human subject's recall of tactile information, which presumably would employ different sets of projection systems, especially in terms of the input stage.

The invention has been described in detail with particular reference to a certain preferred embodiment therof, but it will be understood that variations and modifications can be effected within the spirit and scope of the novel invention and subject to the doctrine of equivalents.

What is claimed is:

1. In a live human subject having a head and having observed or experienced an event, or the like, a method for improving memory of the event, object or the like comprising the steps of exposing the subject to a cognitive task related to the event, object or the like during a session; attaching an electrodes on the head; measuring QEEG brain functions during the session; recording the session and recording the QEEG measurements; converting the QEEG data obtained from the subject's data into an ASCII file; importing the QEEG data into a statistical computer analysis program loaded on a computer; correlating performance on each particular task with the QEEG parameters across a norm derived from a control group of subjects; correlating the QEEG parameters which have positive correlations with memory performance; and communicating the positively correlated QEEG parameters back to the subject in the form of verbal information by coaching the subject whereby after the subject is coached by an operator sufficiently such that an increase the positively correlated QEEG parameters is measured and the memory of the subject is objectively and measurably improved.

2. A method as claimed in claim 1 further comprising determining the electrical output of a brain region in the head of the subject from said electrodes generated via an QEEG unit about the head of a human, obtaining from the electrodes a QEEG electrical signal being first data representative of energy in the brain region in a primary frequency domain, determining from the electrodes an electrical signal being second data representative of energy in the primary frequency domain relative to the energy in a secondary frequency domain, relating the first data with the second data thereby obtaining a value representative of electrical output in the brain region, and presenting such value as determining a selected norm, and wherein relating is effected by determining an increase or decrease of the first data and increase or decrease of the second data relative to the selected norm and indicating a improvement of memory condition when the first data and the second data both increase or decrease relative to the selected norm, and indicating a lack of improvement in memory condition when one of the first data and the second data respectively increase or decrease relative to the selected norm while the other of the first data or second data, respectively, is oppositely directed relative to the selected norm.

3. A method according to claim 1 further comprising the additional step of delineation of a set of specific QEEG variables from a full set of QEEG variables available and identified as responsible for cognitive abilities; and the additional step of identification of the relationship between the resting levels associated with the set of specific QEEG variables wherein eyes are closed and a set of comparison QEEG levels related to auditory attention whereby future success in auditory memory tasks has been defined.

4. A method according to claim 3 further comprising the step of comparing the live human subject's response pattern under activation conditions to a normative reference group's pattern of activation for said specified QEEG variables and the additional step of marking of the specific QEEG variables and associating and selecting a group of QEEG variables wherein said selected QEEG variables are associated with success in performing a pre-specified task.

5. A method according to claim 4 wherein said selected QEEG variables are parameters associated with auditory memory ability, auditory-visual memory ability, spelling ability, mathematical ability, or pronunciation ability.

6. A method for providing a diagnostic test for a brain of a human to ascertain specific weak areas of cognitive functioning, the brain comprising the steps of exposing the subject to a cognitive task related to the event, object or the like during a session; attaching an electrode cap on the head; measuring QEEG brain functions during the session; recording the session and recording the QEEG measurements; converting the QEEG data obtained from the subject's data into an ASCII file; importing the QEEG data into a statistical computer analysis program loaded on a computer; correlating performance on each particular task with the QEEG parameters across a norm derived from a control group of subjects; and then correlating the QEEG parameters which have positive correlations with memory performance.

7. A method for providing a diagnostic test for a brain of a human to ascertain presence of an ineffective use of a recall strategy comprising the steps of exposing the subject to a cognitive task related to the event, object or the like during a session; attaching an electrode cap on the head; measuring QEEG brain functions during the session; recording the session and recording the QEEG measurements; converting the QEEG data obtained from the subject's data into an ASCII file; importing the QEEG data into a statistical computer analysis program loaded on a computer; correlating performance on each particular task with the QEEG parameters across a norm derived from a control group of subjects; and then correlating the QEEG parameters which have positive correlations with memory performance.

* * * * *